US012564651B2

(12) United States Patent　　　(10) Patent No.:　US 12,564,651 B2

Kelly et al.　　　　　　　　　　(45) **Date of Patent:　　*Mar. 3, 2026**

(54) RADIOLABELED ANTI-PD-L1 ANTIBODIES FOR IMMUNO-PET IMAGING

(71) Applicant: Regeneron Pharmaceuticals, Inc., Tarrytown, NY (US)

(72) Inventors: Marcus Kelly, New York, NY (US); Dangshe Ma, Millwood, NY (US); William Olson, Yorktown Heights, NY (US); Gavin Thurston, Briarcliff Manor, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/750,073

(22) Filed: Jun. 21, 2024

(65) Prior Publication Data

US 2024/0335572 A1　　Oct. 10, 2024

Related U.S. Application Data

(60) Continuation of application No. 17/560,003, filed on Dec. 22, 2021, now Pat. No. 12,053,534, which is a continuation of application No. 16/915,894, filed on Jun. 29, 2020, now abandoned, which is a division of application No. 15/829,311, filed on Dec. 1, 2017, now Pat. No. 10,736,976.

(60) Provisional application No. 62/569,773, filed on Oct. 9, 2017, provisional application No. 62/457,267, filed on Feb. 10, 2017, provisional application No. 62/428,672, filed on Dec. 1, 2016.

(51) Int. Cl.

| | |
|---|---|
| *A61K 51/10* | (2006.01) |
| *A61K 51/04* | (2006.01) |
| *C07K 16/22* | (2006.01) |
| *C07K 16/28* | (2006.01) |
| *C07K 19/00* | (2006.01) |

(52) U.S. Cl.

CPC ...... *A61K 51/1045* (2013.01); *A61K 51/0474* (2013.01); *A61K 51/1093* (2013.01); *C07K 16/22* (2013.01); *C07K 16/2827* (2013.01); *C07K 19/00* (2013.01); *A61K 2121/00* (2013.01); *C07K 2317/515* (2013.01); *C07K 2317/565* (2013.01)

(58) Field of Classification Search

CPC ............... A61K 51/00; A61K 51/1045; A61K 51/0474; A61K 51/1093; A61K 2121/00; C07K 16/22; C07K 16/162827; C07K 19/00; C07K 2317/515; C07K 2317/92; A61P 35/00

See application file for complete search history.

(56) References Cited

U.S. PATENT DOCUMENTS

| | | | |
|---|---|---|---|
| 4,680,338 | A | 7/1987 | Sundoro |
| 5,332,567 | A | 7/1994 | Goldenberg |
| 5,639,879 | A | 6/1997 | Mease et al. |
| 6,329,503 | B1 | 12/2001 | Afar et al. |
| 6,814,951 | B1 | 11/2004 | Thiele et al. |
| 7,387,772 | B1 | 6/2008 | Hansen et al. |
| 8,545,809 | B2 | 10/2013 | D'Souza et al. |
| 8,771,966 | B2 | 7/2014 | Dennis et al. |
| 9,359,437 | B2 | 6/2016 | Davis et al. |
| 9,429,584 | B2 | 8/2016 | Matsumura et al. |
| 9,475,874 | B2 | 10/2016 | Sawada et al. |
| 9,546,206 | B2 | 1/2017 | Ring et al. |
| 9,562,087 | B2 | 2/2017 | Ring et al. |
| 9,751,945 | B2 | 9/2017 | Ploegh et al. |
| 9,938,345 | B2 * | 4/2018 | Papadopoulos .. A61K 39/39558 |
| 10,081,684 | B2 | 9/2018 | Ploegh et al. |
| 10,390,522 | B2 | 8/2019 | Burova et al. |
| 10,730,944 | B2 | 8/2020 | Giurleo et al. |
| 10,736,976 | B2 * | 8/2020 | Kelly ................. A61K 51/1045 |
| 10,738,130 | B2 | 8/2020 | Haber et al. |
| 10,905,784 | B2 | 2/2021 | Kelly et al. |
| 11,117,970 | B2 * | 9/2021 | Papadopoulos .. A61K 39/39558 |
| 11,511,001 | B2 | 11/2022 | Kelly et al. |
| 11,525,001 | B2 | 12/2022 | Giurleo et al. |
| 11,896,682 | B2 | 2/2024 | Kelly et al. |
| 12,053,534 | B2 * | 8/2024 | Kelly ................. A61K 51/1045 |
| 12,077,587 | B2 | 9/2024 | Giurleo et al. |
| 2003/0077602 | A1 | 4/2003 | Rosen et al. |
| 2003/0170697 | A1 | 9/2003 | Goldenberg |
| 2004/0018557 | A1 | 1/2004 | Qu et al. |
| 2004/0185040 | A1 | 9/2004 | Garcia-Martinez et al. |

(Continued)

FOREIGN PATENT DOCUMENTS

| | | |
|---|---|---|
| DE | 10339820 A1 | 3/2005 |
| DE | 102012104504 A1 | 11/2013 |

(Continued)

OTHER PUBLICATIONS

Al-Lazikani et al. (1997) "Standard conformations for the canonical structures of immunoglobulins," J. Mol. Biol. 273: 927-948.

(Continued)

*Primary Examiner* — D. L. Jones

(74) *Attorney, Agent, or Firm* — FisherBroyles, LLP; Cara L. Crowley-Weber; Casey Donahoe

(57) ABSTRACT

Radiolabeled anti-PD-L1 antibodies and their use in immuno-PET imaging are provided herein. Included are methods of detecting the presence of PD-L1 proteins in a patient or sample.

15 Claims, 12 Drawing Sheets

Specification includes a Sequence Listing.

(56)  References Cited

U.S. PATENT DOCUMENTS

| | | |
|---|---|---|
| 2004/0253232 A1 | 12/2004 | Jakobovits et al. |
| 2005/0003469 A1 | 1/2005 | Watkins et al. |
| 2005/0208043 A1 | 9/2005 | Adams et al. |
| 2005/0276812 A1 | 12/2005 | Ebens et al. |
| 2006/0177451 A1 | 8/2006 | Van Den Oudenrijn et al. |
| 2006/0246005 A1 | 11/2006 | Yang et al. |
| 2007/0037148 A1 | 2/2007 | Fong et al. |
| 2007/0087005 A1 | 4/2007 | Gregory et al. |
| 2007/0122346 A1 | 5/2007 | Uzgiris et al. |
| 2007/0160530 A1 | 7/2007 | Jakobovits et al. |
| 2007/0280945 A1 | 12/2007 | Stevens et al. |
| 2008/0193376 A1 | 8/2008 | Tawakol et al. |
| 2008/0260650 A1 | 10/2008 | Tawakol et al. |
| 2009/0130108 A1 | 5/2009 | Reiter |
| 2009/0203538 A1 | 8/2009 | Sugioka et al. |
| 2009/0208489 A1 | 8/2009 | Veiby et al. |
| 2009/0208937 A1 | 8/2009 | Chinnaiyan et al. |
| 2009/0297439 A1 | 12/2009 | Comoglio et al. |
| 2010/0111856 A1 | 5/2010 | Gill et al. |
| 2010/0279301 A1 | 11/2010 | Chinnaiyan et al. |
| 2010/0285037 A1 | 11/2010 | Abo et al. |
| 2011/0076287 A1 | 3/2011 | Cohen et al. |
| 2011/0311517 A1 | 12/2011 | Li et al. |
| 2012/0058906 A1 | 3/2012 | Smider et al. |
| 2012/0195905 A1 | 8/2012 | Bedian et al. |
| 2012/0225060 A1 | 9/2012 | Lee et al. |
| 2013/0195845 A1 | 8/2013 | Fendly et al. |
| 2013/0209481 A1 | 8/2013 | Zhou et al. |
| 2014/0112873 A1 | 4/2014 | Gillies et al. |
| 2014/0193424 A1 | 7/2014 | Luo et al. |
| 2014/0249296 A1 | 9/2014 | Ploegh et al. |
| 2014/0322129 A1 | 10/2014 | Leong et al. |
| 2014/0377174 A1 | 12/2014 | Houthoff et al. |
| 2015/0056209 A1 | 2/2015 | Witztum et al. |
| 2015/0191543 A1 | 7/2015 | Wu et al. |
| 2015/0203580 A1 | 7/2015 | Papadopoulos et al. |
| 2015/0299133 A1 | 10/2015 | Osterkamp et al. |
| 2016/0000946 A1 | 1/2016 | Cheng et al. |
| 2016/0011217 A1 | 1/2016 | Matsumura et al. |
| 2016/0136309 A1 | 5/2016 | Rosch et al. |
| 2016/0145350 A1 | 5/2016 | Longberg et al. |
| 2016/0151515 A1 | 6/2016 | Joubert et al. |
| 2016/0157469 A1 | 6/2016 | Burova et al. |
| 2017/0029507 A1 | 2/2017 | Ho et al. |
| 2017/0119913 A1 | 5/2017 | Osterkamp et al. |
| 2017/0258948 A1 | 9/2017 | Morin et al. |
| 2017/0283442 A1 | 10/2017 | D'Souza et al. |
| 2018/0015154 A1 | 1/2018 | Weichert et al. |
| 2018/0043041 A1 | 2/2018 | Bansal et al. |
| 2018/0055947 A1 | 3/2018 | Van Dongen et al. |
| 2018/0071413 A1 | 3/2018 | Olive |
| 2018/0078662 A1 | 3/2018 | Agnew et al. |
| 2018/0126012 A1 | 5/2018 | Weichert et al. |
| 2018/0161464 A1 | 6/2018 | Kelly et al. |
| 2022/0184241 A1 | 6/2022 | Kelly et al. |
| 2023/0270894 A1 | 8/2023 | Kelly et al. |
| 2024/0299601 A1 | 9/2024 | Cheung et al. |
| 2024/0307563 A1 | 9/2024 | Kelly et al. |
| 2024/0409637 A1 | 12/2024 | Giurleo et al. |

FOREIGN PATENT DOCUMENTS

| | | | |
|---|---|---|---|
| EP | 1541680 A1 | 6/2005 |
| EP | 2196541 A1 | 6/2010 |
| EP | 2216344 A1 | 8/2010 |
| EP | 2540745 A1 | 1/2013 |
| EP | 3266465 A1 | 7/2016 |
| WO | 1990/13256 A1 | 11/1990 |
| WO | 1998/17797 A1 | 4/1998 |
| WO | 1998/39027 A2 | 9/1998 |
| WO | 1999/055842 A1 | 11/1999 |
| WO | 2004/016225 A2 | 2/2004 |
| WO | 2004/101756 A2 | 11/2004 |
| WO | 2005/068503 A2 | 7/2005 |
| WO | 2005/113601 A2 | 12/2005 |
| WO | 2006/034488 A2 | 3/2006 |
| WO | 2006/053110 A2 | 5/2006 |
| WO | 2006/099141 A2 | 9/2006 |
| WO | 2006/121168 A1 | 11/2006 |
| WO | 2007/005874 A2 | 1/2007 |
| WO | 2008/052187 A2 | 5/2008 |
| WO | 2008/067283 A2 | 6/2008 |
| WO | 2008/124467 A1 | 10/2008 |
| WO | 2008/141044 A2 | 11/2008 |
| WO | 2009/005809 A2 | 1/2009 |
| WO | 2009/033011 A1 | 3/2009 |
| WO | 2009/045957 A1 | 4/2009 |
| WO | 2009/068204 A1 | 6/2009 |
| WO | 2009/073533 A2 | 6/2009 |
| WO | 2009/120769 A1 | 10/2009 |
| WO | 2009/129578 A1 | 10/2009 |
| WO | 2010/016766 A2 | 2/2010 |
| WO | 2010/111282 A1 | 9/2010 |
| WO | 2011/021014 A2 | 2/2011 |
| WO | 2011/051349 A1 | 5/2011 |
| WO | 2011/056983 A1 | 5/2011 |
| WO | 2011/153346 A1 | 12/2011 |
| WO | 2012/045752 A1 | 4/2012 |
| WO | 2012/087962 A2 | 6/2012 |
| WO | 2012/098407 A1 | 7/2012 |
| WO | 2012/177595 A1 | 12/2012 |
| WO | 2013/010573 A1 | 1/2013 |
| WO | 2013/025779 A1 | 2/2013 |
| WO | 2013/028907 A1 | 2/2013 |
| WO | 2013/061083 A2 | 5/2013 |
| WO | 2013/063312 A1 | 5/2013 |
| WO | 2013/070468 A1 | 5/2013 |
| WO | 2013/071142 A1 | 5/2013 |
| WO | 2013/138696 A1 | 9/2013 |
| WO | 2013/149159 A1 | 10/2013 |
| WO | 2013/165940 A1 | 11/2013 |
| WO | 2013/169625 A1 | 11/2013 |
| WO | 2013/173496 A2 | 11/2013 |
| WO | 2013/177055 A2 | 11/2013 |
| WO | 2014/151634 A1 | 9/2014 |
| WO | 2014/153270 | 9/2014 |
| WO | 2014/159087 A1 | 10/2014 |
| WO | 2014/159835 A1 | 10/2014 |
| WO | 2014/159981 A2 | 10/2014 |
| WO | 2014/183006 A2 | 11/2014 |
| WO | 2014/200969 A2 | 12/2014 |
| WO | 2014/210064 | 12/2014 |
| WO | 2015/053871 A2 | 4/2015 |
| WO | 2015/061209 A1 | 5/2015 |
| WO | 2015/073746 A2 | 5/2015 |
| WO | 2015/075445 A1 | 5/2015 |
| WO | 2015/089344 A1 | 7/2015 |
| WO | 2015/112805 A1 | 7/2015 |
| WO | 2015/132602 A1 | 9/2015 |
| WO | 2015/140212 A1 | 9/2015 |
| WO | 2015/179658 A2 | 11/2015 |
| WO | 2015/191715 A1 | 12/2015 |
| WO | 2016/020502 A1 | 2/2016 |
| WO | 2016/040723 A1 | 3/2016 |
| WO | 2016/040724 A1 | 3/2016 |
| WO | 2016/040868 A1 | 3/2016 |
| WO | 2016/058056 A1 | 4/2016 |
| WO | 2016/061142 A1 | 4/2016 |
| WO | 2016/077518 A1 | 5/2016 |
| WO | 2016/086021 A1 | 6/2016 |
| WO | 2016/144873 A2 | 9/2016 |
| WO | 2016/162368 A1 | 10/2016 |
| WO | 2016/191186 A1 | 12/2016 |
| WO | 2017/059397 A1 | 4/2017 |
| WO | 2017/087826 A1 | 5/2017 |
| WO | 2017/201111 A1 | 11/2017 |
| WO | 2017/213494 A1 | 12/2017 |
| WO | 2017/215590 | 12/2017 |
| WO | 2017/223565 A1 | 12/2017 |
| WO | 2018/049083 A1 | 3/2018 |
| WO | 2018/058125 A1 | 3/2018 |
| WO | 2018/083705 A1 | 5/2018 |
| WO | 2018/128664 A2 | 7/2018 |

(56)             References Cited

FOREIGN PATENT DOCUMENTS

OTHER PUBLICATIONS

Alley et al. (2010) "Antibody-drug conjugates: targeted drug delivery for cancer", Current Opinion in Chemical Biology, 14(4): 529-537.

Altschul et al. (1990) "Basic Local Alignment Search Tool," J. Mol. Biol. 215: 403-410.

Altschul et al. (1997) "Gapped BLAST and PSI-BLAST: a new generation of protein database search programs", Nucleic Acids Res. 25(17):3389-3402.

Alzimami et al. (2014) "Comparison of Zr-89, I-124, and F-18 Imaging Characteristics in PET Using Gate Monte Carlo Simulations: Imaging," International Journal of Radiation Oncology, 88: 502.

Anonymus (2015) "Human MICL/CLEC12A Antibody, Monoclonal Mouse IgG2B Clone# 687317", Catalog No. MAB294611, p. 1.

Askmyr et al. (2013) "Selective killing of candidate AML stem cells by antibody targeting of IL1RAP," Blood, 121(18): 3709-3713.

Bannerman et al. (2009) "Abstract #5635: The Proteasome Inhibitor MLN9708 Has Strong Anti-Tumor Activity in The Murine Bone Marrow Compartment In Vivo," Cancer Research, AACR Annual Meeting, 5 pages.

Bartel et al. (2009) "F18-Fluorodeoxyglucose Positron Emission Tomography in The Context of Other Imaging Techniques and Prognostic Factors in Multiple Myeloma," Blood, 114(10): 2068-2076.

Beaino et al. (2014) "PET Imaging of Very Late Antigen-4 in Melanoma: Comparison of 68Ga- and 64Cu-Labeled NODAGA and CB-TE1A1P-LLP2A Conjugates," The Journal of Nuclear Medicine, 55(11): 1857-1862.

Boerman and Oyen (2011) "Immuno-PET of Cancer: A Revival of Antibody Imaging," Journal of Nuclear Medicine, 52(8): 1171-1172.

Chang et al. (2015) "Metabolic Competition in the Tumor Microenvironment Is a Driver of Cancer Progression," Cell, 162: 1229-1241.

Chatterjee et al. (2016) "A Humanized Antibody for Imaging Immune Checkpoint Ligand PD-L1 Expression in Tumors," Oncotarget 7(9): 10215-10227.

Chattopadhyay et al. (2009) "Sequence, Structure, Function, Immunity: Structural Genomics of Costimulation," Immunol. Rev. 229(1): 356-386.

Chen et al. (2013) "Molecular Mechanisms of T cell co-stimulation and co-inhibition," Nature Rev. Immunol. 13(4): 227-242.

De Lau et al. (2011) "Lgr5 Homologues Associate with Wnt Receptors and Mediate R-spondin Signalling," Nature, 476(7360): 293-297.

De Vries "Antibody immunotherapy Imaging," Department of Medical Oncology University Medical Center Groningen, The Netherlands, 16 pages.

De Vries (2015) "MPDL3280A-imaging-IST-UMCG," ClinicalTrials.gov Identifier: NCT02453984, University Medical Center Groningen, 10 pages.

Deng et al. (2016) "Preclinical Pharmacokinetics, Pharmacodynamics, Tissue Distribution, and Tumor Penetration of Anti-PD-L1 Monoclonal Antibody, an Immune Checkpoint Inhibitor," mAbs, 8(3): 593-603.

Deri et al. (2015) "p-SCN-Bn-HOPO: A Superior Bifunctional Chelator for (89)Zr ImmunoPET," Bioconjugate Chem., 26(12): 2579-2591.

Dijkers et al. (2019) "Biodistribution of 89Zr-trastuzumab and PET Imaging of HER2-Positive Lesions in Patients with Metastatic Breast Cancer," Clinical Pharmacology and Therapeutics, 87(5): 586-592.

Dijkers et al. (2009) "Development and Characterization of Clinical-Grade 89Zr-Trastuzumab for HER2/neu ImmunoPET Imaging," Journal of Nuclear Medicine, 50(6): 974-981.

Dong et al. (1999) "B7-H1, a Third Member of the B7 family, Co-stimulates T-cell Proliferation and Interleukin-10 Secretion," Nature Medicine, 5(12): 1365-1369.

Feng et al. (2013) "Glypican-3 Antibodies: A New Therapeutic Target for Liver Cancer," FEBS Letters, 588(2): 377-382.

Feng et al. (2013) "Therapeutically Targeting Glypican-3 Via a Conformation-specific Single-domain Antibody in Hepatocellular Carcinoma," Proceedings of The National Academy Of Sciences, 110(12): E1083-E1091.

Feng et al. (2009) "A Novel Human Monoclonal Antibody that Binds with High Affinity to Mesothelin-expressing Cells and Kills Them by Antibody-dependent Cell-mediated Cytotoxicity," Molecular Cancer Therapeutics, American Association of Cancer Research, 8(5): 1113-1118.

Fischer et al. (2013) "89Zr, a Radiometal Nuclide with High Potential for Molecular Imaging with PET: Chemistry, Applications and Remaining Challenges," Molecules, 18: 6469-6490.

Fisher et al. (2002) "Generation of Monoclonal Antibodies Specific for Human Kallikrein 2 (hK2) Using hK2-Expresing Tumors," The Prostate, 51: 153-165.

Francisco et al. (2010) "The PD-1 Pathway in Tolerance and Autoimmunity," Immunol Rev., 236: 219-242.

Freeman (2008) "Structures of PD-1 with Its Ligands: Sideways and Dancing Cheek to Cheek," PNAS, 105(30): 10275-10276.

Gao et al. (2014) "Lgr5 Over-Expression is Positively Related to the Tumor Progression and HER2 Expression in Stage pTNM IV Colorectal Cancer," Int. J. Clin. Exp. Pathol., 7(4): 1572-1579.

Garcia-Teijido et al. (2016) "Tumor-Infiltrating Lymphocytes in Triple Negative Breast Cancer: The Future of Immune Targeting," Clin Med Insights Oncol, 10(S1): 31-39.

Gebhart et al. (2015) "Molecular Imaging as a Tool to Investigate Heterogeneity of Advanced HER2-positive Breast Cancer and to Predict Patient Outcome Under Trastuzumab Emtansine (T-DM1); the ZEPHIR Trial," Annals of Oncology Advance Access, 22 pages.

GenBank Accession No. ACV51637.1 TO: Protein [Internet]. Bethesda (MD): National Library of Medicine (US), National Center for Biotechnology Information; [2013]—Accession No. ACV51637.1, "Hypothetical Protein Apar_1209 [Atopobium parvulum DSM 20469]", cited on Dec. 11, 2013, [online], [retrieved on Mar. 15, 2019]. Retrieved from: https://www.ncbi.nlm.nih.gov/protein/ACV51637. 1, 2 pages.

GenBank Accession No. CAJ48864.1 TO: Protein [Internet]. Bethesda (MD): National Library of Medicine (US), National Center for Biotechnology Information; [2015]—Accession No. CAJ48864.1, "Putative Membrane Protein [Bordetella avium 197N]", cited on Feb. 6, 2015, [online], [retrieved on Apr. 3, 2019]. Retrieved from: https://www.ncbi.nlm.nih.gov/protein/CAJ48864.1, 2 pages.

GenBank Accession No. NP_005009.2 TO: Protein [Internet]. Bethesda (MD): National Library of Medicine (US), National Center for Biotechnology Information; [2019]—Accession No. NP_005009.2, "Programmed Cell Death Protein 1 Precursor [*Homo sapiens*]", cited on Feb. 1, 2019, [online], [retrieved on Feb. 14, 2019]. Retrieved from: https://www.ncbi.nlm.nih.gov/protein/NP_005009. 2, 4 pages.

GenBank Accession No. NP_005182.1 TO: Protein [Internet]. Bethesda (MD): National Library of Medicine (US), National Center for Biotechnology Information; [2018]—Accession No. NP_005182.1, "T-lymphocyte Activation Antigen CD80 Precursor [*Homo sapiens*]", cited on Dec. 29, 2018, [online], [retrieved on Feb. 14, 2019]. Retrieved from: https://www.ncbi.nlm.nih.gov/protein/NP_005182. 1, 3 pages.

Glunde et al. (2011) "Magnetic Resonance Spectroscopy and Imaging Guidance in Molecular Medicine: Targeting and Monitoring of Choline and Glucose Metabolism In Cancer," NMR in Biomedicine, 24(6): 673-690.

Gonnet et al. (1992) "Exhaustive Matching of the Entire Protein Sequence Database," Science 256: 1443-1445.

Govindan et al. (2005) "Deferoxamine as A Chelator For $^{67}$Ga in the Preparation of Antibody Conjugates," Nuclear Medicine and Biology, 32(5): 513-519.

(56)            References Cited

OTHER PUBLICATIONS

Gupta et al. (2010) "Clinical Pharmacokinetics of Intravenous and Oral MLN9708, An Investigational Proteasome Inhibitor: An Analysis of Data from Four Phase 1 Monotherapy Studies," Blood, 116: 1813.

Hanaoka et al. (2015) "Glypican-3 Targeted Human Heavy Chain Antibody as a Drug Carrier for Hepatocellular Carcinoma Therapy," Molecular Pharmaceutics, 12(6): 2151-2157.

Hassan et al. (2007) "Preclinical Evaluation of MORAb-009, a Chimeric Antibody Targeting Tumor-associated Mesothelin," Cancer Immunity, Academy of Cancer Immunology, 7: 20.

Herbst et al. (2014) "Predictive Correlates of Response to the Anti-PD-L1 Antibody MPDL3280A in Cancer Patients," Nature 515(7528): 563-567.

Heskamp et al. (2015) "Noninvasive Imaging of Tumor PD-L1 Expression Using Radiolabeled Anti-PD-L1 Antibodies," Cancer Res, 75(14): 2928-2936.

Higashikawa et al. (2014) "64Cu-DOTA-Anti-CTLA-4 mAb Enabled PET Visualization of CTLA-4 on the T-Cell Infiltrating Tumor Tissues," PLoS One, 9(11): e109866, 8 pages.

Holland et al. (2009) "Standardized Methods for the Production of High Specific-Activity Zirconium-89," Nucl. Biol., 36(7): 729-739.

Huang et al. (2010) "Biodistribution, Toxicity and Radiation Dosimetry Studies of the Serotonin Transporter Radioligand 4-[18F]-ADAM in Rats and Monkeys," Eur J Nucl Med Mol Imaging, 37(3): 545-555.

International Commission on Radiological Protection. 1990 Recommendations of the International Commission on Radiological Protection. ICRP Publication 60, Pergamon Press, New York, 1991, 1 page Abstract.

International Search Report and Written Opinion received in PCT/US2017/064215, on Feb. 9, 2018, 16 pages.

Iyer et al. (2011) "Antibody Drug Conjugates—Trojan Horses in the War on Cancer," Journal of Pharmacological and Toxicological Methods, 64(3): 207-212.

Järås et al. (2010) "Isolation and Killing of Candidate Chronic Myeloid Leukemia Stem Cells by Antibody Targeting of IL-1 receptor Accessory Protein," Proceedings of the National Academy of Sciences, National Academy of Sciences, US, 107(37): 16280-16285.

Jauw et al. (2016) "Immuno-Positron Emission Tomography with Zirconium-89-Labeled Monoclonal Antibodies in Oncology: What Can We Learn from Initial Clinical Trials?", Frontiers in Pharmacology, vol. 7, Article 131, 15 pages.

Josefsson et al. (2016) "Imaging Biodistribution, and Dosimetry of Radionuclide-Labeled PD-L1 Antibody in an Immunocompetent Mouse Model of Breast Cancer," Cancer Research, 76(2): 472-479.

Junutula et al. (2008) "Rapid Identification of Reactive Cysteine Residues for Site-specific Labeling of Antibody-Fabs", Journal of Immunological Methods, 332(1-2): 41-52.

Junutula et al. (2008) "Site-specific Conjugation of a Cytotoxic Drug to an Antibody Improves the Therapeutic Index," Nature Biotechnology, 26(8): 925-932.

Kabat (1991) "Sequences of Proteins of Immunological Interest," National Institutes of Health, Bethesda, Md., 147:1709-1719.

Keliher et al. (2011) "89Zr-labeled Dextran Nanoparticles Allow In Vivo Macrophage Imaging," Bioconjugate Chemistry, 22(12): 2383-2389.

Kelly et al. (2017) "Immuno-PET Using Zirconium-89 (89Zr) Radiolabeled Fully Human Anti-PD-L1 Antibody Successfully Images PD-L1 Positive Tumors in Preclinical Mouse Models," Journal of Nuclear Medicine 58(S1): 618.

Lamberts et al. (2015) "ImmunoPET with Anti-Mesothelin Antibody in Patients with Pancreatic and Ovarian Cancer Before Anti-Mesothelin Antibody-Drug Conjugate Treatment," Clinical Cancer Research, 22(7): 1642-1652.

Lasorsa et al. (2016) "Probing the Interaction Between Cisplatin and the Therapeutic Monoclonal Antibody Trastuzumab," RSC Advances, 6(35): 29229-29236.

Le Beau et al. (2013), "Targeting uPAR with Antagonistic Recombinant Human Antibodies in Aggressive Breast Cancer," Cancer Res, 73(7): 2070-2081.

Leong et al. (2015) "An Anti-B7-H4 Antibody-Drug Conjugate for the Treatment of Breast Cancer," Molecular Pharmaceutics, 12(6): 1717-1729.

Lesniak et al. (2016) "PD-L1 Detection in Tumors Using [64 Cu]Atezolizumab with PET," Bioconjugate Chemistry, 27(9): 2103-2110.

Li and Zhu (2016) "Immuno-PET Imagining Using 89Zr Labeled PD-L1 antibody in Non-small Cell Lung Cancer Xenograft," J. Nucl. Med., 57(S2): 337.

Li et al. (2012) "MLN9708 Shows Encouraging Results for The Treatment Of Multiple Myeloma (ASCO 2012)," The Myeloma Beacon, 3pages.

Li et al. (2014) "Addition of Bevacizumab Enhances Antitumor Activity of Erlotinib Against Non-small Cell Lung Cancer Xenografts Depending on VEGF Expression," Cancer Chemother Pharmacol., 74(6): 1297-305; Abstract.

Lloyd (1999) The Art, Science and Technology of Pharmaceutical Compounding, 8pgs.

Lu et al. (2009) "Abstract#1233: Development of Anti-glypican 3 Therapeutic Antibodies," AACR Annual Meeting, 50: 296.

Martin et al. (1989) "Modeling Antibody Hypervariable Loops: A Combined Algorithm," Proc. Natl. Acad. Sci. USA 86: 9268-9272.

Maute et al. (2015) "Engineering High-affinity PD-1 Variants for Optimized Immunotherapy and Immuno-PET Imaging," Proc Natl Acad Sci U S A, 112(47): E6506-E6514.

Meijs et al. (1997) "Zirconium-labeled Monoclonal Antibodies and their Distribution in Tumor-bearing Nude Mice," J Nucl Med, 38(1): 112-118.

Mindt et al. (2014) "Octadetante Bifunctional Chelating Agent for Zr-89 Based Imagining Probes," Technology Opportunity, Ref. No. UZ-15/736, 1 page.

Morita et al. (2004) "Neonatal Lethality of LGR5 Null Mice is Associated with Ankyloglossia and Gastrointestinal Distension," Mol Cell Biol., 24(22): 9736-9743.

Nakano et al. (2010) "Generation of a Humanized Anti-glypican 3 Antibody by CDR Grafting and Stability Optimization," Anti-Cancer Drugs, 21(10): 907-916.

Nakano et al. (2009) "Anti-glypican 3 Antibodies Cause ADCC Against Human Hepatocellular Carcinoma Cells," BBRC, 378(2): 279-284.

Natarajan et al. (2015) "Novel Radiotracer for ImmunoPET Imaging of PD-1 Checkpoint Expression on Tumor Infiltrating Lymphocytes", Bioconjug Chem, 26(10):2062-2069.

Nijland et al. (2019) "Molecular Imaging Using Radiolabeled Atezolizumab to Assess Atezolizumab Biodistribution in Lymphoma Patients," University Medical Center Groningen, ClinicalTrials. gov Identifier: NCT03850028, 11 pages.

Onda et al. (2005) "New Monoclonal Antibodies to Mesothelin Useful for Immunohistochemistry, Fluorescence-activated Cell Sorting, Western Blotting, and ELISA," Clin Cancer Res, 11(16): 5840-5846.

Onda et al. (2006) "Megakaryocyte Potentiation Factor Cleaved from Mesothelin Precursor Is a Useful Tumor Marker in the Serum of Patients with Mesothelioma", Clin Cancer Res, 12(14 Pt 1):4225-4231.

Oosting et al. (2015) "89Zr-Bevacizumab PET Visualizes Heterogeneous Tracer Accumulation in Tumor Lesions of Renal Cell Carcinoma Patients and Differential Effects of Antiangiogenic Treatment," The Journal of Nuclear Medicine, 56(1): 63-69.

Padldan et al. (1995) "Identification of Specificity-determining Residues in Antibodies,", FASEB J. 9: 133-139.

Pandya et al. (2015) "Di-macrocyclic Terephthalamide Ligands as Chelators for the PET Radionuclide Zirconium-89", Chem Commun (Camb), 51(12): 2301-2303.

Pantin et al. (2012) "Optimization of an Intra-Bone Hematopoietic Stem Cell Delivery Technique in a Swine Model (Abstract 2990)," Blood, 120(21): 2990.

Pearson (1994) "Using the FASTA Program to Search Protein and DNA Sequence Databases," Methods Mol. Biol. 24: 307-331.

(56) References Cited

OTHER PUBLICATIONS

Perk et al. (2010) "p-Isothiocyanatobenzyl-desferrioxamine: A New Bifunctional Chelate for Facile Radiolabeling of Monoclonal Antibodies with Zirconium-89 for Immuno-PET Imaging," Eur. J. Nucl. Med. Mol Imaging, 37(2): 250-259.

Petrick et al. (2015) "In Vitro and In Vivo Comparison of Selected Ga-68 and Zr-89 Labelled Siderophores," Mol. Imaging Biol., 18: 344-352.

Phung et al., (2012) "High-affinity Monoclonal Antibodies to Cell Surface Tumor Antigen Glypican-3 Generated Through a Combination of Peptide Immunization and Flow Cytometry Screening," MAbs, 4(5): 592-599.

Price et al. (2014) "Hophospa-trastuzumab: Bifunctional Methylenephosphonate-based Chelator with 89Zr, 111In and 177Lu," Dalton Trans., 43(1): 119-131.

Pritsch et al. (1993) "V Gene Usage by Seven Hybrids Derived from CD5+ B-Cell Chronic Lymphocytic Leukemia and Displaying Autoantibody Activity," Blood, 82(10): 3103-3112.

Ribas (2012) "Tumor Immunotherapy Directed at PD-1," N. Engl. J. Med., 366(26): 2517-2519.

Ricart et al. (2007) "Technology Insight: Cytotoxic Drug Immunoconjugates for Cancer Therapy," Nature Clinical Practice Oncology, 4(4): 245-255.

Rojko et al. (2014) "Formation, Clearance, Deposition, Pathogenicity, and Identification of Biopharmaceutical-related Immune Complexes: Review and Case Studies," Toxicol Pathol. 42(4):725-764.

Sasaki et al. (2010) "Establishment of a Novel Monoclonal Antibody Against LGR5," BBRC, 394(3): 498-502.

Schumacher et al. (2016) "Current Status: Site-Specific Antibody Drug Conjugates," J Clin Immunol., 36(1): S100-S107.

Sheridan (2012) "Cautious Optimism Surrounds Early Clinical Data for PD-1 Blocker," Nature Biotechnology 30(8): 729-730.

Slizys and Widnersson (2016) "The New "Pet" on the Block: Radio Imaging with Zirconium-89," FPA Patent Attorneys, 5 pages.

Smith et al. (2010) "Vascular Endothelial Growth Factor Receptors VEGFR-2 and VEGFR-3 are Localized Primarily to the Vasculature in Human Primary Solid Cancers," Clin Cancer Res., 16(14): 3548-3561.

Souza et al. (2005) "Peripheral B Cells Latently Infected with Epstein-Barr Virus Display Molecular Hallmarks of Classical Antigen-Selected Memory B Cells," Proc Natl Acad Sci USA, 102(50): 18093-18098.

Sugyo et al. (2013) "Evaluation of 89Zr-Labeled Human Anti-CD147 Monoclonal Antibody as a Positron Emission Tomography Probe in a Mouse Model of Pancreatic Cancer," PLOS ONE, 8(4): e61230, 9 pages.

Takahashi et al. (2010) "Significance of Lgr5Cancer Stem Cells in the Colon and Rectum," Annals of Surgical Oncology, 18(4): 1166-1174.

Tavare et al. (2016) "An Effective Immuno-PET Imaging Method to Monitor CD8-Dependent Responses to Immunotherapy," Cancer Research, 76(1): 73-82.

Terrovitis et al. (2010) "Assessment and Optimization of Cell Engraftment After Transplantation into the Heart", Circ Res., 106(3):479-494.

Tinianow et al. (2010) "Site-specifically 89Zr-labeled Monoclonal Antibodies for ImmunoPET," Nucl Med Biol., 37(3): 289-297.

Vajdos et al. (2002) "Comprehensive Functional Maps of the Antigen-binding Site of an Anti-ErbB2 Antibody Obtained with Shotgun Scanning Mutagenesis," J Mol Biol., 320: 415-428.

Valenzuela et al. (2003) "High-throughput Engineering of the Mouse Genome Coupled with High-resolution Expression Analysis," Nat. Biotechnol., 21: 652-659.

Van De Watering et al. (2014) "Zirconium-89 Labeled Antibodies: A New Tool for Molecular Imaging in Cancer Patients", Biomed Research international, Article ID 203601, 2014:1-13.

Van Dongen et al. (2007) "Immuno-PET: A Navigator in Monoclonal Antibody Development and Applications," The Oncologist, 12: 1379-1389.

Vansteenkiste et al. (1999) "Prognostic Importance of the Standardized Uptake Value on 18F-Fluoro-2-Deoxy-Glucose-Positron Emission Tomography Scan In Non-Small-Cell Lung Cancer: An Analysis of 125 Cases", J Clin Oncol., 17(10):3201-3206.

Verel et al. (2003) "89Zr Immuno-PET: Comprehensive Procedures for the Production of 89Zr-labeled Monoclonal Antibodies," J Nucl Med., 44(8): 1271-1281.

Vosjan et al. (2010) "Conjugation and Radiolabeling of Monoclonal Antibodies with Zirconium-89 for PET Imaging Using the Bifunctional Chelate p-isothiocyanatobenzyl-desferrioxamine," Nature Protocols, 5(4): 739-743.

Vugts et al. (2017) "Comparison of the Octadentate Bifunctional Chelator DFO*-pPhe-NCS and the Clinically Used Hexadentate Bifunctional Chelator DFO-pPhe-NCS for 89Zr-immuno-PET," European Journal of Nuclear Medicine and Molecular Imaging, doi:10. 1007/s00259-016-3499-x, 44(2): 286-295.

Waalboer et al. (2015) "Platinum (II) as Bifunctional Linker in Antibody-Drug Conjugate Formation: Coupling of a 4-Nitrobenzo-2-oxa-1,3-diazole Fluorophore to Trastuzumab as a Model," ChemMedChem, 10(5): 797-803.

Walker et al. (2011) "LGR5 Is a Negative Regulator of Tumourigenicity, Antagonizes Wnt Signalling and Regulates Cell Adhesion in Colorectal Cancer Cell Lines," PLoS One, 6(7): e22733.1-20.

Ward et al. (2013) "HDAC Inhibition Induces Increased Choline Uptake and Elevated Phosphocholine Levels in MCF7 Breast Cancer Cells," PLoS One, 8(4): e62610.1-11.

Wu et al. (2012) "Lgr5 Is a Potential Marker of Colorectal Carcinoma Stem Cells that Correlates with Patient Survival," World J Surg Oncol., 10(1): 244.

Yamauchi et al. (2005) "The Glypican 3 Oncofetal Protein is a Promising Diagnostic Marker for Hepatocellular Carcinoma," Modern Pathology, 18(12): 1591-1598.

Yang et al. (2014) "Imaging of Hepatocellular Carcinoma Patient-derived Xenografts Using 89Zr-labeled Anti-glypican-3 Monoclonal Antibody," Biomaterials, 35(25): 6964-6971.

Yasumoto et al. (2004) "Epitope Mapping of the Melanosomal Matrix Protein gp100 (PMEL17) rapid processing in the endoplasmic reticulum and glycosylation in the early Golgi compartment," J Biol Chem., 279(27): 28330-28338.

Yoon et al. (1998) "Antibodies to Domains II and III of the IL-1 Receptor Accessory Protein Inhibit IL-1 Beta Activity but Not Binding: Regulation of IL-1 Responses is Via Type I Receptor, Not the Accessory Protein," J Immunol., 160(7): 3170-3179.

Zhai et al. (2015) "Novel Bifunctional Cyclic Chelator for (89)Zr Labeling-Radiolabeling and Targeting Properties of RGD Conjugates," Mol. Pharmaceutics, 12: 2142-2150.

Zhu et al. (2013) "First-in-Man Phase I Study of GC33, a Novel Recombinant Humanized Antibody Against Glypican-3, in Patients with Advanced Hepatocellular Carcinoma," Clin Cancer Res., 19(4): 920-928.

Jing et al. (2015) "Combined Immune Checkpoint Protein Blockade and Low Dose Whole Body Irradiation as Immunotherapy for Myeloma", J. for Immuno. Therapy of Cancer, 3(2): 1-15.

Patra et al. (2014) "An Octadentate Bifunctional Chelating Agent for the Development of Stable Zirconium-89 Based Molecular Imaging Probes", Chem. Commun., 50: 11523-11525.

Knight et al. (2016) "Scaling-down Antibody Radiolabeling Reactions With Zirconium-89", Dalton Trans., 45: 6343-6347.

Mottaghy et al. (2016) "Molecular Imaging Using PSMA PET/CT Versus Multiparametric MRI for Initial Staging of Prostate Cancer: Comparing Apples with Oranges?" Eur. J. Nucl. Med. Mol. Imaging, 43: 1397-1399.

NCT03780725 on Dec. 19, 2018, ClinicalTrials.gov Archive, "This Study Tests How BI 754111 is Distributed in Patients With Advanced Non-small Cell Lung Cancer or Patients With Head and Neck Cancer Who Are Treated With BI 754091", https://clinicaltrials. gov/ct2/show/NCT03780725.

Perk et al. (2008) "Facile Radiolabeling of Monoclonal Antibodies and Other Proteins with Zirconium-89 or Gallium-68 for PET Imaging Using P-isothiocyatoenzyl-desferrioxamine," Protocol Exchange, XP055750961.

(56)         References Cited

OTHER PUBLICATIONS

Perk et al. (2008) "Quantitative PET Imaging of Met-expressing Human Cancer Xenografts with 89Zr-labelled Monoclonal Antibody DN30," European Journal of Nuclear Medicine and Molecular Imaging, 35(10): 1857-1867.

* cited by examiner

Characterization of H4H8314N-DFO

SDS-PAGE: similar motility profiles of PD-L1 parent and DFO conjugate 1. ladder
2. PD-L1 (L5)        NonRed
3. PD-L1-DFO (L19) NonRed
4. Skip
5. PD-L1 (L5)        Reduced
6. PD-L1-DFO (L19) Reduced 2 µg sample/lane.
Novex 4 – 20% Tris-Glycine Gel;
200V, 300 mA, 60min.

SEC: < 1% aggregate.

H4H8314N-L19 (DFO)

H4H8314N-L5 (parent)

Superdex 200, PBS, 0.75 mL/min, ~25 ug injection

H4H8314N-DFO-Zr$^{89}$

H4H8314N-DFO-Zr$^{89}$

Biodistribution of H4H8314N-DFO-Zr$^{89}$ in Tissues Harvested from
***PD-1$^{hu/hu}$ PD-L1$^{hu/hu}$* Mice**

SEQUENCE LISTING

Sequence total quantity: 344
SEQ ID NO: 1          moltype = DNA  length = 363
FEATURE               Location/Qualifiers
misc_feature          1..363
                      note = synthetic
source                1..363
                      mol_type = other DNA
                      organism = synthetic construct
SEQUENCE: 1
gaggtgcagc tggtggagtc tggggggaggc ttggtccagc ctggggggtc cctgagactc    60
tcctgtgcag cctctggatt caccttttagt aggttttgga tgagctgggt ccgccaggct   120
ccagggaagg ggctggagtg ggtggccaac ataaaccaag atggaactga gaaatactat   180
gtggactctg tgaagggccg attcaccatc tccagagaca acgccaagaa ctcactgtat   240
ctgcaaatga acagcctgag agccggggac acggctgtgt attactgtgc gaatacgtat   300
tacgatttttt ggagtggtca ctttgactac tggggccagg gaaccctggt caccgtctcc   360
tca                                                                  363

SEQ ID NO: 2          moltype = AA  length = 121
FEATURE               Location/Qualifiers
REGION                1..121
                      note = synthetic
source                1..121
                      mol_type = protein
                      organism = synthetic construct

```
SEQUENCE: 2
EVQLVESGGG LVQPGGSLRL SCAASGFTFS RFWMSWVRQA PGKGLEWVAN INQDGTEKYY    60
VDSVKGRFTI SRDNAKNSLY LQMNSLRAGD TAVYYCANTY YDFWSGHFDY WGQGTLVTVS   120
S                                                                  121

SEQ ID NO: 3              moltype = DNA   length = 24
FEATURE                   Location/Qualifiers
misc_feature              1..24
                          note = synthetic
source                    1..24
                          mol_type = other DNA
                          organism = synthetic construct
SEQUENCE: 3
ggattcacct ttagtaggtt ttgg                                          24

SEQ ID NO: 4              moltype = AA   length = 8
FEATURE                   Location/Qualifiers
REGION                    1..8
                          note = synthetic
source                    1..8
                          mol_type = protein
                          organism = synthetic construct
SEQUENCE: 4
GFTFSRFW                                                             8

SEQ ID NO: 5              moltype = DNA   length = 24
FEATURE                   Location/Qualifiers
misc_feature              1..24
                          note = synthetic
source                    1..24
                          mol_type = other DNA
                          organism = synthetic construct
SEQUENCE: 5
ataaaccaag atggaactga gaaa                                          24

SEQ ID NO: 6              moltype = AA   length = 8
FEATURE                   Location/Qualifiers
REGION                    1..8
                          note = synthetic
source                    1..8
                          mol_type = protein
                          organism = synthetic construct
SEQUENCE: 6
INQDGTEK                                                             8

SEQ ID NO: 7              moltype = DNA   length = 42
FEATURE                   Location/Qualifiers
misc_feature              1..42
                          note = synthetic
source                    1..42
                          mol_type = other DNA
                          organism = synthetic construct
SEQUENCE: 7
gcgaatacgt attacgattt ttggagtggt cactttgact ac                      42

SEQ ID NO: 8              moltype = AA   length = 14
FEATURE                   Location/Qualifiers
REGION                    1..14
                          note = synthetic
source                    1..14
                          mol_type = protein
                          organism = synthetic construct
SEQUENCE: 8
ANTYYDFWSG HFDY                                                      14

SEQ ID NO: 9              moltype = DNA   length = 321
FEATURE                   Location/Qualifiers
misc_feature              1..321
                          note = synthetic
source                    1..321
                          mol_type = other DNA
                          organism = synthetic construct
SEQUENCE: 9
gacatccaga tgacccagtc tccttccacc ctgtctgcat ctgtaggaga cagagtcacc    60
atcacttgtc gggccagtca gagtattagt aattggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tatcatagtt attcgtacac ttttggccag   300
gggaccaagc tggagatcaa a                                             321
```

```
SEQ ID NO: 10             moltype = AA   length = 107
FEATURE                   Location/Qualifiers
REGION                    1..107
                          note = synthetic
source                    1..107
                          mol_type = protein
                          organism = synthetic construct
SEQUENCE: 10
DIQMTQSPST LSASVGDRVT ITCRASQSIS NWLAWYQQKP GKAPKLLIYK ASSLESGVPS  60
RFSGSGSGTE FTLTISSLQP DDFATYYCQQ YHSYSYTFGQ GTKLEIK              107

SEQ ID NO: 11             moltype = DNA  length = 18
FEATURE                   Location/Qualifiers
misc_feature              1..18
                          note = synthetic
source                    1..18
                          mol_type = other DNA
                          organism = synthetic construct
SEQUENCE: 11
cagagtatta gtaattgg                                              18

SEQ ID NO: 12             moltype = AA   length = 6
FEATURE                   Location/Qualifiers
REGION                    1..6
                          note = synthetic
source                    1..6
                          mol_type = protein
                          organism = synthetic construct
SEQUENCE: 12
QSISNW                                                           6

SEQ ID NO: 13             moltype =   length =
SEQUENCE: 13
000

SEQ ID NO: 14             moltype =   length =
SEQUENCE: 14
000

SEQ ID NO: 15             moltype = DNA  length = 27
FEATURE                   Location/Qualifiers
misc_feature              1..27
                          note = synthetic
source                    1..27
                          mol_type = other DNA
                          organism = synthetic construct
SEQUENCE: 15
caacagtatc atagttattc gtacact                                   27

SEQ ID NO: 16             moltype = AA   length = 9
FEATURE                   Location/Qualifiers
REGION                    1..9
                          note = synthetic
source                    1..9
                          mol_type = protein
                          organism = synthetic construct
SEQUENCE: 16
QQYHSYSYT                                                        9

SEQ ID NO: 17             moltype = DNA  length = 363
FEATURE                   Location/Qualifiers
misc_feature              1..363
                          note = synthetic
source                    1..363
                          mol_type = other DNA
                          organism = synthetic construct
SEQUENCE: 17
caggagcacc tggtggagtc tgggggaggc gtggtccagc ctgggaggtc cctgagactc  60
tcctgtgaag cgtctggatt caccttcagt aactttggca tgcactgggt ccgccaggct 120
ccaggcaagg ggctggagtg ggtggcagct ttatggtctg atggaagtaa taaatactat 180
gcagactccg tgaagggtcg agtcaccatc tccagagaca attccaagaa cacactgtat 240
ctgcaaatga acagcctgag agccgaggac acggctgtct attactgtgc gagagggaga 300
ggagccccg gtattccgat ttttgggtac tggggccagg gaaccctggt caccgtctcc 360
tca                                                             363

SEQ ID NO: 18             moltype = AA   length = 121
FEATURE                   Location/Qualifiers
REGION                    1..121
```

```
                               note = synthetic
source                         1..121
                               mol_type = protein
                               organism = synthetic construct
SEQUENCE: 18
QEHLVESGGG VVQPGRSLRL SCEASGFTFS NFGMHWVRQA PGKGLEWVAA LWSDGSNKYY    60
ADSVKGRVTI SRDNSKNTLY LQMNSLRAED TAVYYCARGR GAPGIPIFGY WGQGTLVTVS   120
S                                                                   121

SEQ ID NO: 19                  moltype = DNA   length = 24
FEATURE                        Location/Qualifiers
misc_feature                   1..24
                               note = synthetic
source                         1..24
                               mol_type = other DNA
                               organism = synthetic construct
SEQUENCE: 19
ggattcacct tcagtaactt tggc                                          24

SEQ ID NO: 20                  moltype = AA   length = 8
FEATURE                        Location/Qualifiers
REGION                         1..8
                               note = synthetic
source                         1..8
                               mol_type = protein
                               organism = synthetic construct
SEQUENCE: 20
GFTFSNFG                                                             8

SEQ ID NO: 21                  moltype = DNA   length = 24
FEATURE                        Location/Qualifiers
misc_feature                   1..24
                               note = synthetic
source                         1..24
                               mol_type = other DNA
                               organism = synthetic construct
SEQUENCE: 21
ttatggtctg atggaagtaa taaa                                          24

SEQ ID NO: 22                  moltype = AA   length = 8
FEATURE                        Location/Qualifiers
REGION                         1..8
                               note = synthetic
source                         1..8
                               mol_type = protein
                               organism = synthetic construct
SEQUENCE: 22
LWSDGSNK                                                             8

SEQ ID NO: 23                  moltype = DNA   length = 42
FEATURE                        Location/Qualifiers
misc_feature                   1..42
                               note = synthetic
source                         1..42
                               mol_type = other DNA
                               organism = synthetic construct
SEQUENCE: 23
gcgagaggga gaggagcccc cggtattccg atttttgggt ac                      42

SEQ ID NO: 24                  moltype = AA   length = 14
FEATURE                        Location/Qualifiers
REGION                         1..14
                               note = synthetic
source                         1..14
                               mol_type = protein
                               organism = synthetic construct
SEQUENCE: 24
ARGRGAPGIP IFGY                                                     14

SEQ ID NO: 25                  moltype = DNA   length = 321
FEATURE                        Location/Qualifiers
misc_feature                   1..321
                               note = synthetic
source                         1..321
                               mol_type = other DNA
                               organism = synthetic construct
SEQUENCE: 25
gacatccaga tgacccagtc tccatcctcc ctgtctgcat ctgttggaga cagagtcacc   60
atcacttgcc gggcaagtca gggcattaga aatgatttag ctggtatca gcagaaacca  120
```

-continued

```
gggaaagccc ctaagcgcct gatctatact gcatccagtt tgcaaagtgg ggtcccatca   180
agattcagcg gcagtggatc tgggacagaa ttcactctca caatcagcag cctacagcct   240
gaagattttg caacttatta ctgtctacaa cataatagtt accctctcac attcggcgga   300
gggaccaagg tggcgatcaa a                                              321

SEQ ID NO: 26            moltype = AA  length = 107
FEATURE                  Location/Qualifiers
REGION                   1..107
                         note = synthetic
source                   1..107
                         mol_type = protein
                         organism = synthetic construct
SEQUENCE: 26
DIQMTQSPSS LSASVGDRVT ITCRASQGIR NDLGWYQQKP GKAPKRLIYT ASSLQSGVPS   60
RFSGSGSGTE FTLTISSLQP EDFATYYCLQ HNSYPLTFGG GTKVAIK                 107

SEQ ID NO: 27            moltype = DNA  length = 18
FEATURE                  Location/Qualifiers
misc_feature             1..18
                         note = synthetic
source                   1..18
                         mol_type = other DNA
                         organism = synthetic construct
SEQUENCE: 27
cagggcatta gaaatgat                                                  18

SEQ ID NO: 28            moltype = AA  length = 6
FEATURE                  Location/Qualifiers
REGION                   1..6
                         note = synthetic
source                   1..6
                         mol_type = protein
                         organism = synthetic construct
SEQUENCE: 28
QGIRND                                                               6

SEQ ID NO: 29            moltype =   length =
SEQUENCE: 29
000

SEQ ID NO: 30            moltype =   length =
SEQUENCE: 30
000

SEQ ID NO: 31            moltype = DNA  length = 27
FEATURE                  Location/Qualifiers
misc_feature             1..27
                         note = synthetic
source                   1..27
                         mol_type = other DNA
                         organism = synthetic construct
SEQUENCE: 31
ctacaacata atagttaccc tctcaca                                        27

SEQ ID NO: 32            moltype = AA  length = 9
FEATURE                  Location/Qualifiers
REGION                   1..9
                         note = synthetic
source                   1..9
                         mol_type = protein
                         organism = synthetic construct
SEQUENCE: 32
LQHNSYPLT                                                            9

SEQ ID NO: 33            moltype = DNA  length = 390
FEATURE                  Location/Qualifiers
misc_feature             1..390
                         note = synthetic
source                   1..390
                         mol_type = other DNA
                         organism = synthetic construct
SEQUENCE: 33
gaggtgcagc tggtggagtc tggggggaggc ttggtaaagc ctggggggtc ccttagactc   60
tcctgtgcag cctctggatt cactttcagt aacgcctgga tgagctgggt ccgccaggct   120
ccagggaagg ggctggagtg ggttggccgt attaaaagga aaactgatgg tgggacaaca   180
gactacgctg cacccgtgaa aggcagattc accatctcaa gagatgattc aaaaaatacg   240
ctgcatctgc aaatgaacag cctgaaaacc gaggacacag ccgtgtatta ctgtaccaca   300
gatgatattg tagttgtacc agctgttatg agggaatact acttcggtat ggacgtctgg   360
ggccaaggga ccacggtcac cgtctcctca                                    390
```

```
SEQ ID NO: 34              moltype = AA   length = 130
FEATURE                    Location/Qualifiers
REGION                     1..130
                           note = synthetic
source                     1..130
                           mol_type = protein
                           organism = synthetic construct
SEQUENCE: 34
EVQLVESGGG LVKPGGSLRL SCAASGFTFS NAWMSWVRQA PGKGLEWVGR IKRKTDGGTT   60
DYAAPVKGRF TISRDDSKNT LHLQMNSLKT EDTAVYYCTT DDIVVVPAVM REYYFGMDVW   120
GQGTTVTVSS                                                         130

SEQ ID NO: 35              moltype = DNA   length = 24
FEATURE                    Location/Qualifiers
misc_feature               1..24
                           note = synthetic
source                     1..24
                           mol_type = other DNA
                           organism = synthetic construct
SEQUENCE: 35
ggattcactt tcagtaacgc ctgg                                         24

SEQ ID NO: 36              moltype = AA   length = 8
FEATURE                    Location/Qualifiers
REGION                     1..8
                           note = synthetic
source                     1..8
                           mol_type = protein
                           organism = synthetic construct
SEQUENCE: 36
GFTFSNAW                                                           8

SEQ ID NO: 37              moltype = DNA   length = 30
FEATURE                    Location/Qualifiers
misc_feature               1..30
                           note = synthetic
source                     1..30
                           mol_type = other DNA
                           organism = synthetic construct
SEQUENCE: 37
attaaaagga aaactgatgg tgggacaaca                                   30

SEQ ID NO: 38              moltype = AA   length = 10
FEATURE                    Location/Qualifiers
REGION                     1..10
                           note = synthetic
source                     1..10
                           mol_type = protein
                           organism = synthetic construct
SEQUENCE: 38
IKRKTDGGTT                                                         10

SEQ ID NO: 39              moltype = DNA   length = 63
FEATURE                    Location/Qualifiers
misc_feature               1..63
                           note = synthetic
source                     1..63
                           mol_type = other DNA
                           organism = synthetic construct
SEQUENCE: 39
accacagatg atattgtagt tgtaccagct gttatgaggg aatactactt cggtatggac   60
gtc                                                               63

SEQ ID NO: 40              moltype = AA   length = 21
FEATURE                    Location/Qualifiers
REGION                     1..21
                           note = synthetic
source                     1..21
                           mol_type = protein
                           organism = synthetic construct
SEQUENCE: 40
TTDDIVVVPA VMREYYFGMD V                                            21

SEQ ID NO: 41              moltype = DNA   length = 321
FEATURE                    Location/Qualifiers
misc_feature               1..321
                           note = synthetic
source                     1..321
```

```
                        mol_type = other DNA
                        organism = synthetic construct
SEQUENCE: 41
gacatccaga tgacccagtc tccatcctcc ctgtctgcat ctgtaggaga cagagtcacc      60
atcacttgcc ggacaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataataatt acccgtacac ttttggccag     300
gggaccaagc tggagatcaa a                                               321

SEQ ID NO: 42          moltype = AA  length = 107
FEATURE                Location/Qualifiers
REGION                 1..107
                       note = synthetic
source                 1..107
                       mol_type = protein
                       organism = synthetic construct
SEQUENCE: 42
DIQMTQSPSS LSASVGDRVT ITCRTSQGIR NDLGWYQQKP GKAPKRLIYA ASSLQSGVPS      60
RFSGSGSGTE FTLTISSLQP EDFATYYCLQ HNNYPYTFGQ GTKLEIK                   107

SEQ ID NO: 43          moltype = DNA  length = 18
FEATURE                Location/Qualifiers
misc_feature           1..18
                       note = synthetic
source                 1..18
                       mol_type = other DNA
                       organism = synthetic construct
SEQUENCE: 43
cagggcatta gaaatgat                                                    18

SEQ ID NO: 44          moltype = AA  length = 6
FEATURE                Location/Qualifiers
REGION                 1..6
                       note = synthetic
source                 1..6
                       mol_type = protein
                       organism = synthetic construct
SEQUENCE: 44
QGIRND                                                                  6

SEQ ID NO: 45          moltype =   length =
SEQUENCE: 45
000

SEQ ID NO: 46          moltype =   length =
SEQUENCE: 46
000

SEQ ID NO: 47          moltype = DNA  length = 27
FEATURE                Location/Qualifiers
misc_feature           1..27
                       note = synthetic
source                 1..27
                       mol_type = other DNA
                       organism = synthetic construct
SEQUENCE: 47
ctacagcata ataattaccc gtacact                                          27

SEQ ID NO: 48          moltype = AA  length = 9
FEATURE                Location/Qualifiers
REGION                 1..9
                       note = synthetic
source                 1..9
                       mol_type = protein
                       organism = synthetic construct
SEQUENCE: 48
LQHNNYPYT                                                               9

SEQ ID NO: 49          moltype = DNA  length = 363
FEATURE                Location/Qualifiers
misc_feature           1..363
                       note = synthetic
source                 1..363
                       mol_type = other DNA
                       organism = synthetic construct
SEQUENCE: 49
caggtgcaat ggtgcagtc tggggcggag gtgaagaagc ctggggcctc agtgcaggtc      60
tcctgcaagg cttctggata ctccttcacc ggctactata tacactgggt gcgacaggcc    120
```

```
cctggacaag gacttgagtg gatgggatgg atcaaccta acagtggcac caaaaagtat  180
gcacacaagt ttcagggcag ggtcaccatg accagggaca cgtccatcga cacagcctac  240
atgattttga gcagtctgat atccgacgac acggccgtgt attactgtgc gagagatgag  300
gactggaact tgggagctg gttcgactcc tggggccagg gaaccctggt caccgtctcc  360
tca                                                                363

SEQ ID NO: 50           moltype = AA   length = 121
FEATURE                 Location/Qualifiers
REGION                  1..121
                        note = synthetic
source                  1..121
                        mol_type = protein
                        organism = synthetic construct
SEQUENCE: 50
QVQLVQSGAE VKKPGASVQV SCKASGYSFT GYYIHWVRQA PGQGLEWMGW INPNSGTKKY  60
AHKFQGRVTM TRDTSIDTAY MILSSLISDD TAVYYCARDE DWNFGSWFDS WGQGTLVTVS  120
S                                                                  121

SEQ ID NO: 51           moltype = DNA   length = 24
FEATURE                 Location/Qualifiers
misc_feature            1..24
                        note = synthetic
source                  1..24
                        mol_type = other DNA
                        organism = synthetic construct
SEQUENCE: 51
ggatactcct tcaccggcta ctat                                         24

SEQ ID NO: 52           moltype = AA   length = 8
FEATURE                 Location/Qualifiers
REGION                  1..8
                        note = synthetic
source                  1..8
                        mol_type = protein
                        organism = synthetic construct
SEQUENCE: 52
GYSFTGYY                                                           8

SEQ ID NO: 53           moltype = DNA   length = 24
FEATURE                 Location/Qualifiers
misc_feature            1..24
                        note = synthetic
source                  1..24
                        mol_type = other DNA
                        organism = synthetic construct
SEQUENCE: 53
atcaaccta acagtggcac caaa                                          24

SEQ ID NO: 54           moltype = AA   length = 8
FEATURE                 Location/Qualifiers
REGION                  1..8
                        note = synthetic
source                  1..8
                        mol_type = protein
                        organism = synthetic construct
SEQUENCE: 54
INPNSGTK                                                           8

SEQ ID NO: 55           moltype = DNA   length = 42
FEATURE                 Location/Qualifiers
misc_feature            1..42
                        note = synthetic
source                  1..42
                        mol_type = other DNA
                        organism = synthetic construct
SEQUENCE: 55
gcgagagatg aggactggaa ctttgggagc tggttcgact cc                    42

SEQ ID NO: 56           moltype = AA   length = 14
FEATURE                 Location/Qualifiers
REGION                  1..14
                        note = synthetic
source                  1..14
                        mol_type = protein
                        organism = synthetic construct
SEQUENCE: 56
ARDEDWNFGS WFDS                                                    14

SEQ ID NO: 57           moltype = DNA   length = 336
```

```
FEATURE              Location/Qualifiers
misc_feature         1..336
                     note = synthetic
source               1..336
                     mol_type = other DNA
                     organism = synthetic construct
SEQUENCE: 57
gatattgtga tgacccagac tccactctcc tcacctgtca cccttggaca gccggcctcc   60
atctcctgca ggtctagtca aaccctcgta cacggtgatg gaaacacgta cttgagttgg  120
attcagcaga ggccaggcca gcctccgaga ctcctcattt ataaggtttc taatcagttc  180
tctggggtcc cagacagatt cagtggcagt ggggcaggga cagatttcac actgaaaatc  240
agcagggtgg aagctgagga tgtcgggctt tatttctgca tgcaagctac acattttccg  300
atcaccttcg gccaagggac acgactggag attaaa                             336

SEQ ID NO: 58         moltype = AA  length = 112
FEATURE               Location/Qualifiers
REGION                1..112
                      note = synthetic
source                1..112
                      mol_type = protein
                      organism = synthetic construct
SEQUENCE: 58
DIVMTQTPLS SPVTLGQPAS ISCRSSQTLV HGDGNTYLSW IQQRPGQPPR LLIYKVSNQF   60
SGVPDRFSGS GAGTDFTLKI SRVEAEDVGL YFCMQATHFP ITFGQGTRLE IK          112

SEQ ID NO: 59         moltype = DNA  length = 33
FEATURE               Location/Qualifiers
misc_feature          1..33
                      note = synthetic
source                1..33
                      mol_type = other DNA
                      organism = synthetic construct
SEQUENCE: 59
caaaccctcg tacacggtga tggaaacacg tac                                33

SEQ ID NO: 60         moltype = AA  length = 11
FEATURE               Location/Qualifiers
REGION                1..11
                      note = synthetic
source                1..11
                      mol_type = protein
                      organism = synthetic construct
SEQUENCE: 60
QTLVHGDGNT Y                                                         11

SEQ ID NO: 61         moltype =   length =
SEQUENCE: 61
000

SEQ ID NO: 62         moltype =   length =
SEQUENCE: 62
000

SEQ ID NO: 63         moltype = DNA  length = 27
FEATURE               Location/Qualifiers
misc_feature          1..27
                      note = synthetic
source                1..27
                      mol_type = other DNA
                      organism = synthetic construct
SEQUENCE: 63
atgcaagcta cacattttcc gatcacc                                       27

SEQ ID NO: 64         moltype = AA  length = 9
FEATURE               Location/Qualifiers
REGION                1..9
                      note = synthetic
source                1..9
                      mol_type = protein
                      organism = synthetic construct
SEQUENCE: 64
MQATHFPIT                                                            9

SEQ ID NO: 65         moltype = DNA  length = 363
FEATURE               Location/Qualifiers
misc_feature          1..363
                      note = synthetic
source                1..363
                      mol_type = other DNA
```

-continued

```
                            organism = synthetic construct
SEQUENCE: 65
caggtacacc tggtgcagtc tggggctgag gtgaagaagc ctggggcctc agtgaaggtc    60
tcctgcaagg cttctggata caccttcacc ggctactata tacattgggt gcgacaggcc   120
cctggacacg ggcttgagtg gatgggatgg ctcaacccta atactggtac cacaaagtat   180
atacagaact ttcagggcag ggtcaccatg accagggaca cgtccagcag cacagcctac   240
atggagctga ccaggctgag atctgacgac acggccgtgt attactgtgc gagagatgag   300
gactggaatt atgggagctg gttcgacacc tggggccagg gaaccctggt cacagtctcc   360
tca                                                                 363

SEQ ID NO: 66           moltype = AA  length = 121
FEATURE                 Location/Qualifiers
REGION                  1..121
                        note = synthetic
source                  1..121
                        mol_type = protein
                        organism = synthetic construct
SEQUENCE: 66
QVHLVQSGAE VKKPGASVKV SCKASGYTFT GYYIHWVRQA PGHGLEWMGW LNPNTGTTKY    60
IQNFQGRVTM TRDTSSSTAY MELTRLRSDD TAVYYCARDE DWNYGSWFDT WGQGTLVTVS   120
S                                                                   121

SEQ ID NO: 67           moltype = DNA  length = 24
FEATURE                 Location/Qualifiers
misc_feature            1..24
                        note = synthetic
source                  1..24
                        mol_type = other DNA
                        organism = synthetic construct
SEQUENCE: 67
ggatacacct tcaccggcta ctat                                           24

SEQ ID NO: 68           moltype = AA  length = 8
FEATURE                 Location/Qualifiers
REGION                  1..8
                        note = synthetic
source                  1..8
                        mol_type = protein
                        organism = synthetic construct
SEQUENCE: 68
GYTFTGYY                                                              8

SEQ ID NO: 69           moltype = DNA  length = 24
FEATURE                 Location/Qualifiers
misc_feature            1..24
                        note = synthetic
source                  1..24
                        mol_type = other DNA
                        organism = synthetic construct
SEQUENCE: 69
ctcaacccta atactggtac caca                                           24

SEQ ID NO: 70           moltype = AA  length = 8
FEATURE                 Location/Qualifiers
REGION                  1..8
                        note = synthetic
source                  1..8
                        mol_type = protein
                        organism = synthetic construct
SEQUENCE: 70
LNPNTGTT                                                              8

SEQ ID NO: 71           moltype = DNA  length = 42
FEATURE                 Location/Qualifiers
misc_feature            1..42
                        note = synthetic
source                  1..42
                        mol_type = other DNA
                        organism = synthetic construct
SEQUENCE: 71
gcgagagatg aggactggaa ttatgggagc tggttcgaca cc                       42

SEQ ID NO: 72           moltype = AA  length = 14
FEATURE                 Location/Qualifiers
REGION                  1..14
                        note = synthetic
source                  1..14
                        mol_type = protein
                        organism = synthetic construct
```

-continued

```
SEQUENCE: 72
ARDEDWNYGS WFDT                                                            14

SEQ ID NO: 73            moltype = DNA  length = 336
FEATURE                  Location/Qualifiers
misc_feature             1..336
                         note = synthetic
source                   1..336
                         mol_type = other DNA
                         organism = synthetic construct
SEQUENCE: 73
gatattgtaa tgacccagac tccactctcc tcacctgtca cccttggaca gccggcctcc        60
atctcctgca ggtctagtcc aagcctcgta cacagtgatg gaaacaccta cttgagttgg       120
cttcagcaga ggccaggcca gcctccaaga ctcctaattt ataagatttc taaccgattc       180
tctggggtcc cagacagatt cagtggcagt ggggcaggga cagatttcac gctgaaaatc       240
agcagggtgg aagctgagga tgtcgggggtt tattactgca tgcaagctac acattttccg      300
atcaccttcg gccaagggac acgactggag attaga                                 336

SEQ ID NO: 74            moltype = AA  length = 112
FEATURE                  Location/Qualifiers
REGION                   1..112
                         note = synthetic
source                   1..112
                         mol_type = protein
                         organism = synthetic construct
SEQUENCE: 74
DIVMTQTPLS SPVTLGQPAS ISCRSSPSLV HSDGNTYLSW LQQRPGQPPR LLIYKISNRF         60
SGVPDRFSGS GAGTDFTLKI SRVEAEDVGV YYCMQATHFP ITFGQGTRLE IR                112

SEQ ID NO: 75            moltype = DNA  length = 33
FEATURE                  Location/Qualifiers
misc_feature             1..33
                         note = synthetic
source                   1..33
                         mol_type = other DNA
                         organism = synthetic construct
SEQUENCE: 75
ccaagcctcg tacacagtga tggaaacacc tac                                     33

SEQ ID NO: 76            moltype = AA  length = 11
FEATURE                  Location/Qualifiers
REGION                   1..11
                         note = synthetic
source                   1..11
                         mol_type = protein
                         organism = synthetic construct
SEQUENCE: 76
PSLVHSDGNT Y                                                              11

SEQ ID NO: 77            moltype =   length =
SEQUENCE: 77
000

SEQ ID NO: 78            moltype =   length =
SEQUENCE: 78
000

SEQ ID NO: 79            moltype = DNA  length = 27
FEATURE                  Location/Qualifiers
misc_feature             1..27
                         note = synthetic
source                   1..27
                         mol_type = other DNA
                         organism = synthetic construct
SEQUENCE: 79
atgcaagcta cacattttcc gatcacc                                            27

SEQ ID NO: 80            moltype = AA  length = 9
FEATURE                  Location/Qualifiers
REGION                   1..9
                         note = synthetic
source                   1..9
                         mol_type = protein
                         organism = synthetic construct
SEQUENCE: 80
MQATHFPIT                                                                 9

SEQ ID NO: 81            moltype = DNA  length = 360
FEATURE                  Location/Qualifiers
```

```
misc_feature            1..360
                        note = synthetic
source                  1..360
                        mol_type = other DNA
                        organism = synthetic construct
SEQUENCE: 81
gaggtgcagc tggtggaatc tggggggaggt gtggtgcggc ctggggggtc cctgagactc    60
tcctgtgcag cctctggatt cactttgat gattatggca tgacctgggt ccgccaagct     120
ccagggaggg gcctggaatg ggtctctggt attcattggc atggtaaacg cacaggttat    180
gcagactctg tgaagggccg attcaccata tccagagaca acgccaagaa atccctgtat    240
ctgcaaatga acagtctgaa aggcgaggac acggccttgt atcattgtgt gagggggggga    300
atgagtacag gggactggtt cgaccccctgg ggccagggaa ccctggtcat cgtctcctca    360

SEQ ID NO: 82            moltype = AA   length = 120
FEATURE                  Location/Qualifiers
REGION                   1..120
                         note = synthetic
source                   1..120
                         mol_type = protein
                         organism = synthetic construct
SEQUENCE: 82
EVQLVESGGG VVRPGGSLRL SCAASGFTFD DYGMTWVRQA PGRGLEWVSG IHWHGKRTGY     60
ADSVKGRFTI SRDNAKKSLY LQMNSLKGED TALYHCVRGG MSTGDWFDPW GQGTLVIVSS    120

SEQ ID NO: 83            moltype = DNA   length = 24
FEATURE                  Location/Qualifiers
misc_feature             1..24
                         note = synthetic
source                   1..24
                         mol_type = other DNA
                         organism = synthetic construct
SEQUENCE: 83
ggattcactt ttgatgatta tggc                                           24

SEQ ID NO: 84            moltype = AA   length = 8
FEATURE                  Location/Qualifiers
REGION                   1..8
                         note = synthetic
source                   1..8
                         mol_type = protein
                         organism = synthetic construct
SEQUENCE: 84
GFTFDDYG                                                               8

SEQ ID NO: 85            moltype = DNA   length = 24
FEATURE                  Location/Qualifiers
misc_feature             1..24
                         note = synthetic
source                   1..24
                         mol_type = other DNA
                         organism = synthetic construct
SEQUENCE: 85
attcattggc atggtaaacg caca                                           24

SEQ ID NO: 86            moltype = AA   length = 8
FEATURE                  Location/Qualifiers
REGION                   1..8
                         note = synthetic
source                   1..8
                         mol_type = protein
                         organism = synthetic construct
SEQUENCE: 86
IHWHGKRT                                                               8

SEQ ID NO: 87            moltype = DNA   length = 39
FEATURE                  Location/Qualifiers
misc_feature             1..39
                         note = synthetic
source                   1..39
                         mol_type = other DNA
                         organism = synthetic construct
SEQUENCE: 87
gtgaggggggg gaatgagtac aggggactgg ttcgacccc                          39

SEQ ID NO: 88            moltype = AA   length = 13
FEATURE                  Location/Qualifiers
REGION                   1..13
                         note = synthetic
source                   1..13
```

-continued

```
                           mol_type = protein
                           organism = synthetic construct
SEQUENCE: 88
VRGGMSTGDW FDP                                                        13

SEQ ID NO: 89            moltype = DNA   length = 324
FEATURE                  Location/Qualifiers
misc_feature            1..324
                           note = synthetic
source                  1..324
                           mol_type = other DNA
                           organism = synthetic construct
SEQUENCE: 89
gacatccaga tgacccagtc tccatcctcc ctgtctgcat ctctaggaga cagagtcacc   60
atcacttgcc gggcaagtca gagcattaac agttatttaa attggtatca gcagaaacca   120
gggaaagccc ctaaactcct gatctatgtt gcatccagtt tgcaaagtgg ggtcccatca   180
aggttcagtg gcagtggatc tgggacagaa ttcactctca ccatcagcaa tctgcaacct   240
gaagattttg caacttacta ctgtcaacag agttacagta cccctccgat caccttcggc   300
caaggacac gactggagat taaa                                           324

SEQ ID NO: 90            moltype = AA   length = 108
FEATURE                  Location/Qualifiers
REGION                  1..108
                           note = synthetic
source                  1..108
                           mol_type = protein
                           organism = synthetic construct
SEQUENCE: 90
DIQMTQSPSS LSASLGDRVT ITCRASQSIN SYLNWYQQKP GKAPKLLIYV ASSLQSGVPS   60
RFSGSGSGTE FTLTISNLQP EDFATYYCQQ SYSTPPITFG QGTRLEIK               108

SEQ ID NO: 91            moltype = DNA   length = 18
FEATURE                  Location/Qualifiers
misc_feature            1..18
                           note = synthetic
source                  1..18
                           mol_type = other DNA
                           organism = synthetic construct
SEQUENCE: 91
cagagcatta acagttat                                                  18

SEQ ID NO: 92            moltype = AA   length = 6
FEATURE                  Location/Qualifiers
REGION                  1..6
                           note = synthetic
source                  1..6
                           mol_type = protein
                           organism = synthetic construct
SEQUENCE: 92
QSINSY                                                                6

SEQ ID NO: 93            moltype =   length =
SEQUENCE: 93
000

SEQ ID NO: 94            moltype =   length =
SEQUENCE: 94
000

SEQ ID NO: 95            moltype = DNA   length = 30
FEATURE                  Location/Qualifiers
misc_feature            1..30
                           note = synthetic
source                  1..30
                           mol_type = other DNA
                           organism = synthetic construct
SEQUENCE: 95
caacagagtt acagtacccc tccgatcacc                                     30

SEQ ID NO: 96            moltype = AA   length = 10
FEATURE                  Location/Qualifiers
REGION                  1..10
                           note = synthetic
source                  1..10
                           mol_type = protein
                           organism = synthetic construct
SEQUENCE: 96
QQSYSTPPIT                                                            10
```

-continued

```
SEQ ID NO: 97              moltype = DNA   length = 360
FEATURE                    Location/Qualifiers
misc_feature               1..360
                           note = synthetic
source                     1..360
                           mol_type = other DNA
                           organism = synthetic construct
SEQUENCE: 97
gaggtgcagc tggtggagtc tgggggaggt gtggtacggc cggggggtc  cctgagactc   60
tcctgtgcag cctctggatt caccttttgat gattatggca tgacctgggt ccgccaagtt  120
ccagggaagg ggctggagtg ggtctctggt attcattgga gtggtagaag cacaggttat  180
gcagactctg tgaagggccg attcaccatc tccagagaca acgccaagaa ctccctgtat  240
ctgcaaatga acagtctgag agccgaggac acggccttgt attactgtgc gagggggggga  300
atgagtacgg gggactggtt cgacccctgg ggccaggggaa ccctggtcac cgtctcctca  360

SEQ ID NO: 98              moltype = AA   length = 120
FEATURE                    Location/Qualifiers
REGION                     1..120
                           note = synthetic
source                     1..120
                           mol_type = protein
                           organism = synthetic construct
SEQUENCE: 98
EVQLVESGGG VVRPGGSLRL SCAASGFTFD DYGMTWVRQV PGKGLEWVSG IHWSGRSTGY   60
ADSVKGRFTI SRDNAKNSLY LQMNSLRAED TALYYCARGG MSTGDWFDPW GQGTLVTVSS  120

SEQ ID NO: 99              moltype = DNA   length = 24
FEATURE                    Location/Qualifiers
misc_feature               1..24
                           note = synthetic
source                     1..24
                           mol_type = other DNA
                           organism = synthetic construct
SEQUENCE: 99
ggattcacct ttgatgatta tggc                                          24

SEQ ID NO: 100             moltype = AA   length = 8
FEATURE                    Location/Qualifiers
REGION                     1..8
                           note = synthetic
source                     1..8
                           mol_type = protein
                           organism = synthetic construct
SEQUENCE: 100
GFTFDDYG                                                             8

SEQ ID NO: 101             moltype = DNA   length = 24
FEATURE                    Location/Qualifiers
misc_feature               1..24
                           note = synthetic
source                     1..24
                           mol_type = other DNA
                           organism = synthetic construct
SEQUENCE: 101
attcattgga gtggtagaag caca                                          24

SEQ ID NO: 102             moltype = AA   length = 8
FEATURE                    Location/Qualifiers
REGION                     1..8
                           note = synthetic
source                     1..8
                           mol_type = protein
                           organism = synthetic construct
SEQUENCE: 102
IHWSGRST                                                             8

SEQ ID NO: 103             moltype = DNA   length = 39
FEATURE                    Location/Qualifiers
misc_feature               1..39
                           note = synthetic
source                     1..39
                           mol_type = other DNA
                           organism = synthetic construct
SEQUENCE: 103
gcgagggggg gaatgagtac gggggactgg ttcgacccc                          39

SEQ ID NO: 104             moltype = AA   length = 13
FEATURE                    Location/Qualifiers
REGION                     1..13
```

-continued

```
                          note = synthetic
source                    1..13
                          mol_type = protein
                          organism = synthetic construct
SEQUENCE: 104
ARGGMSTGDW FDP                                                       13

SEQ ID NO: 105            moltype = DNA  length = 324
FEATURE                   Location/Qualifiers
misc_feature              1..324
                          note = synthetic
source                    1..324
                          mol_type = other DNA
                          organism = synthetic construct
SEQUENCE: 105
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgtt gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaa                                           324

SEQ ID NO: 106            moltype = AA  length = 108
FEATURE                   Location/Qualifiers
REGION                    1..108
                          note = synthetic
source                    1..108
                          mol_type = protein
                          organism = synthetic construct
SEQUENCE: 106
DIQMTQSPSS LSASVGDRVT ITCRASQSIS SYLNWYQQKP GKAPKLLIYV ASSLQSGVPS     60
RFSGSGSGTD FTLTISSLQP EDFATYYCQQ SYSTPPITFG QGTRLEIK                 108

SEQ ID NO: 107            moltype = DNA  length = 18
FEATURE                   Location/Qualifiers
misc_feature              1..18
                          note = synthetic
source                    1..18
                          mol_type = other DNA
                          organism = synthetic construct
SEQUENCE: 107
cagagcatta gcagctat                                                  18

SEQ ID NO: 108            moltype = AA  length = 6
FEATURE                   Location/Qualifiers
REGION                    1..6
                          note = synthetic
source                    1..6
                          mol_type = protein
                          organism = synthetic construct
SEQUENCE: 108
QSISSY                                                                6

SEQ ID NO: 109            moltype =   length =
SEQUENCE: 109
000

SEQ ID NO: 110            moltype =   length =
SEQUENCE: 110
000

SEQ ID NO: 111            moltype = DNA  length = 30
FEATURE                   Location/Qualifiers
misc_feature              1..30
                          note = synthetic
source                    1..30
                          mol_type = other DNA
                          organism = synthetic construct
SEQUENCE: 111
caacagagtt acagtacccc tccgatcacc                                     30

SEQ ID NO: 112            moltype = AA  length = 10
FEATURE                   Location/Qualifiers
REGION                    1..10
                          note = synthetic
source                    1..10
                          mol_type = protein
                          organism = synthetic construct
SEQUENCE: 112
```

```
QQSYSTPPIT                                                                10

SEQ ID NO: 113              moltype = DNA   length = 345
FEATURE                     Location/Qualifiers
misc_feature                1..345
                            note = synthetic
source                      1..345
                            mol_type = other DNA
                            organism = synthetic construct
SEQUENCE: 113
gaggtgcagt tggtggagtc tggaggaggc ttggtccagc ctggggggtc cctaagactc   60
tcctgtgcag cctctgggtt caccgtcggt agtaactaca tgaactgggt ccgtcaggct  120
ccagggaagg gactggagtg ggtctcagtt atttatagtg gtggtagtac atactacgca  180
gattccgtga agggccgatt caccatctcc agactcactt ccaagaacac actgtatctt  240
caaatgagca gcctgagacc tgaggacacg gccgtgtatt attgtgcgag agggattagg  300
ggtctggacg tctggggcca agggaccacg gtcaccgtct cttca                 345

SEQ ID NO: 114              moltype = AA   length = 115
FEATURE                     Location/Qualifiers
REGION                      1..115
                            note = synthetic
source                      1..115
                            mol_type = protein
                            organism = synthetic construct
SEQUENCE: 114
EVQLVESGGG LVQPGGSLRL SCAASGFTVG SNYMNWVRQA PGKGLEWVSV IYSGGSTYYA   60
DSVKGRFTIS RLTSKNTLYL QMSSLRPEDT AVYYCARGIR GLDVWGQGTT VTVSS       115

SEQ ID NO: 115              moltype = DNA   length = 24
FEATURE                     Location/Qualifiers
misc_feature                1..24
                            note = synthetic
source                      1..24
                            mol_type = other DNA
                            organism = synthetic construct
SEQUENCE: 115
gggttcaccg tcggtagtaa ctac                                          24

SEQ ID NO: 116              moltype = AA   length = 8
FEATURE                     Location/Qualifiers
REGION                      1..8
                            note = synthetic
source                      1..8
                            mol_type = protein
                            organism = synthetic construct
SEQUENCE: 116
GFTVGSNY                                                             8

SEQ ID NO: 117              moltype = DNA   length = 21
FEATURE                     Location/Qualifiers
misc_feature                1..21
                            note = synthetic
source                      1..21
                            mol_type = other DNA
                            organism = synthetic construct
SEQUENCE: 117
atttatagtg gtggtagtac a                                             21

SEQ ID NO: 118              moltype = AA   length = 7
FEATURE                     Location/Qualifiers
REGION                      1..7
                            note = synthetic
source                      1..7
                            mol_type = protein
                            organism = synthetic construct
SEQUENCE: 118
IYSGGST                                                              7

SEQ ID NO: 119              moltype = DNA   length = 27
FEATURE                     Location/Qualifiers
misc_feature                1..27
                            note = synthetic
source                      1..27
                            mol_type = other DNA
                            organism = synthetic construct
SEQUENCE: 119
gcgagaggga ttaggggtct ggacgtc                                       27

SEQ ID NO: 120              moltype = AA   length = 9
```

-continued

```
FEATURE                 Location/Qualifiers
REGION                  1..9
                        note = synthetic
source                  1..9
                        mol_type = protein
                        organism = synthetic construct
SEQUENCE: 120
ARGIRGLDV                                                               9

SEQ ID NO: 121          moltype = DNA   length = 324
FEATURE                 Location/Qualifiers
misc_feature            1..324
                        note = synthetic
source                  1..324
                        mol_type = other DNA
                        organism = synthetic construct
SEQUENCE: 121
gacatccaga tgacccagtc tccatcctcc ctgtctgcat ctgtaggaga cagagtcacc       60
atcacttgcc gggcaagtca gaccattaac atctatttaa attggtatca gcagaaacca      120
gggagagccc ctaggctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaccag agttacagta cccctccgat caccttcggc      300
caagggacac gactggagat taaa                                             324

SEQ ID NO: 122          moltype = AA   length = 108
FEATURE                 Location/Qualifiers
REGION                  1..108
                        note = synthetic
source                  1..108
                        mol_type = protein
                        organism = synthetic construct
SEQUENCE: 122
DIQMTQSPSS LSASVGDRVT ITCRASQTIN IYLNWYQQKP GRAPRLLIYA ASSLQSGVPS       60
RFSGSGSGTD FTLTISSLQP EDFATYYCHQ SYSTPPITFG QGTRLEIK                   108

SEQ ID NO: 123          moltype = DNA   length = 18
FEATURE                 Location/Qualifiers
misc_feature            1..18
                        note = synthetic
source                  1..18
                        mol_type = other DNA
                        organism = synthetic construct
SEQUENCE: 123
cagaccatta acatctat                                                     18

SEQ ID NO: 124          moltype = AA   length = 6
FEATURE                 Location/Qualifiers
REGION                  1..6
                        note = synthetic
source                  1..6
                        mol_type = protein
                        organism = synthetic construct
SEQUENCE: 124
QTINIY                                                                   6

SEQ ID NO: 125          moltype =    length =
SEQUENCE: 125
000

SEQ ID NO: 126          moltype =    length =
SEQUENCE: 126
000

SEQ ID NO: 127          moltype = DNA   length = 30
FEATURE                 Location/Qualifiers
misc_feature            1..30
                        note = synthetic
source                  1..30
                        mol_type = other DNA
                        organism = synthetic construct
SEQUENCE: 127
caccagagtt acagtacccc tccgatcacc                                        30

SEQ ID NO: 128          moltype = AA   length = 10
FEATURE                 Location/Qualifiers
REGION                  1..10
                        note = synthetic
source                  1..10
                        mol_type = protein
```

-continued

```
                          organism = synthetic construct
SEQUENCE: 128
HQSYSTPPIT                                                    10

SEQ ID NO: 129           moltype = DNA   length = 345
FEATURE                  Location/Qualifiers
misc_feature             1..345
                         note = synthetic
source                   1..345
                         mol_type = other DNA
                         organism = synthetic construct
SEQUENCE: 129
gaggaacggt tggtggagtc tggaggagac ttggtccagc ctggggggtc cctgagactc   60
tcctgtgcag cctctggcat caccgtcggt actaattata tgaactgggt ccgccaggct  120
ccagggaagg gactggagtg ggtctcagtt atttctagcg gtggtaatac acactacgca  180
gactccgtga agggccgatt cattatgtcc agacaaactt ccaaaaacac gctgtatctt  240
cagatgaata gcctggaaac tgaggacacg gccgtatatt attgtgcgag ggggatcaga  300
ggtttggacg tctggggcca agggaccatg gtcaccgtct cctca                 345

SEQ ID NO: 130           moltype = AA   length = 115
FEATURE                  Location/Qualifiers
REGION                   1..115
                         note = synthetic
source                   1..115
                         mol_type = protein
                         organism = synthetic construct
SEQUENCE: 130
EERLVESGGD LVQPGGSLRL SCAASGITVG TNYMNWVRQA PGKGLEWVSV ISSGGNTHYA   60
DSVKGRFIMS RQTSKNTLYL QMNSLETEDT AVYYCARGIR GLDVWGQGTM VTVSS       115

SEQ ID NO: 131           moltype = DNA   length = 24
FEATURE                  Location/Qualifiers
misc_feature             1..24
                         note = synthetic
source                   1..24
                         mol_type = other DNA
                         organism = synthetic construct
SEQUENCE: 131
ggcatcaccg tcggtactaa ttat                                         24

SEQ ID NO: 132           moltype = AA   length = 8
FEATURE                  Location/Qualifiers
REGION                   1..8
                         note = synthetic
source                   1..8
                         mol_type = protein
                         organism = synthetic construct
SEQUENCE: 132
GITVGTNY                                                            8

SEQ ID NO: 133           moltype = DNA   length = 21
FEATURE                  Location/Qualifiers
misc_feature             1..21
                         note = synthetic
source                   1..21
                         mol_type = other DNA
                         organism = synthetic construct
SEQUENCE: 133
atttctagcg gtggtaatac a                                            21

SEQ ID NO: 134           moltype = AA   length = 7
FEATURE                  Location/Qualifiers
REGION                   1..7
                         note = synthetic
source                   1..7
                         mol_type = protein
                         organism = synthetic construct
SEQUENCE: 134
ISSGGNT                                                             7

SEQ ID NO: 135           moltype = DNA   length = 27
FEATURE                  Location/Qualifiers
misc_feature             1..27
                         note = synthetic
source                   1..27
                         mol_type = other DNA
                         organism = synthetic construct
SEQUENCE: 135
gcgaggggga tcagaggttt ggacgtc                                      27
```

```
SEQ ID NO: 136          moltype = AA   length = 9
FEATURE                 Location/Qualifiers
REGION                  1..9
                        note = synthetic
source                  1..9
                        mol_type = protein
                        organism = synthetic construct
SEQUENCE: 136
ARGIRGLDV                                                                9

SEQ ID NO: 137          moltype = DNA  length = 324
FEATURE                 Location/Qualifiers
misc_feature            1..324
                        note = synthetic
source                  1..324
                        mol_type = other DNA
                        organism = synthetic construct
SEQUENCE: 137
gacatccaga tgacccagtc tccatcctcc ctgtctgcat ctgtaggaga cagagtcacc      60
atcacttgcc gggcaagtca gagcatgagc agctatttaa attggtatca gcagaaacca     120
gggagagccc ctaagctcct gatctttgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta cccctccgat caccttcggc     300
caagggacac gactggagat taaa                                            324

SEQ ID NO: 138          moltype = AA   length = 108
FEATURE                 Location/Qualifiers
REGION                  1..108
                        note = synthetic
source                  1..108
                        mol_type = protein
                        organism = synthetic construct
SEQUENCE: 138
DIQMTQSPSS LSASVGDRVT ITCRASQSMS SYLNWYQQKP GRAPKLLIFA ASSLQSGVPS      60
RFSGSGSGTD FTLTISSLQP EDFATYYCQQ SYSTPPITFG QGTRLEIK                  108

SEQ ID NO: 139          moltype = DNA  length = 18
FEATURE                 Location/Qualifiers
misc_feature            1..18
                        note = synthetic
source                  1..18
                        mol_type = other DNA
                        organism = synthetic construct
SEQUENCE: 139
cagagcatga gcagctat                                                   18

SEQ ID NO: 140          moltype = AA   length = 6
FEATURE                 Location/Qualifiers
REGION                  1..6
                        note = synthetic
source                  1..6
                        mol_type = protein
                        organism = synthetic construct
SEQUENCE: 140
QSMSSY                                                                 6

SEQ ID NO: 141          moltype =   length =
SEQUENCE: 141
000

SEQ ID NO: 142          moltype =   length =
SEQUENCE: 142
000

SEQ ID NO: 143          moltype = DNA  length = 30
FEATURE                 Location/Qualifiers
misc_feature            1..30
                        note = synthetic
source                  1..30
                        mol_type = other DNA
                        organism = synthetic construct
SEQUENCE: 143
caacagagtt acagtacccc tccgatcacc                                      30

SEQ ID NO: 144          moltype = AA   length = 10
FEATURE                 Location/Qualifiers
REGION                  1..10
                        note = synthetic
```

-continued

```
source                    1..10
                          mol_type = protein
                          organism = synthetic construct
SEQUENCE: 144
QQSYSTPPIT                                                            10

SEQ ID NO: 145            moltype = DNA   length = 354
FEATURE                   Location/Qualifiers
misc_feature              1..354
                          note = synthetic
source                    1..354
                          mol_type = other DNA
                          organism = synthetic construct
SEQUENCE: 145
caggtccagc tggtgcagtc tgggggctgag gtgaagatgc ctgggtcctc ggtgagggtc   60
tcctgcaagg cttctggagg catcttcagc agttctacta tcagttgggt gcgacaggcc  120
cctggacaag ggcttgaatg gatgggagag atcatccctg tctttggtac agtaaactac  180
gcacagaagt tccaggacag agtcatattt accgcggaca atctacgac tacagcctac  240
atggagctga gcagcctgaa atctggggac acggccgtat atttctgtgc gcgaaattgg  300
ggattaggct cttttttatat ctggggccaa gggacaatgg tcaccgtctc ttca       354

SEQ ID NO: 146            moltype = AA   length = 118
FEATURE                   Location/Qualifiers
REGION                    1..118
                          note = synthetic
source                    1..118
                          mol_type = protein
                          organism = synthetic construct
SEQUENCE: 146
QVQLVQSGAE VKMPGSSVRV SCKASGGIFS SSTISWVRQA PGQGLEWMGE IIPVFGTVNY   60
AQKFQDRVIF TADESTTTAY MELSSLKSGD TAVYFCARNW GLGSFYIWGQ GTMVTVSS    118

SEQ ID NO: 147            moltype = DNA   length = 24
FEATURE                   Location/Qualifiers
misc_feature              1..24
                          note = synthetic
source                    1..24
                          mol_type = other DNA
                          organism = synthetic construct
SEQUENCE: 147
ggaggcatct tcagcagttc tact                                            24

SEQ ID NO: 148            moltype = AA   length = 8
FEATURE                   Location/Qualifiers
REGION                    1..8
                          note = synthetic
source                    1..8
                          mol_type = protein
                          organism = synthetic construct
SEQUENCE: 148
GGIFSSST                                                               8

SEQ ID NO: 149            moltype = DNA   length = 24
FEATURE                   Location/Qualifiers
misc_feature              1..24
                          note = synthetic
source                    1..24
                          mol_type = other DNA
                          organism = synthetic construct
SEQUENCE: 149
atcatccctg tctttggtac agta                                            24

SEQ ID NO: 150            moltype = AA   length = 8
FEATURE                   Location/Qualifiers
REGION                    1..8
                          note = synthetic
source                    1..8
                          mol_type = protein
                          organism = synthetic construct
SEQUENCE: 150
IIPVFGTV                                                               8

SEQ ID NO: 151            moltype = DNA   length = 33
FEATURE                   Location/Qualifiers
misc_feature              1..33
                          note = synthetic
source                    1..33
                          mol_type = other DNA
                          organism = synthetic construct
```

-continued

```
SEQUENCE: 151
gcgcgaaatt ggggattagg ctctttttat atc                                 33

SEQ ID NO: 152          moltype = AA  length = 11
FEATURE                 Location/Qualifiers
REGION                  1..11
                        note = synthetic
source                  1..11
                        mol_type = protein
                        organism = synthetic construct
SEQUENCE: 152
ARNWGLGSFY I                                                          11

SEQ ID NO: 153          moltype = DNA  length = 324
FEATURE                 Location/Qualifiers
misc_feature            1..324
                        note = synthetic
source                  1..324
                        mol_type = other DNA
                        organism = synthetic construct
SEQUENCE: 153
gaaattgtgt tgacgcagtc tccaggcacc ctgtctttgt ctccagggga aagagccacc    60
ctctcctgca gggccagtca gagttttaac ttcaactact tagcctggta ccagcagaaa    120
cctggccagg ctcccagact cctcatctat ggtgcatcca gcagggccac tggcatccca    180
gacaggttca gtggcagtgg gtctgggaca gacttcactc tcaccatcaa caggctggag    240
cctgaagatt ttggagtgtt ttattgtcag cagtatgaaa gcgcaccttg gacgttcggc    300
caagggacca aggtggaaat caaa                                           324

SEQ ID NO: 154          moltype = AA  length = 108
FEATURE                 Location/Qualifiers
REGION                  1..108
                        note = synthetic
source                  1..108
                        mol_type = protein
                        organism = synthetic construct
SEQUENCE: 154
EIVLTQSPGT LSLSPGERAT LSCRASQSFN FNYLAWYQQK PGQAPRLLIY GASSRATGIP    60
DRFSGSGSGT DFTLTINRLE PEDFGVFYCQ QYESAPWTFG QGTKVEIK                 108

SEQ ID NO: 155          moltype = DNA  length = 21
FEATURE                 Location/Qualifiers
misc_feature            1..21
                        note = synthetic
source                  1..21
                        mol_type = other DNA
                        organism = synthetic construct
SEQUENCE: 155
cagagtttta acttcaacta c                                              21

SEQ ID NO: 156          moltype = AA  length = 7
FEATURE                 Location/Qualifiers
REGION                  1..7
                        note = synthetic
source                  1..7
                        mol_type = protein
                        organism = synthetic construct
SEQUENCE: 156
QSFNFNY                                                               7

SEQ ID NO: 157          moltype =    length =
SEQUENCE: 157
000

SEQ ID NO: 158          moltype =    length =
SEQUENCE: 158
000

SEQ ID NO: 159          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 159
cagcagtatg aaagcgcacc ttggacg                                        27

SEQ ID NO: 160          moltype = AA  length = 9
FEATURE                 Location/Qualifiers
```

-continued

```
REGION                    1..9
                          note = synthetic
source                    1..9
                          mol_type = protein
                          organism = synthetic construct
SEQUENCE: 160
QQYESAPWT                                                             9

SEQ ID NO: 161            moltype = DNA   length = 345
FEATURE                   Location/Qualifiers
misc_feature              1..345
                          note = synthetic
source                    1..345
                          mol_type = other DNA
                          organism = synthetic construct
SEQUENCE: 161
gaggtgcagc ttgtagagtc tggggggagac ttggtacatc ctggcaggtc cctgagactc  60
tcctgtgcag cctctggtt tcccctttgat gagtatgcca tgcactgggt ccggcaagtt  120
ccagggaagg gcctggagtg ggtctcaggt attagttgga gtaataataa cataggctat  180
gcggactctg tgaagggccg attcaccatc tccagagaca acgccaaaaa ctccctgtat  240
ctacaaatga acagtctgag acctgaggac acggccttt attactgtgc aaaatctgga  300
atctttgact cctggggcca gggaaccctg gtcaccgtct cctca                  345

SEQ ID NO: 162            moltype = AA   length = 115
FEATURE                   Location/Qualifiers
REGION                    1..115
                          note = synthetic
source                    1..115
                          mol_type = protein
                          organism = synthetic construct
SEQUENCE: 162
EVQLVESGGD LVHPGRSLRL SCAASGFPFD EYAMHWVRQV PGKGLEWVSG ISWSNNNIGY    60
ADSVKGRFTI SRDNAKNSLY LQMNSLRPED TAFYYCAKSG IFDSWGQGTL VTVSS         115

SEQ ID NO: 163            moltype = DNA   length = 24
FEATURE                   Location/Qualifiers
misc_feature              1..24
                          note = synthetic
source                    1..24
                          mol_type = other DNA
                          organism = synthetic construct
SEQUENCE: 163
ggtttcccct ttgatgagta tgcc                                          24

SEQ ID NO: 164            moltype = AA   length = 8
FEATURE                   Location/Qualifiers
REGION                    1..8
                          note = synthetic
source                    1..8
                          mol_type = protein
                          organism = synthetic construct
SEQUENCE: 164
GFPFDEYA                                                             8

SEQ ID NO: 165            moltype = DNA   length = 24
FEATURE                   Location/Qualifiers
misc_feature              1..24
                          note = synthetic
source                    1..24
                          mol_type = other DNA
                          organism = synthetic construct
SEQUENCE: 165
attagttgga gtaataataa cata                                          24

SEQ ID NO: 166            moltype = AA   length = 8
FEATURE                   Location/Qualifiers
REGION                    1..8
                          note = synthetic
source                    1..8
                          mol_type = protein
                          organism = synthetic construct
SEQUENCE: 166
ISWSNNNI                                                             8

SEQ ID NO: 167            moltype = DNA   length = 24
FEATURE                   Location/Qualifiers
misc_feature              1..24
                          note = synthetic
source                    1..24
```

```
                              mol_type = other DNA
                              organism = synthetic construct
SEQUENCE: 167
gcaaatctg gaatctttga ctcc                                                    24

SEQ ID NO: 168            moltype = AA   length = 8
FEATURE                   Location/Qualifiers
REGION                    1..8
                          note = synthetic
source                    1..8
                          mol_type = protein
                          organism = synthetic construct
SEQUENCE: 168
AKSGIFDS                                                                      8

SEQ ID NO: 169            moltype = DNA   length = 315
FEATURE                   Location/Qualifiers
misc_feature              1..315
                          note = synthetic
source                    1..315
                          mol_type = other DNA
                          organism = synthetic construct
SEQUENCE: 169
gacatccaga tgacccagtc tccatcctcc ctgtctgcat ctgtaggaga cagagtcacc   60
atcacttgcc gggcaagtca gagcattagc agctatttaa attggtatca gcagaaacca  120
gggaagctcc tgatctatgc tgcatccagt ttgcaaagtg gggtcccatc acggttcagt  180
ggcggtggat ctgggacaga tttcactctc accatcagca gtctgcgacc tgaagatttt  240
gcaacttact actgtcaaca gagttactgt accccctccga tcaccttcgg ccaagggaca  300
cgactggaga ttaaa                                                           315

SEQ ID NO: 170            moltype = AA   length = 105
FEATURE                   Location/Qualifiers
REGION                    1..105
                          note = synthetic
source                    1..105
                          mol_type = protein
                          organism = synthetic construct
SEQUENCE: 170
DIQMTQSPSS LSASVGDRVT ITCRASQSIS SYLNWYQQKP GKLLIYAASS LQSGVPSRFS   60
GGGSGTDFTL TISSLRPEDF ATYYCQQSYC TPPITFGQGT RLEIK                  105

SEQ ID NO: 171            moltype = DNA   length = 18
FEATURE                   Location/Qualifiers
misc_feature              1..18
                          note = synthetic
source                    1..18
                          mol_type = other DNA
                          organism = synthetic construct
SEQUENCE: 171
cagagcatta gcagctat                                                          18

SEQ ID NO: 172            moltype = AA   length = 6
FEATURE                   Location/Qualifiers
REGION                    1..6
                          note = synthetic
source                    1..6
                          mol_type = protein
                          organism = synthetic construct
SEQUENCE: 172
QSISSY                                                                        6

SEQ ID NO: 173            moltype =    length =
SEQUENCE: 173
000

SEQ ID NO: 174            moltype =    length =
SEQUENCE: 174
000

SEQ ID NO: 175            moltype = DNA   length = 30
FEATURE                   Location/Qualifiers
misc_feature              1..30
                          note = synthetic
source                    1..30
                          mol_type = other DNA
                          organism = synthetic construct
SEQUENCE: 175
caacagagtt actgtacccc tccgatcacc                                             30
```

-continued

```
SEQ ID NO: 176          moltype = AA   length = 10
FEATURE                 Location/Qualifiers
REGION                  1..10
                        note = synthetic
source                  1..10
                        mol_type = protein
                        organism = synthetic construct
SEQUENCE: 176
QQSYCTPPIT                                                        10

SEQ ID NO: 177          moltype = DNA   length = 354
FEATURE                 Location/Qualifiers
misc_feature            1..354
                        note = synthetic
source                  1..354
                        mol_type = other DNA
                        organism = synthetic construct
SEQUENCE: 177
gaggtgcagc tggtggagtc cggggggaggc gtggtccagc ctgggaggtc cctgagactc   60
tcctgtgcag cctctggatt caccttcagt agttatggca tgcactgggt ccgccaggct  120
ccaggcaagg gactggagtg ggtgacactt atatcatatg agggaaggaa taaatactat  180
gcagactccg tgaagggccg attcaccatt tccagagaca attccaagaa cacgctgtat  240
ctgcaaatga acagcctgag agctgaggac acggctgtat attactgtgc gaaagatagg  300
acccttttacg gtatggacgt ctggggccaa ggaaccacgg tcaccgtctc ctca        354

SEQ ID NO: 178          moltype = AA   length = 118
FEATURE                 Location/Qualifiers
REGION                  1..118
                        note = synthetic
source                  1..118
                        mol_type = protein
                        organism = synthetic construct
SEQUENCE: 178
EVQLVESGGG VVQPGRSLRL SCAASGFTFS SYGMHWVRQA PGKGLEWVTL ISYEGRNKYY   60
ADSVKGRFTI SRDNSKNTLY LQMNSLRAED TAVYYCAKDR TLYGMDVWGQ GTTVTVSS    118

SEQ ID NO: 179          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 179
ggattcacct tcagtagtta tggc                                         24

SEQ ID NO: 180          moltype = AA   length = 8
FEATURE                 Location/Qualifiers
REGION                  1..8
                        note = synthetic
source                  1..8
                        mol_type = protein
                        organism = synthetic construct
SEQUENCE: 180
GFTFSSYG                                                            8

SEQ ID NO: 181          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 181
atatcatatg agggaaggaa taaa                                         24

SEQ ID NO: 182          moltype = AA   length = 8
FEATURE                 Location/Qualifiers
REGION                  1..8
                        note = synthetic
source                  1..8
                        mol_type = protein
                        organism = synthetic construct
SEQUENCE: 182
ISYEGRNK                                                            8

SEQ ID NO: 183          moltype = DNA   length = 33
FEATURE                 Location/Qualifiers
misc_feature            1..33
```

-continued

```
                              note = synthetic
source                        1..33
                              mol_type = other DNA
                              organism = synthetic construct
SEQUENCE: 183
gcgaaagata ggacccttta cggtatggac gtc                               33

SEQ ID NO: 184         moltype = AA  length = 11
FEATURE                Location/Qualifiers
REGION                 1..11
                       note = synthetic
source                 1..11
                       mol_type = protein
                       organism = synthetic construct
SEQUENCE: 184
AKDRTLYGMD V                                                       11

SEQ ID NO: 185         moltype = DNA  length = 363
FEATURE                Location/Qualifiers
misc_feature           1..363
                       note = synthetic
source                 1..363
                       mol_type = other DNA
                       organism = synthetic construct
SEQUENCE: 185
caggtcacct tgagggagtc tggtcctgcg ctggtgaaaa ccacacagac cctcacactg  60
acctgcacct tctctgggtt ctcactcagc actaatagaa tgtgtgtgac ctggatccgt  120
cagcccccag ggaaggccct ggagtggctt gcgcgcattg attgggatgg tgttaaatac  180
tacaacacat ctctgaagac caggctcacc atctccaagg acacctccaa aaaccaggtg  240
gtccttacaa tgaccaacat ggaccctgtg gacacagcc cttttttactg tgcacggtcg  300
acttcgttga cttttttacta ctttgactac tggggccagg gaaccctggt caccgtctcc  360
tca                                                               363

SEQ ID NO: 186         moltype = AA  length = 121
FEATURE                Location/Qualifiers
REGION                 1..121
                       note = synthetic
source                 1..121
                       mol_type = protein
                       organism = synthetic construct
SEQUENCE: 186
QVTLRESGPA LVKTTQTLTL TCTFSGFSLS TNRMCVTWIR QPPGKALEWL ARIDWDGVKY  60
YNTSLKTRLT ISKDTSKNQV VLTMTNMDPV DTATFYCARS TSLTFYYFDY WGQGTLVTVS  120
S                                                                 121

SEQ ID NO: 187         moltype = DNA  length = 30
FEATURE                Location/Qualifiers
misc_feature           1..30
                       note = synthetic
source                 1..30
                       mol_type = other DNA
                       organism = synthetic construct
SEQUENCE: 187
gggttctcac tcagcactaa tagaatgtgt                                   30

SEQ ID NO: 188         moltype = AA  length = 10
FEATURE                Location/Qualifiers
REGION                 1..10
                       note = synthetic
source                 1..10
                       mol_type = protein
                       organism = synthetic construct
SEQUENCE: 188
GFSLSTNRMC                                                         10

SEQ ID NO: 189         moltype = DNA  length = 21
FEATURE                Location/Qualifiers
misc_feature           1..21
                       note = synthetic
source                 1..21
                       mol_type = other DNA
                       organism = synthetic construct
SEQUENCE: 189
attgattggg atggtgttaa a                                            21

SEQ ID NO: 190         moltype = AA  length = 7
FEATURE                Location/Qualifiers
REGION                 1..7
                       note = synthetic
```

-continued

```
source                     1..7
                           mol_type = protein
                           organism = synthetic construct
SEQUENCE: 190
IDWDGVK                                                                      7

SEQ ID NO: 191             moltype = DNA   length = 39
FEATURE                    Location/Qualifiers
misc_feature               1..39
                           note = synthetic
source                     1..39
                           mol_type = other DNA
                           organism = synthetic construct
SEQUENCE: 191
gcacggtcga cttcgttgac tttttactac tttgactac                                   39

SEQ ID NO: 192             moltype = AA   length = 13
FEATURE                    Location/Qualifiers
REGION                     1..13
                           note = synthetic
source                     1..13
                           mol_type = protein
                           organism = synthetic construct
SEQUENCE: 192
ARSTSLTFYY FDY                                                               13

SEQ ID NO: 193             moltype = DNA   length = 324
FEATURE                    Location/Qualifiers
misc_feature               1..324
                           note = synthetic
source                     1..324
                           mol_type = other DNA
                           organism = synthetic construct
SEQUENCE: 193
gacatccaga tgacccagtc tccatcctcc ctgtctgcat ctgtaggaga cagagtcacc   60
atcacttgcc gggcaagtca gagcattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta cccctccgat caccttcggc  300
caaggacac gactggagat taaa                                          324

SEQ ID NO: 194             moltype = AA   length = 108
FEATURE                    Location/Qualifiers
REGION                     1..108
                           note = synthetic
source                     1..108
                           mol_type = protein
                           organism = synthetic construct
SEQUENCE: 194
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPPITFG QGTRLEIK               108

SEQ ID NO: 195             moltype = DNA   length = 18
FEATURE                    Location/Qualifiers
misc_feature               1..18
                           note = synthetic
source                     1..18
                           mol_type = other DNA
                           organism = synthetic construct
SEQUENCE: 195
cagagcatta gcagctat                                                          18

SEQ ID NO: 196             moltype = AA   length = 6
FEATURE                    Location/Qualifiers
REGION                     1..6
                           note = synthetic
source                     1..6
                           mol_type = protein
                           organism = synthetic construct
SEQUENCE: 196
QSISSY                                                                        6

SEQ ID NO: 197             moltype =    length =
SEQUENCE: 197
000

SEQ ID NO: 198             moltype =    length =
SEQUENCE: 198
000
```

-continued

```
SEQ ID NO: 199          moltype = DNA   length = 30
FEATURE                 Location/Qualifiers
misc_feature            1..30
                        note = synthetic
source                  1..30
                        mol_type = other DNA
                        organism = synthetic construct
SEQUENCE: 199
caacagagtt acagtacccc tccgatcacc                                      30

SEQ ID NO: 200          moltype = AA   length = 10
FEATURE                 Location/Qualifiers
REGION                  1..10
                        note = synthetic
source                  1..10
                        mol_type = protein
                        organism = synthetic construct
SEQUENCE: 200
QQSYSTPPIT                                                             10

SEQ ID NO: 201          moltype = DNA   length = 345
FEATURE                 Location/Qualifiers
misc_feature            1..345
                        note = synthetic
source                  1..345
                        mol_type = other DNA
                        organism = synthetic construct
SEQUENCE: 201
gaggtgcagc tggtggagtc tggaggaggc ttggtccagc cggggggtc cctgagactc     60
tcctgtgcag cctctgagtt caccgtcggt accaaccaca tgaactgggt ccgccaggct    120
ccagggaagg gactggagtg ggtctcagtt atttatagcg gtggtaacac attctacgca    180
gactccgtga agggccgatt caccatctcc agacacactt ccaagaacac gctgtatctt    240
caaatgaaca gcctgacagc agaggacacg gccgtatatt actgtgcgcg aggattgggg    300
ggtatggacg tctggggcca agggaccacg gtcaccgtct cctca                    345

SEQ ID NO: 202          moltype = AA   length = 115
FEATURE                 Location/Qualifiers
REGION                  1..115
                        note = synthetic
source                  1..115
                        mol_type = protein
                        organism = synthetic construct
SEQUENCE: 202
EVQLVESGGG LVQPGGSLRL SCAASEFTVG TNHMNWVRQA PGKGLEWVSV IYSGGNTFYA     60
DSVKGRFTIS RHTSKNTLYL QMNSLTAEDT AVYYCARGLG GMDVWGQGTT VTVSS         115

SEQ ID NO: 203          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 203
gagttcaccg tcggtaccaa ccac                                            24

SEQ ID NO: 204          moltype = AA   length = 8
FEATURE                 Location/Qualifiers
REGION                  1..8
                        note = synthetic
source                  1..8
                        mol_type = protein
                        organism = synthetic construct
SEQUENCE: 204
EFTVGTNH                                                               8

SEQ ID NO: 205          moltype = DNA   length = 21
FEATURE                 Location/Qualifiers
misc_feature            1..21
                        note = synthetic
source                  1..21
                        mol_type = other DNA
                        organism = synthetic construct
SEQUENCE: 205
atttatagcg gtggtaacac a                                               21

SEQ ID NO: 206          moltype = AA   length = 7
FEATURE                 Location/Qualifiers
```

```
REGION                  1..7
                        note = synthetic
source                  1..7
                        mol_type = protein
                        organism = synthetic construct
SEQUENCE: 206
IYSGGNT                                                               7

SEQ ID NO: 207          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 207
gcgcgaggat tggggggtat ggacgtc                                        27

SEQ ID NO: 208          moltype = AA  length = 9
FEATURE                 Location/Qualifiers
REGION                  1..9
                        note = synthetic
source                  1..9
                        mol_type = protein
                        organism = synthetic construct
SEQUENCE: 208
ARGLGGMDV                                                            9

SEQ ID NO: 209          moltype = DNA  length = 321
FEATURE                 Location/Qualifiers
misc_feature            1..321
                        note = synthetic
source                  1..321
                        mol_type = other DNA
                        organism = synthetic construct
SEQUENCE: 209
gacatccaga tgacccagtc tccatcctcc ctgtctgcat ctgtaggaga cagagtcacc   60
atcacttgcc gggcgagtca ggtcattagc aattatttag cctggtatca gcagaaacca  120
gggaaagttc ctaggctcct gatctatgct gcatccactt tgcaatcagg ggtcccatct  180
cgtttcagtg gcagtggatc tgggacagat ttcactctca ccatcagcag cctgcagcct  240
gaagatgttg caacttatta ctgtcaaaag tataacagtg cccctcggac gttcggccaa  300
gggaccaagg tggaaatcaa a                                            321

SEQ ID NO: 210          moltype = AA  length = 107
FEATURE                 Location/Qualifiers
REGION                  1..107
                        note = synthetic
source                  1..107
                        mol_type = protein
                        organism = synthetic construct
SEQUENCE: 210
DIQMTQSPSS LSASVGDRVT ITCRASQVIS NYLAWYQQKP GKVPRLLIYA ASTLQSGVPS   60
RFSGSGSGTD FTLTISSLQP EDVATYYCQK YNSAPRTFGQ GTKVEIK                107

SEQ ID NO: 211          moltype = DNA  length = 18
FEATURE                 Location/Qualifiers
misc_feature            1..18
                        note = synthetic
source                  1..18
                        mol_type = other DNA
                        organism = synthetic construct
SEQUENCE: 211
caggtcatta gcaattat                                                 18

SEQ ID NO: 212          moltype = AA  length = 6
FEATURE                 Location/Qualifiers
REGION                  1..6
                        note = synthetic
source                  1..6
                        mol_type = protein
                        organism = synthetic construct
SEQUENCE: 212
QVISNY                                                               6

SEQ ID NO: 213          moltype =    length =
SEQUENCE: 213
000

SEQ ID NO: 214          moltype =    length =
```

```
SEQUENCE: 214
000

SEQ ID NO: 215          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 215
caaaagtata acagtgcccc tcggacg                                  27

SEQ ID NO: 216          moltype = AA  length = 9
FEATURE                 Location/Qualifiers
REGION                  1..9
                        note = synthetic
source                  1..9
                        mol_type = protein
                        organism = synthetic construct
SEQUENCE: 216
QKYNSAPRT                                                      9

SEQ ID NO: 217          moltype = DNA  length = 360
FEATURE                 Location/Qualifiers
misc_feature            1..360
                        note = synthetic
source                  1..360
                        mol_type = other DNA
                        organism = synthetic construct
SEQUENCE: 217
gaggtgcagc tggtggagtc tggggggaggc ttggtccagc ggggggagtc cctgagactt  60
tactgtgcag cctctggatt caccttttagt aaatattgga tgaactgggt ccgccaggct 120
ccagggaagg ggctggagtg ggtggccaac ataaagggag atggaagtga gaaatactat 180
gtggactctg tgaagggccg gttcaccatc tccagagaca acgccaagaa ctcactatat 240
ctacaaatga acagcctgag agccgaggac acggctgttt attactgtgc gagagattat 300
tggggatcag gctactactt tgacttctgg ggccagggaa ccctggtcac cgtctcctca 360

SEQ ID NO: 218          moltype = AA  length = 120
FEATURE                 Location/Qualifiers
REGION                  1..120
                        note = synthetic
source                  1..120
                        mol_type = protein
                        organism = synthetic construct
SEQUENCE: 218
EVQLVESGGG LVQRGESLRL YCAASGFTFS KYWMNWVRQA PGKGLEWVAN IKGDGSEKYY  60
VDSVKGRFTI SRDNAKNSLY LQMNSLRAED TAVYYCARDY WGSGYYFDFW GQGTLVTVSS 120

SEQ ID NO: 219          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 219
ggattcacct ttagtaaata ttgg                                    24

SEQ ID NO: 220          moltype = AA  length = 8
FEATURE                 Location/Qualifiers
REGION                  1..8
                        note = synthetic
source                  1..8
                        mol_type = protein
                        organism = synthetic construct
SEQUENCE: 220
GFTFSKYW                                                       8

SEQ ID NO: 221          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 221
ataaagggag atggaagtga gaaa                                    24
```

-continued

```
SEQ ID NO: 222          moltype = AA   length = 8
FEATURE                 Location/Qualifiers
REGION                  1..8
                        note = synthetic
source                  1..8
                        mol_type = protein
                        organism = synthetic construct
SEQUENCE: 222
IKGDGSEK                                                          8

SEQ ID NO: 223          moltype = DNA   length = 39
FEATURE                 Location/Qualifiers
misc_feature            1..39
                        note = synthetic
source                  1..39
                        mol_type = other DNA
                        organism = synthetic construct
SEQUENCE: 223
gcgagagatt attggggatc aggctactac tttgacttc                       39

SEQ ID NO: 224          moltype = AA   length = 13
FEATURE                 Location/Qualifiers
REGION                  1..13
                        note = synthetic
source                  1..13
                        mol_type = protein
                        organism = synthetic construct
SEQUENCE: 224
ARDYWGSGYY FDF                                                    13

SEQ ID NO: 225          moltype = DNA   length = 321
FEATURE                 Location/Qualifiers
misc_feature            1..321
                        note = synthetic
source                  1..321
                        mol_type = other DNA
                        organism = synthetic construct
SEQUENCE: 225
gacatccaga tgacccagtc tccatcctcc ctgtctgcat ctgtaggaga cagagtcacc  60
atcacttgcc gggcaagtca gaacattaac aactatttaa attggtatca gcagaaacca  120
gggaaagccc ctaaactcct gatctatgct gcatccagtt tccaaaatgc ggtcccatca  180
aggttcagtg gcagtggatc tgggacagat ttcactctca ccatcagcag tctgcaacct  240
gaagattttg caacttacta ctgtcaacag agttacaata ccccgctcac tttcggcggg  300
gggaccaagg tggagatcaa a                                           321

SEQ ID NO: 226          moltype = AA   length = 107
FEATURE                 Location/Qualifiers
REGION                  1..107
                        note = synthetic
source                  1..107
                        mol_type = protein
                        organism = synthetic construct
SEQUENCE: 226
DIQMTQSPSS LSASVGDRVT ITCRASQNIN NYLNWYQQKP GKAPKLLIYA ASSFQNAVPS  60
RFSGSGSGTD FTLTISSLQP EDFATYYCQQ SYNTPLTFGG GTKVEIK               107

SEQ ID NO: 227          moltype = DNA   length = 18
FEATURE                 Location/Qualifiers
misc_feature            1..18
                        note = synthetic
source                  1..18
                        mol_type = other DNA
                        organism = synthetic construct
SEQUENCE: 227
cagaacatta acaactat                                               18

SEQ ID NO: 228          moltype = AA   length = 6
FEATURE                 Location/Qualifiers
REGION                  1..6
                        note = synthetic
source                  1..6
                        mol_type = protein
                        organism = synthetic construct
SEQUENCE: 228
QNINNY                                                            6

SEQ ID NO: 229          moltype =    length =
SEQUENCE: 229
000
```

```
SEQ ID NO: 230          moltype =   length =
SEQUENCE: 230
000

SEQ ID NO: 231          moltype = DNA   length = 27
FEATURE                 Location/Qualifiers
misc_feature            1..27
                        note = synthetic
source                  1..27
                        mol_type = other DNA
                        organism = synthetic construct
SEQUENCE: 231
caacagagtt acaatacccc gctcact                                            27

SEQ ID NO: 232          moltype = AA   length = 9
FEATURE                 Location/Qualifiers
REGION                  1..9
                        note = synthetic
source                  1..9
                        mol_type = protein
                        organism = synthetic construct
SEQUENCE: 232
QQSYNTPLT                                                                9

SEQ ID NO: 233          moltype = DNA   length = 390
FEATURE                 Location/Qualifiers
misc_feature            1..390
                        note = synthetic
source                  1..390
                        mol_type = other DNA
                        organism = synthetic construct
SEQUENCE: 233
gaggtgcagc tggtggagtc tgggggaggc ttggtccagt ctggggggtc cctgagactc        60
tcctgtgcag cctctggatt cacctttagt agctattgga tgagctgggt ccgccaggct       120
ccagggaagg ggctggagtg ggtggccaac ataaagcaag atggaagtga gaaatactat       180
gtggactctg tgaagggccg attcaccatc tccagagaca cgccaagaa ctcactgtat        240
ctgcaaatga acagcctgag agccgatgac acggctgtgt attactgtgc gagagatgat       300
attgtagtag taccagctcc tatgggatat tactactact acttcggtat ggacgtctgg       360
ggccaaggga ccacggtcac cgtctcctca                                        390

SEQ ID NO: 234          moltype = AA   length = 130
FEATURE                 Location/Qualifiers
REGION                  1..130
                        note = synthetic
source                  1..130
                        mol_type = protein
                        organism = synthetic construct
SEQUENCE: 234
EVQLVESGGG LVQSGGSLRL SCAASGFTFS SYWMSWVRQA PGKGLEWVAN IKQDGSEKYY        60
VDSVKGRFTI SRDNAKNSLY LQMNSLRADD TAVYYCARDD IVVVPAPMGY YYYYFGMDVW       120
GQGTTVTVSS                                                              130

SEQ ID NO: 235          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 235
ggattcacct ttagtagcta ttgg                                              24

SEQ ID NO: 236          moltype = AA   length = 8
FEATURE                 Location/Qualifiers
REGION                  1..8
                        note = synthetic
source                  1..8
                        mol_type = protein
                        organism = synthetic construct
SEQUENCE: 236
GFTFSSYW                                                                8

SEQ ID NO: 237          moltype = DNA   length = 24
FEATURE                 Location/Qualifiers
misc_feature            1..24
                        note = synthetic
source                  1..24
                        mol_type = other DNA
```

-continued

```
                              organism = synthetic construct
SEQUENCE: 237
ataaagcaag atggaagtga gaaa                                               24

SEQ ID NO: 238           moltype = AA   length = 8
FEATURE                  Location/Qualifiers
REGION                   1..8
                         note = synthetic
source                   1..8
                         mol_type = protein
                         organism = synthetic construct
SEQUENCE: 238
IKQDGSEK                                                                 8

SEQ ID NO: 239           moltype = DNA   length = 69
FEATURE                  Location/Qualifiers
misc_feature             1..69
                         note = synthetic
source                   1..69
                         mol_type = other DNA
                         organism = synthetic construct
SEQUENCE: 239
gcgagagatg atattgtagt agtaccagct cctatgggat attactacta ctacttcggt   60
atggacgtc                                                               69

SEQ ID NO: 240           moltype = AA   length = 23
FEATURE                  Location/Qualifiers
REGION                   1..23
                         note = synthetic
source                   1..23
                         mol_type = protein
                         organism = synthetic construct
SEQUENCE: 240
ARDDIVVVPA PMGYYYYYFG MDV                                               23

SEQ ID NO: 241           moltype = DNA   length = 321
FEATURE                  Location/Qualifiers
misc_feature             1..321
                         note = synthetic
source                   1..321
                         mol_type = other DNA
                         organism = synthetic construct
SEQUENCE: 241
gacatccaga tgacccagtc tccatcctcc ctgtctgcat ctgtaggaga cagagtcacc   60
atcacttgcc gggcaagtca gggcattaga aatgatttag ctggtatca gcagaaacca    120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccgtacac ttttggccag   300
gggaccaagc tggagatcaa a                                                321

SEQ ID NO: 242           moltype = AA   length = 107
FEATURE                  Location/Qualifiers
REGION                   1..107
                         note = synthetic
source                   1..107
                         mol_type = protein
                         organism = synthetic construct
SEQUENCE: 242
DIQMTQSPSS LSASVGDRVT ITCRASQGIR NDLGWYQQKP GKAPKRLIYA ASSLQSGVPS   60
RFSGSGSGTE FTLTISSLQP EDFATYYCLQ HNSYPYTFGQ GTKLEIK                   107

SEQ ID NO: 243           moltype = DNA   length = 18
FEATURE                  Location/Qualifiers
misc_feature             1..18
                         note = synthetic
source                   1..18
                         mol_type = other DNA
                         organism = synthetic construct
SEQUENCE: 243
cagggcatta gaaatgat                                                     18

SEQ ID NO: 244           moltype = AA   length = 6
FEATURE                  Location/Qualifiers
REGION                   1..6
                         note = synthetic
source                   1..6
                         mol_type = protein
                         organism = synthetic construct
SEQUENCE: 244
```

-continued

```
QGIRND                                                             6

SEQ ID NO: 245          moltype =   length =
SEQUENCE: 245
000

SEQ ID NO: 246          moltype =   length =
SEQUENCE: 246
000

SEQ ID NO: 247          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 247
ctacagcata atagttaccc gtacact                                      27

SEQ ID NO: 248          moltype = AA  length = 9
FEATURE                 Location/Qualifiers
REGION                  1..9
                        note = synthetic
source                  1..9
                        mol_type = protein
                        organism = synthetic construct
SEQUENCE: 248
LQHNSYPYT                                                          9

SEQ ID NO: 249          moltype = DNA  length = 369
FEATURE                 Location/Qualifiers
misc_feature            1..369
                        note = synthetic
source                  1..369
                        mol_type = other DNA
                        organism = synthetic construct
SEQUENCE: 249
gaagtgcagc tggtggagtc tggggggaggc ttggttcagc ctggcaggtc cctgagactc   60
tcctgtgcag cctctggatt caccttlgat gattttgcca tgcactgggt ccgacaagct  120
ccagggaagg gcctggagtg ggtctcaggt attagtgga ctggtggtaa catggactat  180
gcgaactctg tgaagggccg attcaccatc tccagagagg acgccaagaa ttccctgtat  240
ctgcaaatga acagtctgag agctgcggac acggccttgt attactgtgt aaaagatata  300
aggggatag tggctacggg gggggctttt gatatctggg gccgagggac aatggtcacc  360
gtctcttca                                                         369

SEQ ID NO: 250          moltype = AA  length = 123
FEATURE                 Location/Qualifiers
REGION                  1..123
                        note = synthetic
source                  1..123
                        mol_type = protein
                        organism = synthetic construct
SEQUENCE: 250
EVQLVESGGG LVQPGRSLRL SCAASGFTFD DFAMHWVRQA PGKGLEWVSG ISWTGGNMDY   60
ANSVKGRFTI SREDAKNSLY LQMNSLRAAD TALYYCVKDI RGIVATGGAF DIWGRGTMVT  120
VSS                                                                123

SEQ ID NO: 251          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 251
ggattcacct ttgatgattt tgcc                                         24

SEQ ID NO: 252          moltype = AA  length = 8
FEATURE                 Location/Qualifiers
REGION                  1..8
                        note = synthetic
source                  1..8
                        mol_type = protein
                        organism = synthetic construct
SEQUENCE: 252
GFTFDDFA                                                           8

SEQ ID NO: 253          moltype = DNA  length = 24
```

```
FEATURE              Location/Qualifiers
misc_feature         1..24
                     note = synthetic
source               1..24
                     mol_type = other DNA
                     organism = synthetic construct
SEQUENCE: 253
attagttgga ctggtggtaa catg                                              24

SEQ ID NO: 254       moltype = AA   length = 8
FEATURE              Location/Qualifiers
REGION               1..8
                     note = synthetic
source               1..8
                     mol_type = protein
                     organism = synthetic construct
SEQUENCE: 254
ISWTGGNM                                                                8

SEQ ID NO: 255       moltype = DNA   length = 48
FEATURE              Location/Qualifiers
misc_feature         1..48
                     note = synthetic
source               1..48
                     mol_type = other DNA
                     organism = synthetic construct
SEQUENCE: 255
gtaaaagata taaggggat agtggctacg gggggggctt ttgatatc                    48

SEQ ID NO: 256       moltype = AA   length = 16
FEATURE              Location/Qualifiers
REGION               1..16
                     note = synthetic
source               1..16
                     mol_type = protein
                     organism = synthetic construct
SEQUENCE: 256
VKDIRGIVAT GGAFDI                                                       16

SEQ ID NO: 257       moltype = DNA   length = 321
FEATURE              Location/Qualifiers
misc_feature         1..321
                     note = synthetic
source               1..321
                     mol_type = other DNA
                     organism = synthetic construct
SEQUENCE: 257
gacatccaga tgacccagtc tccatcctcc ctgtctgcat ctgtaggaga cagagtcacc   60
atctcttgcc gggcaagtca gaccattagc acttatttaa attggtttca gcagaaacca  120
gggaaagccc ctaagctcct gatctatgtt gtgtccagtt tgcaaagtgg ggtcccatca  180
aggttcagtg gcagtggatc tgggacagat ttcactctca ccatcagcag tctgcaacct  240
gaagattttg caacttatta ctgtcaacag agttacagta ccccattcac tttcggccct  300
gggaccaaag tggatatcaa a                                              321

SEQ ID NO: 258       moltype = AA   length = 107
FEATURE              Location/Qualifiers
REGION               1..107
                     note = synthetic
source               1..107
                     mol_type = protein
                     organism = synthetic construct
SEQUENCE: 258
DIQMTQSPSS LSASVGDRVT ISCRASQTIS TYLNWFQQKP GKAPKLLIYV VSSLQSGVPS   60
RFSGSGSGTD FTLTISSLQP EDFATYYCQQ SYSTPFTFGP GTKVDIK                 107

SEQ ID NO: 259       moltype = DNA   length = 18
FEATURE              Location/Qualifiers
misc_feature         1..18
                     note = synthetic
source               1..18
                     mol_type = other DNA
                     organism = synthetic construct
SEQUENCE: 259
cagaccatta gcacttat                                                    18

SEQ ID NO: 260       moltype = AA   length = 6
FEATURE              Location/Qualifiers
REGION               1..6
                     note = synthetic
```

-continued

```
source                    1..6
                          mol_type = protein
                          organism = synthetic construct
SEQUENCE: 260
QTISTY                                                            6

SEQ ID NO: 261            moltype =   length =
SEQUENCE: 261
000

SEQ ID NO: 262            moltype =   length =
SEQUENCE: 262
000

SEQ ID NO: 263            moltype = DNA   length = 27
FEATURE                   Location/Qualifiers
misc_feature              1..27
                          note = synthetic
source                    1..27
                          mol_type = other DNA
                          organism = synthetic construct
SEQUENCE: 263
caacagagtt acagtacccc attcact                                    27

SEQ ID NO: 264            moltype = AA   length = 9
FEATURE                   Location/Qualifiers
REGION                    1..9
                          note = synthetic
source                    1..9
                          mol_type = protein
                          organism = synthetic construct
SEQUENCE: 264
QQSYSTPFT                                                         9

SEQ ID NO: 265            moltype = DNA   length = 345
FEATURE                   Location/Qualifiers
misc_feature              1..345
                          note = synthetic
source                    1..345
                          mol_type = other DNA
                          organism = synthetic construct
SEQUENCE: 265
gaggtgcagc tggtggagtc tggaggaggc ttggtccagc cggggggtc cctgagactc    60
tcctgtgcag cctctggatt caccgtcggt accaactaca tgaactgggt ccgccaggct   120
ccagggaagg gactggagtg gatctcagtt atttatagcg gtggtagcac attctacgca   180
gactccgtga agggccgatt caccatctcc agacagactt cccagaacac gctgtatctt   240
caaatgaaca gcctgagacc tgaggacacg gccgtatatt actgtgcgag aggtatacgt   300
ggttttgata tctggggcca aggggacaatg gtcaccgtct cttca                 345

SEQ ID NO: 266            moltype = AA   length = 115
FEATURE                   Location/Qualifiers
REGION                    1..115
                          note = synthetic
source                    1..115
                          mol_type = protein
                          organism = synthetic construct
SEQUENCE: 266
EVQLVESGGG LVQPGGSLRL SCAASGFTVG TNYMNWVRQA PGKGLEWISV IYSGGSTFYA    60
DSVKGRFTIS RQTSQNTLYL QMNSLRPEDT AVYYCARGIR GFDIWGQGTM VTVSS         115

SEQ ID NO: 267            moltype = DNA   length = 24
FEATURE                   Location/Qualifiers
misc_feature              1..24
                          note = synthetic
source                    1..24
                          mol_type = other DNA
                          organism = synthetic construct
SEQUENCE: 267
ggattcaccg tcggtaccaa ctac                                        24

SEQ ID NO: 268            moltype = AA   length = 8
FEATURE                   Location/Qualifiers
REGION                    1..8
                          note = synthetic
source                    1..8
                          mol_type = protein
                          organism = synthetic construct
SEQUENCE: 268
GFTVGTNY                                                          8
```

-continued

```
SEQ ID NO: 269            moltype = DNA   length = 21
FEATURE                   Location/Qualifiers
misc_feature              1..21
                          note = synthetic
source                    1..21
                          mol_type = other DNA
                          organism = synthetic construct
SEQUENCE: 269
atttatagcg gtggtagcac a                                        21

SEQ ID NO: 270            moltype = AA   length = 7
FEATURE                   Location/Qualifiers
REGION                    1..7
                          note = synthetic
source                    1..7
                          mol_type = protein
                          organism = synthetic construct
SEQUENCE: 270
IYSGGST                                                         7

SEQ ID NO: 271            moltype = DNA   length = 27
FEATURE                   Location/Qualifiers
misc_feature              1..27
                          note = synthetic
source                    1..27
                          mol_type = other DNA
                          organism = synthetic construct
SEQUENCE: 271
gcgagaggta tacgtggttt tgatatc                                  27

SEQ ID NO: 272            moltype = AA   length = 9
FEATURE                   Location/Qualifiers
REGION                    1..9
                          note = synthetic
source                    1..9
                          mol_type = protein
                          organism = synthetic construct
SEQUENCE: 272
ARGIRGFDI                                                       9

SEQ ID NO: 273            moltype = DNA   length = 324
FEATURE                   Location/Qualifiers
misc_feature              1..324
                          note = synthetic
source                    1..324
                          mol_type = other DNA
                          organism = synthetic construct
SEQUENCE: 273
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                     324

SEQ ID NO: 274            moltype = AA   length = 108
FEATURE                   Location/Qualifiers
REGION                    1..108
                          note = synthetic
source                    1..108
                          mol_type = protein
                          organism = synthetic construct
SEQUENCE: 274
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK            108

SEQ ID NO: 275            moltype = DNA   length = 18
FEATURE                   Location/Qualifiers
misc_feature              1..18
                          note = synthetic
source                    1..18
                          mol_type = other DNA
                          organism = synthetic construct
SEQUENCE: 275
cagagcatta gcagctat                                            18

SEQ ID NO: 276            moltype = AA   length = 6
FEATURE                   Location/Qualifiers
```

```
REGION                    1..6
                          note = synthetic
source                    1..6
                          mol_type = protein
                          organism = synthetic construct
SEQUENCE: 276
QSISSY                                                              6

SEQ ID NO: 277            moltype =   length =
SEQUENCE: 277
000

SEQ ID NO: 278            moltype =   length =
SEQUENCE: 278
000

SEQ ID NO: 279            moltype = DNA  length = 30
FEATURE                   Location/Qualifiers
misc_feature              1..30
                          note = synthetic
source                    1..30
                          mol_type = other DNA
                          organism = synthetic construct
SEQUENCE: 279
caacagagtt acagtacccc tccgatcacc                                   30

SEQ ID NO: 280            moltype = AA  length = 10
FEATURE                   Location/Qualifiers
REGION                    1..10
                          note = synthetic
source                    1..10
                          mol_type = protein
                          organism = synthetic construct
SEQUENCE: 280
QQSYSTPPIT                                                          10

SEQ ID NO: 281            moltype = DNA  length = 345
FEATURE                   Location/Qualifiers
misc_feature              1..345
                          note = synthetic
source                    1..345
                          mol_type = other DNA
                          organism = synthetic construct
SEQUENCE: 281
gaggtgcagc tggtggagtc tggaggaggc ttggtccagc cggggggggtc cctgagactc  60
tcctgtgcag cctctgggtt taccatcagt accaactaca tgaactgggt ccgccaggct  120
ccagggaagg ggctggagtg ggtcgcagtt atttatagca gtggttccac atactatatc  180
gactccgtga agggccgatt caccatctcc agactcactt ccaagaacac ggtgtatctt  240
caaatgagca gcctgaattc tgaagacacg gccgtgtatt actgtgcgag ggggatcagg  300
ggttttgata tttggggcca agggacaatg gtcaccgtct cttca                  345

SEQ ID NO: 282            moltype = AA  length = 115
FEATURE                   Location/Qualifiers
REGION                    1..115
                          note = synthetic
source                    1..115
                          mol_type = protein
                          organism = synthetic construct
SEQUENCE: 282
EVQLVESGGG LVQPGGSLRL SCAASGFTIS TNYMNWVRQA PGKGLEWVAV IYSSGSTYYI  60
DSVKGRFTIS RLTSKNTVYL QMSSLNSEDT AVYYCARGIR GFDIWGQGTM VTVSS        115

SEQ ID NO: 283            moltype = DNA  length = 24
FEATURE                   Location/Qualifiers
misc_feature              1..24
                          note = synthetic
source                    1..24
                          mol_type = other DNA
                          organism = synthetic construct
SEQUENCE: 283
gggtttacca tcagtaccaa ctac                                         24

SEQ ID NO: 284            moltype = AA  length = 8
FEATURE                   Location/Qualifiers
REGION                    1..8
                          note = synthetic
source                    1..8
                          mol_type = protein
                          organism = synthetic construct
```

-continued

```
SEQUENCE: 284
GFTISTNY                                                                                           8

SEQ ID NO: 285          moltype = DNA   length = 21
FEATURE                 Location/Qualifiers
misc_feature            1..21
                        note = synthetic
source                  1..21
                        mol_type = other DNA
                        organism = synthetic construct
SEQUENCE: 285
atttatagca gtggttccac a                                                                            21

SEQ ID NO: 286          moltype = AA   length = 7
FEATURE                 Location/Qualifiers
REGION                  1..7
                        note = synthetic
source                  1..7
                        mol_type = protein
                        organism = synthetic construct
SEQUENCE: 286
IYSSGST                                                                                            7

SEQ ID NO: 287          moltype = DNA   length = 27
FEATURE                 Location/Qualifiers
misc_feature            1..27
                        note = synthetic
source                  1..27
                        mol_type = other DNA
                        organism = synthetic construct
SEQUENCE: 287
gcgaggggga tcaggggttt tgatatt                                                                      27

SEQ ID NO: 288          moltype = AA   length = 9
FEATURE                 Location/Qualifiers
REGION                  1..9
                        note = synthetic
source                  1..9
                        mol_type = protein
                        organism = synthetic construct
SEQUENCE: 288
ARGIRGFDI                                                                                          9

SEQ ID NO: 289          moltype = DNA   length = 372
FEATURE                 Location/Qualifiers
misc_feature            1..372
                        note = synthetic
source                  1..372
                        mol_type = other DNA
                        organism = synthetic construct
SEQUENCE: 289
gaagtgcagc tggtggagtc ggggggaggc ttggtacagc ctggcaggtc cctgagactc       60
tcctgtgcag cctctggatt caccattgat gatagtgcca tgcactgggt ccggcaaact      120
ccagggaagg gcctggagtg ggtctcaggt attagttgga aaagtggtag cataggttat      180
gcggactctg tgaggggccg attcaccatc tccagagaca cgccaagaa ttccctctat       240
ctgcaaatga acagtctgag agttgaggac acggccttgt attactgtgt aaaaagatata      300
aggggcaact ggaactacgg gggaaactgg ttcgacccct ggggccaggg aaccctggtc      360
actgtctcct ca                                                          372

SEQ ID NO: 290          moltype = AA   length = 124
FEATURE                 Location/Qualifiers
REGION                  1..124
                        note = synthetic
source                  1..124
                        mol_type = protein
                        organism = synthetic construct
SEQUENCE: 290
EVQLVESGGG LVQPGRSLRL SCAASGFTID DSAMHWVRQT PGKGLEWVSG ISWKSGSIGY        60
ADSVRGRFTI SRDNAKNSLY LQMNSLRVED TALYYCVKDI RGNWNYGGNW FDPWGQGTLV       120
TVSS                                                                   124

SEQ ID NO: 291          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 291
```

-continued

```
ggattcacca ttgatgatag tgcc                                     24

SEQ ID NO: 292          moltype = AA   length = 8
FEATURE                 Location/Qualifiers
REGION                  1..8
                        note = synthetic
source                  1..8
                        mol_type = protein
                        organism = synthetic construct
SEQUENCE: 292
GFTIDDSA                                                        8

SEQ ID NO: 293          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 293
attagttgga aaagtggtag cata                                     24

SEQ ID NO: 294          moltype = AA   length = 8
FEATURE                 Location/Qualifiers
REGION                  1..8
                        note = synthetic
source                  1..8
                        mol_type = protein
                        organism = synthetic construct
SEQUENCE: 294
ISWKSGSI                                                        8

SEQ ID NO: 295          moltype = DNA   length = 51
FEATURE                 Location/Qualifiers
misc_feature            1..51
                        note = synthetic
source                  1..51
                        mol_type = other DNA
                        organism = synthetic construct
SEQUENCE: 295
gtaaaagata taaggggcaa ctggaactac gggggaaact ggttcgaccc c        51

SEQ ID NO: 296          moltype = AA   length = 17
FEATURE                 Location/Qualifiers
REGION                  1..17
                        note = synthetic
source                  1..17
                        mol_type = protein
                        organism = synthetic construct
SEQUENCE: 296
VKDIRGNWNY GGNWFDP                                              17

SEQ ID NO: 297          moltype = DNA   length = 345
FEATURE                 Location/Qualifiers
misc_feature            1..345
                        note = synthetic
source                  1..345
                        mol_type = other DNA
                        organism = synthetic construct
SEQUENCE: 297
gaggtgcagc tggtggagtc tggaggaggc ttggtccagc ctggggggtc cctgagactc  60
tcatgtgaag cctctgggtt caccgtcggt gtcaaccaca tgaactgggt ccgccaggct  120
ccagggaagg gtctggagtg ggtctcagtt attttcagta gtggtaggac attctacgga  180
gactacgtga agggccgatt aaccatcttc agacaaacct cccagaacac ggtgtatctt  240
caaatgaata gcctgagaag tgaggacacg gccatatatt actgtgcgag agggattggc  300
ggtttggaca tctggggccg agggacaatg gtcaccgtct cttca               345

SEQ ID NO: 298          moltype = AA   length = 115
FEATURE                 Location/Qualifiers
REGION                  1..115
                        note = synthetic
source                  1..115
                        mol_type = protein
                        organism = synthetic construct
SEQUENCE: 298
EVQLVESGGG LVQPGGSLRL SCEASGFTVG VNHMNWVRQA PGKGLEWVSV IFSSGRTFYG  60
DYVKGRLTIF RQTSQNTVYL QMNSLRSEDT AIYYCARGIG GLDIWGRGTM VTVSS        115

SEQ ID NO: 299          moltype = DNA   length = 24
```

```
FEATURE               Location/Qualifiers
misc_feature          1..24
                      note = synthetic
source                1..24
                      mol_type = other DNA
                      organism = synthetic construct
SEQUENCE: 299
gggttcaccg tcggtgtcaa ccac                                                24

SEQ ID NO: 300        moltype = AA   length = 8
FEATURE               Location/Qualifiers
REGION                1..8
                      note = synthetic
source                1..8
                      mol_type = protein
                      organism = synthetic construct
SEQUENCE: 300
GFTVGVNH                                                                  8

SEQ ID NO: 301        moltype = DNA   length = 21
FEATURE               Location/Qualifiers
misc_feature          1..21
                      note = synthetic
source                1..21
                      mol_type = other DNA
                      organism = synthetic construct
SEQUENCE: 301
attttcagta gtggtaggac a                                                   21

SEQ ID NO: 302        moltype = AA   length = 7
FEATURE               Location/Qualifiers
REGION                1..7
                      note = synthetic
source                1..7
                      mol_type = protein
                      organism = synthetic construct
SEQUENCE: 302
IFSSGRT                                                                   7

SEQ ID NO: 303        moltype = DNA   length = 27
FEATURE               Location/Qualifiers
misc_feature          1..27
                      note = synthetic
source                1..27
                      mol_type = other DNA
                      organism = synthetic construct
SEQUENCE: 303
gcgagaggga ttggcggttt ggacatc                                            27

SEQ ID NO: 304        moltype = AA   length = 9
FEATURE               Location/Qualifiers
REGION                1..9
                      note = synthetic
source                1..9
                      mol_type = protein
                      organism = synthetic construct
SEQUENCE: 304
ARGIGGLDI                                                                 9

SEQ ID NO: 305        moltype = DNA   length = 369
FEATURE               Location/Qualifiers
misc_feature          1..369
                      note = synthetic
source                1..369
                      mol_type = other DNA
                      organism = synthetic construct
SEQUENCE: 305
gaagtgcagc tggtggagtc tggggggggc ttggttcagc ctggcaggtc cctaagactc   60
tcctgtgcag cctctggatt caccttgat gattatgcct tgcactgggt ccggcaagct  120
ccagggaagg gcctggagtg ggtctcaggt attagttgga ctggtggtac tatagactat  180
gcggactctg tgaagggccg attcaccatc tccagagaca acgccaagaa ctccctgtat  240
ctgcaaatga gcagtctgag aactgaggac acggccatat attactgtac aagagatatc  300
cgggggaact ggaagtacgg aggctggttc gaccctgg gccagggaac cctggtcacc  360
gtctcctca                                                           369

SEQ ID NO: 306        moltype = AA   length = 123
FEATURE               Location/Qualifiers
REGION                1..123
                      note = synthetic
```

```
source                  1..123
                        mol_type = protein
                        organism = synthetic construct
SEQUENCE: 306
EVQLVESGGG LVQPGRSLRL SCAASGFTFD DYALHWVRQA PGKGLEWVSG ISWTGGTIDY   60
ADSVKGRFTI SRDNAKNSLY LQMSSLRTED TAIYYCTRDI RGNWKYGGWF DPWGQGTLVT  120
VSS                                                                123

SEQ ID NO: 307          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 307
ggattcacct ttgatgatta tgcc                                          24

SEQ ID NO: 308          moltype = AA  length = 8
FEATURE                 Location/Qualifiers
REGION                  1..8
                        note = synthetic
source                  1..8
                        mol_type = protein
                        organism = synthetic construct
SEQUENCE: 308
GFTFDDYA                                                             8

SEQ ID NO: 309          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 309
attagttgga ctggtggtac tata                                          24

SEQ ID NO: 310          moltype = AA  length = 8
FEATURE                 Location/Qualifiers
REGION                  1..8
                        note = synthetic
source                  1..8
                        mol_type = protein
                        organism = synthetic construct
SEQUENCE: 310
ISWTGGTI                                                             8

SEQ ID NO: 311          moltype = DNA  length = 48
FEATURE                 Location/Qualifiers
misc_feature            1..48
                        note = synthetic
source                  1..48
                        mol_type = other DNA
                        organism = synthetic construct
SEQUENCE: 311
acaagagata tccgggggaa ctggaagtac ggaggctggt tcgacccc                48

SEQ ID NO: 312          moltype = AA  length = 16
FEATURE                 Location/Qualifiers
REGION                  1..16
                        note = synthetic
source                  1..16
                        mol_type = protein
                        organism = synthetic construct
SEQUENCE: 312
TRDIRGNWKY GGWFDP                                                    16

SEQ ID NO: 313          moltype = DNA  length = 360
FEATURE                 Location/Qualifiers
misc_feature            1..360
                        note = synthetic
source                  1..360
                        mol_type = other DNA
                        organism = synthetic construct
SEQUENCE: 313
caggtgcagc tggtgcagtc tgggactgag gtgaagaagc ctggggcctc agtgaaggtc   60
tcctgcaagg cttctggata caccttcacc gcctactata tgcactgggt gcgacaggcc  120
cctggtcaag gacttgactg gatgggatgg atcagcccta acagtggttt cacaaactat  180
```

```
gcacagaagt ttcagggcag ggtcaccatg accagggaca cgtccatcaa cacattttat   240
atggagctga gtggactgag atctgacgac acggccgtat attactgtgc gcgagagggt   300
tctactcacc acaattcttt cgacccctgg ggccagggaa ccctggtcac cgtctcctca   360

SEQ ID NO: 314          moltype = AA   length = 120
FEATURE                 Location/Qualifiers
REGION                  1..120
                        note = synthetic
source                  1..120
                        mol_type = protein
                        organism = synthetic construct
SEQUENCE: 314
QVQLVQSGTE VKKPGASVKV SCKASGYTFT AYYMHWVRQA PGQGLDWMGW ISPNSGFTNY   60
AQKFQGRVTM TRDTSINTFY MELSGLRSDD TAVYYCAREG STHHNSFDPW GQGTLVTVSS  120

SEQ ID NO: 315          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 315
ggatacacct tcaccgccta ctat                                           24

SEQ ID NO: 316          moltype = AA   length = 8
FEATURE                 Location/Qualifiers
REGION                  1..8
                        note = synthetic
source                  1..8
                        mol_type = protein
                        organism = synthetic construct
SEQUENCE: 316
GYTFTAYY                                                              8

SEQ ID NO: 317          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 317
atcagcccta acagtggttt caca                                           24

SEQ ID NO: 318          moltype = AA   length = 8
FEATURE                 Location/Qualifiers
REGION                  1..8
                        note = synthetic
source                  1..8
                        mol_type = protein
                        organism = synthetic construct
SEQUENCE: 318
ISPNSGFT                                                              8

SEQ ID NO: 319          moltype = DNA   length = 39
FEATURE                 Location/Qualifiers
misc_feature            1..39
                        note = synthetic
source                  1..39
                        mol_type = other DNA
                        organism = synthetic construct
SEQUENCE: 319
gcgcgagagg gttctactca ccacaattct ttcgacccc                           39

SEQ ID NO: 320          moltype = AA   length = 13
FEATURE                 Location/Qualifiers
REGION                  1..13
                        note = synthetic
source                  1..13
                        mol_type = protein
                        organism = synthetic construct
SEQUENCE: 320
AREGSTHHNS FDP                                                        13

SEQ ID NO: 321          moltype = DNA   length = 342
FEATURE                 Location/Qualifiers
misc_feature            1..342
                        note = synthetic
```

```
source                          1..342
                                mol_type = other DNA
                                organism = synthetic construct
SEQUENCE: 321
gaggtgcagc tggtggagtc tggaggaggc ttggtccaac cggggggtc cctgaggctc      60
tcctgtgcag cctctgggtt caccgtcggt actaacttca tgaattgggt ccgccaggct     120
ccagggaagg ggctggagtg ggtctcagcg atttatagcg gtggtaccgc taactacgca     180
gactccgtga agggccgatt caccatttcc agagacactt ccaggaacac gctgtatctt     240
caaatgaaca gcctgagaac tgaggacacg gccgtttatt attgtgcgag aggggggggt     300
atggacgtct ggggccaagg gaccacggtc accgtctcct ca                        342

SEQ ID NO: 322                  moltype = AA   length = 114
FEATURE                         Location/Qualifiers
REGION                          1..114
                                note = synthetic
source                          1..114
                                mol_type = protein
                                organism = synthetic construct
SEQUENCE: 322
EVQLVESGGG LVQPGGSLRL SCAASGFTVG TNFMNWVRQA PGKGLEWVSA IYSGGTANYA      60
DSVKGRFTIS RDTSRNTLYL QMNSLRTEDT AVYYCARGGG MDVWGQGTTV TVSS           114

SEQ ID NO: 323                  moltype = DNA   length = 24
FEATURE                         Location/Qualifiers
misc_feature                    1..24
                                note = synthetic
source                          1..24
                                mol_type = other DNA
                                organism = synthetic construct
SEQUENCE: 323
gggttcaccg tcggtactaa cttc                                            24

SEQ ID NO: 324                  moltype = AA   length = 8
FEATURE                         Location/Qualifiers
REGION                          1..8
                                note = synthetic
source                          1..8
                                mol_type = protein
                                organism = synthetic construct
SEQUENCE: 324
GFTVGTNF                                                               8

SEQ ID NO: 325                  moltype = DNA   length = 21
FEATURE                         Location/Qualifiers
misc_feature                    1..21
                                note = synthetic
source                          1..21
                                mol_type = other DNA
                                organism = synthetic construct
SEQUENCE: 325
atttatagcg gtggtaccgc t                                               21

SEQ ID NO: 326                  moltype = AA   length = 7
FEATURE                         Location/Qualifiers
REGION                          1..7
                                note = synthetic
source                          1..7
                                mol_type = protein
                                organism = synthetic construct
SEQUENCE: 326
IYSGGTA                                                                7

SEQ ID NO: 327                  moltype = DNA   length = 24
FEATURE                         Location/Qualifiers
misc_feature                    1..24
                                note = synthetic
source                          1..24
                                mol_type = other DNA
                                organism = synthetic construct
SEQUENCE: 327
gcgagagggg ggggtatgga cgtc                                            24

SEQ ID NO: 328                  moltype = AA   length = 8
FEATURE                         Location/Qualifiers
REGION                          1..8
                                note = synthetic
source                          1..8
                                mol_type = protein
                                organism = synthetic construct
```

```
SEQUENCE: 328
ARGGGMDV                                                                          8

SEQ ID NO: 329          moltype = DNA  length = 354
FEATURE                 Location/Qualifiers
misc_feature            1..354
                        note = synthetic
source                  1..354
                        mol_type = other DNA
                        organism = synthetic construct
SEQUENCE: 329
caggtccagc tggtgcagtc tggggctgag gtgaagaagc ctgggtcctc ggtgaaggtc   60
tcctgcaagg cttctggagg caccttcaac acctatgttc tcagctgggt gcgacaggcc  120
cctggacaag ggcttgagtg gatgggagag atcatcccta tcttaggtgc agcaaactac  180
gcacagaact ccagggcag agtcacttt accacggacg aatccacgaa tacagcctac   240
atggacctga gcagcctaag atctgaggac acggccgtgt attactgtgc gagagatcgg  300
acctccgggg ggttcgaccc ctggggccag ggaaccctgg tcactgtctc ctca        354

SEQ ID NO: 330          moltype = AA  length = 118
FEATURE                 Location/Qualifiers
REGION                  1..118
                        note = synthetic
source                  1..118
                        mol_type = protein
                        organism = synthetic construct
SEQUENCE: 330
QVQLVQSGAE VKKPGSSVKV SCKASGGTFN TYVLSWVRQA PGQGLEWMGE IIPILGAANY   60
AQNFQGRVTF TTDESTNTAY MDLSSLRSED TAVYYCARDR TSGGFDPWGQ GTLVTVSS    118

SEQ ID NO: 331          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 331
ggaggcacct caacaccta tgtt                                          24

SEQ ID NO: 332          moltype = AA  length = 8
FEATURE                 Location/Qualifiers
REGION                  1..8
                        note = synthetic
source                  1..8
                        mol_type = protein
                        organism = synthetic construct
SEQUENCE: 332
GGTFNTYV                                                                           8

SEQ ID NO: 333          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 333
atcatcccta tcttaggtgc agca                                         24

SEQ ID NO: 334          moltype = AA  length = 8
FEATURE                 Location/Qualifiers
REGION                  1..8
                        note = synthetic
source                  1..8
                        mol_type = protein
                        organism = synthetic construct
SEQUENCE: 334
IIPILGAA                                                                           8

SEQ ID NO: 335          moltype = DNA  length = 33
FEATURE                 Location/Qualifiers
misc_feature            1..33
                        note = synthetic
source                  1..33
                        mol_type = other DNA
                        organism = synthetic construct
SEQUENCE: 335
gcgagagatc ggacctccgg ggggttcgac ccc                               33
```

-continued

```
SEQ ID NO: 336          moltype = AA   length = 11
FEATURE                 Location/Qualifiers
REGION                  1..11
                        note = synthetic
source                  1..11
                        mol_type = protein
                        organism = synthetic construct
SEQUENCE: 336
ARDRTSGGFD P                                                    11

SEQ ID NO: 337          moltype = DNA   length = 357
FEATURE                 Location/Qualifiers
misc_feature            1..357
                        note = synthetic
source                  1..357
                        mol_type = other DNA
                        organism = synthetic construct
SEQUENCE: 337
caggttcagc tggtgcagtc tggagctgag gtggagaagc ctggggcctc agtgaaggtc   60
tcctgcaagg cttctggtta catctttacc cactatggta tcagctgggt gcgacaggcc  120
cctgacaag gacttgagtg ggtgggctgg atcagccctt acaatggtta cacagactat  180
gcacagaaac tccagggcag agtcaccttg accacagcac catccacgac cacagcctac  240
atggagctga ggaacctgag atctgacgac acggccatgt attactgttc gagagggagg  300
ggcccttact ggtccttcga tctctggggc cgtggcaccc tggtcaccgt ctcctca     357

SEQ ID NO: 338          moltype = AA   length = 119
FEATURE                 Location/Qualifiers
REGION                  1..119
                        note = synthetic
source                  1..119
                        mol_type = protein
                        organism = synthetic construct
SEQUENCE: 338
QVQLVQSGAE VEKPGASVKV SCKASGYIFT HYGISWVRQA PGQGLEWVGW ISPYNGYTDY   60
AQKLQGRVTL TTDTSTTTAY MELRNLRSDD TAMYYCSRGR GPYWSFDLWG RGTLVTVSS   119

SEQ ID NO: 339          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 339
ggttacatct ttacccacta tggt                                          24

SEQ ID NO: 340          moltype = AA   length = 8
FEATURE                 Location/Qualifiers
REGION                  1..8
                        note = synthetic
source                  1..8
                        mol_type = protein
                        organism = synthetic construct
SEQUENCE: 340
GYIFTHYG                                                             8

SEQ ID NO: 341          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 341
atcagccctt acaatggtta caca                                          24

SEQ ID NO: 342          moltype = AA   length = 8
FEATURE                 Location/Qualifiers
REGION                  1..8
                        note = synthetic
source                  1..8
                        mol_type = protein
                        organism = synthetic construct
SEQUENCE: 342
ISPYNGYT                                                             8

SEQ ID NO: 343          moltype = DNA   length = 36
FEATURE                 Location/Qualifiers
misc_feature            1..36
```

-continued

```
                          note = synthetic
source                    1..36
                          mol_type = other DNA
                          organism = synthetic construct
SEQUENCE: 343
tcgagaggga ggggcccctta ctggtccttc gatctc                                      36

SEQ ID NO: 344            moltype = AA  length = 12
FEATURE                   Location/Qualifiers
REGION                    1..12
                          note = synthetic
source                    1..12
                          mol_type = protein
                          organism = synthetic construct
SEQUENCE: 344
SRGRGPYWSF DL                                                                  12
```

RADIOLABELED ANTI-PD-L1 ANTIBODIES FOR IMMUNO-PET IMAGING

CROSS-REFERENCE TO RELATED APPLICATIONS

This application is a continuation of U.S. patent application Ser. No. 17/560,003, filed Dec. 22, 2021, which is a continuation application of U.S. patent application Ser. No. 16/915,894, filed Jun. 29, 2020, which is a divisional application of U.S. patent application Ser. No. 15/829,311, filed Dec. 1, 2017, now U.S. Pat. No. 10,736,976 which claims the benefit under 34 U.S.C. § 119(e) of U.S. Provisional Application Ser. No. 62/428,672, filed Dec. 1, 2016, U.S. Provisional Application Ser. No. 62/457,267, filed Feb. 10, 2017, and U.S. Provisional Application Ser. No. 62/569,773, filed Oct. 9, 2017, all of which are herein specifically incorporated by reference in their entireties.

FIELD

This disclosure relates to radiolabeled anti-PD-L1 antibodies and their use in immuno-PET imaging.

SEQUENCE LISTING

A copy of the sequence listing is submitted concurrently with the specification electronically via Patent Center. The content of the electronic sequence listing (10305US04_Sequence_Listing_ST26.xml; Size 413,696 bytes; and Date of Creation: Jun. 7, 2024) is herein incorporated by reference in its entirety.

BACKGROUND

Programmed death-ligand 1 (PD-L1) (also called B7-H1 or CD274) is a 290 amino acid protein receptor ligand expressed widely on both lymphoid and non-lymphoid tissues such as CD4 and CD8 T-cells, macrophage lineage cells, peripheral tissues as well as on tumor cells, and virally-infected cells (Dong et al 1999, Nature Med.). PD-L1 binds to receptors PD-1 and B7-1 which belong to the CD28/CTLA-4 (cytotoxic T lymphocyte antigen)/ICOS (inducible co-stimulator) family of T-cell co-inhibitory receptors (Chen et al 2013, Nature Rev. Immunol. 13:227-242) and attenuates the immune response by inhibiting T-cell activation. PD-L1 binding to PD-1 or B7-1 results in decreased T-cell proliferation and cytokine secretion, compromising humoral and cellular immune responses in diseases such as cancer, and viral infection. The expression of PD-L1 on tumor cells and virally-infected cells is exploited by tumors and chronic viral infections to evade immune response. PD-L1 is expressed on a wide variety of tumors and studies on animal models have shown that PD-L1 on tumors inhibits T-cell activation and lysis of tumor cells and may lead to increased death of tumor-specific T-cells. In chronic viral infections, PD-L1 expressed on virally-infected cells binds to PD-1 on virus-specific T-cells and these T-cells become "exhausted" with loss of effector functions and proliferative capacity (Freeman 2008, PNAS 105: 10275-10276). The PD-1: PD-L1 system also plays an important role in induced T-regulatory (Treg) cell development and in sustaining Treg function (Francisco et al 2010, Immunol. Rev. 236:219-242). Blocking PD-L1 with antagonists, including monoclonal antibodies, has been studied in treatments of cancer and chronic viral infections (Ribas 2012, NEJM 366:2517-2519; Freeman 2008, PNAS 105: 10275-10276; Sheridan 2012, Nature Biotechnology 30:729-730).

Immuno-positron emission tomography (PET) is a diagnostic imaging tool that utilizes monoclonal antibodies labeled with positron emitters, combining the targeting properties of an antibody with the sensitivity of positron emission tomography cameras. See, e.g., The Oncologist, 12:1379 (2007); Journal of Nuclear Medicine, 52 (8): 1171 (2011). Immuno-PET enables the visualization and quantification of antigen and antibody accumulation in vivo and, as such, can serve as an important tool for diagnostics and complementing therapy. For example, immuno-PET can aid in the selection of potential patient candidates for a particular therapy, as well as in the monitoring of treatment.

As both PD1 and PD-L1 have emerged as targets for immunotherapy, there is need for diagnostic tools for anti-PD1 and/or anti-PD-L1 therapy, including, inter alia, diagnostic tools that enable the detection of suitable patient candidates for said therapy.

BRIEF SUMMARY

Included in this disclosure are radiolabeled anti-PD-L1 antibody conjugates for use in immuno-PET imaging.

In one aspect, the conjugate comprises an anti-PD-L1 antibody or antigen-binding fragment thereof, a chelating moiety, and a positron emitter.

Provided herein are also processes for synthesizing said conjugates and synthetic intermediates useful for the same.

Provided herein are also methods of imaging a tissue that expresses PD-L1, the methods comprising administering a radiolabeled anti-PD-L1 antibody conjugate described herein to the tissue; and visualizing the PD-L1 expression by positron emission tomography (PET) imaging.

Provided herein are also methods for detecting PD-L1 in a tissue, the methods comprising administering a radiolabeled anti-PD-L1 antibody conjugate described herein to the tissue; and visualizing the PD-L1 expression by PET imaging. In one embodiment, the tissue is present in a human subject. In certain embodiments, the subject is a non-human mammal. In certain embodiments, the subject has a disease or disorder such as cancer, an inflammatory disease, or an infection.

In some aspects, the subject is administered a dose of 5 mg, or 10 mg, or 20 mg, of a radiolabeled anti-PD-L1 antibody conjugate.

Provided herein are also methods for identifying a patient to be suitable for anti-tumor therapy comprising an inhibitor of the PD-1/PD-L1 signaling axis, the methods comprising selecting a patient with a solid tumor, administering a radiolabeled antibody conjugate described herein, and visualizing the administered radiolabeled antibody conjugate in the tumor by PET imaging wherein presence of the radiolabeled antibody conjugate in the tumor identifies the patient as suitable for anti-tumor therapy comprising an inhibitor of the PD-1/PD-L1 signaling axis.

Provided herein are also methods of treating a tumor, the methods comprising selecting a subject with a solid tumor; determining that the solid tumor is PD-L1-positive; and administering an anti-tumor therapy to the subject in need thereof. In certain embodiments, the anti-tumor therapy comprises an inhibitor of the PD-1/PD-L1 signaling axis (e.g., an anti-PD-1 antibody or an anti-PD-L1 antibody). In certain embodiments, the subject is administered a radiolabeled antibody conjugate described herein, and localization of the radiolabeled antibody conjugate is imaged via positron emission tomography (PET) imaging to determine if the tumor is PD-L1-positive.

Provided herein are also methods for monitoring the efficacy of an anti-tumor therapy in a subject, wherein the methods comprise selecting a subject with a solid tumor wherein the subject is being treated with an anti-tumor therapy; administering a radiolabeled conjugate described herein to the subject; imaging the localization of the administered radiolabeled conjugate in the tumor by PET imaging; and determining tumor growth, wherein a decrease from the baseline in uptake of the conjugate or radiolabeled signal indicates tumor regression and efficacy of the anti-tumor therapy. In certain embodiments, the anti-tumor therapy comprises an inhibitor of the PD-1/PD-L1 signaling axis (e.g., an anti-PD-1 antibody).

Provided herein are also methods for predicting response of a patient to an anti-tumor therapy comprising an inhibitor of the PD-1/PD-L1 signaling axis, the methods comprising selecting a patient with a solid tumor; and determining if the tumor is PD-L1-positive, wherein if the tumor is PD-L1-positive it indicates a positive response of the patient to an anti-tumor therapy comprising an inhibitor of the PD-1/PD-L1 signaling axis. In certain embodiments, the tumor is determined positive by administering a radiolabeled antibody conjugate of the present disclosure and localizing the radiolabeled antibody conjugate in the tumor by PET imaging wherein presence of the radiolabeled antibody conjugate in the tumor indicates that the tumor is PD-L1-positive.

BRIEF DESCRIPTION OF THE FIGURES

In FIG. 8A-FIG. 8C, elution of buffer components was also detected. These peaks of salts in the sample buffer (retention time >25 min, asterisk "*") were excluded from the integration of peak areas. Peaks are labeled to indicate HMW (high molecular weight) immunoconjugate ("1"), monomeric immunoconjugate ("2"), unincorporated $^{89}$Zr ("3"), and salts in the sample buffer ("*"). Abbreviations: mAU=milli absorbance units; cps=counts per second.

DETAILED DESCRIPTION

I. Definitions

Figures 1A, 1B:
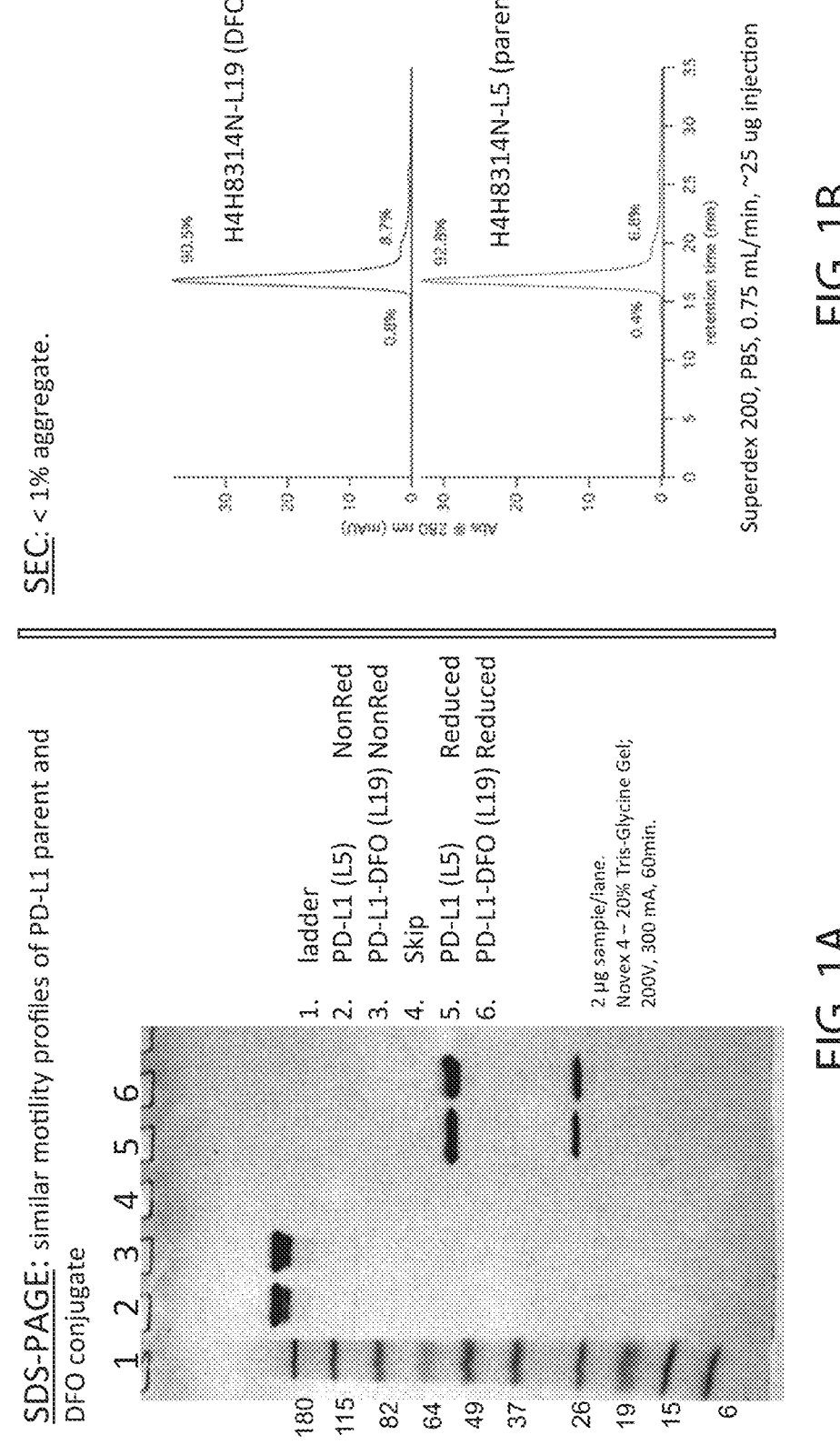
FIG. 1A depicts SDS-PAGE and FIG. 1B depicts SEC of un-modified anti-PD-L1 antibody and anti-PD-L1 DFO modified antibody.

Unless defined otherwise herein, all technical and scientific terms used herein have the same meaning as commonly understood by one of ordinary skill in the art to which the disclosed subject matter belongs.

The term "PD-L1" refers to programmed death-ligand 1, also known as CD274 and B7H1. The amino acid sequence of full-length PD-L1 is provided in GenBank as accession number NP 054862.1. The term "PD-L1" also includes protein variants of PD-L1. The term "PD-L1" includes recombinant PD-L1 or a fragment thereof. The term also encompasses PD-L1 or a fragment thereof coupled to, for example, histidine tag, mouse or human Fc, or a signal sequence such as ROR1. For example, the term includes sequences comprising a mouse Fc (mIgG2a) or human Fc (hIgG1) at the C-terminal, coupled to amino acid residues 19-239 of full-length PD-L1 (NP_054862.1). Protein variants comprise a histidine tag at the C-terminal, coupled to amino acid residues 19-239 of NP_054862.1. Unless specified as being from a non-human species, the term "PD-L1" means human PD-L1. PD-L1 is a 290 amino acid protein with extracellular IgV-like and IgC-like domains (amino acids 19-239 of full length PD-L1), a transmembrane domain and an intracellular domain of approximately 30 amino acids. PD-L1 is constitutively expressed on many cells such as antigen presenting cells (e.g., dendritic cells, macrophages, and B-cells) and on hematopoietic and non-hematopoietic cells (e.g., vascular endothelial cells, pancreatic islets, and sites of immune privilege). PD-L1 is also expressed on a wide variety of tumors, and virally-infected cells and is a component of the immunosuppressive milieu (Ribas 2012, NEJM 366:2517-2519). PD-L1 binds to one of two T-cell co-inhibitors PD-1 and B7-1.

The term "PD-1" refers to the programmed death-1 protein, a T-cell co-inhibitor, also known as CD279. The amino acid sequence of full-length PD-1 is provided in GenBank as accession number NP_005009.2. The term also encompasses PD-1 or a fragment thereof coupled to, for example, histidine tag, mouse or human Fc, or a signal sequence such as ROR1. For example, the term includes sequences comprising a mouse Fc (mIgG2a) or human Fc (hIgG1) at the C-terminal, coupled to amino acid residues 25-170 of NP_005009.2 with a C93S change. PD-1 is a member of the CD28/CTLA-4/ICOS family of T-cell co-inhibitors. PD-1 is a 288-amino acid protein with an extracellular N-terminal domain which is IgV-like, a transmembrane domain and an intracellular domain containing an immunoreceptor tyrosine-based inhibitory (ITIM) motif and an immunoreceptor tyrosine-based switch (ITSM) motif (Chattopadhyay et al 2009, Immunol. Rev.). The PD-1 receptor has two ligands, PD-L1 and PD-L2.

The term "B7-1" refers to the T-lymphocyte activation antigen, also known as costimulatory factor CD80. B7-1 is a 288 amino acid membrane receptor with an extracellular N-terminal domain which comprises IgV-like (aa 37-138) and IgC-like (aa 154-232) regions, a transmembrane domain (aa 243-263) and a C-terminal intracellular region (aa 263-288). The amino acid sequence of full-length B7-1 is provided in GenBank as accession number NP_005182.1.

As used herein, the term "T-cell co-inhibitor" refers to a ligand and/or receptor which modulates the immune response via T-cell activation or suppression. The term "T-cell co-inhibitor", also known as T-cell co-signaling molecule, includes, but is not limited to, PD-1, lymphocyte activation gene 3 protein (LAG-3, also known as CD223), cytotoxic T-lymphocyte antigen-4 (CTLA-4), B and T lymphocyte attenuator (BTLA), CD-28, 2B4, LY108, T-cell immunoglobulin and mucin-3 (TIM3), T-cell immunoreceptor with immunoglobulin and ITIM (TIGIT; also known as VSIG9), leucocyte associated immunoglobulin-like receptor 1 (LAIR1; also known as CD305), inducible T-cell costimulator (ICOS; also known as CD278), B7-1 (CD80), and CD160.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-PD-L1 monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The present disclosure also includes fully human anti-PD-L1 monoclonal antibodies comprising variants of any of the HCVR, LCVR, and/or CDR amino acid sequences disclosed herein having one or more conservative substitutions. For example, the present disclosure includes anti-PD-L1 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The term "multi-specific antigen-binding molecules", as used herein refers to bispecific, tri-specific or multi-specific antigen-binding molecules, and antigen-binding fragments thereof. Multi-specific antigen-binding molecules may be specific for different epitopes of one target polypeptide or may contain antigen-binding domains specific for epitopes of more than one target polypeptide. A multi-specific antigen-binding molecule can be a single multifunctional polypeptide, or it can be a multimeric complex of two or more polypeptides that are covalently or non-covalently associated with one another. The term "multi-specific antigen-binding molecules" includes antibodies of the present disclosure that may be linked to or co-expressed with another functional molecule, e.g., another peptide or protein. For example, an antibody or fragment thereof can be functionally linked (e.g., by chemical coupling, genetic fusion, non-covalent association or otherwise) to one or more other molecular entities, such as a protein or fragment thereof to produce a bi-specific or a multi-specific antigen-binding molecule with a second binding specificity. According to the present disclosure, the term "multi-specific antigen-binding molecules" also includes bi-specific, tri-specific or multi-specific antibodies or antigen-binding fragments thereof. In certain embodiments, an antibody of the present disclosure is functionally linked to another antibody or antigen-binding fragment thereof to produce a bispecific antibody with a second binding specificity. Bispecific and multi-specific antibodies of the present disclosure are described elsewhere herein.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to PD-L1. Moreover, multi-specific antibodies that bind to one domain in PD-L1 and one or more additional antigens or a bi-specific that binds to two different regions of PD-L1 are nonetheless considered antibodies that "specifically bind", as used herein.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to PD-L1.

An "isolated antibody", as used herein, is intended to refer to an antibody that is substantially free of other antibodies (Abs) having different antigenic specificities (e.g., an isolated antibody that specifically binds PD-L1, or a fragment thereof, is substantially free of Abs that specifically bind antigens other than PD-L1.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24:307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256:1443 45, herein incorporated by reference. A "moderately conservative" replacement is any change having a nonnegative value in the PAM250 log-likelihood matrix. Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215:403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, in need of amelioration, prevention and/or treatment of a disease or disorder such as chronic viral infection, cancer or autoimmune disease.

II. Radiolabeled Immunoconjugates of PD-L1 Antibodies for Immuno-PET Imaging

Provided herein are radiolabeled antigen-binding proteins that bind programmed death-ligand 1 (PD-L1). In some embodiments, the radiolabeled antigen-binding proteins comprise an antigen-binding protein covalently linked to one or more chelating moieties, which are chemical moieties that are capable of chelating a positron emitter.

In some embodiments, provided herein are antigen-binding proteins that bind PD-L1, e.g., antibodies, wherein said antigen-binding proteins that bind PD-L1 are covalently bonded to one or more moieties having the following structure:

$$-L-M_Z$$

wherein L is a chelating moiety; M is a positron emitter; and z, independently at each occurrence, is 0 or 1; and wherein at least one of z is 1.

In some embodiments, the radiolabeled antigen-binding protein is a compound of Formula (I):

$$M-L-A-[L-M_Z]_k \tag{I}$$

A is a protein that binds PD-L1; L is a chelating moiety; M is a positron emitter; z is 0 or 1; and k is an integer from 0-30. In some embodiments, k is 1.

In certain embodiments, the radiolabeled antigen-binding protein is a compound of Formula (II):

$$A-[L-M]_k \tag{II}$$

wherein A is a protein that binds PD-L1; L is a chelating moiety; M is a positron emitter; and k is an integer from 1-30.

In some embodiments, provided herein are compositions comprising a conjugate having the following structure:

$$A-L_k$$

wherein A is a protein that binds PD-L1; L is a chelating moiety; and k is an integer from 1-30; wherein the conjugate is chelated with a positron emitter in an amount sufficient to provide a specific activity suitable for clinical PET imaging.

Suitable binding proteins, chelating moieties, and positron emitters are provided below.

A. PD-L1 Binding Proteins

Suitable PD-L1 binding protein are proteins that specifically bind to PD-L1, including those described in US Patent Publication No. US 2015-0203580 A1, incorporated herein by reference in its entirety. Exemplary anti-PD-L1 antibodies of the present disclosure are listed in Table 1 of US Patent Publication No. US 2015-0203580 A1, also presented below.

TABLE 1

| Antibody | SEQ ID NOs: | | | | | | | |
|---|---|---|---|---|---|---|---|---|
| Designation | HCVR | HCDR1 | HCDR2 | HCDR3 | LCVR | LCDR1 | LCDR2 | LCDR3 |
| H2M8306N | 2 | 4 | 6 | 8 | 10 | 12 | 14 | 16 |
| H2M8307N | 18 | 20 | 22 | 24 | 26 | 28 | 30 | 32 |
| H2M8309N | 34 | 36 | 38 | 40 | 42 | 44 | 46 | 48 |
| H2M8310N | 50 | 52 | 54 | 56 | 58 | 60 | 62 | 64 |
| H2M8312N | 66 | 68 | 70 | 72 | 74 | 76 | 78 | 80 |
| H2M8314N | 82 | 84 | 86 | 88 | 90 | 92 | 94 | 96 |
| H2M8316N | 98 | 100 | 102 | 104 | 106 | 108 | 110 | 112 |
| H2M8317N | 114 | 116 | 118 | 120 | 122 | 124 | 126 | 128 |
| H2M8321N | 130 | 132 | 134 | 136 | 138 | 140 | 142 | 144 |
| H2M8323N | 146 | 148 | 150 | 152 | 154 | 156 | 158 | 160 |
| H2M8718N | 162 | 164 | 166 | 168 | 170 | 172 | 174 | 176 |

TABLE 1-continued

| Antibody | Amino Acid Sequence Identifiers | | | | | | | |
| | SEQ ID NOs: | | | | | | | |
| Designation | HCVR | HCDR1 | HCDR2 | HCDR3 | LCVR | LCDR1 | LCDR2 | LCDR3 |
| --- | --- | --- | --- | --- | --- | --- | --- | --- |
| H2M8718N2 | 178 | 180 | 182 | 184 | 170 | 172 | 174 | 176 |
| H2M8719N | 186 | 188 | 190 | 192 | 194 | 196 | 198 | 200 |
| H1H9323P | 202 | 204 | 206 | 208 | 210 | 212 | 214 | 216 |
| H1H9327P | 218 | 220 | 222 | 224 | 226 | 228 | 230 | 232 |
| H1H9329P | 234 | 236 | 238 | 240 | 242 | 244 | 246 | 248 |
| H1H9336P | 250 | 252 | 254 | 256 | 258 | 260 | 262 | 264 |
| H1H9344P2 | 266 | 268 | 270 | 272 | 274 | 276 | 278 | 280 |
| H1H9345P2 | 282 | 284 | 286 | 288 | 274 | 276 | 278 | 280 |
| H1H9351P2 | 290 | 292 | 294 | 296 | 274 | 276 | 278 | 280 |
| H1H9354P2 | 298 | 300 | 302 | 304 | 274 | 276 | 278 | 280 |
| H1H9364P2 | 306 | 308 | 310 | 312 | 274 | 276 | 278 | 280 |
| H1H9373P2 | 314 | 316 | 318 | 320 | 274 | 276 | 278 | 280 |
| H1H9382P2 | 322 | 324 | 326 | 328 | 274 | 276 | 278 | 280 |
| H1H9387P2 | 330 | 332 | 334 | 336 | 274 | 276 | 278 | 280 |
| H1H9396P2 | 338 | 340 | 342 | 344 | 274 | 276 | 278 | 280 |

Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-PD-L1 antibodies.

In some embodiments, the binding protein is an antibody or antigen binding fragment comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

In some embodiments, the binding protein is an antibody or antigen binding fragment comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

In some embodiments, the binding protein is an antibody or antigen binding fragment comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present disclosure provides antibodies, or antigen-binding fragments thereof, comprising an HCVR/LCVR amino acid sequence pair contained within any of the exemplary anti-PD-L1 antibodies listed in Table 1. In certain embodiments, the HCVR/LCVR amino acid sequence pair is selected from the group consisting of SEQ ID NOs: 2/10, 18/26, 34/42, 50/58, 66/74, 82/90, 98/106, 114/122, 130/138, 146/154, 162/170, 178/170, 186/194, 202/210, 218/226, 234/242, 250/258, 266/274, 282/274, 290/274, 298/274, 306/274, 314/274, 322/274, 330/274, and 338/274. In certain embodiments, the HCVR/LCVR amino acid sequence pair is selected from one of SEQ ID NOs: 82/90 (e.g., H2M8314N), 162/170 (e.g., H2M8718N), 306/274 (e.g., H1H9364P2), and 314/274 (e.g., H1H9373P2). In certain other embodiments, the HCVR/LCVR amino acid sequence pair is selected from one of SEQ ID NOs: 98/106 (e.g., H2M8316N), 146/154 (e.g., H2M8323N), 290/274 (e.g., H1H9351P2), and 330/274 (e.g., H1H9387P2).

In some embodiments, the binding protein is an antibody or antigen binding fragment comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

In some embodiments, the binding protein is an antibody or antigen binding fragment comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present disclosure provides antibodies, or antigen-binding fragments thereof, comprising an HCDR3/LCDR3 amino acid sequence pair contained within any of the exemplary anti-PD-L1 antibodies listed in Table 1. In certain embodiments, the HCDR3/LCDR3 amino acid sequence pair is selected from the group consisting of SEQ ID NOs: 88/96 (e.g., H2M8314N), 168/176 (e.g., H2M8718N), 312/280 (e.g., H1H9364P2), and 320/280 (e.g., H1H9373P2). In certain other embodiments, the HCDR3/LCDR3 amino acid sequence pair is selected from the group consisting of SEQ ID NOs: 104/112 (e.g., H2M8316N), 152/160 (e.g., H2M8323N), 296/280 (e.g., H1H9351P2), and 336/280 (e.g., H1H9387P2).

In some embodiments, the binding protein is an antibody or antigen binding fragment comprising a set of six CDRs (i.e., HCDR1-HCDR2-HCDR3-LCDR1-LCDR2-LCDR3) contained within any of the exemplary anti-PD-L1 antibodies listed in Table 1. In certain embodiments, the HCDR1-HCDR2-HCDR3-LCDR1-LCDR2-LCDR3 amino acid sequence set is selected from the group consisting of SEQ ID NOs: 84-86-88-92-VAS-96 (e.g., H2M8314N); 164-166-168-172-AAS-176 (e.g., H2M8718N); 308-310-312-276-AAS-280 (e.g., H1H9364P2); and 316-318-320-276-AAS-280 (e.g., H1H9373P2). In certain other embodiments, the HCDR1-HCDR2-HCDR3-LCDR1-LCDR2-LCDR3 amino acid sequence set is selected from the group consisting of SEQ ID NOs: 100-102-104-108-VAS-112 (e.g., H2M8316N); 148-150-152-156-GAS-160 (e.g., H2M8323N); 292-294-296-276-AAS-280 (e.g., H1H9351P2); and 332-334-336-276-AAS-280 (e.g., H1H9387P2).

In some embodiments, the binding protein is an antibody or antigen binding fragment comprising a set of six CDRs (i.e., HCDR1-HCDR2-HCDR3-LCDR1-LCDR2-LCDR3) contained within an HCVR/LCVR amino acid sequence pair as defined by any of the exemplary anti-PD-L1 antibodies listed in Table 1. For example, in some embodiments, the binding protein is an antibody or antigen binding fragment comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 82/90 (e.g., H2M8314N), 98/106 (e.g., H2M8316N), 146/154 (e.g., H2M8323N), 162/170 (e.g., H2M8718N), 290/274 (e.g., H1H9351P2), 306/274 (e.g., H1H9364P2), 314/274 (e.g., H1H9373P2) and 330/274 (e.g., H1H9387P2). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In some embodiments, binding proteins are antibodies and antigen-binding fragments thereof that compete for specific binding to PD-L1 with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

In some embodiments, the binding proteins are isolated antibodies and antigen-binding fragments thereof that block PD-L1 binding to PD-1 or to B7-1. In some embodiments, the antibody or antigen-binding fragment thereof that blocks PD-L1 binding to PD-1 or to B7-1 may bind to the same epitope on PD-L1 as PD-1/B7-1 or may bind to a different epitope on PD-L1 as PD-1/B7-1. In certain embodiments, the antibodies of the disclosure that block PD-L1 binding to PD-1 or to B7-1 comprise the CDRs of an HCVR having an amino acid sequence selected from the group consisting of HCVR sequences listed in Table 1; and the CDRs of a LCVR having an amino acid sequence selected from the group consisting of LCVR sequences listed in Table 1.

In alternate embodiments, the present disclosure provides antibodies and antigen-binding fragments thereof that do not block PD-L1 binding to PD-1 or to B7-1. In certain embodiments, the present disclosure provides isolated antibodies or antigen-binding fragments thereof that bind PD-L1, wherein the antibodies or antigen-binding fragments thereof enhance PD-L1 binding to PD-1 or to B7-1. In some embodiments, the isolated antibodies or antigen-binding fragments thereof that enhance PD-L1 binding to PD-1/B7-1 comprise the CDRs of a HCVR, wherein the HCVR has an amino acid sequence selected from the group consisting of SEQ ID NOs: 18, 66, 114, 130, 202, 218, 266, 282, 298, 322 and 338; and the CDRs of a LCVR, wherein the LCVR has an amino acid sequence selected from the group consisting of SEQ ID NOs: 26, 74, 122, 138, 210, 226, and 274. In some embodiments, the isolated antibodies or antigen-binding fragments thereof comprise an HCVR/LCVR amino acid sequence pair selected from the group consisting of SEQ ID NOs: 18/26 (e.g., H2M8307N), 66/74 (e.g., H2M8312N), 114/122 (e.g., H2M8317N), 130/138 (e.g., H2M8321N), 202/210 (e.g., H1H9323P), 218/226 (e.g., H1H9327P), 266/274 (e.g., H1H9344P2), 282/274 (e.g., H1H9345P2), 298/274 (e.g., H1H9354P2), 322/274 (e.g., H1H9382P2), and 338/274 (e.g., H1H9396P2).

In some embodiments, the binding proteins are antibodies and antigen-binding fragments thereof that bind specifically to PD-L1 from human or other species. In certain embodiments, the antibodies may bind to human PD-L1 and/or to cynomolgus PD-L1.

In some embodiments, the binding proteins are antibodies and antigen-binding fragments thereof that cross-compete for binding to PD-L1 with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

In one embodiment, the binding protein is an isolated antibody or antigen-binding fragment that has one or more of the following characteristics: (a) blocks the binding of PD-L1 to PD-1 or to B7-1; (b) binds specifically to human PD-L1 and/or cynomolgus PD-L1; (c) inhibits T-cell proliferation in a mixed lymphocyte reaction (MLR) assay; and (d) increases IL-2 and/or interferon-gamma secretion in a MLR assay.

In some embodiments, the binding protein is an antibody or antigen binding fragment thereof may bind specifically to PD-L1 in an agonist manner, i.e., it enhances or stimulates PD-L1 binding and/or activity; in other embodiments, the antibody can bind specifically to PD-L1 in an antagonist manner, i.e., it blocks PD-L1 from binding to its receptor.

In certain embodiments, the antibodies or antigen-binding fragments are bispecific comprising a first binding specificity to PD-L1 and a second binding specificity for a second target epitope. The second target epitope may be another epitope on PD-L1 or on a different protein such as a T-cell co-inhibitor. In certain embodiments, the target epitope may be on a different cell including e.g., a different T-cell, a B-cell, a tumor cell, an autoimmune tissue cell or a virally infected cell.

In some embodiments, the antibodies and antigen-binding fragments of antibodies bind monomeric PD-L1 (e.g., at 25° C. or at 37° C.) with a $K_D$ of less than about 318 pM as measured by surface plasmon resonance, e.g., using the assay format as defined in Example 3 of US Patent Publication No. US 2015-0203580 A1, or substantially similar assay. In certain embodiments, the antibodies or antigen-binding fragments thereof bind monomeric PD-L1 with a $K_D$ of less than about 300 pM, less than about 250 pM, less than about 150 pM, less than about 100 pM, or less than about 50 pM, as measured by surface plasmon resonance, e.g., using the assay format as defined in Example 3 of US Patent Publication No. US 2015-0203580 A1, or a substantially similar assay.

In some embodiments, the antibodies and antigen-binding fragments thereof bind dimeric PD-L1 (e.g., at 25° C. or at 37° C.) with a $K_D$ of less than about 15 pM as measured by surface plasmon resonance, e.g., using the assay format as defined in Example 3 of US Patent Publication No. US 2015-0203580 A1 or sustainably similar assay. In certain embodiments, the antibodies or antigen-binding fragments thereof bind dimeric PD-L1 with a $K_D$ of less than about 12 pM, less than about 10 pM, less than about 8 pM, or less than about 5 pM, as measured by surface plasmon resonance, e.g., using the assay format as defined in Example 3 of US Patent Publication No. US 2015-0203580 A1, or a substantially similar assay.

In some embodiments, the antibodies or antigen-binding fragments thereof bind cynomolgus (*Macaca fascicularis*) PD-L1 (e.g., at 25° C. or at 37° C.) with a $K_D$ of less than about 28 nM as measured by surface plasmon resonance, e.g., using the assay format as defined in Example 3 of US Patent Publication No. US 2015-0203580 A1. In certain embodiments, the antibodies or antigen-binding fragments thereof bind cynomolgus PD-L1 with a $K_D$ of less than about 25 nM, less than about 20 nM, less than about 15 nM, less than about 10 nM, or less than about 5 nM, as measured by surface plasmon resonance, e.g., using the assay format as defined in Example 3 of US Patent Publication No. US 2015-0203580 A1, or a substantially similar assay.

In some embodiments, the antibodies and antigen-binding fragments thereof bind PD-L1 with a dissociative half-life (t1/2) of greater than about 1 minute as measured by surface plasmon resonance at 25° C. or 37° C., e.g., using an assay format as defined in Example 3 of US Patent Publication No. US 2015-0203580 A1, or a substantially similar assay. In certain embodiments, the antibodies or antigen-binding fragments bind PD-L1 with a t1/2 of greater than about 5 minutes, greater than about 10 minutes, greater than about 30 minutes, greater than about 50 minutes, greater than about 60 minutes, greater than about 70 minutes, greater than about 80 minutes, greater than about 90 minutes, greater than about 100 minutes, greater than about 200 minutes, greater than about 300 minutes, greater than about 400 minutes, greater than about 500 minutes, greater than about 600 minutes, greater than about 700 minutes, or greater than about 800 minutes, as measured by surface plasmon resonance at 25° C. or 37° C., e.g., using an assay format as defined in Example 3 of US Patent Publication No. US 2015-0203580 A1 (e.g., mAb-capture or antigen-capture format), or a substantially similar assay.

In some embodiments, the antibodies or antigen-binding fragments thereof block PD-L1 binding to PD-1 with an $IC_{50}$ of less than about 770 pM as determined using a ELISA-based immunoassay assay, e.g., as shown in Example 4 of US Patent Publication No. US 2015-0203580 A1, or a substantially similar assay. In some embodiments, the antibodies or antigen-binding fragments thereof block PD-L1 binding to B7-1 with an $IC_{50}$ of less than about 10 nM as determined using a ELISA-based immunoassay assay, e.g., as shown in Example 4 of US Patent Publication No. US 2015-0203580 A1, or a substantially similar assay. In some embodiments, the antibodies and antigen-binding fragments thereof bind to PD-L1 and enhance the binding of PD-L1 to PD-1 or to B7-1.

In some embodiments, the antibodies bind to the extracellular domain of PD-L1 or to a fragment of the domain. In some embodiments, the antibodies bind to more than one domain (cross-reactive antibodies). In certain embodiments, the antibodies of the bind to an epitope located in the extracellular domain comprising amino acid residues 19-239 of NP_054862.1.

In certain embodiments, the antibodies function by blocking or inhibiting the PD-1-binding or the B7-1-binding activity associated with PD-L1 by binding to any other region or fragment of the full length protein. In certain embodiments, the antibodies attenuate or modulate the interaction between PD-L1 and PD-1/B7-1.

In certain embodiments, the antibodies are bi-specific antibodies. The bi-specific antibodies can bind one epitope in one domain and can also bind a second epitope in a different domain of PD-L1. In certain embodiments, the bi-specific antibodies bind two different epitopes in the same domain. In one embodiment, the multi-specific antigen-binding molecule comprises a first antigen-binding specificity wherein the first binding specificity comprises the extracellular domain or fragment thereof of PD-1; and a second antigen-binding specificity to another epitope of PD-L1. In another embodiment, the multi-specific antigen-binding molecule comprises a first antigen-binding specificity wherein the first binding specificity comprises the extracellular domain or fragment thereof of B7-1; and a second antigen-binding specificity to another epitope of PD-L1.

In one embodiment, the antibody or fragment thereof is a fully human monoclonal antibody or antigen-binding fragment thereof that binds to PD-L1, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 186, 202, 218, 234, 250, 258, 266, 274, 282, 290, 298, 306, 314, 322, 330 and 338, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 194, 210, 226, 242, 258, and 274, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 192, 208, 224, 240, 256, 272, 280, 288, 296, 304, 312, 320, 328, 336 and 344, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 200, 216, 232, 248, 264, and 280, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 188, 204, 220, 236, 252, 268, 284, 292, 300, 308, 316, 324, 332, and 340, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 190, 206, 222, 238, 254, 270, 286, 294, 302, 310, 318, 326, 334, and 342, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 196, 212, 228, 244, 260, and 276, or a substantially similar sequence thereof having at least 90%, at least 95%, at least 98% or at least 99% sequence identity; and a LCDR2 domain having an amino acid sequence selected from the group consisting of SEQ ID NO: KAS, TAS, AAS, KVS, KIS, VAS, VAS, AAS, AAS, GAS, AAS, AAS, AAS, AAS, AAS, VVS, and AAS, or a substantially similar sequence thereof having at least 90%, at least 95%, at least 98% or at least 99% sequence identity; (v) is a multi-specific antigen-binding molecule comprising a first binding specificity to PD-L1 and a second binding specificity to an antigen selected from the group consisting of PD-L1, a tumor specific antigen, a virally infected cell antigen, and a T-cell co-inhibitor; (vi) binds to human PD-L1 with a $K_D$ of about 4 pM to about 645 nM; (vii) binds to cynomolgus PD-L1 with a $K_D$ of about 70 pM to about 400 nM; (viii) blocks or enhances the binding of PD-L1 to PD-1 with an IC50≤770 pM; (ix) blocks or enhances the binding of PD-L1 to B7-1 with an IC50≤10 nM; (x) blocks PD-1-induced T-cell down-regulation and/or rescues T-cell signaling in a T-cell/APC luciferase reporter assay; (xi) stimulates T-cell proliferation and activity in a mixed lymphocyte reaction (MLR) assay; (xii) induces IL-2 and/or IFNγ production in a MLR assay; and (xiii) suppresses tumor growth and increases survival in subjects with cancer.

In one embodiment, the antibody or fragment thereof is a fully human monoclonal antibody or antigen-binding fragment thereof that blocks PD-L1 binding to PD-1 or to B7-1, wherein the antibody or fragment thereof exhibits one or more of the following characteristics: (i) comprises a HCVR having an amino acid sequence selected from the group consisting of SEQ ID NO: 82, 98, 146, 162, 290, 306, 314, and 330, or a substantially similar sequence thereof having at least 90%, at least 95%, at least 98% or at least 99% sequence identity; (ii) comprises a LCVR having an amino acid sequence selected from the group consisting of SEQ ID NO: 90, 106, 154, 170, and 274, or a substantially similar sequence thereof having at least 90%, at least 95%, at least 98% or at least 99% sequence identity; (iii) comprises a HCDR3 domain having an amino acid sequence selected from the group consisting of SEQ ID NO: 88, 104, 152, 168, 296, 312, 320, and 336, or a substantially similar sequence thereof having at least 90%, at least 95%, at least 98% or at least 99% sequence identity; and a LCDR3 domain having an amino acid sequence selected from the group consisting of SEQ ID NO: 96, 112, 160, 176, and 280, or a substantially similar sequence thereof having at least 90%, at least 95%, at least 98% or at least 99% sequence identity; (iv) comprises a HCDR1 domain having an amino acid sequence selected from the group consisting of SEQ ID NO: 84, 100, 148, 164, 292, 308, 316, and 332, or a substantially similar sequence thereof having at least 90%, at least 95%, at least 98% or at least 99% sequence identity; a HCDR2 domain having an amino acid sequence selected from the group consisting of SEQ ID NO: 86, 102, 150, 166, 294, 310, 318, and 334, or a substantially similar sequence thereof having at least 90%, at least 95%, at least 98% or at least 99% sequence identity; a LCDR1 domain having an amino acid sequence selected from the group consisting of SEQ ID NO: 92, 108, 156, 172, and 276, or a substantially similar sequence thereof having at least 90%, at least 95%, at least 98% or at least 99% sequence identity; and a LCDR2 domain having an amino acid sequence selected from the group consisting of SEQ ID NO: VAS, VAS, GAS, AAS, and AAS, or a substantially similar sequence thereof having at least 90%, at least 95%, at least 98% or at least 99% sequence identity; (v) is a multi-specific antigen-binding molecule comprising a first binding specificity to PD-L1 and a second binding specificity to an antigen selected from the group consisting of a different epitope of PD-L1, a tumor specific antigen, a virally-infected cell antigen, and a T-cell co-inhibitor; (vi) binds to human PD-L1 with a $K_D \le 10^{-10}$M; (vii) binds to cynomolgus PD-L1 with a $K_D \le 10^{-7}$M; (viii) blocks the binding of PD-L1 to PD-1 or to B7-1; (ix) blocks PD-1-induced T-cell down-regulation and/or rescues T-cell signaling in a T-cell/APC luciferase reporter assay; (xi) stimulates T-cell proliferation and activity in a mixed lymphocyte reaction (MLR) assay; (xii) induces IL-2 and/or IFNγ production in a MLR assay; and (xiii) suppresses tumor growth and increases survival in subjects with cancer.

In certain embodiments, the anti-PD-L1 antibodies or antigen-binding fragments thereof bind an epitope within any one or more of the regions exemplified in PD-L1, either in natural form, or recombinantly produced, or to a fragment thereof. In some embodiments, the antibodies of the disclosure bind to an extracellular region comprising one or more amino acids selected from the group consisting of amino acid residues 19-239 of PD-L1. In some embodiments, the antibodies of the disclosure bind to a region comprising one or more amino acids selected from the group consisting of amino acid residues 1-221 of cynomolgus PD-L1.

In certain embodiments, the antibodies of the disclosure, as shown in Table 1, interact with at least one amino acid sequence selected from the group consisting of amino acid residues ranging from about position 19 to about position 130 of PD-L1; or amino acid residues ranging from about position 130 to about position 153 of PD-L1; or amino acid residues ranging from about position 153 to about position 210 of PD-L1; or to amino acid residues ranging from about position 210 to about position 239 of PD-L1.

In some embodiments, the anti-PD-L1 antibodies bind to the same epitope, or a portion of the epitope, as any of the specific exemplary antibodies described herein in Table 1, or an antibody having the CDR sequences of any of the exemplary antibodies described in Table 1. Likewise, suitable antibodies also include anti-PD-L1 antibodies that compete for binding to PD-L1 or a PD-L1 fragment with any of the specific exemplary antibodies described herein in Table 1, or an antibody having the CDR sequences of any of the exemplary antibodies described in Table 1. For example, suitable antibodies include anti-PD-L1 antibodies that cross-compete for binding to PD-L1 with one or more antibodies as defined in Example 6 of herein (e.g., H2aM8309N, H1H9329P, H1H9336P, H2aM8314N, H2aM8316N, H2AM8718N, H1H9387P2, H1H9351P2, H1H9364P2, H1H9373P2, and H2aM8306N). The present disclosure also includes anti-PD-L1 antibodies that cross-compete for binding to PD-L1 with one or more antibodies as defined in Example 6 of US Patent Publication No. US 2015-0203580

A1 (e.g., H1H9396P2, H2aM8317N, H2aM8321N, H1H9323P, H1H9382P2, H1H9344P2, H1H9345P2 and H1H9354P2).

The antibodies and antigen-binding fragments described herein specifically bind to PD-L1 and modulate the interaction of PD-L1 with PD-1 or with B7-1. The anti-PD-L1 antibodies may bind to PD-L1 with high affinity or with low affinity. In certain embodiments, the antibodies are blocking antibodies wherein the antibodies bind to PD-L1 and block the interaction of PD-L1 with PD-1 or with B7-1. In some embodiments, the blocking antibodies of the disclosure block the binding of PD-L1 to PD-1 or to B7-1 and/or stimulate or enhance T-cell activation. In some embodiments, the blocking antibodies are useful for stimulating or enhancing the immune response and/or for treating a subject suffering from cancer, or a chronic viral infection. The antibodies when administered to a subject in need thereof may reduce the chronic infection by a virus such as HIV, LCMV or HBV in the subject. They may be used to inhibit the growth of tumor cells in a subject. They may be used alone or as adjunct therapy with other therapeutic moieties or modalities known in the art for treating cancer, or viral infection. In certain embodiments, the anti-PD-L1 antibodies that bind to PD-L1 with a low affinity are used as multi-specific antigen-binding molecules wherein the first binding specificity binds to PD-L1 with a low affinity and the second binding specificity binds to an antigen selected from the group consisting of a different epitope of PD-L1, a T-cell co-inhibitor such as PD-1, a tumor specific antigen and an infected-cell-specific antigen.

In certain embodiments, the antibodies of the present disclosure are agonist antibodies, wherein the antibodies bind to PD-L1 and enhance the interaction of PD-L1 and PD-1/B7-1. In some embodiments, the activating antibodies enhance binding of PD-L1 to PD-1 or to B7-1 and/or inhibit or suppress T-cell activation. The activating antibodies of the present disclosure may be useful for inhibiting the immune response in a subject and/or for treating autoimmune disease.

In certain embodiments, the anti-PD-L1 antibodies are multi-specific antigen-binding molecules, wherein they comprise a first binding specificity to PD-L1 and a second binding specificity to an antigen selected from the group consisting of a different epitope of PD-L1, a T-cell co-inhibitor such as PD-1, a tumor specific antigen and an infected-cell-specific antigen. In certain embodiments, the first binding specificity binds to PD-L1 with low affinity, e.g., with a $K_D$ of $10^{-8}$ M, $10^{-7}$ M or more.

Certain anti-PD-L1 antibodies of the present disclosure are able to bind to and neutralize the activity of PD-L1, as determined by in vitro or in vivo assays. The ability of the antibodies of the disclosure to bind to and neutralize the activity of PD-L1 may be measured using any standard method known to those skilled in the art, including binding assays, or activity assays, as described herein.

Non-limiting, exemplary in vitro assays for measuring binding activity are illustrated in Example 3 of US Patent Publication No. US 2015-0203580 A1. In Example 3, the binding affinities and kinetic constants of human anti-PD-L1 antibodies for human PD-L1 and cynomolgus PD-L1 were determined by surface plasmon resonance and the measurements were conducted on a T200 Biacore instrument. In Examples 4 and 5 of US Patent Publication No. US 2015-0203580 A1, blocking assays were used to determine the ability of the anti-PD-L1 antibodies to block PD-L1-binding ability of PD-1 or to B7-1 in vitro. In Example 6 of US Patent Publication No. US 2015-0203580 A1, blocking assays were used to determine cross-competition between different anti-PD-L1 antibodies. Example 7 of US Patent Publication No. US 2015-0203580 A1 describes the binding of the antibodies to cells overexpressing PD-L1. In Example 8 of US 2015-0203580 A1, a luciferase assay was used to determine the ability of anti-PD-L1 antibodies to antagonize PD-1/PD-L1 signaling in T-cells.

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to PD-L1. An antibody fragment may include a Fab fragment, a F(ab') 2 fragment, a Fv fragment, a dAb fragment, a fragment containing a CDR, or an isolated CDR. In certain embodiments, the term "antigen-binding fragment" refers to a polypeptide or fragment thereof of a multi-specific antigen-binding molecule. In such embodiments, the term "antigen-binding fragment" includes, e.g., an extracellular domain of PD-1 which binds specifically to PD-L1. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present disclosure using routine techniques available in the art.

The anti-PD-L1 antibodies and antibody fragments of the present disclosure encompass proteins having amino acid sequences that vary from those of the described antibodies, but that retain the ability to bind PD-L1. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present disclosure encompass sequences that comprise one or more additions, deletions, or substitutions of nucleotides when compared to the disclosed sequence, but that encode an antibody or antibody fragment that is essentially bioequivalent to an antibody or antibody fragment of the disclosure.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the disclosure may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

According to certain embodiments of the present disclosure, anti-PD-L1 antibodies comprise an Fc domain comprising one or more mutations which enhance or diminish antibody binding to the FcRn receptor, e.g., at acidic pH as compared to neutral pH. For example, the present disclosure includes anti-PD-L1 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 2591 (e.g., V2591), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present disclosure includes anti-PD-L1 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). In one embodiment, the present disclosure includes anti-PD-L1 antibodies comprising an Fc domain comprising a S108P mutation in the hinge region of IgG4 to promote dimer stabilization. All possible combinations of the foregoing Fc domain mutations, and other mutations within the antibody variable domains disclosed herein, are contemplated within the scope of the present disclosure.

The present disclosure also includes anti-PD-L1 antibodies comprising a chimeric heavy chain constant ($C_H$) region, wherein the chimeric $C_H$ region comprises segments derived from the $C_H$ regions of more than one immunoglobulin isotype. For example, the antibodies of the disclosure may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the disclosure comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Ser. No. 14/170,166, filed Jan. 31, 2014, the disclosure of which is hereby incorporated by reference in its entirety).

B. Positron Emitters and Chelating Moieties

Suitable positron emitters include, but are not limited to, those that form stable complexes with the chelating moiety and have physical half-lives suitable for immuno-PET imaging purposes. Illustrative positron emitters include, but are not limited to, $^{89}$Zr, $^{68}$Ga, $^{64}$Cu, $^{44}$Sc, and $^{86}$Y. Suitable positron emitters also include those that directly bond with the PD-L1 binding protein, including, but not limited to, $^{76}$Br and $^{124}$I, and those that are introduced via prosthetic group, e.g., $^{18}$F.

The chelating moieties described herein are chemical moieties that are covalently linked to the PD-L1 binding protein, e.g., anti-PD-L1 antibody and comprise a portion capable of chelating a positron emitter, i.e., capable of reacting with a positron emitter to form a coordinated chelate complex. Suitable moieties include those that allow efficient loading of the particular metal and form metal-chelator complexes that are sufficiently stable in vivo for diagnostic uses, e.g., immuno-PET imaging. Illustrative chelating moieties include those that minimize dissociation of the positron emitter and accumulation in mineral bone, plasma proteins, and/or bone marrow depositing to an extent suitable for diagnostic uses.

Examples of chelating moieties include, but are not limited to, those that form stable complexes with positron emitters $^{89}$Zr, $^{68}$Ga, $^{64}$Cu, $^{44}$Sc, and/or $^{86}$Y. Illustrative chelating moieties include, but are not limited to, those described in *Nature Protocols,* 5 (4): 739, 2010; *Bioconjugate Chem.,* 26 (12): 2579 (2015); *Chem Commun (Camb),* 51 (12): 2301 (2015); *Mol. Pharmaceutics,* 12:2142 (2015); *Mol. Imaging Biol.,* 18:344 (2015); *Eur. J. Nucl. Med. Mol. Imaging,* 37:250 (2010); *Eur. J. Nucl. Med. Mol. Imaging* (2016). doi: 10.1007/s00259-016-3499-x; Bioconjugate Chem., 26 (12): 2579 (2015); WO 2015/140212A1; and U.S. Pat. No. 5,639,879, incorporated by reference in their entireties.

Illustrative chelating moieties also include, but are not limited to, those that comprise desferrioxamine (DFO), 1,4,7,10-tetraacetic acid (DOTA), diethylenetriaminepentaacetic acid (DTPA), ethylenediaminetetraacetic acid (EDTA), (1,4,7,10-Tetraazacyclododecane-1,4,7,10-tetra (methylene phosphonic) acid (DOTP), 1R,4R,7R,10R)-α'α"α'"-Tetramethyl-1,4,7,10-tetraazacyclododecane-1,4,7, 10-tetraacetic acid (DOTMA), 1,4,8,11-Tetraazacyclotetradecane-1,4,8,11-tetraacetic acid (TETA), $H_4$octapa, $H_6$phospa, $H_2$dedpa, $H_5$decapa, $H_2$azapa, HOPO, DO2A, 1,4,7,10-Tetrakis(carbamoylmethyl)-1,4,7,10-tetraazacyclododecane (DOTAM), 1,4,7-triazacyclononane-N, N',N"-triacetic acid (NOTA), 1,4,7,10-Tetrakis(carbamoylmethyl)-1,4,7,10-tetraazacyclododecane (DOTAM), 1,4,8, 11-tetraazabicyclo[6.6.2]hexadecane-4,11-dicetic acid (CB-TE2A), 1,4,7,10-Tetraazacyclododecane (Cyclen), 1,4,8,11-Tetraazacyclotetradecane (Cyclam), octadentate chelators, hexadentate chelators, phosphonate-based chelators, macrocyclic chelators, chelators comprising macrocyclic terephthalamide ligands, bifunctional chelators, fusarinine C and fusarinine C derivative chelators, triacetylfusarinine C (TAFC), ferrioxamine E (FOXE), ferrioxamine B (FOXB), ferrichrome A (FCHA), and the like.

In some embodiments, the chelating moieties are covalently bonded to the PD-L1 binding protein, e.g., antibody or antigen binding fragment thereof, via a linker moiety, which covalently attaches the chelating portion of the chelating moiety to the binding protein. In some embodiments, these linker moieties are formed from a reaction between a reactive moiety of the PD-L1 binding protein, e.g., cysteine or lysine of an antibody, and reactive moiety that is attached to a chelator, including, for example, a p-isothiocyanatobenyl group and the reactive moieties provided in the conjugation methods below. In addition, such linker moieties optionally comprise chemical groups used for purposes of adjusting polarity, solubility, steric interactions, rigidity, and/or the length between the chelating portion and PD-L1 binding protein.

C. Preparation of Radiolabeled Anti-PD-L1 Conjugates

The radiolabeled anti-PD-L1 protein conjugates can be prepared by (1) reacting a PD-L1 binding protein, e.g., antibody, with a molecule comprising a positron emitter chelator and a moiety reactive to the desirable conjugation site of the PD-L1 binding protein and (2) loading the desirable positron emitter.

Suitable conjugation sites include, but are not limited to, lysine and cysteine, both of which can be, for example, native or engineered, and can be, for example, present on the heavy or light chain of an antibody. Cysteine conjugation sites include, but are not limited to, those obtained from mutation, insertion, or reduction of antibody disulfide bonds. Methods for making cysteine engineered antibodies include, but are not limited to, those disclosed in WO2011/056983. Site-specific conjugation methods can also be used to direct the conjugation reaction to specific sites of an antibody, achieve desirable stoichiometry, and/or achieve desirable drug-to-antibody (DAR) ratios. Such conjugation methods are known to those of ordinary skill in the art and include, but are not limited to cysteine engineering and enzymatic and chemo-enzymatic methods, including, but not limited to, glutamine conjugation, Q295 conjugation, and transglutaminase-mediated conjugation, as well as those described in *J. Clin. Immunol.,* 36:100 (2016), incorporated herein by reference in its entirety. Suitable moieties reactive to the desirable conjugation site generally enable efficient and facile coupling of the PD-L1 binding protein, e.g., antibody and positron emitter chelator. Moieties reactive to lysine and cysteine sites include electrophilic groups, which are known to those of ordinary skill. In certain aspects, when the desired conjugation site is lysine, the reactive moiety is an isothiocyanate, e.g., p-isothiocyanatobenyl group or reactive ester. In certain aspects, when the desired conjugation site is cysteine, the reactive moiety is a maleimide.

When the chelator is desferrioxamine (DFO), suitable reactive moieties include, but are not limited to, an isothiocyantatobenzyl group, an n-hydroxysuccinimide ester,2,3, 5,6 tetraflurorphenol ester, n-succinimidyl-S-acetylthioacetate, and those described in BioMed Research International, Vol 2014, Article ID 203601, incorporated herein by reference in its entirety. In certain embodiments, the PD-L1 binding protein is an antibody and the molecule comprising a positron emitter chelator and moiety reactive to the conjugation site is p-isothiocyantatobenzyl-desferrioxamine (p-SCN-Bn-DFO):

Positron emitter loading is accomplished by incubating the PD-L1 binding protein chelator conjugate with the positron emitter for a time sufficient to allow coordination of said positron emitter to the chelator, e.g., by performing the methods described in the examples provided herein, or substantially similar method.

D. Illustrative Embodiments of Conjugates

Included in the instant disclosure are radiolabeled antibody conjugates comprising an antibody or antigen binding fragment thereof, that binds human program death ligand 1 (PD-L1), a chelating moiety, and a positron emitter.

In some embodiments, the chelating moiety comprises a chelator capable of forming a complex with $^{89}$Zr. In certain embodiments, the chelating moiety comprises desferrioxamine. In certain embodiments, the chelating moiety is p-isothiocyanatobenzyl-desferrioxamine.

In some embodiments, the positron emitter is $^{89}$Zr.

In some embodiments, the chelating moiety-to-antibody ratio of the conjugate is from 1 to 2.

In a particular embodiment, chelating moiety is p-isothiocyanatobenzyl-desferrioxamine and the positron emitter is $^{89}$Zr. In another particular embodiment, the chelating moiety is p-isothiocyanatobenzyl-desferrioxamine and the positron emitter is $^{89}$Zr, and the chelating moiety-to-antibody ratio of the conjugate is from 1 to 2.

In some embodiments, provided herein are antigen-binding proteins that bind PD-L1, wherein said antigen-binding proteins that bind PD-L1 are covalently bonded to one or more moieties having the following structure:

$$-L-M_Z$$

wherein L is a chelating moiety; M is a positron emitter; and z, independently at each occurrence, is 0 or 1; and wherein at least one of z is 1. In certain embodiments, the radiolabeled antigen-binding protein is a compound of Formula (I):

$$M-L-A-[L-M_Z]_k \qquad (I)$$

A is a protein that binds PD-L1; L is a chelating moiety; M is a positron emitter; z is 0 or 1; and k is an integer from 0-30. In some embodiments, k is 1.

In some embodiments, L is:

In some embodiments, M is $^{89}$Zr.

In some embodiments, k is an integer from 1 to 2. In some embodiments, k is 1.

In some embodiments, -L-M is

Included in the instant disclosure are also methods of synthesizing a radiolabeled antibody conjugates comprising contacting a compound of Formula (III):

(III)

with $^{89}$Zr, wherein A is an antibody or antigen-binding fragment thereof that binds PD-L1. In certain embodiments, the compound of Formula (III) is synthesized by contacting an antibody, or antigen binding fragment thereof, that binds PD-L1, with p-SCN-Bn-DFO.

Provided herein is also the product of the reaction between a compound of Formula (III) with $^{89}$Zr.

Provided herein are compounds of Formula (III):

wherein A is an antibody or antigen binding fragment thereof that binds PD-L1 and k is an integer from 1-30. In some embodiments, k is 1 or 2.

In some embodiments, provided herein are compositions comprising a conjugate having the following structure:

A-L$_k$ wherein A is a protein that binds PD-L1; L is a chelating moiety; and k is an integer from 1-30; wherein the conjugate is chelated with a positron emitter in an amount sufficient to provide a specific activity suitable for clinical PET imaging. In some embodiments, the amount of chelated positron emitter is an amount sufficient to provide a specific activity of 1-3 mCi per 1-50 mg of the protein that binds PD-L1.

In some embodiments, the antibody or antigen-binding fragment thereof binds monomeric human programmed death-ligand 1 (PD-L1) with a binding dissociation equilibrium constant ($K_D$) of less than about 310 pM as measured in a surface plasmon resonance assay at 37° C.

In some embodiments, the antibody or antigen-binding fragment thereof binds monomeric human PD-L1 with a $K_D$ less than about 180 pM in a surface plasmon resonance assay at 25° C.

In some embodiments, the antibody or antigen-binding fragment thereof binds dimeric human PD-L1 with a $K_D$ of less than about 15 pM as measured in a surface plasmon resonance assay at 37° C.

In some embodiments, the antibody or antigen-binding fragment thereof that binds dimeric human PD-L1 with a $K_D$ less than about 8 pM in a surface plasmon resonance assay at 25° C.

In some embodiments, the antibody or antigen-binding fragment thereof competes for binding to human PD-L1 with a reference antibody comprising the complementarity determining regions (CDRs) of a HCVR, wherein the HCVR has an amino acid sequence selected from the group consisting of HCVR sequences listed in Table 1; and the CDRs of a LCVR, wherein the LCVR has an amino acid sequence selected from the group consisting of LCVR sequences listed in Table 1. In some embodiments, the reference antibody or antigen-binding fragment thereof comprises an HCVR/LCVR amino acid sequence pair as set forth in Table 1. In some embodiments, the reference antibody comprises an HCVR/LCVR amino acid sequence pair selected from the group consisting of SEQ ID NOs: 82/90, 98/106, 146/154, 162/170, 290/274, 306/274, 314/274 and 330/274.

In some embodiments, the antibody or antigen-binding fragment thereof enhances PD-L1 binding to one of PD-1 or B7-1. In some embodiments, the antibody or antigen binding fragment thereof blocks PD-L1 binding to PD-1 and/or B7-1. In some embodiments, the antibody or antigen binding fragment thereof do not increase or decrease PD-L1 binding to its ligands.

In some embodiments, the antibody or antigen-binding fragment thereof comprises the complementarity determining regions (CDRs) of a HCVR, wherein the HCVR has an amino acid sequence selected from the group consisting of SEQ ID NOs: 18, 66, 114, 130, 202, 218, 266, 282, 298, 322, and 338; and the CDRs of a LCVR, wherein the LCVR has an amino acid sequence selected from the group consisting of SEQ ID NOs: 26, 74, 122, 138, 210, 226, and 274. In certain embodiments, the isolated antibody comprises an HCVR/LCVR amino acid sequence pair selected from the group consisting of SEQ ID NOs: 18/26, 66/74, 114/122, 130/138, 202/210, 218/226, 266/274, 282/274, 298/274, 322/274, and 338/274.

In some embodiments, the antibody is a human mono-clonal antibody or antigen-binding fragment thereof that binds specifically to human PD-L1, wherein the antibody or antigen-binding fragment thereof comprises a heavy chain variable region (HCVR) having an amino acid sequence selected from the group consisting of HCVR sequences listed in Table 1.

In some embodiments, the antibody is a human mono-clonal antibody or antigen-binding fragment thereof that binds specifically to human PD-L1, wherein the antibody or antigen-binding fragment thereof comprises a light chain variable region (LCVR) having an amino acid sequence selected from the group consisting of LCVR sequences listed in Table 1.

In some embodiments, the antibody a human monoclonal antibody or antigen-binding fragment thereof that binds specifically to human PD-L1, wherein the antibody or antigen-binding fragment thereof comprises (a) a HCVR having an amino acid sequence selected from the group consisting of HCVR sequences listed in Table 1; and (b) a LCVR having an amino acid sequence selected from the group consisting of LCVR sequences listed in Table 1.

In some embodiments, the antibody or antigen-binding fragment thereof comprises three heavy chain complementarity determining regions (CDRs) (HCDR1, HCDR2 and HCDR3) contained within any one of the heavy chain variable region (HCVR) sequences listed in Table 1; and three light chain CDRs (LCDR1, LCDR2 and LCDR3) contained within any one of the light chain variable region (LCVR) sequences listed in Table 1.

In some embodiments, the antibody or antigen-binding fragment thereof comprises:

(a) a HCDR1 domain having an amino acid sequence selected from the group consisting of SEQ ID NOs: 4, 20, 36, 52, 68, 84, 100, 116, 132, 148, 164, 180, 188, 204, 220, 236, 252, 268, 284, 292, 300, 308, 316, 324, 332, and 340;

(b) a HCDR2 domain having an amino acid sequence selected from the group consisting of SEQ ID NOs: 6, 22, 38, 54, 70, 86, 102, 118, 134, 150, 166, 182, 190, 206, 222, 238, 254, 270, 286, 294, 302, 310, 318, 326, 334, and 342;

(c) a HCDR3 domain having an amino acid sequence selected from the group consisting of SEQ ID NOs: 8, 24, 40, 56, 72, 88, 104, 120, 136, 152, 168, 184, 192, 208, 224, 240, 256, 272, 288, 296, 304, 312, 320, 328, 336, and 344;

(d) a LCDR1 domain having an amino acid sequence selected from the group consisting of SEQ ID NOs: 12, 28, 44, 60, 76, 92, 108, 124, 140, 156, 172, 196, 212, 228, 244, 260, and 276;

(e) a LCDR2 domain having an amino acid sequence selected from the group consisting of SEQ ID NOs: KAS, TAS, AAS, KVS, KIS, VAS, VAS, AAS, AAS, GAS, AAS, AAS, AAS, AAS, AAS, VVS, and AAS; and (f) a LCDR3 domain having an amino acid sequence selected from the group consisting of SEQ ID NOs: 16, 32, 48, 64, 80, 96, 112, 128, 144, 160, 176, 200, 216, 232, 248, 264, and 280.

In some embodiments, the antibody or antigen-binding fragment comprises a HCVR/LCVR amino acid sequence pair selected from the group consisting of SEQ ID NOs: 82/90, 98/106, 146/154, 162/170, 290/274, 306/274, 314/274 and 330/274.

In some embodiments, the antibody or antigen-binding fragment thereof comprises the CDRs of a HCVR, wherein the HCVR has an amino acid sequence selected from the group consisting of SEQ ID NOs: 2, 34, 50, 82, 98, 146, 162, 178, 186, 234, 250, 290, 306, 314, and 330; and the CDRs of a LCVR, wherein the LCVR has an amino acid sequence selected from the group consisting of SEQ ID NOs: 10, 42, 58, 90, 106, 154, 170, 194, 242, 258, and 274.

E. Scaled Manufacturing for Production of Anti-PD-L1 Antibody-Chelator Conjugates Included in the present disclosure are scaled-up manufacturing processes for producing anti-PD-L1 antibodies conjugated to a chelator. The anti-PD-L1 antibody-chelator conjugates are in a form suitable for radiolabeling.

Good manufacturing processes are adhered to in all aspects of production, including maintaining a sterile environment, practicing aseptic procedures, keeping records of all processes, and documenting product quality, purity, strength, and identity, and any deviations therefrom.

The scaled-up manufacturing process is, in some embodiments, much faster than the manufacturing process for research and development. In some embodiments, the scaled-up manufacturing process can take less than 12 hours, or less than 10 hours, or less than 8 hours, or less than 6 hours, or less than 4 hours, or less than or about 2 hours.

In some embodiments, a first step comprises ultrafiltration and diafiltration (UFDF), using a 30-50 kDa membrane, of the anti-PD-L1 antibody to remove excipients, conjugation interfering species, and salts that inhibit the conjugation process. Exemplary membrane polymers include polyethersulfone (PES), cellulose acetate (CA), and regenerated cellulose (RC). In this step, the antibody is buffer exchanged in a low ionic strength and non-interfering buffer solution. The buffer pH can be between about 4.5 to about 6, or about 5 to about 6, or about 5.3 to about 5.7, or about 5.5. Buffer systems contemplated as useful herein include any buffer system lacking a primary amine. Exemplary buffers include acetate, phosphate, or citrate buffers. The buffer provides protein stability during pre-conjugation processing. The process volume can be further reduced to concentrate the antibody, then sterile filtered.

Following the pre-conjugation UFDF, the concentrated and filtered antibody can be transferred into an amine free carbonate buffer system. The carbonate buffer system can have a pH in a range from about 8.5 to about 9.6, or from about 9.0 to about 9.6, or from about 9.2 to about 9.4, or from about 9.4 to about 9.6, or a pH of about 9.4.

A chelator, for example, DFO, in solvent is added to a target concentration into the buffer system containing the antibody, and additional solvent can be added to the solution to a desired percentage. The chelator can be added in molar excess of the antibody, for example, 3.5-5:1 chelator to antibody. The total reaction volume can be up to 5 L.

The reaction temperature and the reaction time are inversely related. For example, if the reaction temperature is higher, the reaction time is lower. If the reaction temperature is lower, the reaction time is higher. Illustratively, at a temperature above about 18° C., the reaction may take less than 2 hours; at a temperature below 18° C., the reaction may take more than 2 hours.

The conjugation reaction can be terminated by quenching, for example, by the addition of acetic acid.

In some embodiments, conjugation of the antibody with deferoxamine is performed to produce DFO-mAb conjugates. In some embodiments, conjugation of the antibody with p-SCN-Bn-deferoxamine is performed to produce DFO-mAb conjugates.

Exemplary solvents for the chelator include DMSO and DMA. Subsequent UFDF steps utilize membranes, and the membrane is chosen based on the solvent system used in the conjugation step. For example, DMA dissolves PES membranes, so the two could not be used in the same system.

Carbonate buffers are not preferred for stability of the conjugate during long term storage. Thus, once the antibody-chelator conjugates have been formed, they can be buffer exchanged into a buffer chosen specifically for long term storage and stability. Exemplary buffers include citrate, acetate, phosphate, arginine, and histidine buffers. A further UFDF step can be performed to remove residual salts and to provide a suitable concentration, excipient level, and pH of the conjugated monoclonal antibody. The resulting antibody-chelator conjugates can be sterile filtered and stored for subsequent formulation.

III. Methods of Using Radiolabeled Immunoconjugates

In certain aspects, the present disclosure provides diagnostic and therapeutic methods of use of the radiolabeled antibody conjugates of the present disclosure.

According to one aspect, the present disclosure provides methods of detecting PD-L1 in a tissue, the methods comprising administering a radiolabeled antibody conjugate of the provided herein to the tissue; and visualizing the PD-L1 expression by positron emission tomography (PET) imaging. In certain embodiments, the tissue comprises cells or cell lines. In certain embodiments, the tissue is present in a subject, wherein the subject is a mammal. In certain embodiments, the subject is a human subject. In certain embodiments, the subject has a disease or disorder selected from the group consisting of cancer, infectious disease and inflammatory disease. In one embodiment, the subject has cancer. In certain embodiments, the infectious disease is bacterial or viral infection caused by, for example, hepatitis B virus (HBV), hepatitis C virus (HCV), human immunodeficiency virus (HIV), and *Mycobacterium tuberculosis*.

According to one aspect, the present disclosure provides methods of imaging a tissue that expresses PD-L1 comprising administering a radiolabeled antibody conjugate of the present disclosure to the tissue; and visualizing the PD-L1 expression by positron emission tomography (PET) imaging. In one embodiment, the tissue is comprised in a tumor. In one embodiment, the tissue is comprised in a tumor cell culture or tumor cell line. In one embodiment, the tissue is comprised in a tumor lesion in a subject.

According to one aspect, the present disclosure provides methods for measuring response to a therapy, wherein the response to a therapy is measured by measuring inflammation. The methods, according to this aspect, comprise administering a radiolabeled antibody conjugate provided herein to a subject in need thereof and visualizing the PD-L1 expression by positron emission tomography (PET) imaging. In certain embodiments, the inflammation is present in a tumor in the subject. In certain embodiments, an increase in PD-L1 expression correlates to increase in inflammation in the tumor.

According to one aspect, the present disclosure provides methods for determining if a patient is suitable for anti-tumor therapy comprising an inhibitor of the PD-1/PD-L1 signaling axis, the methods comprising selecting a patient with a solid tumor, administering a radiolabeled antibody conjugate of the present disclosure, and localizing the administered radiolabeled antibody conjugate in the tumor by PET imaging wherein presence of the radiolabeled antibody conjugate in the tumor identifies the patient as suitable for anti-tumor therapy comprising an inhibitor of the PD-1/PD-L1 signaling axis.

According to one aspect, the present disclosure provides methods for identifying a candidate for anti-tumor therapy comprising an inhibitor of the PD-1/PD-L1 signaling axis, the methods comprising selecting a patient with a solid tumor, administering a radiolabeled antibody conjugate of the present disclosure, and localizing the administered radiolabeled antibody conjugate in the tumor by PET imaging wherein presence of the radiolabeled antibody conjugate in the tumor identifies the patient as suitable for anti-tumor therapy comprising an inhibitor of the PD-1/PD-L1 signaling axis.

According to one aspect, the present disclosure provides methods for predicting response of a patient to an anti-tumor therapy comprising an inhibitor of the PD-1/PD-L1 signaling axis, the methods comprising selecting a patient with a solid tumor, determining if the tumor is PD-L1-positive, wherein a positive response of the patient is predicted if the tumor is PD-L1-positive. In certain embodiments, the tumor is determined positive by administering a radiolabeled antibody conjugate of the present disclosure and localizing the radiolabeled antibody conjugate in the tumor by PET imaging wherein presence of the radiolabeled antibody conjugate in the tumor indicates that the tumor is PD-L1-positive.

According to one aspect, the present disclosure provides methods for detecting a PD-L1-positive tumor in a subject. The methods, according to this aspect, comprise selecting a subject with a solid tumor; administering a radiolabeled antibody conjugate of the present disclosure to the subject; and determining localization of the radiolabeled antibody conjugate by PET imaging, wherein presence of the radiolabeled antibody conjugate in a tumor indicates that the tumor is PD-L1-positive.

As used herein, the expression "a subject in need thereof" means a human or non-human mammal that exhibits one or more symptoms or indications of cancer, and/or who has been diagnosed with cancer, including a solid tumor and who needs treatment for the same. In many embodiments, the term "subject" may be interchangeably used with the term "patient". For example, a human subject may be diagnosed with a primary or a metastatic tumor and/or with one or more symptoms or indications including, but not limited to, unexplained weight loss, general weakness, persistent fatigue, loss of appetite, fever, night sweats, bone pain, shortness of breath, swollen abdomen, chest pain/pressure, enlargement of spleen, and elevation in the level of a cancer-related biomarker (e.g., CA125). The expression includes subjects with primary or established tumors. In specific embodiments, the expression includes human subjects that have and/or need treatment for a solid tumor, e.g., colon cancer, breast cancer, lung cancer, prostate cancer, skin cancer, liver cancer, bone cancer, ovarian cancer, cervical cancer, pancreatic cancer, head and neck cancer, and brain cancer. The term includes subjects with primary or metastatic tumors (advanced malignancies). In certain embodiments, the expression "a subject in need thereof" includes patients with a solid tumor that is resistant to or refractory to or is inadequately controlled by prior therapy (e.g., treatment with an anti-cancer agent). For example, the expression includes subjects who have been treated with one or more lines of prior therapy such as treatment with chemotherapy (e.g., carboplatin or docetaxel). In certain embodiments, the expression "a subject in need thereof" includes patients with a solid tumor which has been treated with one or more lines of prior therapy but which has subsequently relapsed or metastasized. In certain embodiments, the term includes subjects having an inflammatory disease or disorder including, but not limited to, cancer, rheumatoid arthritis, atherosclerosis, periodontitis, hay fever, heart disease, coronary artery disease, infectious disease, bronchitis, dermatitis, meningitis, asthma, tuberculosis, ulcerative colitis, Crohn's disease, inflammatory bowel disease, hepatitis, sinusitis, psoriasis, allergy, fibrosis, lupus, vasiculitis, ankylosing spondylitis, Graves' disease, Celiac disease, fibromyalgia, and transplant rejection.

In certain embodiments, the methods of the present disclosure are used in a subject with a solid tumor. The terms "tumor", "cancer" and "malignancy" are interchangeably used herein. As used herein, the term "solid tumor" refers to an abnormal mass of tissue that usually does not contain cysts or liquid areas. Solid tumors may be benign (not cancer) or malignant (cancer). For the purposes of the present disclosure, the term "solid tumor" means malignant solid tumors. The term includes different types of solid tumors named for the cell types that form them, viz. sarcomas, carcinomas and lymphomas. In certain embodiments, the term "solid tumor" includes cancers including, but not limited to, colorectal cancer, ovarian cancer, prostate cancer, breast cancer, brain cancer, cervical cancer, bladder cancer, anal cancer, uterine cancer, colon cancer, liver cancer, pancreatic cancer, lung cancer, endometrial cancer, bone cancer, testicular cancer, skin cancer, kidney cancer, stomach cancer, esophageal cancer, head and neck cancer, salivary gland cancer, and myeloma.

According to one aspect, the present disclosure provides methods of treating a tumor in a subject. The methods, according to this aspect, comprise selecting a subject with a solid tumor; determining that the tumor is PD-L1-positive; and administering one or more doses of an inhibitor of the PD-1/PD-L1 signaling axis. In certain embodiments, the tumor is determined to be PD-L1-positive by administering a radiolabeled antibody conjugate of the present disclosure to the subject; and visualizing the radiolabeled antibody conjugate in the tumor by PET imaging, wherein presence of the radiolabeled antibody conjugate in the tumor indicates that the tumor is PD-L1-positive.

As used herein, the terms "treat", "treating", or the like, mean to alleviate symptoms, eliminate the causation of symptoms either on a temporary or permanent basis, to delay or inhibit tumor growth, to reduce tumor cell load or tumor burden, to promote tumor regression, to cause tumor shrinkage, necrosis and/or disappearance, to prevent tumor recurrence, to prevent or inhibit metastasis, to inhibit metastatic tumor growth, and/or to increase duration of survival of the subject.

According to one aspect, the present disclosure provides methods for monitoring the efficacy of an anti-tumor therapy in a subject, wherein the methods comprise selecting a subject with a solid tumor wherein the subject is being treated with an anti-tumor therapy; administering a radiolabeled antibody conjugate of the present disclosure to the subject; imaging the localization of the administered radiolabeled conjugate in the tumor by PET imaging; and determining tumor growth, wherein a decrease from the baseline in radiolabeled signal indicates tumor regression and efficacy of the anti-tumor therapy. In certain embodiments, the anti-tumor therapy comprises an inhibitor of the PD-1/PD-L1 signaling axis (e.g., an anti-PD-1 antibody).

In certain embodiments, the present disclosure provides methods to assess changes in the inflammatory state of a tumor, the methods comprising selecting a subject with a solid tumor wherein the subject is being treated with an anti-tumor therapy; administering a radiolabeled antibody conjugate provided herein to the subject; and imaging the localization of the administered radiolabeled conjugate in the tumor by PET imaging, wherein an increase from the baseline in radiolabeled signal indicates increase in inflammation and efficacy of the anti-tumor therapy. In certain embodiments, the anti-tumor therapy comprises an inhibitor of the PD-1/PD-L1 signaling axis (e.g., an anti-PD-1 antibody).

As used herein, the term "baseline," with respect to the PD-L1 expression in the tumor, means the numerical value of uptake of the radiolabeled conjugate for a subject prior to or at the time of administration of a dose of anti-tumor therapy. The uptake of the radiolabeled conjugate is determined using methods known in the art (see, for example, Oosting et al 2015, J. Nucl. Med. 56:63-69). In certain embodiments, the anti-tumor therapy comprises an inhibitor of the PD-1/PD-L1 signaling axis.

To determine whether there is tumor regression, the uptake of the radiolabeled conjugate is quantified at baseline and at one or more time points after administration of the inhibitor of the PD-1/PD-L1 signaling axis (e.g., an anti-PD-1 antibody). For example, the uptake of the administered radiolabeled antibody conjugate (e.g., radiolabeled anti-PD-L1 antibody conjugate) may be measured at day 2, day 3, day 4, day 5, day 6, day 7, day 8, day 9, day 10, day 11, day 12, day 14, day 15, day 22, day 25, day 29, day 36, day 43, day 50, day 57, day 64, day 71, day 85; or at the end of week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with the inhibitor of the PD-1/PD-L1 signaling axis (e.g., an anti-PD-1 antibody). The difference between the value of the uptake at a particular time point following initiation of treatment and the value of the uptake at baseline is used to establish whether there has been a difference in amount of tumor tissue (tumor regression or progression). For example, a decrease from baseline in the uptake upon treatment with at least one dose of the inhibitor of the PD-1/PD-L1 signaling axis means tumor regression and indicates efficacy of the anti-tumor therapy.

In certain embodiments, the radiolabeled antibody conjugate is administered intravenously or subcutaneously to the subject. In certain embodiments, the radiolabeled antibody conjugate is administered intra-tumorally. Upon administration, the radiolabeled antibody conjugate is localized in the tumor. The localized radiolabeled antibody conjugate is imaged by PET imaging and the uptake of the radiolabeled antibody conjugate by the tumor is measured by methods known in the art. In certain embodiments, the imaging is carried out 1, 2, 3, 4, 5, 6 or 7 days after administration of the radiolabeled conjugate. In certain embodiments, the imaging is carried out on the same day upon administration of the radiolabeled antibody conjugate.

In certain embodiments, the antibody or antigen-binding fragment thereof that binds specifically to PD-L1. In certain embodiments, the anti-PD-L1 antibody comprises the CDRs of a HCVR, wherein the HCVR has an amino acid sequence selected from the group consisting of SEQ ID NOs: 2, 34, 50, 82, 98, 146, 162, 178, 186, 234, 250, 290, 306, 314, and 330; and the CDRs of a LCVR, wherein the LCVR has an amino acid sequence selected from the group consisting of SEQ ID NOs: 10, 42, 58, 90, 106, 154, 170, 194, 242, 258, and 274.

In certain embodiments, the inhibitor of the PD-1/PD-L1 signaling axis comprises an antibody or antigen-binding fragment thereof that binds specifically to PD-1. In certain embodiments, the anti-PD-1 antibody is selected from the group consisting of nivolumab, pembrolizumab and REGN2810. In certain other embodiments, the inhibitor of the PD-1/PD-L1 signaling axis comprises an antibody or antigen-binding fragment thereof that binds specifically to PD-L1. In one embodiment, the anti-PD-L1 antibody is atezolizumab. In one embodiment, the anti-PD-L1 antibody comprises an HCVR of SEQ ID NO: 82 and a LCVR of SEQ ID NO: 90.

IV. Examples

Certain embodiments of the disclosure are illustrated by the following non-limiting examples.

Example 1: Generation of Human Antibodies to PD-L1

Human anti PD-L1 antibodies, including those listed in Table 1, were prepared and characterized as described in US Patent Publication No. US 2015-0203580 A1, which is incorporated herein by reference in its entirety. In brief, human antibodies to PD-L1 were generated using a fragment of PD-L1 that ranges from about amino acids 19-239 of PD-L1 (Genbank Accession No. NP_054862.1). The immunogen was administered directly, with an adjuvant to stimulate the immune response, to a VELOCIMMUNE® mouse comprising DNA encoding human Immunoglobulin heavy and kappa light chain variable regions. The antibody immune response was monitored by a PD-L1-specific immunoassay. When a desired immune response was achieved splenocytes were harvested and fused with mouse myeloma cells to preserve their viability and form hybridoma cell lines. The hybridoma cell lines were screened and selected to identify cell lines that produce PD-L1-specific antibodies. Using this technique, and the immunogen described above, several anti-PD-L1 chimeric antibodies (i.e., antibodies possessing human variable domains and mouse constant domains) were obtained; exemplary antibodies generated in this manner were designated as H2M8306N, H2M8307N, H2M8309N, H2M8310N, H2M8312N, H2M8314N, H2M8316N, H2M8317N, H2M8321N, H2M8323N, H2M8718N, H2M8718N2, and H2M8719N.

Anti-PD-L1 antibodies were also isolated directly from antigen-positive B cells without fusion to myeloma cells, as described in U.S. 2007/0280945A1, herein specifically incorporated by reference in its entirety. Using this method, several fully human anti-PD-L1 antibodies (i.e., antibodies possessing human variable domains and human constant domains) were obtained; exemplary antibodies generated in this manner were designated as follows: H1H9323P, H1H9327P, H1H9329P, H1H9336P, H1H9344P2, H1H9345P2, H1H9351P2, H1H9354P2, H1H9364P2, H1H9373P2, H1H9382P2, H1H9387P2, and H1H9396P2.

Example 2: Conjugation of anti-PD-L1 antibody H4H8314N with p-SCN-Bn-DFO

In order to modify the parental anti-PD-L1 antibody, H4H8314N, and an isotype control antibody to be suitable for ImmunoPET studies with radiolabeling, a chelator, p-SCN-bn-Deferoxamine (DFO; Macrocyclics, Cat #: B-705), was attached to the antibodies.

For the modification, H4H8314N was first buffer exchanged into PBS, pH 7.2 from histidine buffer by dialysis at 4° C. overnight (Slide-A-Lyzer Dialysis Cassette G2 10k MWCO; ThermoScientific) then buffer exchanged again using a PD-10 column (GE Healthcare, Cat. #: 17-0851-01) into a buffer composed of 50 mM carbonate buffer, 150 mM NaCl, pH 9.0 (conjugation buffer). To determine the concentration following the buffer exchanges, the samples were measured on a Nanodrop 2000 UV/VIS spectrometer (Thermo Scientific) using the MacVector sequence based extinction coefficient of 1.46 g/L (see Table 2). In 15 a mL polypropylene tube, 773.9 uL of H4H8314N (12.5 mg) was added to 1676.1 uL of conjugation buffer. In a separate vial, 29.3 uL of DMSO was added to 20.7 uL of DFO. In one-quarter increments, this DFO solution was added to the H1H8314N solution, each time gently being mixed by pipetting up-and-down. The final solution was 5 mg/mL H4H8314N in conjugation buffer, 2% DMSO with 6-fold mole-to-mole excess of DFO. This solution was allowed to incubate in a 37° C. water bath with no additional stirring.

After 30 minutes at 37° C., the solution was promptly passed through a PD-10 desalting column (GE Healthcare, Cat. #: 17-0851-01), pre-equilibrated with a buffer containing 250 mM NaAcO at pH 5.4 (formulation buffer). The final solution was sterile-filtered via a syringe filter (Acrodisc 13 mm syringe filter, Pall Corporation, Cat #: 4602). The concentration and DFO-to-Antibody Ratio (DAR) was subsequently measured by UV/VIS spectroscopy. For the absorbance measurement, the DFO-conjugated antibody was measured against the formulation buffer at 252 nm (A252), 280 nm (A280) and 600 nm (A600). For the calculation, the background was corrected at each absorbance value using the equation:

$$A'_\lambda = A_\lambda - A_{600}$$

The antibody conjugate was tested for aggregation using SEC chromatography, with 25 μg of the sample injected onto a Superdex 200 column (GE Healthcare, Cat. No. 17-5175-01) monitored at 280 nm with a PBS mobile phase (0.75 mL/min). The antibody integrity was evaluated by SDS-PAGE 4-20% Tris/Gly pre-cast gel (Novex) with 2 μg of the sample loaded. The gel is shown in FIG. 1. The antibody concentration, conjugate concentration, and DAR were calculated using the equations below:

Antibody Concentration Calculation $$ConcmAb\,(\text{mg/mL}) = \frac{A'_{280}}{\epsilon_{280}}$$

Conjugate Concentration Calculation $$Conc\ \text{conjugate}\,(\text{mg/mL}) = \frac{A'_{252} - 1.53A'_{280}}{\epsilon_{252} - 1.53\epsilon_{280}}$$

DAR Calculation $$DAR = \frac{\epsilon_{252}A'_{280} - \epsilon_{280}A'_{252}}{18800A'_{252} - 28700A'_{280}}$$

TABLE 2

Molar extinction coefficients and molecular weight

| Antibody | MW (g mol$^{-1}$) | $\epsilon$280 (L g$^{-1}$cm$^{-1}$) | $\epsilon$252 (L g$^{-1}$cm$^{-1}$) |
|---|---|---|---|
| H4H8314N | 144984 | 1.46 | 0.553 |

TABLE 3

UV DAR, percent aggregate and concentration post DFO-attachment

| Antibody | UV DAR | Concentration (mg/mL) | % aggregate |
|---|---|---|---|
| H4H8314N | 1.2 | 3.34 | <1% |

Example 3: $^{89}$Zr Chelation of DFO Conjugated Monoclonal Antibodies

For use in ImmunoPET in vivo studies, the DFO-conjugated anti-PD-L1 antibody, H4H8314N, and a DFO-conjugated isotype control antibody were radiolabeled with $^{89}$Zr.

DFO-conjugated antibody (250 or 750 ug) was first brought to 1.25 mg/ml in 1 M HEPES, pH 7.2. The recipe matography) to determine radiolabeling reaction yield and the remaining reaction mixtures were transferred to pre-equilibrated PD-10 columns (Vendor) with 250 mM sodium acetate at pH 5.4 for gravity fed desalting. Each PD-10 column took no more than 1.2 mL of reaction mixture (otherwise multiple columns were used). After the contents of the reaction entered the column bed, 1.6 mL of 250 mM sodium acetate at pH 5.4 (formulation buffer) was added; the flow through was discarded. An additional 1.8 mL of formulation buffer was added to the column, and the eluate was collected from each column. Next, approximately 500 μL of each solution was analyzed using a Nanodrop spectrophotometer (ThermoScientific). The final Ab concentration was calculated using the appropriate extinction coefficient and the absorption at 280 nm using the equation:

Concentration in mg/mL = Absorption at 280 nm ÷ Extinction coefficient at 280 nm (found in Table 6)

The final mass measured in grams was recorded in Table 4. The radioactivity was then measured using the dose calibrator and reported in Table 5. The final material along with the material prior to the PD-10 column treatment, were then analyzed by iTLC. For this assay, 1 μL of each solution was added to the iTLC-SG-Glass microfiber chromatography paper impregnated with silica gel (Agilent Technologies, Cat #SG10001), developed in a TLC chamber with 20 mM citric acid buffer solution. The final material was also analyzed using a SEC-HPLC with UV 280 and radioisotope detector connected in series (Agilent 1260 with Lablogic Radio-TLC/HPLC Detector, SCAN-RAM) using a Superdex 200 column with PBS mobile phase at a flow rate of 0.75 mL/min. The radiotrace was used for the determining radiochemical purity by comparing the integration of the protein peak (~10 to 16 min) and free $^{89}$Zr peak (~ 25 min). The monomeric purity was determined by comparing the integration of the oligomeric peak (10 min to ~ 15 min) to the monomer (~16 min).

The specific activity and protein recovery (%) of each radiolabeled conjugate was determined using the following equations:

a. Mass of conjugate in mg = concentration in mg/mL × mass of solution in grams b. Specific activitiy in mCi/mg = activity of vial in mCi ÷ mass of conjugate in mg c. Protein recovery = starting conjugate mass (mg) ÷ Mass of conjugate in mg of DFO-Ab conjugate solution for each study is listed in Table 4. Separately, $^{89}$Zr solution was prepared using the recipe for each corresponding study shown in Table 5. Stock $^{89}$Zr-oxalic acid solution was obtained from PerkinElmer or 3D Imaging. If the radioactivity concentration of the stock solution was low (see Table 5), a neutralization step was performed with 1 M borate, pH 9.0. The final radioactivity of the solution was first confirmed using a Capintec CRC-25R dose calibrator (Capintec #520), then immediately combined with the DFO-Ab conjugate solution, gently mixed (pipetting up-and-down) and subsequently incubated for 45 minutes at room temperature.

After the incubation, a small sample of each reaction mixture was taken for iTLC (instant thin layer liquid chro- Finally the appearance was noted and recorded in Table 7. Both UV280 and iTLC traces were performed on purified product.

Figure 2A:
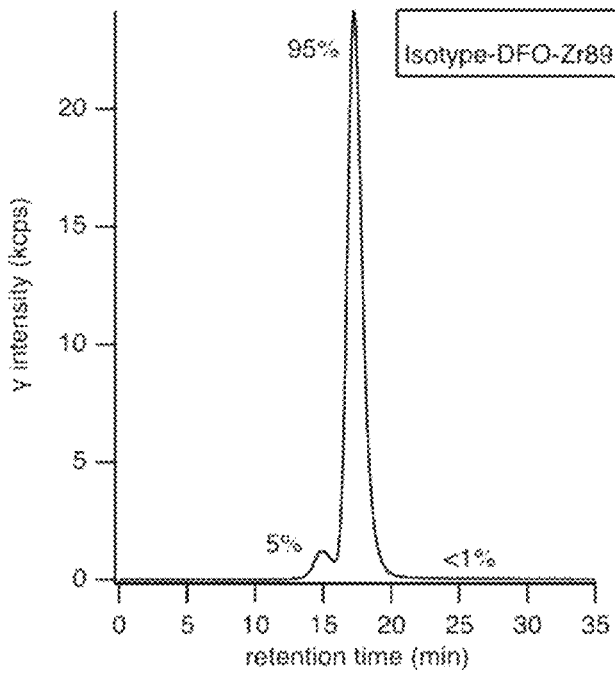
FIGS. 2A and 2B depict radio-SEC-HPLC after $^{89}$Zr radiolabeling for Study 1.
Figure 2B:
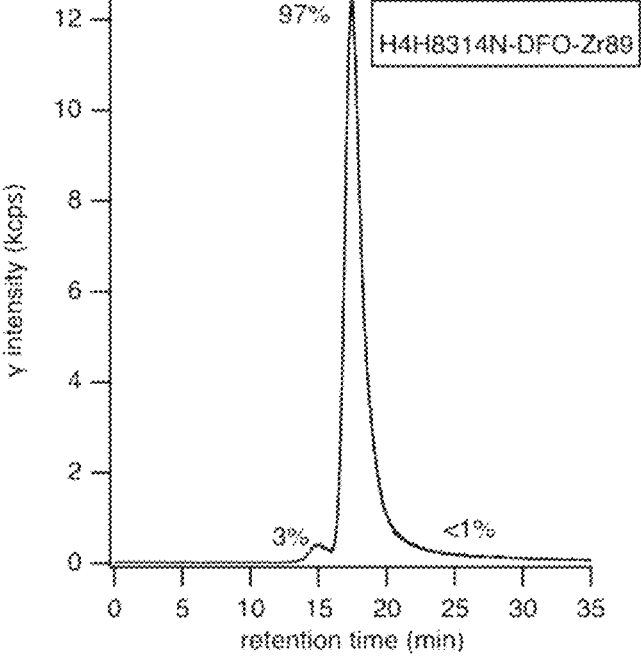
Figure 3:
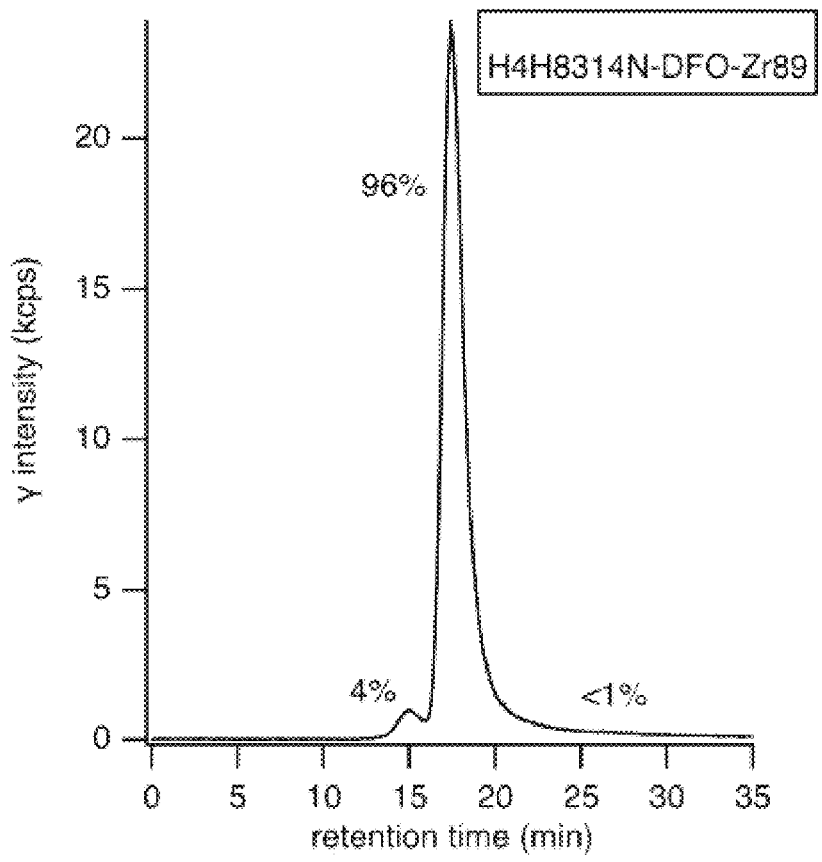
FIG. 3 depicts radio-SEC-HPLC of DFO-conjugate (anti-PD-L1) after $^{89}$Zr radiolabeling for Study 2.
Figure 4:
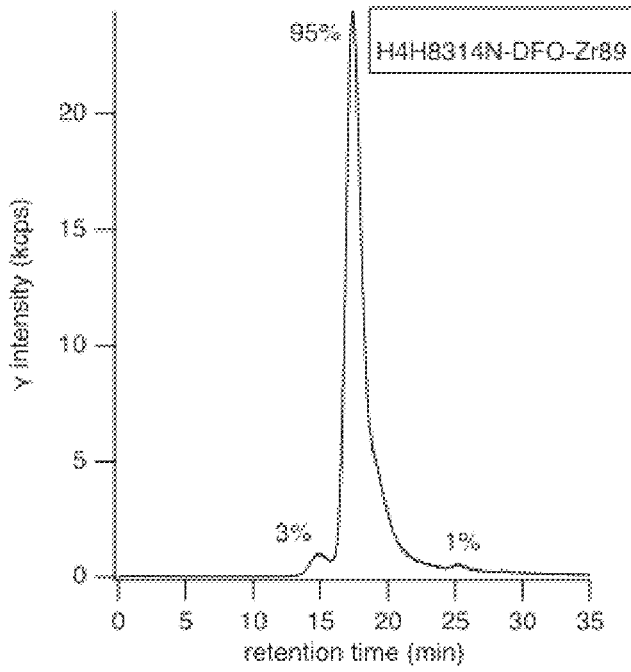
FIG. 4 depicts radio-SEC-HPLC SEC after $^{89}$Zr radiolabeling Study 3.
Figure 5A:
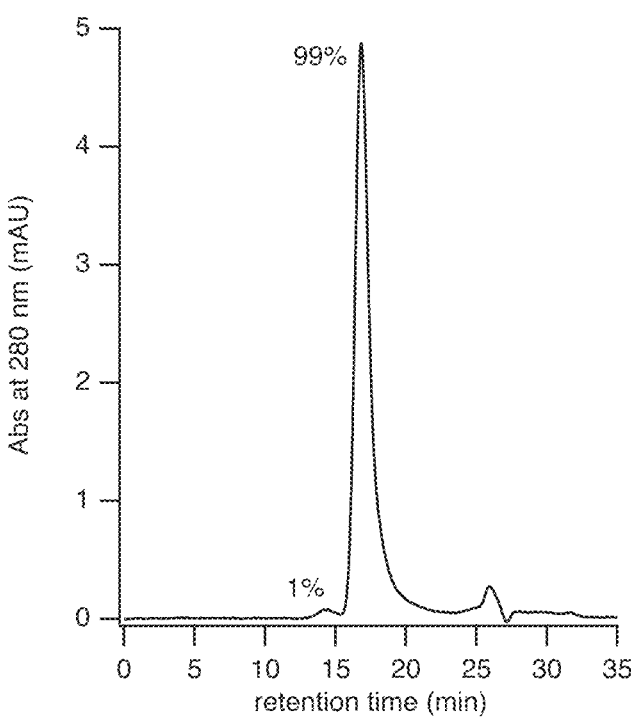
FIG. 5A depicts UV280-SEC-HPLC chromatogram and FIG. 5B depicts radio-iTLC trace after $^{89}$Zr radiolabeling for Study 1.
Figure 5B:
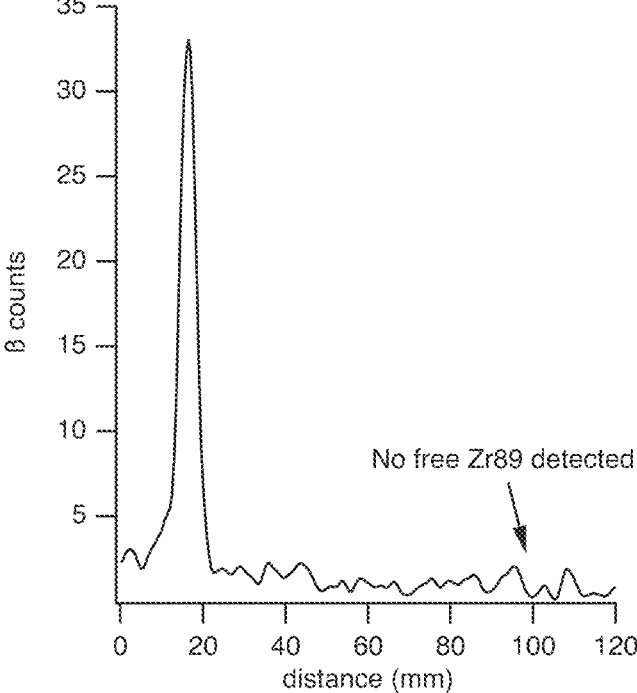
Figure 6A:
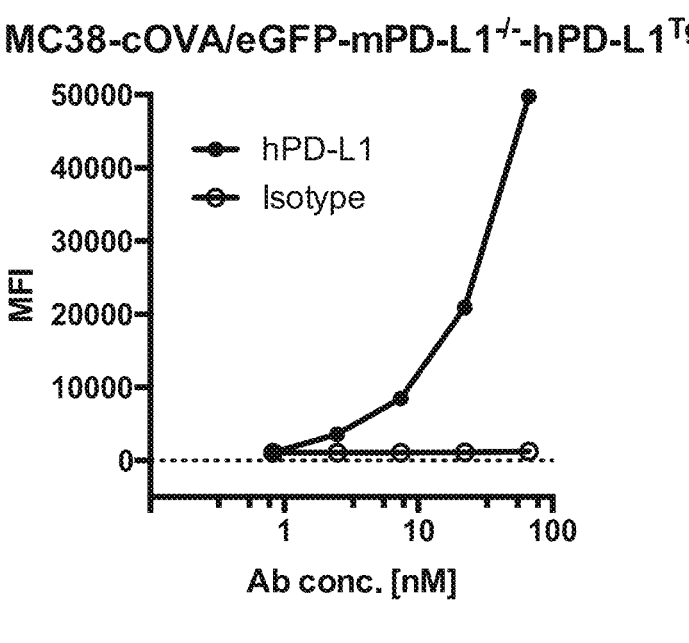
FIGS. 6A, 6B, 6C, and 6D shows hPD-L1 expression by tumor cell lines MC38-cOVA/eGFP-mPD-L1-/-hPD-L1$^{Tg}$ (FIG. 6A), LOX-IMVI (FIG. 6B), MDA-MB-231 (FIG. 6C), and SK-Br-3 (FIG. 6D) in vitro, as described in Example 5 herein.
Figure 6B:
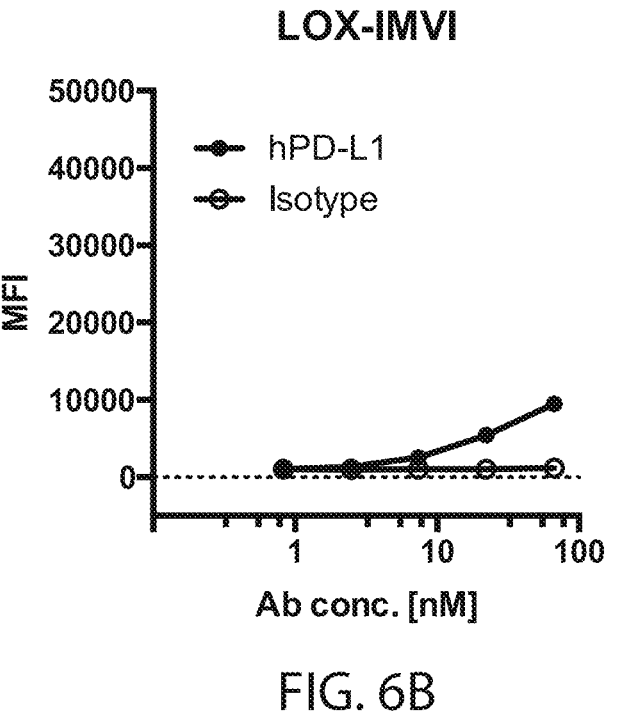
Figure 6C:
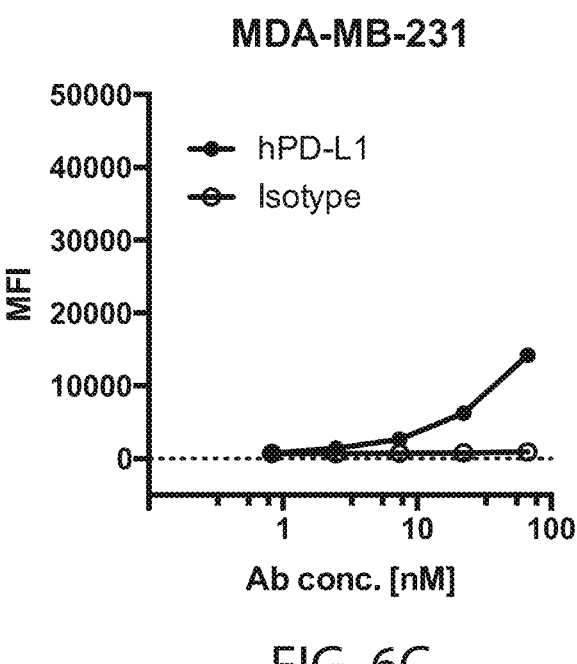
Figure 6D:
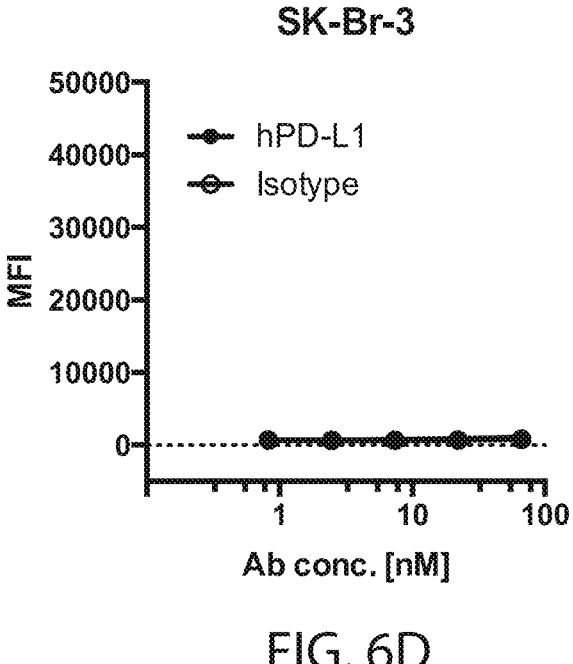

The results are consolidated in Table 7. The radio-SEC-HPLC chromatograms are shown in FIGS. 2-4. An example of UV280 HPLC SEC chromatogram and radio-iTLC is shown in FIG. 5 for the $^{89}$Zr radiolabeling, Study 1. The UV280-HPLC SEC chromatogram confirms the highly monomeric product (99%). The radio-iTLC trace was processed with a 7-point binomial smoothing function. The origin and solvent front was approximately 16 and 100 mm, respectively. No detectable $^{89}$Zr was observed beyond 22 mm and corroborates the radiochemical purity determined by radio-SEC-HPLC SEC in FIG. 2B.

TABLE 4

DFO-antibody conjugate preparation for radiolabeling

| Radio-labeling # | Study # | Radiolabeling Lots | Concentration (mg/mL) | DAR * | Conjugate mass (mg) | Total volume (uL) | Final Concentration (mg/mL) |
|---|---|---|---|---|---|---|---|
| 1 | 1 | Isotype-DFO-$^{89}$Zr | 3.7 | 1.6 | 250 | 200 | 1.25 |
| 2 | 1 | H4H8314N-DFO-$^{89}$Zr | 3.34 | 1.2 | 250 | 200 | 1.25 |
| 3 | 2 | H4H8314N-DFO-$^{89}$Zr | 3.34 | 1.2 | 750 | 600 | 1.25 |
| 4 | 3 | Isotype-DFO-$^{89}$Zr | 3.7 | 1.6 | 250 | 200 | 1.25 |
| 5 | 3 | H4H8314N-DFO-$^{89}$Zr | 3.34 | 1.2 | 250 | 200 | 1.25 |

* DAR is defined as the DFO to Antibody Ratio

TABLE 5

$^{89}$Zr reaction solution preparation for radiolabeling

| Radio-labeling | Study # | Radiolabeling Lots | $^{89}$Zr-oxalate (uL) | Add'l 1 M oxalic acid added (uL) | 1 M borate, pH 9.0 added (uL) | 1 M HEPES, pH 7.2 (uL) | Final Vol (uL) | Final Activity (uCi) | Specific Activity (uCi/uL) |
|---|---|---|---|---|---|---|---|---|---|
| 1 | 1 | Isotype-DFO-$^{89}$Zr | 50 | 50 | 400 | 500 | 1000 | 1009 | 1.01 |
| 2 | 1 | H4H8314N-DFO-$^{89}$Zr | 50 | 50 | 400 | 500 | 1000 | 1000 | 1 |
| 3 | 2 | H4H8314N-DFO-$^{89}$Zr | 150 | 150 | 1200 | 1500 | 3000 | 3070 | 1.02 |
| 4 | 3 | Isotype-DFO-$^{89}$Zr | ~1 | 0 | 0 | 1000 | 1000 | 1680 | 1.68 |
| 5 | 3 | H4H8314N-DFO-$^{89}$Zr | ~1 | 0 | 0 | 1000 | 1000 | 1640 | 1.64 |

TABLE 6

Extinction coefficients for conjugate lots

| Radiolabeling Lot | $\varepsilon_{280}$ (AU ml mg$^{-1}$ cm$^{-1}$) |
|---|---|
| Isotype-DFO-$^{89}$Zr | 1.71 |
| H4H8314N-DFO-$^{89}$Zr | 1.61 |

40

45

TABLE 7

Summary of $^{89}$Zr labeled DFO-Ab conjugates for in vivo imaging and biodistribution studies

| Radio-labeling | Study # | Conjugate Lots | Appea-rance | Radio-chemical Purity* (%) | Mono-meric Purity* (%) | Protein Recovery (%) | Conc. (mg/mL) | Specific Activity (mCi/mg) |
|---|---|---|---|---|---|---|---|---|
| 1 | 1 | Isotype-DFO-$^{89}$Zr | Clear | >99% | >95% | 60% | 0.106 | 3.35 |
| 2 | 1 | H4H8341N-DFO-$^{89}$Zr | Clear | >99% | >95% | 63% | 0.121 | 2.75 |
| 3 | 2 | H4H8341N-DFO-$^{89}$Zr | Clear | >99% | >95% | 62% | 0.134 | 3.58 |
| 4 | 3 | Isotype-DFO-$^{89}$Zr | Clear | >99% | >95% | 66% | 0.074 | 5.38 |

TABLE 7-continued

Summary of [89]Zr labeled DFO-Ab conjugates for in vivo imaging and biodistribution studies

| Radio-labeling | Study # | Conjugate Lots | Appea-r-ance | Radio-chemical Purity* (%) | Mono-meric Purity* (%) | Protein Recovery (%) | Conc. (mg/mL) | Specific Activity (mCi/mg) |
|---|---|---|---|---|---|---|---|---|
| 5 | 3 | H4H8341N-DFO-[89]Zr | Clear | >99% | >95% | 74% | 0.084 | 5.13 |

*by radio-SEC-HPLC

Example 4: Immunoreactivity

The immunoreactivity (IR) of the radiolabeled anti-PD-L1 antibody and isotype control antibody was measured as follows. For the initial studies, MC38-cOVA/eGFP-mPD-L1/hPD-L1[Tg] cells were used and subsequently LOX-IMVI cells (see detailed description of cell lines in Example 5) were also used in the later study. In these assays, 20 ng of the respective [89]Zr labeled antibodies were added to $15 \times 10^6$ MC38-cOVA/eGFP-mPD-L1[-/-]hPD-L1[Tg] or $30 \times 10^6$ LOX-IMVI cells in a final volume of 1 mL. Samples were incubated for 45 minutes with continuous mixing before undergoing 3 washes with media to remove any unbound antibody. The radioactivity of the test cell pellets was then counted in an automatic gamma counter (Wizard 2470, Perkin Elmer) against 2 reference standards containing the same 20 ng of [89]Zr labeled antibody. The percentage immunoreactivity was determined for the samples using the average of the standards as a measure of total activity.

As seen in Table 8, 89Zr labeled anti-PD-L1 antibody retained immunoreactivity following conjugation and radio-labeling, with % IR ranging from 88 to 98% across the studies. The specificity of binding is apparent in the control antibodies having a background % IR of less than 1%.

Gene® technology (Valenzuela et al 2003, Nat. Biotechnol. 21:652-659; US Patent Application Publication US2016/0157469).

Cell lines used in these studies include: 1) a murine colon carcinoma cell line MC38 (obtained from NCI at Frederick, MD, Laboratory of Tumor Immunology and Biology), which has been engineered in house to knock out murine PD-L1, but over-express full-length human PD-L1 and full-length chicken ovalbumin fused with eGFP, thus referred here as MC38-cOVA/eGFP-mPD-L1[-/-]hPD-L1[Tg]; 2) several human tumor cell lines: human melanoma cell line LOX-IMVI (endogenous PD-L1 positive line, obtained from NCI at Frederick, MD, Division of Cancer Treatment and Diagnosis, Tumor Repository), human breast cancer cell lines MDA-MB-231 (endogenous PD-L1 positive line) and SK-Br-3 (PD-L1 negative cell line) (both obtained from ATCC). In some cases, human PD-L1 was directly evaluated without any induction in vitro; in some cases, human PD-L1 expression was evaluated with overnight murine or human IFNγ (100 ng/ml) treatment (obtained from Peprotech); in some cases, human PD-L1 was evaluated ex vivo on enzy-matically dissociated tumor cells extracted from tumor bear-ing nude mice or humanized mice. All surface staining of human PD-L1 was performed following a standard protocol.

TABLE 8

Immunoreactivity of [89]Zr chelated DFO-conjugates

| Study | Study 1 | | Study 2 | | Study 3 | | | |
|---|---|---|---|---|---|---|---|---|
| Cell Line | MC38-cOVA/eGFP-mPD-L1[-/-]hPD-L1[Tg] | | MC38-cOVA/eGFP-mPD-L1[-/-]hPD-L1[Tg] | | MC38-cOVA/eGFP-mPD-L1[-/-]hPD-L1[Tg] | | LOX-IMVI | |
| Antibody | [89]Zr-Anti-PD-L1 | [89]Zr-Control | [89]Zr-Anti-PD-L1 | [89]Zr-Control | [89]Zr-Anti-PD-L1 | [89]Zr-Control | [89]Zr-Anti-PD-L1 | [89]Zr-Control |
| Cell pellet activity | 4048.4 | 29.6 | 8311.9 | na | 6262.4 | 68 | 5587.54 | 65.4 |
| Average Standard activity | 4536.5 | 6432.4 | 8567.2 | na | 6386.6 | 9544.8 | 6386.6 | 9544.8 |
| Percent IR | 89.2 | 0.5 | 97.0 | na | 98.1 | 0.7 | 87.5 | 0.7 |

Example 5: In Vitro and Ex Vivo Characterization of Human PD-L1 Expression on Tumor Cell Lines Several tumor cell lines were studied to evaluate the expression level of human PD-L1, aiming at the detection of human PD-L1 expressed endogenously by tumors in vivo in either male NCr nude (Taconic, Hudson NY) mice or in mice that were engineered to be homozygous for the expression of the extracellular domain of human PD-L1 in place of extracellular domain of mouse PD-L1 (PD-L1 HumIn mice) on a 75% C57/Bl6/25% 129 strain background using Veloci- Briefly, tumor cells were washed with PBS once, washed with ice cold staining buffer once, stained with commercial available fluorochrome directly conjugated anti-human PD-L1 antibody (eBioscience, clone MIH1) in staining buffer for 30 minutes on ice in the dark, and then washed with 2 mL of PBS once again. Fixable dye eFluor506 was also included following manufacturer's protocol (eBiosci-ence, Cat #17-5983). Samples were acquired on BD FACSCanto II™ IVD10 equipped with DIVA v8. Data were further analyzed with FlowJo v10.0.6 or above.

PD-L1 expression by MC38-cOVA/eGFP-mPD-L1$^{-/-}$ hPD-L1$^{Tg}$ cells prior to implantation and seven days post implantation in nude mice is shown in Table 9.

TABLE 9

| | | | |
|---|---|---|---|
| Percentage of human PD-L1 positive MC38-cOVA/eGFP-mPD-L1$^{-/-}$hPD-L1$^{Tg}$ cells prior to implantation and 7 days post implantation in nude mice | | | |
| | Isotype staining | hPD-L1 staining | |
| Prior to implantation | 0.6% | 94.7% | |
| Post implantation | 1.09% | 74.0% | |

Prior to implantation, a vast majority of MC38-cOVA/eGFP-mPD-L1$^{-/-}$hPD-L1$^{Tg}$ cells were human PD-L1 positive, compared to isotype control staining. Seven days post implantation in nude mice and upon enzymatic and mechanical processing for tumor dissociation, ~70% of MC38-cOVA/eGFP-mPD-L1$^{-/-}$hPD-L1$^{Tg}$ cells were still human PD-L1 positive.

PD-L1 expression by MC38-cOVA/eGFP-mPD-L1$^{-/-}$ hPD-L1$^{Tg}$ cells prior to implantation and fourteen days post implantation in PD-L1 humanized mice is shown in Table 10.

TABLE 10

| | | |
|---|---|---|
| Percentage of human PD-L1 positive MC38-cOVA/eGFP-mPD-L1$^{-/-}$hPD-L1$^{Tg}$ cells prior to implantation and 14 days post implantation in PD-L1 humanized mice | | |
| | Isotype staining | hPD-L1 staining |
| Prior to implantation | 0.2% | 92.5% |
| Post implantation | 3.6 | 46.2% |

Prior to implantation, a vast majority of MC38-cOVA/eGFP-mPD-L1$^{-/-}$hPD-L1$^{Tg}$ cells were human PD-L1 positive, compared to isotype control staining. Fourteen days post implantation in PD-1/PD-L1 double humanized mice and upon enzymatic and mechanical processing for tumor dissociation; ~50% of MC38-cOVA/eGFP-mPD-L1$^{-/-}$hPD-L1$^{Tg}$ cells were still human PD-L1 positive.

PD-L1 expression by multiple tumor cell lines in vitro is shown in FIG. 6. To evaluate how comparable the expression level of PD-L1 by the engineered cell line (MC38-cOVA/eGFP-mPD-L1$^{-/-}$hPD-L1$^{Tg}$) and other human tumor cell lines (LOX-IMVI melanoma cells, MDA-MB-231 breast cancer cells, and SK-Br-3 breast cancer cells) was, dose titration of anti-PD-L1 antibody staining was performed. FIG. 6 illustrates that MC38-cOVA/eGFP-mPD-L1$^{-/-}$hPD-L1$^{Tg}$ had the highest level of human PD-L1 expression (FIG. 6A) and SK-Br-3 had the lowest expression with no PD-L1 detectable (FIG. 6D), whereas PD-L1 expression by LOX-IMVI and MDA-MB-231 was moderate (about 5 times lower than MC38-cOVA/eGFP-mPD-L1$^{-/-}$hPD-L1$^{Tg}$) (FIGS. 6B and 6C).

Figure 7:
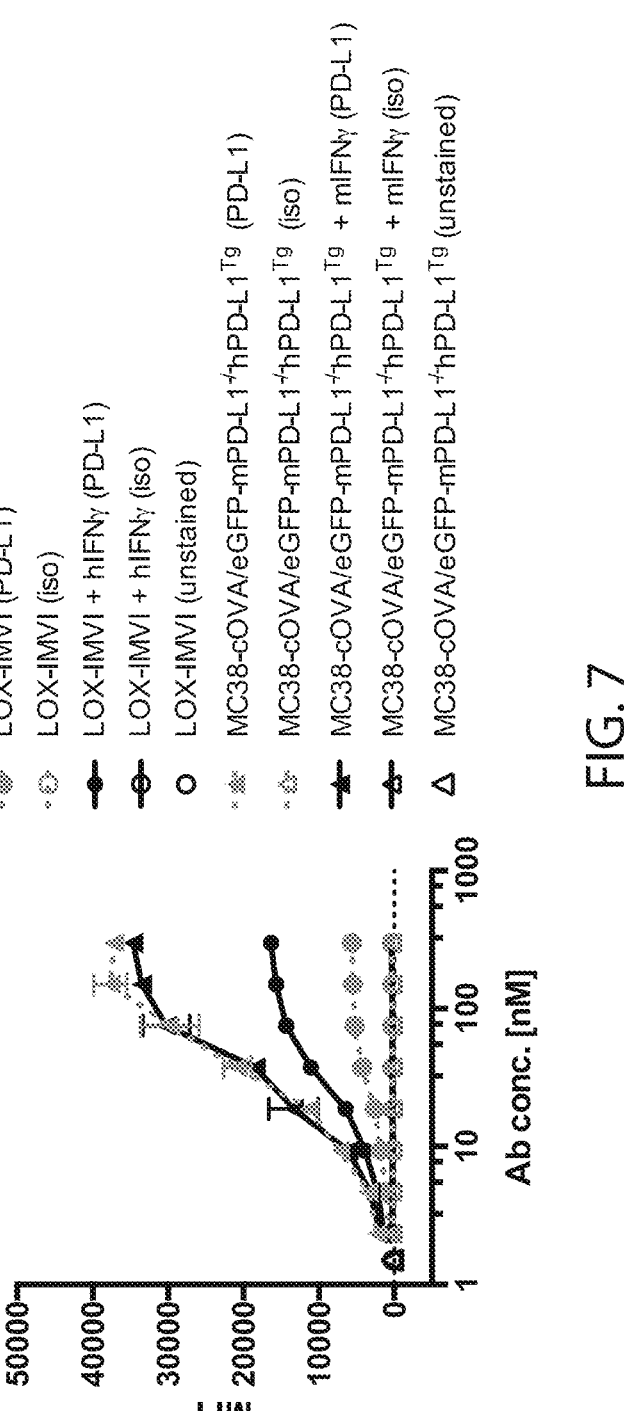
FIG. 7 shows hPD-L1 expression by MC38-cOVA/eGFP-mPD-L1-/-hPD-L1$^{Tg}$ and LOX-IMVI tumor cells with or without interferon-gamma treatment in vitro in a second experiment, as described in Example 5 herein.
Figure 8A:
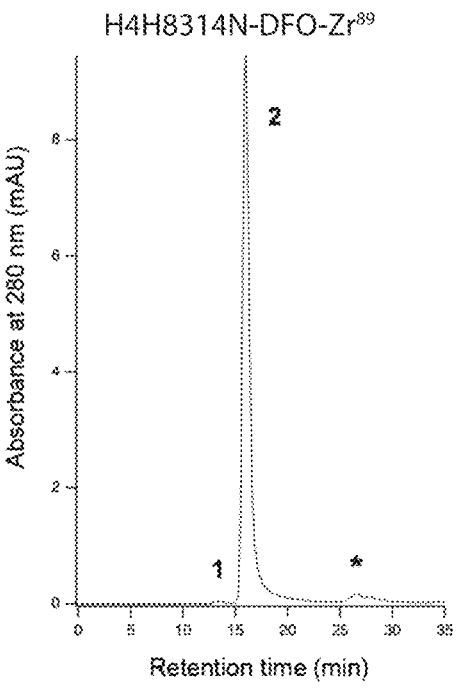
FIGS. 8A, 8B, 8C, 8D, 8E, and 8F depict chromatograms generated by SEC-HPLC analysis using samples from radio-immunoconjugate preparations of $^{89}$Zr-DFO-anti-PD-L1 antibody conjugate for studies shown in FIG. 8A, FIG. 8B, FIG. 8D, and FIG. 8E, and of isotype control radioimmunoconjugate $^{89}$Zr-DFO-IgG4$^P$ for studies shown in FIG. 8C and FIG. 8F. Chromatograms for absorbance at 280 nm are shown in FIG. 8A-FIG. 8C and radio-chromatograms for intensity of γ-emission are shown in FIG. 8D-FIG. 8F.
Figure 8B:
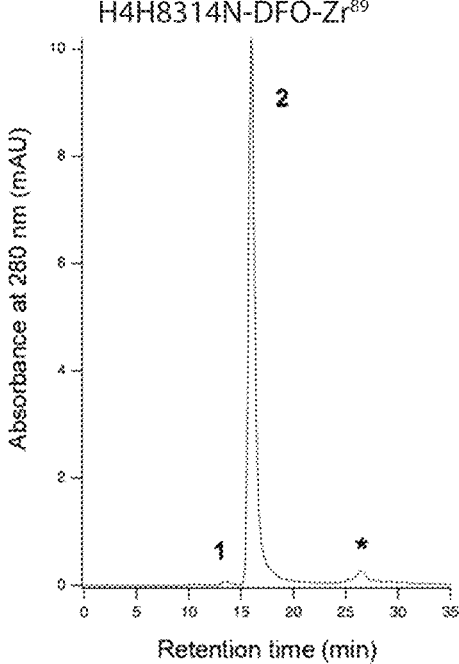
Figure 8C:
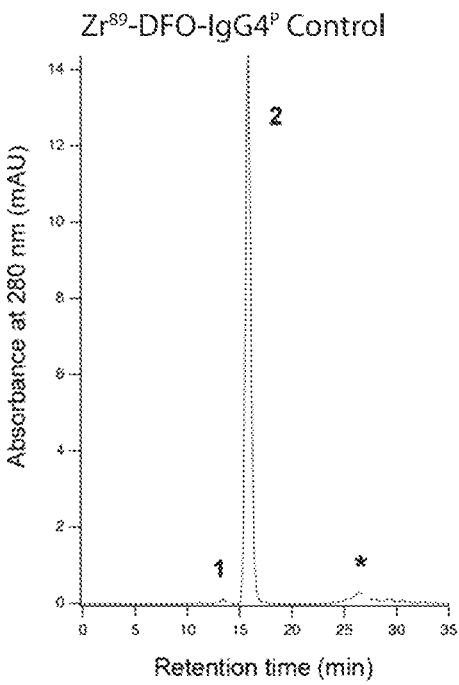
Figure 8D:
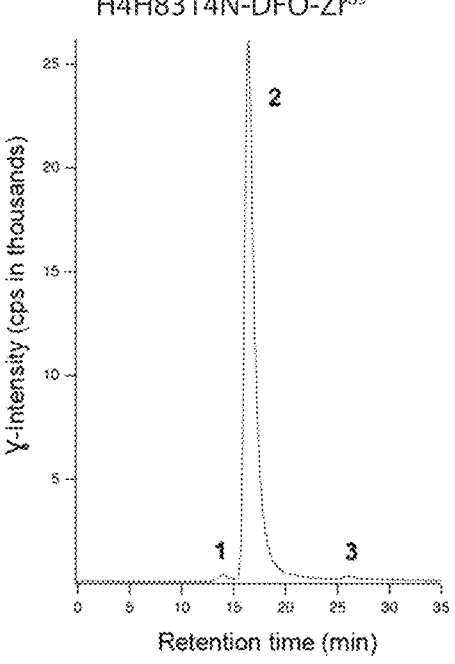
Figure 8E:
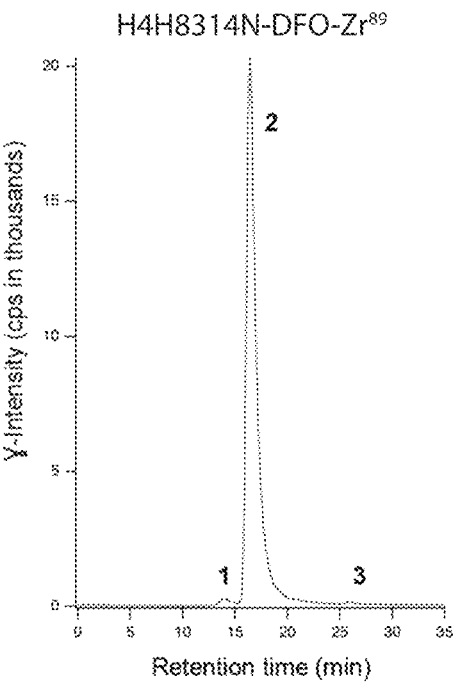
Figure 8F:
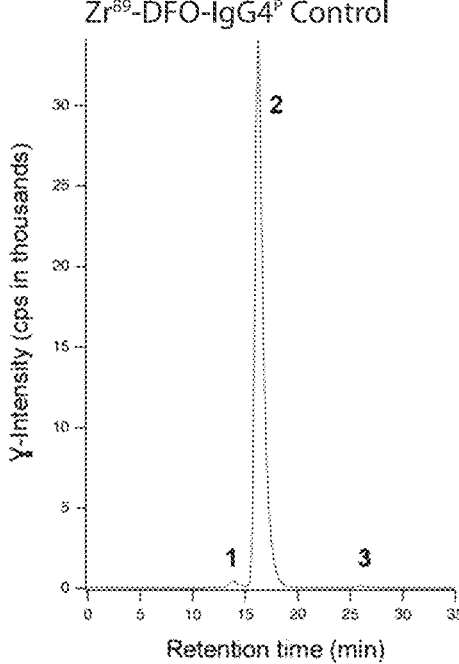

In a second experiment, further comparison between LOX-IMVI and MC38-cOVA/eGFP-mPD-L1$^{-/-}$hPD-L1$^{Tg}$ was done with or without in vitro treatment by 100 ng/ml of hIFNy/mIFNY overnight, respectively. FIG. 7 illustrated that median fluorescence intensity of PD-L1 reached the plateau at ~150 nM of anti-PD-L1 antibody used for staining. At the baseline, PD-L1 expression by LOX-IMVI was moderate (about 6-7 times lower than MC38-cOVA/eGFP-mPD-L1$^{-/-}$hPD-L1$^{Tg}$). Upon treatment with mIFNy, there was no change for PD-L1 staining on MC38-cOVA/eGFPmPD-L1$^{-/-}$hPD-L1$^{Tg}$, whereas 3-fold increase of human PD-L1 staining was seen in LOX-IMVI after treatment with hIFNy.

Ex vivo PD-L1 expression by LOX-IMVI and MC38-cOVA/eGFP-mPD-L1$^{-/-}$hPD-L1$^{Tg}$ cells about three weeks post implantation in nude mice were shown in Tables 11 and 12.

TABLE 11

| | | |
|---|---|---|
| Percentage of PD-L1 positive LOX-IMVI and MC38-cOVA/eGFP-mPD-L1$^{-/-}$hPD-L1$^{Tg}$ cells ~3 weeks post implantation in nude mice | | |
| | Isotype staining | hPD-L1 staining |
| LOX-IMVI | 0.2% | 56.6% |
| MC38-cOVA/eGFP-mPD-L1$^{-/-}$hPD-L1$^{Tg}$ | 0.2% | 96.2% |

TABLE 12

| | | |
|---|---|---|
| Mean fluorescence intensity of PD-L1 by LOX-IMVI and MC38-cOVA/eGFP-mPD-L1$^{-/-}$hPD-L1$^{Tg}$ cells ~3 weeks post implantation in nude mice | | |
| | Tumor 1 | Tumor 2 |
| LOX-IMVI | 8479.1 | 12121.5 |
| MC38-cOVA/eGFP-mPD-L1$^{-/-}$hPD-L1$^{Tg}$ | 49589.1 | 51445.0 |

Upon enzymatic and mechanical processing to allow for tumor dissociation, cells were stained with the anti-PD-L1 antibody (20 ug/mL). The PD-L1 expression level on LOX-IMVI was about 5 times lower than that on MC38-cOVA/eGFP-mPD-L1$^{-/-}$hPD-L1$^{Tg}$ tumor cells.

Example 6: Selective Localization of Radiolabeled Anti-PD-L1 Antibody to hPD-L1 Positive Tumors in Nude Mice To determine the in vivo localization of anti-PD-L1 antibody, Zirconium-89 labeled DFO-antibody conjugate was administered intravenously to nude mice bearing PD-L1 positive tumors.

The tumor line used for the study was a murine colon carcinoma cell-line referred to as MC38-cOVA/eGFP-mPD-L1$^{-/-}$hPD-L1$^{Tg}$, which has been engineered to knock out murine PD-L1 off the wild type MC38, but over-express full-length human PD-L1 and full-length chicken ovalbumin fused with eGFP. For the second study of tumors with endogenous expression of human PD-L1, the human melanoma cell line LOX-IMVI was used to establish tumors in vivo for subsequent anti-PD-L1 antibody localization studies.

The exemplary radiolabeled anti-PD-L1 antibody used for this study was H1H8314N, comprising HCVR/LCVR of SEQ ID NOs: 82/90.

For the first study, 1×10$^6$ MC38-cOVA/eGFP-mPD-L1–/–hPD-L1$^{Tg}$ cells were implanted subcutaneously into the left flank of male 8-10 week old NCr nude mice (Taconic, Hudson NY). For LOX-IMVI tumors, 1×10$^6$ cells were implanted subcutaneously into the left flank of male 8-10 week old NCr nude mice. Once tumors had reached an average volume of 50-150 mm$^3$ (~Day 7-10), mice were randomized into groups, and dosed with either $^{89}$Zr labeled anti-PD-L1 DFO-antibody conjugate (H1H8314N) or a $^{89}$Zr labeled non-binding isotype control DFO-antibody conjugate. The nude mice bearing MC38-cOVA/eGFP-mPD- L1−/−hPD-L1$^{Tg}$ tumors received 50±1 uCi of $^{89}$Zr labeled antibody with a protein dose ~0.6 mg/kg. In the study using mice bearing LOX-IMVI tumors, mice received 35±1 uCi of $^{89}$Zr labeled antibody with a final antibody dose of 0.3 or 1 mg/kg.

PET imaging of antibody localization was assessed 6 days after administration of the antibodies. A Sofie Biosciences G8 PET/CT (Sofie Biosciences and Perkin Elmer) was used to acquire images). The instrument was pre-calibrated for detection of $^{89}$Zr prior to image acquisition. The energy window ranged from 150 to 650 keV with a reconstructed resolution of 1.4 mm at the center of the field of view. Mice underwent induction anesthesia using isoflurane and were kept under continuous flow of isoflurane during imaging. Static 10-minute images were acquired using the G8 acquisition software and subsequently reconstructed using the pre-configured settings. Image data was corrected for decay and other parameters. CT images were acquired following PET acquisition and later co-registered with the PET images. Images were prepared using VivoQuant post-processing software (inviCRO Imaging Services).

For bio distribution, mice were euthanized at the final time-point (5-6 days post-dosing) and blood was collected via cardiac puncture. Tumors and normal tissues were then excised and placed in counting tubes. Weight for each sample were measured and recorded. Count data for $^{89}$Zr in CPM was then collected by measuring samples on an automatic gamma counter (Wizard 2470, Perkin Elmer). The percent-injected dose per gram (% ID/g) was calculated for each sample using standards prepared from the injected material.

The average % ID/g for each antibody is presented in Table 13.

TABLE 13

| | | | | |
|---|---|---|---|---|
| Average % ID/g in analyzed tissues | | | | |
| | $^{89}$Zr-H1H8314N | | $^{89}$Zr-Isotype Control Antibody | |
| SAMPLE | AVERAGE % ID/g | STDEV % ID/g | AVERAGE % ID/g | STDEV % ID/g |
| LIVER | 3.1 | 0.4 | 0.9 | 0.9 |
| SPLEEN | 4.4 | 1.1 | 1.5 | 1.3 |
| KIDNEY | 4.0 | 0.7 | 1.4 | 1.6 |

TABLE 13-continued

| | | | | |
|---|---|---|---|---|
| Average % ID/g in analyzed tissues | | | | |
| | $^{89}$Zr-H1H8314N | | $^{89}$Zr-Isotype Control Antibody | |
| SAMPLE | AVERAGE % ID/g | STDEV % ID/g | AVERAGE % ID/g | STDEV % ID/g |
| BONE | 5.1 | 2.6 | 1.7 | 1.6 |
| LUNG | 5.1 | 1.1 | 2.5 | 3.0 |
| HEART | 2.4 | 0.2 | 1.3 | 1.4 |
| BLOOD | 7.6 | 1.6 | 3.8 | 4.6 |
| THYMUS | 5.3 | 3.0 | 2.8 | 2.2 |
| MC38-cOVA/eGFP-mPD-L1$^{-/-}$hPD-L1$^{Tg}$ | 55.3 | 12.2 | 3.0 | 3.3 |
| S. BOWEL | 1.5 | 0.3 | 0.6 | 0.6 |

From this, the clear high uptake in MC38-cOVA/eGFP-mPD-L1−/−hPD-L1$^{Tg}$ tumors was apparent over other normal tissues, with tumor uptake of 55.3% ID/g being significantly higher than the next highest uptake of 5.3% ID/g observed in the thymus. Tumor uptake was 7.3-fold and 17.8-fold higher than activity in blood and liver, respectively. The specificity of anti-PD-L1 uptake into tumor (55.3% ID/g) was apparent as compared to significantly reduced tumor uptake of 3% observed for the non-binding isotype control antibody. Pilot PET imaging performed here demonstrated a clear localization of the $^{89}$Zr labeled anti-PD-L1 DFO-antibody conjugate to the MC38-cOVA/eGFP-mPD-L1−/−hPD-L1$^{Tg}$ tumors. Little background signal was observed in the animals at this Day 6 post-dosing time-point. In contrast to the clear tumor localization that was apparent using anti-PD-L1 antibody, only faint background activity was apparent in imaging of the control antibody in this model. Imaging clearly indicated high, specific uptake of anti-PD-L1 antibody in human PD-L1 positive tumor, showing the localization of $^{89}$Zr radiolabeled anti-PD-L1 antibody to a MC38-cOVA/eGFP-mPD-L1−/−hPD-L1$^{Tg}$ tumor in an NCr nude mouse.

In a second study, the ability of anti-PD-L1 antibody to selectively target tumors expressing endogenous levels of human PD-L1 antigen was assessed. Here, mice bearing human LOX-IMVI melanoma tumors received $^{89}$Zr labeled antibody at doses of 0.3 and 1 mg/kg. Again, blood, tumor and tissues were taken at Day 6 post-injection and the % ID/g for the samples was calculated. The average % ID/g for each antibody is presented in Table 14.

TABLE 14

| | | | | | | |
|---|---|---|---|---|---|---|
| Average % ID/G in analyzed tissues from second study (LOX-IMVI tumors) | | | | | | |
| | $^{89}$Zr-DFO-H1H8314N 0.3 mg/kg | | $^{89}$Zr-DFO-H1H8314N 1 mg/kg | | $^{89}$Zr-Isotype control antibody 1 mg/kg | |
| SAMPLE | AVERAGE % ID/g | STDEV % ID/g | AVERAGE % ID/g | STDEV % ID/g | AVERAGE % ID/g | STDEV % ID/g |
| LIVER | 2.9 | 0.3 | 3.3 | 0.2 | 3.9 | 0.3 |
| SPLEEN | 4.2 | 0.2 | 4.3 | 0.9 | 4.2 | 0.7 |
| KIDNEY | 4.3 | 0.4 | 4.3 | 0.8 | 3.4 | 0.4 |
| BONE | 3.2 | 0.6 | 2.7 | 0.5 | 3.6 | 0.4 |
| LUNG | 5.7 | 1.0 | 6.6 | 1.6 | 5.9 | 1.2 |
| HEART | 3.2 | 0.8 | 3.2 | 0.4 | 2.9 | 0.6 |
| BLOOD | 8.1 | 1.4 | 9.5 | 1.0 | 11.1 | 6.2 |
| THYMUS | 5.3 | 2.3 | 5.6 | 0.7 | 4.9 | 1.4 |
| LOX-IMVI TUMOR | 20.6 | 2.7 | 10.6 | 2.6 | 12.0 | 1.8 |
| S. BOWEL | 1.5 | 0.2 | 1.8 | 0.4 | 2.0 | 0.3 |

At the lower 0.3 mg/kg dose, clear targeting to tumor over normal tissues was observed, with a 20.6% ID/g observed in the LOX-IMVI tumors. When mice received the higher 1 mg/kg dose, reduced tumor uptake 10.6% ID/g of was observed relative to the 0.3 mg/kg level. This suggests that the higher protein dose and possibly the subsequent higher fraction of unlabeled antibody led to blocking of tumor uptake by the $^{89}$Zr labeled anti-PD-L1 antibody. In accordance with this, PET imaging conducted immediately prior to the biodistribution study also showed that uptake of anti-PD-L1 antibody at the 1 mg/kg dose was roughly equivalent to that of the control antibody. At the lower dose of 0.3 mg/kg, a clear increase in tumor localization of the anti-PD-L1 antibody was apparent relative to control antibody. Overall, the PET images and the biodistribution data demonstrate specific targeting of the LOX-IMVI tumors at the 0.3 mg/kg dose of anti-PD-L1 antibody.

Example 7: Selective Localization of Radiolabeled Anti-PD-L1 Antibody to hPD-L1 Positive Tumors in Mice This Example describes the in vivo localization of a Zirconium-89 labeled DFO-anti-PD-L1 antibody conjugate in mice humanized for PD-L1. The exemplary antibody used in this Example was H1H8314N, comprising HCVR/LCVR of SEQ ID NOs: 82/90.

Mice humanized for PD-L1 were engineered using VelociGene® technology (Valenzuela et al 2003, Nat. Biotechnol. 21:652-659; US Patent Application PublicationnUS2016/0157469).

The tumor line used was a murine colon carcinoma cell-line referred to as MC38-COVA/eGFP-mPD-L1$^{-/-}$hPD-L1$^{Tg}$, engineered in-house to express full-length chicken ovalbumin fused with eGFP and to knock out murine PD-L1 off the wild type MC38, but over-express full-length human PD-L1.

1×10$^6$ cells of MC38-cOVA/eGFP-mPD-L1$^{-/-}$hPD-L1$^{Tg}$ were implanted subcutaneously into the left flank of male humanized PD-L1 mice. Once tumors had reached an average volume of 50-150 mm$^3$ (~Day 7), mice were randomized into groups, and dosed with either $^{89}$Zr labeled anti-PD-L1 DFO-antibody conjugate or a $^{89}$Zr labeled non-binding isotype control DFO-antibody conjugate. The mice received 50±1 uCi of $^{89}$Zr labeled antibody with a final protein dose of 1 or 3 mg/kg.

PET imaging of antibody localization was assessed 6 days after administration of the antibodies. A Sofie Biosciences G8 PET/CT (Sofie Biosciences and Perkin Elmer) was used to acquire images). The instrument was pre-calibrated for detection of $^{89}$Zr prior to image acquisition. The energy window ranged from 150 to 650 keV with a reconstructed resolution of 1.4 mm at the center of the field of view. Mice underwent induction anesthesia using isoflurane and were kept under continuous flow of isoflurane during imaging. Static 10-minute images were acquired using the G8 acquisition software and subsequently reconstructed using the pre-configured settings. Image data was corrected for decay and other parameters. CT images were acquired following PET acquisition and later co-registered with the PET images. Images were prepared using VivoQuant post-processing software (inviCRO Imaging Services).

For biodistribution, mice were euthanized at the final time-point (5-6 days post-dosing) and blood was collected via cardiac puncture. Tumors and normal tissues were then excised and placed in counting tubes. Weight for each sample were measured and recorded. Count data for $^{89}$Zr in CPM was then collected by measuring samples on an automatic gamma counter (Wizard 2470, Perkin Elmer). The percent-injected dose per gram (% ID/g) was calculated for each sample using standards prepared from the injected material.

Results

Humanized PD-L1 mice bearing MC38-cOVA/eGFP-mPD-L1$^{-/-}$hPD-L1$^{Tg}$ tumors received $^{89}$Zr labeled anti-PD-L1 DFO-antibody conjugate at a final antibody dose of 1 or 3 mg/kg. Blood, tumor and tissues were taken and weighed at Day 6 post-injection and the % ID/g for the samples was calculated based on the counts from each sample. The average % ID/g for dose at 1 and 3 mg/kg is presented in Table 15 and Table 16 respectively.

TABLE 15

Average % ID/g in analyzed tissues of anti-PD-L1 antibody at 1 mg/kg

| SAMPLE | AVERAGE % ID/g | STDEV % ID/g |
|---|---|---|
| LIVER | 8.6 | 1.5 |
| SPLEEN | 14.1 | 1.1 |
| KIDNEY | 7.8 | 1.0 |
| BONE | 4.5 | 1.4 |
| LUNG | 7.9 | 3.0 |
| HEART | 4.3 | 1.1 |
| BLOOD | 9.1 | 4.6 |
| THYMUS | 9.7 | 3.5 |
| MC38-cOVA/eGFP-mPD-L1$^{-/-}$hPD-L1$^{Tg}$ | 34.1 | 18.0 |
| S. BOWEL | 2.4 | 0.9 |

At the 1 mg/kg dose level, clear tumor targeting of the MC38-cOVA/eGFP-mPD-L1$^{-/-}$hPD-L1$^{Tg}$ tumors is apparent with a % ID/g of 34.1% despite the expression of PD-L1 in normal tissues in these humanized mice. At this dose, some localization of the $^{89}$Zr labeled anti-PD-L1 antibody was apparent in the spleen, where antibody uptake of 14.1% ID/g was observed. Such uptake is expected because of the normal expression of human PD-L1 in place of mouse PD-L1 expression of human PD-L1 in the spleen. At the 3 mg/kg antibody dose, localization of $^{89}$Zr-DFO-anti-PD-L1 antibody conjugate to the spleen was reduced, as uptake now averaged 9.7% ID/g in mice that received this antibody dose (Table 16).

TABLE 16

Average % ID/g in analyzed tissues of anti-PD-L1 antibody at 3 mg/kg

| SAMPLE | AVERAGE % ID/g | STDEV % ID/g |
|---|---|---|
| LIVER | 6.7 | 1.4 |
| SPLEEN | 9.7 | 1.3 |
| KIDNEY | 7.0 | 1.1 |
| BONE | 3.6 | 0.6 |
| LUNG | 11.0 | 1.0 |
| HEART | 4.7 | 0.7 |
| BLOOD | 12.4 | 2.1 |
| THYMUS | 7.6 | 0.5 |
| MC38-cOVA/eGFP-mPD-L1$^{-/-}$hPD-L1$^{Tg}$ | 28.7 | 13.1 |
| S. BOWEL | 0.4 | 0.2 |

Clear tumor targeting was still observed at the 3 mg/kg dose, with an average of 28.7% ID/g taken up by the MC38-cOVA/eGFP-mPD-L1$^{-/-}$hPD-L1$^{Tg}$ tumors. Therefore although reduced normal tissue localization was apparent in imaging the 3 mg/kg dose, clear localization of anti-PD-L1 labeled antibody to the MC38-cOVA/eGFPmPD-L1$^{-/-}$hPD-L1$^{Tg}$ tumors remained clear at this dose. Overall, these results indicate that clear targeting of the MC38-cOVA/eGFP-mPD-L1$^{-/-}$hPD-L1$^{Tg}$ tumors was possible in mice expressing PD-L1 on regular sites of normal tissue expression.

The results from the studies performed here clearly demonstrate that anti-PD-L1 antibody labeled with $^{89}$Zr can significantly and specifically localize to tumors. One may envisage a scenario where the anti-PD-L1 antibody is used in the selection of patients with PD-L1 positive tumors for subsequent treatment with inhibitors of the PD-1/PD-L1 signaling axis.

Example 8: Scaled-Up Manufacturing Process for Producing DFO-Anti-PD-L1 Antibody Conjugates This example details the scaled-up manufacturing process for preparing the anti-PD-L1 antibody to be suitable for radiolabeling by attaching p-SCN-bn-Deferoxamine (DFO) to the anti-PD-L1 antibody (mAb, H4H8314N) described herein: (1) ultrafiltration and diafiltration (UFDF) processes prior to mAb conjugation removes excipients that inhibit the conjugation process; (2) following the pre-conjugation UFDF, conjugation of the mAb with p-SCN-Bn-deferoxamine is performed to produce DFO-mAb conjugates; and (3) a post-conjugation UFDF to remove residual salts provides a suitable concentration, excipient level, and pH of the conjugated monoclonal antibody. The resulting DFO-mAb conjugates are then provided in a buffered state with improved stability for subsequent formulation.

(1) Pre-Conjugation Ultrafiltration and Diafiltration (UFDF)

100 g anti-PD-L1 antibody was buffer exchanged into a 5 mM acetate buffer solution having a pH of 5.50 using a Sius Prostream (TangenX Technology Corporation) membrane (membrane capacity of ≤500 g/m²) to remove residual salts prior to conjugation. The process volume was reduced to further concentrate the antibody, then the antibody was sterile filtered using a Sartopore 2 (Sartorius) membrane having a 0.45/0.2 μm (heterogeneous PES double layer) or equivalent pore size. The acetate buffer temperature was kept at a target temperature of 20±5° C. The solutions were well mixed.

(2) Conjugation

The concentrated and filtered antibody (20 g) was transferred into a conjugation vessel containing an amine free carbonate buffer system (56 mM Carbonate, 167 mM Sodium Chloride, pH 9.40) resulting in negligible levels of residual acetate. DFO (25 mM p-SCN-Bn-Deferoxamine) was solubilized in DMSO and added to the conjugation vessel, along with additional DMSO such that the DMSO was present in a final amount of 5%. DFO was added in molar excess at a ratio of 4.5:1 DFO to mAb. The total reaction volume equaled 2.0 L. The buffer system was mixed throughout the addition of the reaction ingredients and throughout the reaction time.

The reaction temperature was controlled for specific time by using an equation which relates temperature to reaction time. In this instance, the reaction temperature was held at 18° C. for 120 minutes. The reaction was quenched by the addition of 2M acetic acid (23 mL/L), resulting in the solution having a pH of 6.

(3) Post-Conjugation UFDF

After the conjugation step, the quenched DFO-mAb conjugation solution was buffer exchanged into histidine buffer (10 mM Histidine, pH 5.50 with 0.0005% (w/v) super refined polysorbate 80 added as a shear protectant) to remove residual process salts, DMSO, and unreacted DFO.

Once diafiltered, the solution was then concentrated and subsequently formulated. The histidine buffer was selected for long term storage of protein at −80° C. The same Sius Prostream membrane mentioned in step (1) was used in the final UFDF step. The resulting concentrated DFO-mAb conjugate solution was sterile filtered using the Sartopore 2 filter mentioned above.

UV-DAR (target of 1.5) and protein concentration determination was performed as described in Example 2.

TABLE 17

| Molar Extinction Coefficients and Molecular Weight | | | |
|---|---|---|---|
| Antibody | MW (g mol$^{-1}$) | ε280 (L g$^{-1}$cm$^{-1}$) | ε252 (L g$^{-1}$cm$^{-1}$) |
| H4H8314N | 144984 | 211480 | 80172 |

Example 9: Predicted Whole Body and Tissue Exposure of Radioactivity in Human Subjects to be Given an IV Dose of $^{89}$Zr-DFO-Anti-PD-L1 Antibody Conjugate The purpose of the following experiment was to estimate the predicted whole body and tissue exposures to radioactivity in human subjects due to an intravenous (IV) dose of $^{89}$Zr-DFO-anti-PD-L1 antibody conjugate. The exemplary anti-PD-L1 antibody used in the radiolabeled conjugate was H4H8314N.

Characterization of Radioimmunoconjugates

Anti-PD-L1 immunoconjugate (DFO-Ab) and isotype control immunoconjugate (DFO-IgG4P Control) were radiolabeled and purified for use in in vivo imaging and biodistribution studies. SEC-HPLC analysis and a MC38/mPD-L1$^{-/-}$hPD-L1 (murine MC38 colon adenocarcinoma cells engineered to knock out mouse PD-L1 and stably express human PD-L1) cell-based in vitro assay were performed to characterize the resultant radioimmunoconjugates.

Monomeric and Radiochemical Purity

SEC-HPLC using UV- and γ-emission detectors was performed to assess monomeric and radiochemical purity. Results for radioimmunoconjugate preparations of $^{89}$Zr-DFO-anti-PD-L1 antibody conjugate and of isotype control radioimmunoconjugate $^{89}$Zr-DFO-IgG4$^P$ are shown in FIG. 8.

Analysis of chromatograms for absorption at 280 nm was performed to evaluate the relative amounts of high molecular weight (HMW) and monomeric protein in the radioimmunoconjugate preparations. As summarized in Table 18, the monomeric peaks (a readout of monomeric purity) constitute 99.6, 99.2, and 98.6%, respectively, of the total protein peak area for preparations of $^{89}$Zr-DFO-anti-PD-L1 antibody conjugate and isotype control $^{89}$Zr-DFO-IgG4P; low levels of HMW species (0.4, 0.8, and 1.4%, respectively) were also detected. Low molecular weight (LMW) species were not observed for any of the tested samples.

Analysis of radio-chromatograms for γ-emission was performed to evaluate the relative amounts of $^{89}$Zr incorporated into radioimmunoconjugates compared with unincorporated $^{89}$Zr (such as free $^{89}$Zr or $^{89}$Zr chelated with free DFO-derivatives). As summarized in Table 18, the peaks for unincorporated $^{89}$Zr constitute ≤1.1% of the total γ-emission peak area, while the combined peaks for radiolabeled monomeric and HMW species (a readout of radiochemical purity) constitute 98.9, 99.5, and 99.5%, respectively, of the total γ-emission peak area for preparations of [89]Zr-DFO-anti-PD-L1 antibody conjugate and isotype control [89]Zr-DFO-IgG4P.

TABLE 18

Summary of SEC-HPLC Data

| Peak Number | Species | Approximate Retention Time (min) | Peak Area (%) | |
| | | | UV-Chroma-togram | Radio-Chroma-togram |
|---|---|---|---|---|
| | [89]Zr-DFO-H4H8314N Study 1 | | | |
| 1 | HMW | 13 | 0.4 | 1.1 |
| 2 | Monomer | 16 | 99.6 | 97.8 |
| 3 | Unincorporated [89]Zr | 26 | n/a | 1.1 |
| | [89]Zr-DFO-H4H8314N Study 2 | | | |
| 1 | HMW | 14 | 0.8 | 1.3 |
| 2 | Monomer | 16 | 99.2 | 98.2 |
| 3 | Unincorporated [89]Zr | 26 | n/a | 0.5 |
| | [89]Zr-DFO-IgG4P Control | | | |
| 1 | HMW | 13 | 1.4 | 1.5 |
| 2 | Monomer | 16 | 98.6 | 98.0 |
| 3 | Unincorporated [89]Zr | 26 | n/a | 0.5 |

Numerical values for SEC-HPLC analysis graphically represented in FIG. 8. UV-chromatogram indicated the chromatogram for absorption at 280 nm and radio-chromatogram indicates the chromatogram for intensity of γ-emission. HMW: high molecular weight; n/a: not applicable.

Immunoreactivity

The immunoreactivity, a measure of the percent of radio-labeled, conjugated antibody that is capable of binding its antigen, was determined by incubating [89]Zr-DFO-anti-PD-L1 antibody conjugate with MC38/mPD-L1[−/−]hPD-L1 cells. The 2 tested lots of [89]Zr-DFO-anti-PD-L1 antibody conjugate demonstrated 84.5 and 88.8% immunoreactivity on MC38/mPD-L1[−/−]hPD-L1 cells (Table 19). Background, nonspecific immunoreactivity of 8.8% was observed for the isotype control radioimmunoconjugate.

TABLE 19

Immunoreactivity of [89]Zr labeled anti-PD-L1 DFO-antibody conjugate and isotype control [89]Zr-DFO-IgG4P

| Radioimmunoconjugate | Immunoreactivity |
|---|---|
| [89]Zr-DFO-anti-PD-L1 antibody conjugate (lot 1) | 84.5% |
| [89]Zr-DFO-anti-PD-L1 antibody conjugate (lot 2) | 88.8% |
| isotype control [89]Zr-DFO-IgG4P | 8.8% |

In conclusion, two separate lots of [89]Zr-DFO-anti-PD-L1 antibody conjugate showed high immunoreactivity, percentage of monomer, and radiochemical purity.

[89]Zr-DFO-anti-PD-L1 Biodistribution in Mice

This experiment evaluated the biodistribution of the anti-human PD-L1 radioimmunoconjugate, [89]Zr-DFO-anti-PD-L1 antibody conjugate, over time following administration of a single 50 μCi (1 mg/kg) intravenous (IV) dose to PD-L1/PD-1-humanized mice (PD-1hu/huPD-L1hu/hu). Since H4H8314N does not bind mouse PD-L1, the portion of the mouse PD-L1 gene encoding the PD-L1 ectodomain was replaced by the corresponding human sequence in PD-1hu/hu-PD-L1hu/hu mice. In this strain, the ectodomain of mouse PD-1 was similarly humanized. These mice were not subjected to immune/inflammatory challenge, and are therefore expected to have unstimulated levels of PD-L1 expression on immune cells. Two groups of 8 animals each were sacrificed 6 days (144 hours) or 10 days (240 hours) post dosing, blood was collected and the following tissues were harvested: heart, lungs, liver, spleen, kidneys, stomach, small intestine, caecum, large intestine, bone (femur), thymus, muscle, bladder, and brain. The percentage of radio-activity of the total injected dose (% ID) localized to specific tissues or blood was determined and reported as average % ID per gram (% ID/g) of tissue. In advance of sacrifice, immuno-PET/computed tomography (CT) images were acquired 1, 24, 48, 72, 144, 192 (10-day group only), and 240 (10-day group only) hours post dosing from the same animals.

Figure 9:
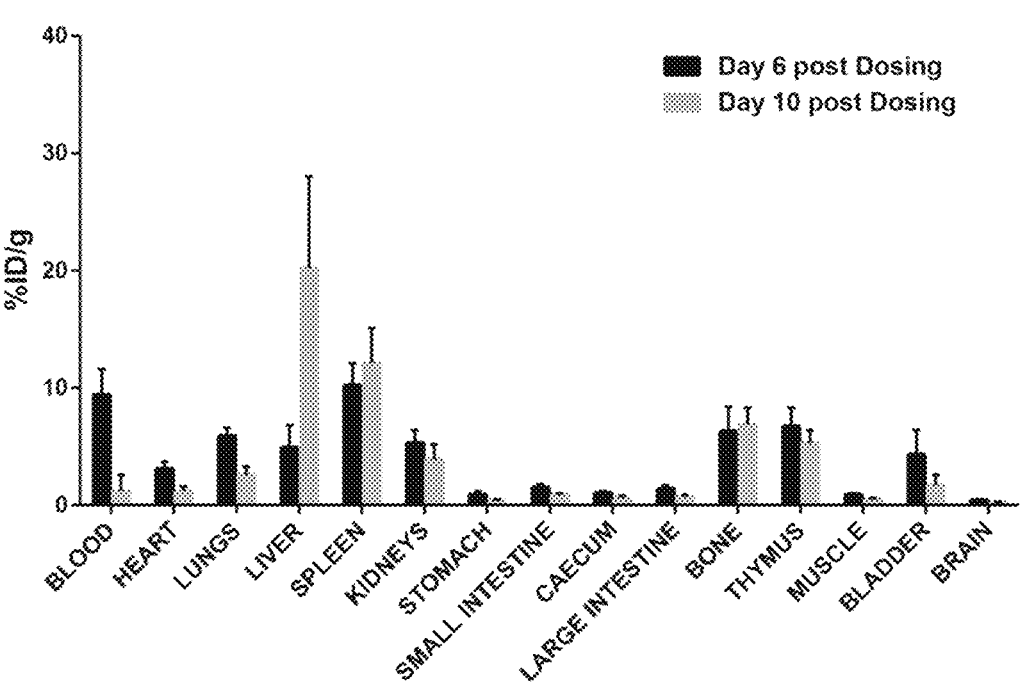
FIG. 9 provides ex vivo biodistribution data for $^{89}$Zr-DFO-anti-PD-L1 antibody conjugate in PD-1hu/hu-PD-L1hu/hu mice. Sixteen mice (2 groups of 8 animals each) were administered a single IV dose of 50 μCi (1 mg/kg) $^{89}$Zr-DFO-anti-PD-L1 antibody conjugate on day 0 and were sacrificed on day 6 (black columns) or day 10 (gray columns) post dosing. Blood, collected via cardiac puncture, and the indicated harvested tissues were weighed and radioactivity was determined. The percent injected dose per gram (% ID/g) values for individual samples collected on day 6 or 10 were calculated relative to the radioactivity of a dose-standard from injected material ($^{89}$Zr-DFO-anti-PD-L1 antibody conjugate) and the weight of the individual samples. Data are plotted as mean±SD.

Relative to [89]Zr levels in blood, uptake of [89]Zr-DFO-anti-PD-L1 antibody conjugate into specific tissues was negligible throughout the 10-day study period, as evaluated by ex vivo tissue analysis (Table 20 and FIG. 9) and in vivo imaging. Compared with blood (9.4±2.2% ID/g), all harvested tissues, with the exception of spleen, demonstrated lower [89]Zr levels (≤6.7% ID/g) on day 6 post dosing. A small degree of target-mediated [89]Zr-DFO-anti-PD-L1 antibody conjugate uptake (10.2±1.9% ID/g) was observed in the spleen, in agreement with PD-L1 expression on splenocytes, as demonstrated by flow cytometry. At 10 days post-dosing, [89]Zr levels in blood had decreased 7.8-fold relative to day 6 post dosing, suggesting a mouse-anti-human antibody (MAHA) response affecting [89]Zr-DFO-anti-PD-L1 antibody conjugate levels. This observed MAHA response is likely due to the fact that the target, PD-L1, is expressed on antigen-presenting cells (Francisco, 2010), leading to the presentation of the human antibody to the mouse immune system and subsequent MAHA formation. In parallel, [89]Zr levels in the liver were 4.1-fold increased on day 10 compared with day 6 post dosing, possibly as a result of MAHA/[89]Zr-DFO-anti-PD-L1 antibody conjugate immune complex (IC) formation and subsequent liver-mediated IC clearance (Rojko, 2014). Whole animal in vivo PET imaging did not uncover marked tissue-specific uptake of [89]Zr-DFO-anti-PD-L1 antibody conjugate beyond a low signal for spleen and the MAHA-mediated accumulation in the liver described above.

In summary, marked target-mediated uptake of [89]Zr-DFO-anti-PD-L1 antibody conjugate into specific tissues above [89]Zr levels in blood was not observed over a 6-day period in PD-L1/PD-1-humanized mice administered a single IV dose of 1 mg/kg (50 μCi) of [89]Zr-DFO-anti-PD-L1 antibody conjugate with the exception of the spleen, where a small degree of target-mediated uptake was observed in agreement with the demonstrated expression of PD-L1 on splenocytes. Data collected beyond day 6 until the end of the study on day 10 post dosing were affected by a MAHA response.

TABLE 20

Average Ex Vivo Biodistribution Data

| Tissue | [89]Zr Levels on Day 6 post Dosing (% ID/g) | | [89]Zr Levels on Day 10 post Dosing (% ID/g) | |
| | Average | SD | Average | SD |
|---|---|---|---|---|
| Blood | 9.4 | 2.2 | 1.2 | 1.4 |
| Heart | 3.1 | 0.6 | 1.2 | 0.4 |
| Lungs | 5.9 | 0.7 | 2.6 | 0.7 |
| Liver | 4.9 | 1.9 | 20.2 | 7.8 |
| Spleen | 10.2 | 1.9 | 12.1 | 3.0 |
| Kidneys | 5.3 | 1.1 | 3.9 | 1.3 |
| Stomach | 0.9 | 0.3 | 0.4 | 0.1 |
| Small Intestine | 1.5 | 0.3 | 0.9 | 0.1 |

TABLE 20-continued

| Average Ex Vivo Biodistribution Data | | | | |
|---|---|---|---|---|
| | [89]Zr Levels on Day 6 post Dosing (% ID/g) | | [89]Zr Levels on Day 10 post Dosing (% ID/g) | |
| Tissue | Average | SD | Average | SD |
| Caecum | 1.0 | 0.2 | 0.6 | 0.2 |
| Large Intestine | 1.4 | 0.3 | 0.7 | 0.2 |
| Bone (Femur) | 6.3 | 2.1 | 6.9 | 1.4 |
| Thymus | 6.7 | 1.6 | 5.3 | 1.1 |
| Muscle | 0.9 | 0.1 | 0.5 | 0.1 |
| Bladder | 4.3 | 2.1 | 1.7 | 0.9 |
| Brain | 0.4 | 0.1 | 0.2 | 0.1 |

Abbreviation: % ID/g = Percent injected dose per gram (of tissue)

Estimates of Whole Body and Tissue Exposures to Radioactivity in Humans

This experiment used PET/CT image data for four PD-1/PD-L1-humanized male mice and four PD-1/PD-L1-humanized female mice imaged at 1, 24, 48, 72, 144, 192, and 240 hours following single IV administration of 50 µCi (1 mg/kg) of [89]Zr-DFO-anti-PD-L1 antibody conjugate. The data generated by administration of this clinically relevant dose was used in calculating estimates of human exposure to radioactivity. Tissue concentration data was determined using volume of interest (VOI) analysis.

For radiation dosimetry estimation, the mean residence time was determined for the following regions: brain, stomach contents, heart contents, kidneys, liver, lungs, muscle, red marrow, spleen, bladder contents, and remainder of body. These mean residence time values were used as an input into the OLINDA/EXM 1.1 software program to estimate the mean absorbed tissue doses and effective dose in humans.

The effective human dose for [89]Zr-DFO-anti-PD-L1 antibody conjugate was estimated to be 0.513 mSv/MBq (millisievert/megabecquerel) in the adult male and 0.622 mSv/MBq in the adult female. The organs predicted to have the highest absorbed dose in humans were the spleen and liver. The estimated absorbed dose in the spleen was 0.856 mSv/MBq in the adult male and 1.12 mSv/MBq in the adult female. The estimated absorbed dose in the liver was 0.764 mSv/MBq in the adult male and 0.974 mSv/MBq in the adult female.

Average decay-corrected percent of the injected dose per mL (DC % ID/mL) values for male and female mice (n=4 male, n=4 female) for each VOI are summarized in Table 21.

TABLE 21

| Biodistribution Data | | | | | | | | | | |
|---|---|---|---|---|---|---|---|---|---|---|
| Average Decay-corrected Percent Injected Dose Per mL (DC % ID/mL) ± SD | | | | | | | | | | |
| Time (h) | 1 | | 24 | | 48 | | 72 | | 144 | |
| Sex | Female | Male | Female | Male | Female | Male | Female | Male | Female | Male |
| Brain | 1.365 ± 0.115 | 1.190 ± 0.050 | 0.903 ± 0.115 | 0.538 ± 0.071 | 0.640 ± 0.079 | 0.548 ± 0.218 | 0.685 ± 0.096 | 0.623 ± 0.224 | 0.465 ± 0.231 | 0.398 ± 0.073 |
| Lungs | 12.503 ± 1.146 | 12.498 ± 0.414 | 8.293 ± 0.635 | 7.155 ± 1.175 | 6.715 ± 0.370 | 5.888 ± 0.990 | 6.060 ± 0.708 | 5.558 ± 0.385 | 4.863 ± 0.316 | 4.585 ± 0.339 |
| Liver | 12.298 ± 0.664 | 12.078 ± 0.372 | 9.058 ± 0.793 | 7.200 ± 0.499 | 8.113 ± 0.969 | 6.125 ± 0.858 | 7.838 ± 0.932 | 6.203 ± 0.483 | 9.423 ± 1.885 | 6.208 ± 1.428 |
| Heart | 27.688 ± 1.942 | 25.695 ± 0.934 | 15.685 ± 1.223 | 13.323 ± 1.133 | 12.088 ± 0.883 | 10.25 ± 1.335 | 11.740 ± 1.553 | 9.915 ± 0.171 | 8.140 ± 0.598 | 7.463 ± 0.768 |
| Kidneys | 11.430 ± 0.387 | 12.100 ± 0.872 | 7.345 ± 0.322 | 6.783 ± 0.811 | 6.418 ± 0.761 | 5.565 ± 0.680 | 6.475 ± 0.493 | 5.568 ± 0.550 | 5.643 ± 0.222 | 4.815 ± 0.450 |
| Spleen | 15.263 ± 2.166 | 15.860 ± 0.974 | 14.135 ± 2.010 | 11.265 ± 1.706 | 13.675 ± 2.195 | 9.388 ± 1.389 | 13.655 ± 3.606 | 9.920 ± 1.414 | 15.105 ± 2.959 | 10.303 ± 1.102 |
| Bladder | 6.045 ± 3.910 | 9.688 ± 4.991 | 1.653 ± 0.107 | 1.820 ± 0.283 | 1.443 ± 0.205 | 1.403 ± 0.160 | 1.318 ± 0.108 | 1.710 ± 0.346 | 1.115 ± 0.224 | 1.293 ± 0.430 |
| Muscle | 1.608 ± 0.182 | 1.435 ± 0.198 | 2.608 ± 0.196 | 1.780 ± 0.137 | 2.368 ± 0.259 | 1.955 ± 0.339 | 2.408 ± 0.181 | 2.148 ± 0.176 | 2.095 ± 0.168 | 1.918 ± 0.144 |
| Stomach | 3.238 ± 1.063 | 3.978 ± 0.632 | 2.875 ± 0.921 | 3.073 ± 0.566 | 2.478 ± 0.296 | 2.238 ± 0.487 | 2.260 ± 0.306 | 2.233 ± 0.491 | 2.380 ± 0.405 | 1.665 ± 0.148 |
| Bone | 3.683 ± 1.418 | 3.023 ± 0.244 | 3.310 ± 0.330 | 2.738 ± 0.171 | 4.600 ± 0.511 | 3.493 ± 0.716 | 4.850 ± 1.292 | 4.658 ± 1.399 | 8.993 ± 1.057 | 7.635 ± 0.872 |

Estimated human mean residence time (MRT) values are provided in Table 22 for each of the source organs. MRT in the remainder of the body was obtained by subtracting the sum of all source organ residence times from the reciprocal of the [89]Zr decay constant (Huang et al., Biodistribution, toxicity and radiation dosimetry studies of the serotonin transporter radioligand 4-[18F]-ADAM in rats and monkeys. Eur J Nucl Med Mol Imaging, 2010; 37:545-555). This represents a conservative estimation of the cumulative tissue radioactivity.

TABLE 22

| Human Mean Residence Times (h) | | | | |
|---|---|---|---|---|
| Organ/ | Physical Decay[1] | | Biexponential Fit[2] | |
| Tissue | Female | Male | Female | Male |
| Brain | 0.398 | 0.364 | 0.372 | 0.344 |
| Stomach Contents | 0.511 | 0.476 | 0.492 | 0.480 |
| Heart Contents | 2.433 | 2.279 | 2.290 | 2.154 |
| Kidneys | 0.868 | 0.818 | 0.832 | 0.794 |

TABLE 22-continued

| Human Mean Residence Times (h) | | | | |
|---|---|---|---|---|
| Organ/ | Physical Decay[1] | | Biexponential Fit[2] | |
| Tissue | Female | Male | Female | Male |
| Liver | 5.902 | 5.919 | 8.240 | 5.938 |
| Lungs | 2.508 | 2.772 | 2.411 | 2.642 |
| Muscle | 17.635 | 23.677 | 13.348 | 17.182 |
| Red Marrow | 2.777 | 2.024 | 2.613 | 1.913 |
| Spleen | 0.996 | 0.871 | 1.053 | 0.910 |
| Bladder Contents | 0.299 | 0.491 | 0.315 | 0.405 |
| Remainder of Body | 78.794 | 73.430 | 81.157 | 80.361 |

[1]Mean residence time calculated assuming only physical decay following day 6 time point
[2]Mean residence time calculated from a biexponential fit of the data The estimated absorbed tissue doses for all target organs for the OLINDA/EXM 1.1 adult male and adult female phantoms are provided in Table 23. The effective dose, defined by the International Commission on Radiological Protection (ICRP) (International Commission on Radiological Protection. 1990 Recommendations of the International Commission on Radiological Protection. ICRP Publication 60, Pergamon Press, New York, 1991) is a quantity that is calculated by multiplying the absorbed dose for a given organ by a stochastic risk weighting factor and adding the weighted doses together. Estimated effective doses are provided at the end of Table 23. These values represent a conservative estimation of radioactive absorbed doses.

TABLE 23

| Estimated Human Tissue Absorbed Doses and Effective Dose | | | | |
|---|---|---|---|---|
| | Physical Decay[1] | | Biexponential Fit[2] | |
| Organ/Tissue | Adult Male (mSv/MBq) | Adult Female (mSv/MBq) | Adult Male (mSv/MBq) | Adult Female (mSv/MBq) |
| Adrenals | 0.561 | 0.702 | 0.567 | 0.726 |
| Brain | 0.179 | 0.237 | 0.182 | 0.234 |
| Breasts | 0.366 | 0.459 | 0.379 | 0.466 |
| Gallbladder Wall | 0.601 | 0.692 | 0.610 | 0.751 |
| LLI Wall | 0.519 | 0.652 | 0.530 | 0.651 |
| Small Intestine | 0.563 | 0.600 | 0.582 | 0.605 |
| Stomach Wall | 0.575 | 0.714 | 0.584 | 0.718 |
| ULI Wall | 0.553 | 0.685 | 0.571 | 0.700 |
| Heart Wall | 0.789 | 0.973 | 0.781 | 0.964 |
| Kidney | 0.650 | 0.773 | 0.641 | 0.774 |
| Liver | 0.764 | 0.974 | 0.764 | 1.220 |
| Lungs | 0.575 | 0.705 | 0.561 | 0.700 |
| Muscle | 0.396 | 0.481 | 0.381 | 0.464 |
| Ovaries | 0.533 | 0.645 | 0.542 | 0.642 |
| Pancreas | 0.597 | 0.743 | 0.606 | 0.765 |
| Red Marrow | 0.480 | 0.591 | 0.483 | 0.587 |
| Osteogenic Cells | 0.604 | 0.777 | 0.625 | 0.779 |
| Skin | 0.291 | 0.373 | 0.297 | 0.374 |
| Spleen | 0.856 | 1.120 | 0.876 | 1.160 |
| Testes | 0.399 | NA | 0.407 | NA |
| Thymus | 0.481 | 0.605 | 0.484 | 0.601 |
| Thyroid | 0.417 | 0.484 | 0.423 | 0.480 |
| Urinary Bladder Wall | 0.580 | 0.496 | 0.559 | 0.494 |
| Uterus | 0.545 | 0.638 | 0.554 | 0.636 |
| Total Body | 0.440 | 0.550 | 0.440 | 0.554 |
| Effective Dose | 0.513 | 0.622 | 0.516 | 0.625 |

[1]Absorbed doses calculated from MRT assuming only physicadecay following day 6 time point
[2]Absorbed doses calculated from MRT with a biexponential fit of the data
Abbreviations: LLI = lower large intestine, ULI = upper large intestine, NA = not applicable The estimated human tissue absorbed doses and effective human dose (Table 23) from the physical decay and the biexponential fit methods were similar. The physical decay method was selected to produce the final set of estimated human tissue absorbed doses and effective dose due to the apparent MAHA response in this murine model. Therefore, the effective human dose for $^{89}$Zr-DFO-anti-PD-L1 antibody conjugate was estimated to be 0.513 mSv/MBq in the adult male and 0.622 mSv/MBq in the adult female. The organs predicted to have the highest absorbed dose in humans are the spleen and liver. The estimated absorbed dose in the spleen was 0.856 mSv/MBq in the adult male and 1.12 mSv/MBq in the adult female. The estimated absorbed dose in the liver was 0.764 mSv/MBq in the adult male and 0.974 mSv/MBq in the adult female.

Example 10: ImmunoPET Imaging of PD-L1 in Tumors Using an $^{89}$Zr-DFO-Anti-PD-L1 Antibody Conjugate in Patients with Advanced Thoracic Malignancies The primary objective of this study is to determine the safety and tolerability of $^{89}$Zr-DFO-anti-PD-L1 antibody conjugate, in which the anti-PD-L1 antibody used in the radiolabeled conjugate is H4H8314N. The secondary objectives of the study are:

Study part A only: To establish adequate mass dose of $^{89}$Zr-DFO-anti-PD-L1 antibody conjugate and optimal post-infusion imaging time, as assessed by imaging and blood draw after tracer infusion.

Study part B only: To establish test/re-test reliability of PET measures as assessed on two separate tracer infusions at optimal mass dose and imaging time point as determined in Part A.

To characterize the pharmacokinetic (PK) profile of $^{89}$Zr-DFO-anti-PD-L1 antibody conjugate based on tracer plasma activity concentration.

This is an open label, 2-part study designed to evaluate the safety and tolerability of $^{89}$Zr-DFO-anti-PD-L1. Study Part A will establish an adequate mass dose and activity dose of $^{89}$Zr-DFO-anti-PD-L1 and an optimal post-infusion imaging time. Test/re-test variability of $^{89}$Zr-DFO-anti-PD-L1 will be evaluated in Part B.

All patients will undergo screening procedures. Patients who meet the eligibility criteria will undergo $^{18}$F-fluorodeoxyglucose ($^{18}$F-FDG) PET/computed tomography (CT) and diagnostic CT scans to assess lesion viability, location, and dimensions. These scans will not be required if adequate quality images are available that were acquired within 28 days of the expected first dose of $^{89}$Zr-DFO-anti-PD-L1.

Part A

Three sequential dose cohorts are planned to be treated open-label with $^{89}$Zr-DFO-anti-PD-L1 at 5 mg, 10 mg, or 20 mg.

After infusion with $^{89}$Zr-DFO-anti-PD-L1, patients will undergo $^{89}$Zr-DFO-anti-PD-L1 PET/CT scans on day 1, day 4±1 and day 7±1. Additional imaging may be performed up to day 10. Patients will undergo safety assessments and provide samples for hematology, chemistry, immune safety assays, pharmacokinetics, anti-drug antibody analysis, and biomarker analysis.

Patients will continue to undergo safety evaluations, including physical examination, vital signs, and documentation of Adverse Events (AEs), up to day 21 after the infusion of the $^{89}$Zr-DFO-anti-PD-L1 tracer.

Dose escalation decisions to identify an adequate dose will be informed by safety and tolerability data and by evaluation of immune-positron emission tomography (iPET) positivity and tracer plasma activity concentration, as described below.

Dose Cohorts in Part A

Up to 3 ascending mass dose cohorts are planned. For each mass dose cohort, an initial 2 patients will be dosed, with at a minimum 48-hour interval between the dosing of each patient. Upon completion of the day 7±1 day PET/CT scan for the second patient at a given mass dose, all available imaging, tracer plasma activity concentration, clinical dosimetry, and safety data will be reviewed. Based upon this review, a decision will be made to:

Expand the cohort 6 patients, if there is tumor uptake positivity/tumor localization in at least 1 patient, as defined by a tumor-to-blood ratio >1.

Ascend to the next mass dose cohort if there is inadequate tumor uptake and plasma tracer activity concentration, with adequate defined by blood standardized uptake value (SUV) range of 1 to 5 at the optimum imaging time point.

Proceed with the next mass dose cohort at a lower mass dose, based on inadequate tumor uptake and adequate plasma tracer activity concentration.

If tumor localization is inadequate in at least 2 patients at all three proposed mass dose levels, and this is determined to be due to low image signal-to-noise, the activity dose will be increased up to a maximum of 185 MBq for further expansion of previously tested mass dose cohorts.

Part B

Study Part B will begin once an adequate [89]Zr-DFO-anti-PD-L1 dose and an optimal imaging time have been determined in Part A. On day 1 of Part B, patients will receive the tracer mass dose. Subsequent to receiving the tracer, patients will undergo a scan at the optimal time as identified in Part A. Patients in Part B will receive a second tracer dose and scan after an inter-dose interval of 14 to 28 days. The actual timing of the second tracer dose after the interval will be determined based on results from Part A.

Patients will undergo safety assessments, including physical examination, vital signs, and documentation of adverse events (AEs) during and after visits where [89]Zr-DFO-anti-PD-L1 tracer is administered. During these visits, patients will provide samples for PK, hematology, chemistry, and immune safety assays.

For both Part A and Part B, patients will continue to undergo safety evaluations, including physical examination, vital signs, and documentation of AEs, up to 21 days after the last infusion of the [89]Zr-DFO-anti-PD-L1 tracer.

Study Duration

For Part A, patients will have a screening period of up to 28 days (4 weeks) and a follow-up period of up to 21 days (approximately 3 weeks) after infusion of the tracer dose. The duration of study Part A is approximately 7 weeks, including the screening period.

For Part B, patients will have a screening period of up to 28 days (4 weeks), an inter-infusion interval of up to 28 days (4 weeks), and a 21-day (3 week) safety follow-up period that includes the second scan period. The total duration of the study for each patient will be up to 11 weeks, including the screening period.

The end of study for this study is defined as the last visit of the last patient.

For study Part A, 3 sequential dose levels of up to 6 patients each are planned per cohort, with 3 cohorts planned, for a total of up to 18 patients. For study Part B, up to 10 patients will be enrolled. Enrollment of a maximum of 28 patients in a single study site is planned for the entire study.

Patient Target Population

The target population will consist of patients 18 years of age or older with advanced thoracic malignancies and PD-L1 IHC score on a diagnostic or subsequent biopsy of ≥1% (positive PD-L1 IHC score by 22C3 PharmDx assay, Dako North America Inc.).

For Part A, the thoracic malignancies will be limited to NSCLC, gastro-esophageal junction adenocarcinoma, and gastric cancer, with PD-L1 score of ≥1% by IHC.

For Part B, all patients with advanced thoracic malignancies and a PD-L1 score of ≥1% by IHC will be eligible. Patients must also have stable disease as per RECIST 1.1 between the two most recent imaging studies.

All patients requiring therapy should be on standard of care therapy.

Treatment

[89]Zr-DFO-anti-PD-L1, a radioimmunoconjugate formed by covalently conjugating bifunctional chelator (p-SCN-Bn-DFO) to H4H8314N (anti-PD-L1 monoclonal antibody) and radiolabeling this compound with [89]Zr. [89]Zr-DFO-anti-PD-L1 is supplied in an aqueous buffered vehicle.

For Part A, [89]Zr-DFO-anti-PD-L1 will be administered IV on day 1 (baseline). For Part B, [89]Zr-DFO-anti-PD-L1 will be administered IV on day 1 and day 7±3. Actual timing of the second dose in Part B will be determined from results in Part A.

The [89]Zr-DFO-anti-PD-L1 tracer will be administered at a dose level well below the estimated cumulative exposure levels in humans based on PK models and lower than the levels at which currently available anti-PD-1 agents are used for anti-cancer treatment. This study will exclude patients who are currently treated with anti-PD-L1 to avoid competition for target.

Endpoints

The primary endpoint in the study is the incidence and severity of Treatment-emergent adverse events (TEAEs) through day 21 of the last dose of tracer infusion in patients with thoracic malignancies dosed with [89]Zr-DFO-anti-PD-L1.

For Part A only, the study will establish an adequate mass dose and activity dose of [89]Zr-DFO-anti-PD-L1 and optimal post-infusion imaging time, and the following will be determined via blood drawing and imaging at day 1, 4, and 7 after tracer infusion:

Standardized uptake value of [89]Zr-DFO-anti-PD-L1 in the blood pool, with subsequent calculation of tumor-to-blood ratios at the time of imaging.

Clinical dosimetry based on the absorbed dose and effective tissue radiation, as calculated from PET image acquisition data and tracer activity concentration in blood Standardized Uptake Values (SUVs) across the tumor regions of interest (ROIs)

Maximal SUVs (SUVmax) within tumor ROIs.

Plasma tracer activity concentration, expressed as SUV, with calculation of area under the curve through day 7 ($AUC_{0-7}$)

For Part B only, the study will establish the test/re-test reliability of [89]Zr-DFO-anti-PD-L1 PET measures, and the following will be determined from measures of 2 separate tracer infusions at an adequate mass dose and optimal imaging time points, as determined from Part A:

Blood pool SUV with subsequent calculation of tumor-to-blood ratio.

SUVs across the tumor ROIs

SUVmax within the tumor ROIs.

Biodistribution of [89]Zr-DFO-anti-PD-L1

The resulting data will be indicative of the safety and tolerability of $^{89}$Zr-DFO-anti-PD-L1 in humans.

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

TABLE 24

| | Informal Sequence Listing | |
|---|---|---|
| SEQ. ID. NO. | SEQUENCE | DESCRIPTION |
| 1 | gaggtgcagc tggtggagtc tgggggaggc ttggtccagc ctggggggtc cctgagactc tcctgtgcag cctctggatt cacctttagt aggttttgga tgagctgggt ccgccaggct ccagggaagg ggctggagtg ggtggccaac ataaaccaag atggaactga gaaatactat gtggactctg tgaagggccg attcaccato tccagagaca acgccaagaa ctcactgtat ctgcaaatga acagcctgag agccggggac acggctgtgt attactgtgc gaatacgtat tacgatttt ggagtggtca ctttgactac tggggccagg gaaccctggt caccgtctcc tca | DNA nucleotide sequence |
| 2 | EVQLVESGGG LVQPGGSLRL SCAASGFTFS RFWMSWVRQA PGKGLEWVAN INQDGTEKYY VDSVKGRFTI SRDNAKNSLY LQMNSLRAGD TAVYYCANTY YDFWSGHFDY WGQGTLVTVS S | AA amino acid sequence |
| 3 | ggattcacct ttagtaggtt ttgg | DNA nucleotide sequence |
| 4 | GFTFSRFW | AA amino acid sequence |
| 5 | ataaaccaag atggaactga gaaa | DNA nucleotide sequence |
| 6 | INQDGTEK | AA amino acid sequence |
| 7 | gcgaatacgt attacgattt ttggagtggt cactttgact ac | DNA nucleotide sequence |
| 8 | ANTYYDFWSG HFDY | AA amino acid sequence |
| 9 | gacatccaga tgacccagtc tccttccacc ctgtctgcat ctgtaggaga cagagtcacc atcacttgtc gggccagtca gagtattagt aattggttgg cctggtatca gcagaaacca gggaaagccc ctaagctcct gatctataag gcgtctagtt tagaaagtgg ggtcccatca aggttcagtg gcagtggatc tgggacagaa ttcactctca ccatcagcag cctgcagcct gatgatttg caacttatta ctgccaacag tatcatagtt attcgtacac ttttggccag gggaccaagc tggagatcaa a | DNA nucleotide sequence |
| 10 | DIQMTQSPST LSASVGDRVT ITCRASQSIS NWLAWYQQKP GKAPKLLIYK ASSLESGVPS RFSGSGSGTE FTLTISSLQP DDFATYYCQQ YHSYSYTFGQ GTKLEIK | AA amino acid sequence |
| 11 | cagagtatta gtaattgg | DNA nucleotide sequence |
| 12 | QSISNW | AA amino acid sequence |
| 13 | aaggcgtct | DNA nucleotide sequence |
| 14 | KAS | AA amino acid sequence |
| 15 | caacagtatc atagttattc gtacact | DNA nucleotide sequence |

TABLE 24-continued

Informal Sequence Listing

| SEQ. ID. NO. | SEQUENCE | DESCRIPTION |
|---|---|---|
| 16 | QQYHSYSYT | AA amino acid sequence |
| 17 | caggagcacc tggtggagtc tggggggaggc gtggtccagc ctgggaggtc cctgagactc tcctgtgaag cgtctggatt caccttcagt aactttggca tgcactgggt ccgccaggct ccaggcaagg ggctggagtg ggtggcagct ttatggtctg atggaagtaa taaatactat gcagactccg tgaagggtcg agtcaccatc tccagagaca attccaagaa cacactgtat ctgcaaatga acagcctgag agccgaggac acggctgtct attactgtgc gagagggaga ggagcccccg gtattccgat ttttgggtac tggggccagg gaaccctggt caccgtctcc tca | DNA nucleotide sequence |
| 18 | QEHLVESGGG VVQPGRSLRL SCEASGFTFS NFGMHWVRQA PGKGLEWVAA LWSDGSNKYY ADSVKGRVTI SRDNSKNTLY LQMNSLRAED TAVYYCARGR GAPGIPIFGY WGQGTLVTVS S | AA amino acid sequence |
| 19 | ggattcacct tcagtaactt tggc | DNA nucleotide sequence |
| 20 | GFTFSNFG | AA amino acid sequence |
| 21 | ttatggtctg atggaagtaa taaa | DNA nucleotide sequence |
| 22 | LWSDGSNK | AA amino acid sequence |
| 23 | gcgagaggga gaggagcccc cggtattccg atttttgggt ac | DNA nucleotide sequence |
| 24 | ARGRGAPGIP IFGY | AA amino acid sequence |
| 25 | gacatccaga tgacccagtc tccatcctcc ctgtctgcat ctgttggaga cagagtcacc atcacttgcc gggcaagtca gggcattaga aatgatttag gctggtatca gcagaaacca gggaaagccc ctaagcgcct gatctatact gcatccagtt tgcaaagtgg ggtcccatca agattcagcg gcagtggatc tgggacagaa ttcactctca caatcagcag cctacagcct gaagattttg caacttatta ctgtctacaa cataatagtt accctctcac attcggcgga gggaccaagg tggcgatcaa a | DNA nucleotide sequence |
| 26 | DIQMTQSPSS LSASVGDRVT ITCRASQGIR NDLGWYQQKP GKAPKRLIYT ASSLQSGVPS RFSGSGSGTE FTLTISSLQP EDFATYYCLQ HNSYPLTFGG GTKVAIK | AA amino acid sequence |
| 27 | cagggcatta gaaatgat | DNA nucleotide sequence |
| 28 | QGIRND | AA amino acid sequence |
| 29 | actgcatcc | DNA nucleotide sequence |
| 30 | TAS | AA amino acid sequence |
| 31 | ctacaacata atagttaccc tctcaca | DNA nucleotide sequence |
| 32 | LQHNSYPLT | AA amino acid sequence |
| 33 | gaggtgcagc tggtggagtc tggggggaggc ttggtaaagc ctggggggtc ccttagactc tcctgtgcag cctctggatt cactttcagt aacgcctgga tgagctgggt ccgccaggct ccagggaagg ggctggagtg ggttggccgt attaaaagga aaactgatgg tgggacaaca gactacgctg cacccgtgaa aggcagattc accatctcaa gagatgattc aaaaaaatacg ctgcatctgc | DNA nucleotide sequence |

TABLE 24-continued

Informal Sequence Listing

| SEQ. ID. NO. | SEQUENCE | DESCRIPTION |
|---|---|---|
| | aaatgaacag cctgaaaacc gaggacacag ccgtgtatta ctgtaccaca<br>gatgatattg tagttgtacc agctgttatg agggaatact acttcggtat<br>ggacgtctgg ggccaaggga ccacggtcac cgtctcctca | |
| 34 | EVQLVESGGG LVKPGGSLRL SCAASGFTFS NAWMSWVRQA PGKGLEWVGR<br>IKRKTDGGTT DYAAPVKGRF TISRDDSKNT LHLQMNSLKT EDTAVYYCTT<br>DDIVVVPAVM REYYFGMDVW GQGTTVTVSS | AA amino acid sequence |
| 35 | ggattcactt tcagtaacgc ctgg | DNA<br>nucleotide<br>sequence |
| 36 | GFTFSNAW | AA amino acid sequence |
| 37 | attaaaagga aaactgatgg tgggacaaca | DNA<br>nucleotide<br>sequence |
| 38 | IKRKTDGGTT | AA amino acid sequence |
| 39 | accacagatg atattgtagt tgtaccagct gttatgaggg aatactactt<br>cggtatggac gtc | DNA<br>nucleotide<br>sequence |
| 40 | TTDDIVVVPA VMREYYFGMD V | AA amino acid sequence |
| 41 | gacatccaga tgacccagtc tccatcctcc ctgtctgcat ctgtaggaga<br>cagagtcacc atcacttgcc ggacaagtca gggcattaga aatgatttag<br>gctggtatca gcagaaacca gggaaagccc ctaagcgcct gatctatgct<br>gcatccagtt tgcaaagtgg ggtcccatca aggttcagcg gcagtggatc<br>tgggacagaa ttcactctca caatcagcag cctgcagcct gaagattttg<br>caacttatta ctgtctacag cataataatt acccgtacac ttttggccag<br>gggaccaagc tggagatcaa a | DNA<br>nucleotide<br>sequence |
| 42 | DIQMTQSPSS LSASVGDRVT ITCRTSQGIR NDLGWYQQKP GKAPKRLIYA<br>ASSLQSGVPS RFSGSGSGTE FTLTISSLQP EDFATYYCLQ HNNYPYTFGQ<br>GTKLEIK | AA amino acid sequence |
| 43 | cagggcatta gaaatgat | DNA<br>nucleotide<br>sequence |
| 44 | QGIRND | AA amino acid sequence |
| 45 | gctgcatcc | DNA<br>nucleotide<br>sequence |
| 46 | AAS | AA amino acid sequence |
| 47 | ctacagcata ataattacco gtacact | DNA<br>nucleotide<br>sequence |
| 48 | LQHNNYPYT | AA amino acid sequence |
| 49 | caggtgcaat tggtgcagtc tggggcggag gtgaagaagc ctggggcctc<br>agtgcaggtc tcctgcaagg cttctggata ctccttcacc ggctactata<br>tacactgggt gcgacaggcc cctggacaag gacttgagtg gatgggatgg<br>atcaacccta acagtggcac caaaaagtat gcacacaagt ttcagggcag<br>ggtcaccatg accaggggaca cgtccatcga cacagcctac atgattttga<br>gcagtctgat atccgacgac acggccgtgt attactgtgc gagagatgag<br>gactggaact ttgggagctg gttcgactcc tggggccagg gaaccctggt<br>caccgtctcc tca | DNA<br>nucleotide<br>sequence |
| 50 | QVQLVQSGAE VKKPGASVQV SCKASGYSFT GYYIHWVRQA PGQGLEWMGW<br>INPNSGTKKY AHKFQGRVTM TRDTSIDTAY MILSSLISDD TAVYYCARDE<br>DWNFGSWFDS WGQGTLVTVS S | AA amino acid sequence |

TABLE 24-continued

Informal Sequence Listing

| SEQ. ID. NO. | SEQUENCE | DESCRIPTION |
|---|---|---|
| 51 | ggatactcct tcaccggcta ctat | DNA nucleotide sequence |
| 52 | GYSFTGYY | AA amino acid sequence |
| 53 | atcaacccta acagtggcac caaa | DNA nucleotide sequence |
| 54 | INPNSGTK | AA amino acid sequence |
| 55 | gcgagagatg aggactggaa ctttgggagc tggttcgact cc | DNA nucleotide sequence |
| 56 | ARDEDWNFGS WFDS | AA amino acid sequence |
| 57 | gatattgtga tgacccagac tccactctcc tcacctgtca cccttggaca gccggcctcc atctcctgca ggtctagtca aaccctcgta cacggtgatg gaaacacgta cttgagttgg attcagcaga ggccaggcca gcctccgaga ctcctcattt ataaggtttc taatcagttc tctggggtcc cagacagatt cagtggcagt ggggcaggga cagattcac actgaaaatc agcagggtgg aagctgagga tgtcgggctt tatttctgca tgcaagctac acattttccg atcaccttcg gccaagggac acgactggag attaaa | DNA nucleotide sequence |
| 58 | DIVMTQTPLS SPVTLGQPAS ISCRSSQTLV HGDGNTYLSW IQQRPGQPPR LLIYKVSNQF SGVPDRFSGS GAGTDFTLKI SRVEAEDVGL YFCMQATHFP ITFGQGTRLE IK | AA amino acid sequence |
| 59 | caaaccctcg tacacggtga tggaaacacg tac | DNA nucleotide sequence |
| 60 | QTLVHGDGNT Y | AA amino acid sequence |
| 61 | aaggtttct | DNA nucleotide sequence |
| 62 | KVS | AA amino acid sequence |
| 63 | atgcaagcta cacattttcc gatcacc | DNA nucleotide sequence |
| 64 | MQATHFPIT | AA amino acid sequence |
| 65 | caggtacacc tggtgcagtc tggggctgag gtgaagaagc ctggggcctc agtgaaggtc tcctgcaagg cttctggata caccttcacc ggctactata cacattgggt gcgacaggcc cctggacacg gccttgagtg gatgggatgg ctcaaccta atactggtac cacaaagtat atacagaact ttcagggcag ggtcaccatg accagggaca cgtccagcag cacagcctac atggagctga ccaggctgag atctgacgac acggccgtgt attactgtgc gagagatgag gactggaatt atgggagctg gttcgacacc tggggccagg gaaccctggt cacagtctcc tca | DNA nucleotide sequence |
| 66 | QVHLVQSGAE VKKPGASVKV SCKASGYTFT GYYIHWVRQA PGHGLEWMGW LNPNTGTTKY IQNFQGRVTM TRDTSSSTAY MELTRLRSDD TAVYYCARDE DWNYGSWFDT WGQGTLVTVS S | AA amino acid sequence |
| 67 | ggatacacct tcacoggcta ctat | DNA nucleotide sequence |

TABLE 24-continued

Informal Sequence Listing

| SEQ. ID. NO. | SEQUENCE | DESCRIPTION |
|---|---|---|
| 68 | GYTFTGYY | AA amino acid sequence |
| 69 | ctcaaccta atactggtac caca | DNA nucleotide sequence |
| 70 | LNPNTGTT | AA amino acid sequence |
| 71 | gcgagagatg aggactggaa ttatgggagc tggttcgaca cc | DNA nucleotide sequence |
| 72 | ARDEDWNYGS WFDT | AA amino acid sequence |
| 73 | gatattgtaa tgacccagac tccactctcc tcacctgtca cccttggaca gccggcctcc atctcctgca ggtctagtcc aagcctcgta cacagtgatg gaaacaccta cttgagttgg cttcagcaga ggccaggcca gcctccaaga ctcctaattt ataagatttc taaccgattc totggggtcc cagacagatt cagtggcagt ggggcaggga cagattcac gctgaaaatc agcagggtgg aagctgagga tgtcggggtt tattactgca tgcaagctac acattttccg atcaccttcg gccaagggac acgactggag attaga | DNA nucleotide sequence |
| 74 | DIVMTQTPLS SPVTLGQPAS ISCRSSPSLV HSDGNTYLSW LQQRPGQPPR LLIYKISNRF SGVPDRFSGS GAGTDFTLKI SRVEAEDVGV YYCMQATHFP ITFGQGTRLE IR | AA amino acid sequence |
| 75 | ccaagcctcg tacacagtga tggaaacacc tac | DNA nucleotide sequence |
| 76 | PSLVHSDGNT Y | AA amino acid sequence |
| 77 | aagatttct | DNA nucleotide sequence |
| 78 | KIS | AA amino acid sequence |
| 79 | atgcaagcta cacattttcc gatcacc | DNA nucleotide sequence |
| 80 | MQATHFPIT | AA amino acid sequence |
| 81 | gaggtgcagc tggtggaatc tgggggaggt gtggtgcggc ctggggggtc cctgagactc tcctgtgcag cctctggatt cacttttgat gattatggca tgacctgggt ccgccaagct ccagggaggg gcctggaatg ggtctctggt attcattggc atggtaaacg cacaggttat gcagactctg tgaagggccg attcaccata tccagagaca acgccaagaa atccctgtat ctgcaaatga acagtctgaa aggcgaggac acggccttgt atcattgtgt gaggggggga atgagtacag gggactggtt cgacccctgg ggccagggaa ccctggtcat cgtctcctca | DNA nucleotide sequence |
| 82 | EVQLVESGGG VVRPGGSLRL SCAASGFTFD DYGMTWVRQA PGRGLEWVSG IHWHGKRTGY ADSVKGRFTI SRDNAKKSLY LQMNSLKGED TALYHCVRGG MSTGDWFDPW GQGTLVIVSS | AA amino acid sequence |
| 83 | ggattcactt ttgatgatta tggc | DNA nucleotide sequence |
| 84 | GFTFDDYG | AA amino acid sequence |

TABLE 24-continued

Informal Sequence Listing

| SEQ. ID. NO. | SEQUENCE | DESCRIPTION |
|---|---|---|
| 85 | attcattggc atggtaaacg caca | DNA nucleotide sequence |
| 86 | IHWHGKRT | AA amino acid sequence |
| 87 | gtgaggggg gaatgagtac aggggactgg ttcgacccc | DNA nucleotide sequence |
| 88 | VRGGMSTGDW FDP | AA amino acid sequence |
| 89 | gacatccaga tgacccagtc tocatcctcc ctgtctgcat ctctaggaga cagagtcacc atcacttgcc gggcaagtca gagcattaac agttatttaa attggtatca gcagaaacca gggaaagccc ctaaactcct gatctatgtt gcatccagtt tgcaaagtgg ggtcccatca aggttcagtg gcagtggatc tgggacagaa ttcactctca ccatcagcaa totgcaacct gaagattttg caacttacta ctgtcaacag agttacagta cccctccgat caccttcggc caagggacac gactggagat taaa | DNA nucleotide sequence |
| 90 | DIQMTQSPSS LSASLGDRVT ITCRASQSIN SYLNWYQQKP GKAPKLLIYV ASSLQSGVPS RFSGSGSGTE FTLTISNLQP EDFATYYCQQ SYSTPPITFG QGTRLEIK | AA amino acid sequence |
| 91 | cagagcatta acagttat | DNA nucleotide sequence |
| 92 | QSINSY | AA amino acid sequence |
| 93 | gttgcatcc | DNA nucleotide sequence |
| 94 | VAS | AA amino acid sequence |
| 95 | caacagagtt acagtacccc tccgatcaco | DNA nucleotide sequence |
| 96 | QQSYSTPPIT | AA amino acid sequence |
| 97 | gaggtgcagc tggtggagtc tggggggaggt gtggtacggc cggggggggtc cctgagactc tcctgtgcag cctctggatt cacctttgat gattatggca tgacctgggt ccgccaagtt ccagggaagg ggctggagtg ggtctctggt attcattgga gtggtagaag cacaggttat gcagactctg tgaagggccg attcaccatc tccagagaca acgccaagaa ctccctgtat ctgcaaatga acagtctgag agccgaggac acggccttgt attactgtgc gaggggggga atgagtacgg gggactggtt cgaccctgg ggccagggaa ccctggtcac cgtctcctca | DNA nucleotide sequence |
| 98 | EVQLVESGGG VVRPGGSLRL SCAASGFTFD DYGMTWVRQV PGKGLEWVSG IHWSGRSTGY ADSVKGRFTI SRDNAKNSLY LQMNSLRAED TALYYCARGG MSTGDWFDPW GQGTLVTVSS | AA amino acid sequence |
| 99 | ggattcacct ttgatgatta tggc | DNA nucleotide sequence |
| 100 | GFTFDDYG | AA amino acid sequence |
| 101 | attcattgga gtggtagaag caca | DNA nucleotide sequence |

TABLE 24-continued

Informal Sequence Listing

| SEQ. ID. NO. | SEQUENCE | DESCRIPTION |
|---|---|---|
| 102 | IHWSGRST | AA amino acid sequence |
| 103 | gcgagggggg gaatgagtac gggggactgg ttcgacccc | DNA nucleotide sequence |
| 104 | ARGGMSTGDW FDP | AA amino acid sequence |
| 105 | gacatccaga tgacccagtc tccatcctcc ctgtctgcat ctgtaggaga cagagtcacc atcacttgcc gggcaagtca gagcattagc agctatttaa attggtatca gcagaaacca gggaaagccc ctaagctcct gatctatgtt gcatccagtt tgcaaagtgg ggtcccatca aggttcagtg gcagtggatc tgggacagat ttcactctca ccatcagcag tctgcaacct gaagattttg caacttacta ctgtcaacag agttacagta cccctccgat caccttcggc caagggacac gactggagat taaa | DNA nucleotide sequence |
| 106 | DIQMTQSPSS LSASVGDRVT ITCRASQSIS SYLNWYQQKP GKAPKLLIYV ASSLQSGVPS RFSGSGSGTD FTLTISSLQP EDFATYYCQQ SYSTPPITFG QGTRLEIK | AA amino acid sequence |
| 107 | cagagcatta gcagctat | DNA nucleotide sequence |
| 108 | QSISSY | AA amino acid sequence |
| 109 | gttgcatcc | DNA nucleotide sequence |
| 110 | VAS | AA amino acid sequence |
| 111 | caacagagtt acagtacccc tccgatcacc | DNA nucleotide sequence |
| 112 | QQSYSTPPIT | AA amino acid sequence |
| 113 | gaggtgcagt tggtggagtc tggaggaggc ttggtccagc ctggggggtc cctaagactc toctgtgcag cctctgggtt caccgtcggt agtaactaca tgaactgggt ccgtcaggct ccagggaagg gactggagtg ggtctcagtt atttatagtg gtggtagtac atactacgca gattccgtga agggccgatt caccatctcc agactcactt ccaagaacac actgtatctt caaatgagca gcctgagacc tgaggacacg gccgtgtatt attgtgcgag agggattagg ggtctggacg tctggggcca agggaccacg gtcaccgtct cttca | DNA nucleotide sequence |
| 114 | EVQLVESGGG LVQPGGSLRL SCAASGFTVG SNYMNWVRQA PGKGLEWVSV IYSGGSTYYA DSVKGRFTIS RLTSKNTLYL QMSSLRPEDT AVYYCARGIR GLDVWGQGTT VTVSS | AA amino acid sequence |
| 115 | gggttcaccg tcggtagtaa ctac | DNA nucleotide sequence |
| 116 | GFTVGSNY | AA amino acid sequence |
| 117 | atttatagtg gtggtagtac a | DNA nucleotide sequence |
| 118 | IYSGGST | AA amino acid sequence |
| 119 | gcgagaggga ttaggggtct ggacgtc | DNA nucleotide sequence |
| 120 | ARGIRGLDV | AA amino acid sequence |

TABLE 24-continued

Informal Sequence Listing

| SEQ. ID. NO. | SEQUENCE | DESCRIPTION |
|---|---|---|
| 121 | gacatccaga tgacccagtc tccatcctcc ctgtctgcat ctgtaggaga<br>cagagtcacc atcacttgcc gggcaagtca gaccattaac atctatttaa<br>attggtatca gcagaaacca gggagagccc ctaggctcct gatctatgct<br>gcatccagtt tgcaaagtgg ggtcccatca aggttcagtg gcagtggatc<br>tgggacagat ttcactctca ccatcagcag tctgcaacct gaagattttg<br>caacttacta ctgtcaccag agttacagta cccctccgat caccttcggc<br>caagggacac gactggagat taaa | DNA<br>nucleotide<br>sequence |
| 122 | DIQMTQSPSS LSASVGDRVT ITCRASQTIN IYLNWYQQKP GRAPRLLIYA<br>ASSLQSGVPS RFSGSGSGTD FTLTISSLQP EDFATYYCHQ SYSTPPITFG<br>QGTRLEIK | AA amino acid<br>sequence |
| 123 | cagaccatta acatctat | DNA<br>nucleotide<br>sequence |
| 124 | QTINIY | AA amino acid<br>sequence |
| 125 | gctgcatcc | DNA<br>nucleotide<br>sequence |
| 126 | AAS | AA amino acid<br>sequence |
| 127 | caccagagtt acagtacccc tccgatcacc | DNA<br>nucleotide<br>sequence |
| 128 | HQSYSTPPIT | AA amino acid<br>sequence |
| 129 | gaggaacggt tggtggagtc tggaggagac ttggtccagc ctggggggtc<br>cctgagactc tcctgtgcag cctctggcat caccgtcggt actaattata<br>tgaactgggt ccgccaggct ccagggaagg gactggagtg ggtctcagtt<br>atttctagcg gtggtaatac acactacgca gactccgtga agggccgatt<br>cattatgtcc agacaaactc ccaaaaacac gctgtatctt cagatgaata<br>gcctggaaac tgaggacacg gccgtatatt attgtgcgag ggggatcaga<br>ggtttggacg tctgggggcca agggaccatg gtcaccgtct cctca | DNA<br>nucleotide<br>sequence |
| 130 | EERLVESGGD LVQPGGSLRL SCAASGITVG TNYMNWVRQA PGKGLEWVSV<br>ISSGGNTHYA DSVKGRFIMS RQTSKNTLYL QMNSLETEDT AVYYCARGIR<br>GLDVWGQGTM VTVSS | AA amino acid<br>sequence |
| 131 | ggcatcaccg tcggtactaa ttat | DNA<br>nucleotide<br>sequence |
| 132 | GITVGTNY | AA amino acid<br>sequence |
| 133 | atttctagcg gtggtaatac a | DNA<br>nucleotide<br>sequence |
| 134 | ISSGGNT | AA amino acid<br>sequence |
| 135 | gcgaggggga tcagaggttt ggacgtc | DNA<br>nucleotide<br>sequence |
| 136 | ARGIRGLDV | AA amino acid<br>sequence |
| 137 | gacatccaga tgacccagtc tccatcctcc ctgtctgcat ctgtaggaga<br>cagagtcacc atcacttgcc gggcaagtca gagcatgagc agctatttaa<br>attggtatca gcagaaacca gggagagccc ctaagctcct gatctttgct<br>gcatccagtt tgcaaagtgg ggtcccatca aggttcagtg gcagtggato<br>tgggacagat ttcactctca ccatcagcag tctgcaacct gaagattttg<br>caacttacta ctgtcaacag agttacagta cccctccgat caccttcggc<br>caagggacac gactggagat taaa | DNA<br>nucleotide<br>sequence |

TABLE 24-continued

| | Informal Sequence Listing | |
|---|---|---|

| SEQ.<br>ID. NO. | SEQUENCE | DESCRIPTION |
|---|---|---|
| 138 | DIQMTQSPSS LSASVGDRVT ITCRASQSMS SYLNWYQQKP GRAPKLLIFA<br>ASSLQSGVPS RFSGSGSGTD FTLTISSLQP EDFATYYCQQ SYSTPPITFG<br>QGTRLEIK | AA amino acid<br>sequence |
| 139 | cagagcatga gcagctat | DNA<br>nucleotide<br>sequence |
| 140 | QSMSSY | AA amino acid<br>sequence |
| 141 | gctgcatcc | DNA<br>nucleotide<br>sequence |
| 142 | AAS | AA amino acid<br>sequence |
| 143 | caacagagtt acagtacccc tccgatcacc | DNA<br>nucleotide<br>sequence |
| 144 | QQSYSTPPIT | AA amino acid<br>sequence |
| 145 | caggtccagc tggtgcagtc tggggctgag gtgaagatgc ctgggtcctc<br>ggtgagggtc tcctgcaagg cttctggagg catcttcagc agttctacta<br>tcagttgggt gcgacaggcc cctggacaag ggcttgaatg gatgggagag<br>atcatccctg tctttggtac agtaaactac gcacagaagt tccaggacag<br>agtcatattt accgcggacg aatctacgac tacagcctac atggagctga<br>gcagcctgaa atctggggac acggccgtat atttctgtgc gcgaaattgg<br>ggattaggct cttttttatat ctggggccaa gggacaatgg tcaccgtctc<br>ttca | DNA<br>nucleotide<br>sequence |
| 146 | QVQLVQSGAE VKMPGSSVRV SCKASGGIFS SSTISWVRQA PGQGLEWMGE<br>IIPVFGTVNY AQKFQDRVIF TADESTTTAY MELSSLKSGD TAVYFCARNW<br>GLGSFYIWGQ GTMVTVSS | AA amino acid<br>sequence |
| 147 | ggaggcatct tagcagttc tact | DNA<br>nucleotide<br>sequence |
| 148 | GGIFSSST | AA amino acid<br>sequence |
| 149 | atcatccctg tctttggtac agta | DNA<br>nucleotide<br>sequence |
| 150 | IIPVFGTV | AA amino acid<br>sequence |
| 151 | gcgcgaaatt ggggattagg ctcttttttat atc | DNA<br>nucleotide<br>sequence |
| 152 | ARNWGLGSFY I | AA amino acid<br>sequence |
| 153 | gaaattgtgt tgacgcagtc tccaggcacc ctgtctttgt ctccagggga<br>aagagccacc ctctcctgca gggccagtca gagttttaac ttcaactact<br>tagcctggta ccagcagaaa cctggccagg ctcccagact cctcatctat<br>ggtgcatcca gcagggccac tggcatccca gacaggttca gtggcagtgg<br>gtctgggaca gacttcactc tcaccatcaa caggctggag cctgaagatt<br>ttgagtgtt ttattgtcag cagtatgaaa gcgcaccttg gacgttcggc<br>caagggacca aggtggaaat caaa | DNA<br>nucleotide<br>sequence |
| 154 | EIVLTQSPGT LSLSPGERAT LSCRASQSFN FNYLAWYQQK PGQAPRLLIY<br>GASSRATGIP DRFSGSGSGT DFTLTINRLE PEDFGVFYCQ QYESAPWTFG<br>QGTKVEIK | AA amino acid<br>sequence |
| 155 | cagagtttta acttcaacta c | DNA<br>nucleotide<br>sequence |

TABLE 24-continued

Informal Sequence Listing

| SEQ. ID. NO. | SEQUENCE | DESCRIPTION |
|---|---|---|
| 156 | QSFNFNY | AA amino acid sequence |
| 157 | ggtgcatcc | DNA nucleotide sequence |
| 158 | GAS | AA amino acid sequence |
| 159 | cagcagtatg aaagcgcacc ttggacg | DNA nucleotide sequence |
| 160 | QQYESAPWT | AA amino acid sequence |
| 161 | gaggtgcagc ttgtagagtc tggggggagac ttggtacatc ctggcaggtc cctgagactc tcctgtgcag cctctggttt ccctttgat gagtatgcca tgcactgggt ccggcaagtt ccaggaagg gcctggagtg ggtctcaggt attagttgga gtaataataa cataggctat gcggactctg tgaagggccg attcaccato tccagagaca acgccaaaaa ctccctgtat ctacaaatga acagtctgag acctgaggac acggcctttt attactgtgc aaaatctgga atctttgact cctggggcca gggaaccctg gtcaccgtct cctca | DNA nucleotide sequence |
| 162 | EVQLVESGGD LVHPGRSLRL SCAASGFPFD EYAMHWVRQV PGKGLEWVSG ISWSNNNIGY ADSVKGRFTI SRDNAKNSLY LQMNSLRPED TAFYYCAKSG IFDSWGQGTL VTVSS | AA amino acid sequence |
| 163 | ggtttcccct ttgatgagta tgcc | DNA nucleotide sequence |
| 164 | GFPFDEYA | AA amino acid sequence |
| 165 | attagttgga gtaataataa cata | DNA nucleotide sequence |
| 166 | ISWSNNNI | AA amino acid sequence |
| 167 | gcaaaatctg gaatctttga ctcc | DNA nucleotide sequence |
| 168 | AKSGIFDS | AA amino acid sequence |
| 169 | gacatccaga tgacccagtc tccatcctcc ctgtctgcat ctgtaggaga cagagtcacc atcacttgcc gggcaagtca gagcattagc agctatttaa attggtatca gcagaaacca gggaagctcc tgatctatgc tgcatccagt ttgcaaagtg gggtcccatc acggttcagt ggcggtggat ctgggacaga tttcactctc accatcagca gtctgcgacc tgaagatttt gcaacttact actgtcaaca gagttactgt acccctccga tcaccttcgg ccaagggaca cgactggaga ttaaa | DNA nucleotide sequence |
| 170 | DIQMTQSPSS LSASVGDRVT ITCRASQSIS SYLNWYQQKP GKLLIYAASS LQSGVPSRFS GGGSGTDFTL TISSLRPEDF ATYYCQQSYC TPPITFGQGT RLEIK | AA amino acid sequence |
| 171 | cagagcatta gcagctat | DNA nucleotide sequence |
| 172 | QSISSY | AA amino acid sequence |
| 173 | gctgcatcc | DNA nucleotide sequence |
| 174 | AAS | AA amino acid sequence |

TABLE 24-continued

Informal Sequence Listing

| SEQ. ID. NO. | SEQUENCE | DESCRIPTION |
|---|---|---|
| 175 | caacagagtt actgtacccc tccgatcacc | DNA nucleotide sequence |
| 176 | QQSYCTPPIT | AA amino acid sequence |
| 177 | gaggtgcagc tggtggagtc cggggggaggc gtggtccagc ctgggaggtc cctgagactc tcctgtgcag cctctggatt caccttcagt agttatggca tgcactgggt ccgccaggct ccaggcaagg gactggagtg ggtgacactt atatcatatg agggaaggaa taaatactat gcagactccg tgaagggccg attcaccatt tccagagaca attccaagaa cacgctgtat ctgcaaatga acagcctgag agctgaggac acggctgtat attactgtgc gaaagatagg acccttacg gtatggacgt ctggggccaa ggaaccacgg tcaccgtctc ctca | DNA nucleotide sequence |
| 178 | EVQLVESGGG VVQPGRSLRL SCAASGFTFS SYGMHWVRQA PGKGLEWVTL ISYEGRNKYY ADSVKGRFTI SRDNSKNTLY LQMNSLRAED TAVYYCAKDR TLYGMDVWGQ GTTVTVSS | AA amino acid sequence |
| 179 | ggattcacct tcagtagtta tggc | DNA nucleotide sequence |
| 180 | GFTFSSYG | AA amino acid sequence |
| 181 | atatcatatg agggaaggaa taaa | DNA nucleotide sequence |
| 182 | ISYEGRNK | AA amino acid sequence |
| 183 | gcgaaagata ggaccctta cggtatggac gtc | DNA nucleotide sequence |
| 184 | AKDRTLYGMD V | AA amino acid sequence |
| 185 | caggtcacct tgagggagtc tggtcctgcg ctggtgaaaa ccacacagac cctcacactg acctgcacct tctctgggtt ctcactcagc actaatagaa tgtgtgtgac ctggatccgt cagcccccag ggaaggccct ggagtggctt gcgcgcattg attgggatgg tgttaaatac tacaacacat ctctgaagac caggctcacc atctccaagg acacctccaa aaaccaggtg gtccttacaa tgaccaacat ggaccctgtg gacacagcca cttttttactg tgcacggtcg acttcgttga cttttttacta ctttgactac tggggccagg gaaccctggt caccgtctcc tca | DNA nucleotide sequence |
| 186 | QVTLRESGPA LVKTTQTLTL TCTFSGFSLS TNRMCVTWIR QPPGKALEWL ARIDWDGVKY YNTSLKTRLT ISKDTSKNQV VLTMTNMDPV DTATFYCARS TSLTFYYFDY WGQGTLVTVS S | AA amino acid sequence |
| 187 | gggttctcac tcagcactaa tagaatgtgt | DNA nucleotide sequence |
| 188 | GFSLSTNRMC | AA amino acid sequence |
| 189 | attgattggg atggtgttaa a | DNA nucleotide sequence |
| 190 | IDWDGVK | AA amino acid sequence |
| 191 | gcacggtcga cttcgttgac tttttactac tttgactac | DNA nucleotide sequence |
| 192 | ARSTSLTFYY FDY | AA amino acid sequence |

TABLE 24-continued

Informal Sequence Listing

| SEQ. ID. NO. | SEQUENCE | DESCRIPTION |
|---|---|---|
| 193 | gacatccaga tgacccagtc tccatcctcc ctgtctgcat ctgtaggaga cagagtcacc atcacttgcc gggcaagtca gagcattagc agctatttaa attggtatca gcagaaacca gggaaagccc ctaagctcct gatctatgct gcatccagtt tgcaaagtgg ggtcccatca aggttcagtg gcagtggatc tgggacagat ttcactctca ccatcagcag tctgcaacct gaagattttg caacttacta ctgtcaacag agttacagta cccctccgat caccttcggc caagggacac gactggagat taaa | DNA nucleotide sequence |
| 194 | DIQMTQSPSS LSASVGDRVT ITCRASQSIS SYLNWYQQKP GKAPKLLIYA ASSLQSGVPS RFSGSGSGTD FTLTISSLQP EDFATYYCQQ SYSTPPITFG QGTRLEIK | AA amino acid sequence |
| 195 | cagagcatta gcagctat | DNA nucleotide sequence |
| 196 | QSISSY | AA amino acid sequence |
| 197 | gctgcatcc | DNA nucleotide sequence |
| 198 | AAS | AA amino acid sequence |
| 199 | caacagagtt acagtacccc tccgatcacc | DNA nucleotide sequence |
| 200 | QQSYSTPPIT | AA amino acid sequence |
| 201 | gaggtgcagc tggtggagtc tggaggaggc ttggtccagc cggggggtc cctgagactc tcctgtgcag cctctgagtt caccgtcggt accaaccaca tgaactgggt ccgccaggct ccagggaagg gactggagtg ggtctcagtt atttatagcg gtggtaacac attctacgca gactccgtga agggccgatt caccatctcc agacacactt ccaagaacac gctgtatctt caaatgaaca gcctgacagc agaggacacg gccgtatatt actgtgcgcg aggattgggg ggtatggacg tctggggcca aggaccacg gtcaccgtct cctca | DNA nucleotide sequence |
| 202 | EVQLVESGGG LVQPGGSLRL SCAASEFTVG TNHMNWVRQA PGKGLEWVSV IYSGGNTFYA DSVKGRFTIS RHTSKNTLYL QMNSLTAEDT AVYYCARGLG GMDVWGQGTT VTVSS | AA amino acid sequence |
| 203 | gagttcaccg tcggtaccaa ccac | DNA nucleotide sequence |
| 204 | EFTVGTNH | AA amino acid sequence |
| 205 | atttatagcg gtggtaacac a | DNA nucleotide sequence |
| 206 | IYSGGNT | AA amino acid sequence |
| 207 | gcgcgaggat tggggggtat ggacgtc | DNA nucleotide sequence |
| 208 | ARGLGGMDV | AA amino acid sequence |
| 209 | gacatccaga tgacccagtc tccatcctcc ctgtctgcat ctgtaggaga cagagtcacc atcacttgcc gggcgagtca ggtcattagc aattatttag cctggtatca gcagaaacca gggaaagttc ctaggctcct gatctatgct gcatccactt tgcaatcagg ggtcccatct cgtttcagtg gcagtggatc tgggacagat ttcactctca ccatcagcag cctgcagcct gaagatgttg caacttatta ctgtcaaaag tataacagtg cccctcggac gttoggccaa gggaccaagg tggaaatcaa a | DNA nucleotide sequence |

TABLE 24-continued

Informal Sequence Listing

| SEQ. ID. NO. | SEQUENCE | DESCRIPTION |
|---|---|---|
| 210 | DIQMTQSPSS LSASVGDRVT ITCRASQVIS NYLAWYQQKP GKVPRLLIYA ASTLQSGVPS RFSGSGSGTD FTLTISSLQP EDVATYYCQK YNSAPRTFGQ GTKVEIK | AA amino acid sequence |
| 211 | caggtcatta gcaattat | DNA nucleotide sequence |
| 212 | QVISNY | AA amino acid sequence |
| 213 | gctgcatcc | DNA nucleotide sequence |
| 214 | AAS | AA amino acid sequence |
| 215 | caaaagtata acagtgcccc tcggacg | DNA nucleotide sequence |
| 216 | QKYNSAPRT | AA amino acid sequence |
| 217 | gaggtgcagc tggtggagtc tgggggaggc ttggtccagc ggggggagtc cctgagactt tactgtgcag cctctggatt cacctttagt aaatattgga tgaactgggt ccgccaggct ccagggaagg ggctggagtg ggtggccaac ataaagggag atggaagtga gaaatactat gtggactctg tgaagggccg gttcaccatc tccagagaca acgccaagaa ctcactatat ctacaaatga acagcctgag agccgaggac acggctgttt attactgtgc gagagattat tggggatcag gctactactt tgacttctgg ggccagggaa ccctggtcac cgtctcctca | DNA nucleotide sequence |
| 218 | EVQLVESGGG LVQRGESLRL YCAASGFTFS KYWMNWVRQA PGKGLEWVAN IKGDGSEKYY VDSVKGRFTI SRDNAKNSLY LQMNSLRAED TAVYYCARDY WGSGYYFDFW GQGTLVTVSS | AA amino acid sequence |
| 219 | ggattcacct ttagtaaata ttgg | DNA nucleotide sequence |
| 220 | GFTFSKYW | AA amino acid sequence |
| 221 | ataaagggag atggaagtga gaaa | DNA nucleotide sequence |
| 222 | IKGDGSEK | AA amino acid sequence |
| 223 | gcgagagatt attggggatc aggctactac tttgactto | DNA nucleotide sequence |
| 224 | ARDYWGSGYY FDF | AA amino acid sequence |
| 225 | gacatccaga tgacccagtc tccatcctcc ctgtctgcat ctgtaggaga cagagtcacc atcacttgcc gggcaagtca gaacattaac aactatttaa attggtatca gcagaaacca gggaaagccc ctaaactcct gatctatgct gcatccagtt tccaaaatgc ggtcccatca aggttcagtg gcagtggatc tgggacagat ttcactctca ccatcagcag tctgcaacct gaagattttg caacttacta ctgtcaacag agttacaata ccccgctcac tttcggcggg gggaccaagg tggagatcaa a | DNA nucleotide sequence |
| 226 | DIQMTQSPSS LSASVGDRVT ITCRASQNIN NYLNWYQQKP GKAPKLLIYA ASSFQNAVPS RFSGSGSGTD FTLTISSLQP EDFATYYCQQ SYNTPLTFGG GTKVEIK | AA amino acid sequence |
| 227 | cagaacatta acaactat | DNA nucleotide sequence |

TABLE 24-continued

Informal Sequence Listing

| SEQ. ID. NO. | SEQUENCE | DESCRIPTION |
|---|---|---|
| 228 | QNINNY | AA amino acid sequence |
| 229 | gctgcatcc | DNA nucleotide sequence |
| 230 | AAS | AA amino acid sequence |
| 231 | caacagagtt acaatacccc gctcact | DNA nucleotide sequence |
| 232 | QQSYNTPLT | AA amino acid sequence |
| 233 | gaggtgcagc tggtggagtc tggggggaggc ttggtccagt ctggggggtc cctgagactc tcctgtgcag cctctggatt caccttttagt agctattgga tgagctgggt ccgccaggct ccagggaagg ggctggagtg ggtggccaac ataaagcaag atggaagtga gaaatactat gtggactctg tgaagggccg attcaccatc tccagagaca acgccaagaa ctcactgtat ctgcaaatga acagcctgag agccgatgac acggctgtgt attactgtgc gagagatgat attgtagtag taccagctcc tatgggatat tactactact acttcggtat ggacgtctgg ggccaaggga ccacggtcac cgtctcctca | DNA nucleotide sequence |
| 234 | EVQLVESGGG LVQSGGSLRL SCAASGFTFS SYWMSWVRQA PGKGLEWVAN IKQDGSEKYY VDSVKGRFTI SRDNAKNSLY LQMNSLRADD TAVYYCARDD IVVVPAPMGY YYYYFGMDVW GQGTTVTVSS | AA amino acid sequence |
| 235 | ggattcacct ttagtagcta ttgg | DNA nucleotide sequence |
| 236 | GFTFSSYW | AA amino acid sequence |
| 237 | ataaagcaag atggaagtga gaaa | DNA nucleotide sequence |
| 238 | IKQDGSEK | AA amino acid sequence |
| 239 | gcgagagatg atattgtagt agtaccagct cctatgggat attactacta ctacttcggt atggacgtc | DNA nucleotide sequence |
| 240 | ARDDIVVVPA PMGYYYYYFG MDV | AA amino acid sequence |
| 241 | gacatccaga tgacccagtc tccatcctcc ctgtctgcat ctgtaggaga cagagtcacc atcacttgcc gggcaagtca gggcattaga aatgatttag gctggtatca gcagaaacca gggaaagccc ctaagcgcct gatctatgct gcatccagtt tgcaaagtgg ggtcccatca aggttcagcg gcagtggatc tgggacagaa ttcactctca caatcagcag cctgcagcct gaagattttg caacttatta ctgtctacag cataatagtt acccgtacac ttttggccag gggaccaagc tggagatcaa a | DNA nucleotide sequence |
| 242 | DIQMTQSPSS LSASVGDRVT ITCRASQGIR NDLGWYQQKP GKAPKRLIYA ASSLQSGVPS RFSGSGSGTE FTLTISSLQP EDFATYYCLQ HNSYPYTFGQ GTKLEIK | AA amino acid sequence |
| 243 | caggggcatta gaaatgat | DNA nucleotide sequence |
| 244 | QGIRND | AA amino acid sequence |
| 245 | gctgcatcc | DNA nucleotide sequence |

TABLE 24-continued

Informal Sequence Listing

| SEQ. ID. NO. | SEQUENCE | DESCRIPTION |
|---|---|---|
| 246 | AAS | AA amino acid sequence |
| 247 | ctacagcata atagttaccc gtacact | DNA nucleotide sequence |
| 248 | LQHNSYPYT | AA amino acid sequence |
| 249 | gaagtgcagc tggtggagtc tgggggaggc ttggttcagc ctggcaggtc cctgagactc tcctgtgcag cctctggatt cacctttgat gattttgcca tgcactgggt ccgacaagct ccagggaagg gcctggagtg ggtctcaggt attagttgga ctggtggtaa catggactat gcgaactctg tgaagggccg attcaccatc tccagagagg acgccaagaa ttccctgtat ctgcaaatga acagtctgag agctgcggac acggccttgt attactgtgt aaaagatata aggggggatag tggctacggg ggggggcttt gatatctggg gccgaggggac aatggtcacc gtctcttca | DNA nucleotide sequence |
| 250 | EVQLVESGGG LVQPGRSLRL SCAASGFTFD DFAMHWVRQA PGKGLEWVSG ISWTGGNMDY ANSVKGRFTI SREDAKNSLY LQMNSLRAAD TALYYCVKDI RGIVATGGAF DIWGRGTMVT VSS | AA amino acid sequence |
| 251 | ggattcacct ttgatgattt tgcc | DNA nucleotide sequence |
| 252 | GFTFDDFA | AA amino acid sequence |
| 253 | attagttgga ctggtggtaa catg | DNA nucleotide sequence |
| 254 | ISWTGGNM | AA amino acid sequence |
| 255 | gtaaaagata taagggggat agtggctacg ggggggcttt ttgatatc | DNA nucleotide sequence |
| 256 | VKDIRGIVAT GGAFDI | AA amino acid sequence |
| 257 | gacatccaga tgacccagtc tccatcctcc ctgtctgcat ctgtaggaga cagagtcacc atctcttgcc gggcaagtca gaccattagc acttatttaa attggtttca gcagaaacca gggaaagccc ctaagctcct gatctatgtt gtgtccagtt tgcaaagtgg ggtcccatca aggttcagtg gcagtggatc tgggacagat ttcactctca ccatcagcag tctgcaacct gaagattttg caacttatta ctgtcaacag agttacagta ccccattcac tttcggccct gggaccaaag tggatatcaa a | DNA nucleotide sequence |
| 258 | DIQMTQSPSS LSASVGDRVT ISCRASQTIS TYLNWFQQKP GKAPKLLIYV VSSLQSGVPS RFSGSGSGTD FTLTISSLQP EDFATYYCQQ SYSTPFTFGP GTKVDIK | AA amino acid sequence |
| 259 | cagaccatta gcacttat | DNA nucleotide sequence |
| 260 | QTISTY | AA amino acid sequence |
| 261 | gttgtgtcc | DNA nucleotide sequence |
| 262 | VVS | AA amino acid sequence |
| 263 | caacagagtt acagtacccc attcact | DNA nucleotide sequence |

TABLE 24-continued

Informal Sequence Listing

| SEQ. ID. NO. | SEQUENCE | DESCRIPTION |
|---|---|---|
| 264 | QQSYSTPFT | AA amino acid sequence |
| 265 | gaggtgcagc tggtggagtc tggaggaggc ttggtccagc cggggggtc cctgagactc tcctgtgcag cctctggatt caccgtcggt accaactaca tgaactgggt ccgccaggct ccagggaagg gactggagtg gatctcagtt atttatagcg gtggtagcac attctacgca gactccgtga agggccgatt caccatctcc agacagactt cccagaacac gctgtatctt caaatgaaca gcctgagacc tgaggacacg gccgtatatt actgtgcgag aggtatacgt ggttttgata tctggggcca aggacaatg gtcaccgtct cttca | DNA nucleotide sequence |
| 266 | EVQLVESGGG LVQPGGSLRL SCAASGFTVG TNYMNWVRQA PGKGLEWISV IYSGGSTFYA DSVKGRFTIS RQTSQNTLYL QMNSLRPEDT AVYYCARGIR GFDIWGQGTM VTVSS | AA amino acid sequence |
| 267 | ggattcaccg tcggtaccaa ctac | DNA nucleotide sequence |
| 268 | GFTVGTNY | AA amino acid sequence |
| 269 | atttatagcg gtggtagcac a | DNA nucleotide sequence |
| 270 | IYSGGST | AA amino acid sequence |
| 271 | gcgagaggta tacgtggttt tgatatc | DNA nucleotide sequence |
| 272 | ARGIRGFDI | AA amino acid sequence |
| 273 | gacatccaga tgacccagtc tccatcctcc ctgtctgcat ctgtaggaga cagagtcacc atcacttgcc gggcaagtca gagcattagc agctatttaa attggtatca gcagaaacca gggaaagccc ctaagctcct gatctatgct gcatccagtt tgcaaagtgg ggtcccgtca aggttcagtg gcagtggatc tgggacagat ttcactctca ccatcagcag tctgcaacct gaagattttg caacttacta ctgtcaacag agttacagta cccctccgat caccttcggc caagggacac gactggagat taaa | DNA nucleotide sequence |
| 274 | DIQMTQSPSS LSASVGDRVT ITCRASQSIS SYLNWYQQKP GKAPKLLIYA ASSLQSGVPS RFSGSGSGTD FTLTISSLQP EDFATYYCQQ SYSTPPITFG QGTRLEIK | AA amino acid sequence |
| 275 | cagagcatta gcagctat | DNA nucleotide sequence |
| 276 | QSISSY | AA amino acid sequence |
| 277 | gctgcatcc | DNA nucleotide sequence |
| 278 | AAS | AA amino acid sequence |
| 279 | caacagagtt acagtacccc tccgatcacc | DNA nucleotide sequence |
| 280 | QQSYSTPPIT | AA amino acid sequence |
| 281 | gaggtgcagc tggtggagtc tggaggaggc ttggtccagc cggggggtc cctgagactc tcctgtgcag cctctgggtt taccatcagt accaactaca tgaactgggt ccgccaggct ccagggaagg ggctggagtg ggtcgcagtt atttatagca gtggttccac atactatatc gactccgtga agggccgatt caccatctcc agactcactt ccaagaacac ggtgtatctt caaatgagca gcctgaattc tgaagacacg gccgtgtatt actgtgcgag ggggatcagg | DNA nucleotide sequence |

TABLE 24-continued

Informal Sequence Listing

| SEQ. ID. NO. | SEQUENCE | DESCRIPTION |
|---|---|---|
| | ggttttgata tttggggcca agggacaatg gtcaccgtct cttca | |
| 282 | EVQLVESGGG LVQPGGSLRL SCAASGFTIS TNYMNWVRQA PGKGLEWVAV IYSSGSTYYI DSVKGRFTIS RLTSKNTVYL QMSSLNSEDT AVYYCARGIR GFDIWGQGTM VTVSS | AA amino acid sequence |
| 283 | gggtttacca tcagtaccaa ctac | DNA nucleotide sequence |
| 284 | GFTISTNY | AA amino acid sequence |
| 285 | atttatagca gtggttccac a | DNA nucleotide sequence |
| 286 | IYSSGST | AA amino acid sequence |
| 287 | gcgaggggga tcaggggttt tgatatt | DNA nucleotide sequence |
| 288 | ARGIRGFDI | AA amino acid sequence |
| 289 | gaagtgcagc tggtggagtc ggggggaggc ttggtacagc ctggcaggtc cctgagactc tcctgtgcag cctctggatt caccattgat gatagtgcca tgcactgggt ccggcaaact ccagggaagg gcctggagtg ggtctcaggt attagttgga aaagtggtag cataggttat gcggactctg tgaggggccg attcaccato tccagagaca acgccaagaa ttccctctat ctgcaaatga acagtctgag agttgaggac acggccttgt attactgtgt aaaagatata aggggcaact ggaactacgg gggaaactgg ttcgacccct ggggccaggg aaccctggtc actgtctcct ca | DNA nucleotide sequence |
| 290 | EVQLVESGGG LVQPGRSLRL SCAASGFTID DSAMHWVRQT PGKGLEWVSG ISWKSGSIGY ADSVRGRFTI SRDNAKNSLY LQMNSLRVED TALYYCVKDI RGNWNYGGNW FDPWGQGTLV TVSS | AA amino acid sequence |
| 291 | ggattcacca ttgatgatag tgcc | DNA nucleotide sequence |
| 292 | GFTIDDSA | AA amino acid sequence |
| 293 | attagttgga aaagtggtag cata | DNA nucleotide sequence |
| 294 | ISWKSGSI | AA amino acid sequence |
| 295 | gtaaaagata taaggggcaa ctggaactac gggggaaact ggttcgaccc c | DNA nucleotide sequence |
| 296 | VKDIRGNWNY GGNWFDP | AA amino acid sequence |
| 297 | gaggtgcagc tggtggagtc tggaggaggc ttggtccagc ctggggggtc cctgagactc tcatgtgaag cctctgggtt caccgtcggt gtcaaccaca tgaactgggt ccgccaggct ccagggaagg gtctggagtg ggtctcagtt attttcagta gtggtaggac attctacgga gactacgtga aggggcgatt aaccatcttc agacaaacct cccagaacac ggtgtatctt caaatgaata gcctgagaag tgaggacacg gccatatatt actgtgcgag agggattggc ggttttggaca tctggggccg aggacaatg gtcaccgtct cttca | DNA nucleotide sequence |
| 298 | EVQLVESGGG LVQPGGSLRL SCEASGFTVGV NHMNWVRQA PGKGLEWVSV IFSSGRTFYG DYVKGRLTIF RQTSQNTVYL QMNSLRSEDT AIYYCARGIG GLDIWGRGTM VTVSS | AA amino acid sequence |

TABLE 24-continued

Informal Sequence Listing

| SEQ. ID. NO. | SEQUENCE | DESCRIPTION |
|---|---|---|
| 299 | gggttcaccg tcggtgtcaa ccac | DNA nucleotide sequence |
| 300 | GFTVGVNH | AA amino acid sequence |
| 301 | attttcagta gtggtaggac a | DNA nucleotide sequence |
| 302 | IFSSGRT | AA amino acid sequence |
| 303 | gcgagaggga ttggcggttt ggacatc | DNA nucleotide sequence |
| 304 | ARGIGGLDI | AA amino acid sequence |
| 305 | gaagtgcagc tggtggagtc tggggggaggc ttggttcagc ctggcaggtc cctaagactc tcctgtgcag cctctggatt cacctttgat gattatgcct tgcactgggt ccggcaagct ccagggaagg gcctggagtg ggtctcaggt attagttgga ctggtggtac tatagactat gcggactctg tgaagggccg attcaccatc tccagagaca acgccaagaa ctccctgtat ctgcaaatga gcagtctgag aactgaggac acggccatat attactgtac aagagatatc cggggggaact ggaagtacgg aggctggttc gaccccctgggg gccagggaac cctggtcacc gtctcctca | DNA nucleotide sequence |
| 306 | EVQLVESGGG LVQPGRSLRL SCAASGFTFD DYALHWVRQA PGKGLEWVSG ISWTGGTIDY ADSVKGRFTI SRDNAKNSLY LQMSSLRTED TAIYYCTRDI RGNWKYGGWF DPWGQGTLVT VSS | AA amino acid sequence |
| 307 | ggattcacct ttgatgatta tgcc | DNA nucleotide sequence |
| 308 | GFTFDDYA | AA amino acid sequence |
| 309 | attagttgga ctggtggtac tata | DNA nucleotide sequence |
| 310 | ISWTGGTI | AA amino acid sequence |
| 311 | acaagagata tccgggggaa ctggaagtac ggaggctggt tcgaccccc | DNA nucleotide sequence |
| 312 | TRDIRGNWKY GGWFDP | AA amino acid sequence |
| 313 | caggtgcagc tggtgcagtc tgggactgag gtgaagaagc ctggggcctc agtgaaggtc tcctgcaagg cttctggata caccttcacc gcctactata tgcactgggt gcgacaggcc cctggtcaag gacttgactg gatgggatgg atcagcccta acagtggttt cacaaactat gcacagaagt ttcagggcag ggtcaccatg accagggaca cgtccatcaa cacattttat atggagctga gtggactgag atctgacgac acggccgtat attactgtgc gcgagagggt tctactcacc acaattcttt cgaccccctgg ggccagggaa ccctggtcac cgtctcctca | DNA nucleotide sequence |
| 314 | QVQLVQSGTE VKKPGASVKV SCKASGYTFT AYYMHWVRQA PGQGLDWMGW ISPNSGFTNY AQKFQGRVTM TRDTSINTFY MELSGLRSDD TAVYYCAREG STHHNSFDPW GQGTLVTVSS | AA amino acid sequence |
| 315 | ggatacacct tcaccgccta ctat | DNA nucleotide sequence |
| 316 | GYTFTAYY | AA amino acid sequence |

TABLE 24-continued

Informal Sequence Listing

| SEQ. ID. NO. | SEQUENCE | DESCRIPTION |
|---|---|---|
| 317 | atcagcccta acagtggttt caca | DNA nucleotide sequence |
| 318 | ISPNSGFT | AA amino acid sequence |
| 319 | gcgcgagagg gttctactca ccacaattct ttcgacccc | DNA nucleotide sequence |
| 320 | AREGSTHHNS FDP | AA amino acid sequence |
| 321 | gaggtgcagc tggtggagtc tggaggaggc ttggtccaac cggggggggtc cctgaggctc tcctgtgcag cctctgggtt caccgtcggt actaacttca tgaattgggt ccgccaggct ccagggaagg ggctggagtg ggtctcagcg atttatagcg gtggtaccgc taactacgca gactccgtga agggccgatt caccatttcc agagacactt ccaggaacaa gctgtatctt caaatgaaca gcctgagaac tgaggacacg gccgtttatt attgtgcgag agggggggggt atggacgtct ggggccaagg gaccacggtc accgtctct ca | DNA nucleotide sequence |
| 322 | EVQLVESGGG LVQPGGSLRL SCAASGFTVG TNFMNWVRQA PGKGLEWVSA IYSGGTANYA DSVKGRFTIS RDTSRNTLYL QMNSLRTEDT AVYYCARGGG MDVWGQGTTV TVSS | AA amino acid sequence |
| 323 | gggttcaccg tcggtactaa cttc | DNA nucleotide sequence |
| 324 | GFTVGTNF | AA amino acid sequence |
| 325 | atttatagcg gtggtaccgc t | DNA nucleotide sequence |
| 326 | IYSGGTA | AA amino acid sequence |
| 327 | gcgagagggg ggggtatgga cgtc | DNA nucleotide sequence |
| 328 | ARGGGMDV | AA amino acid sequence |
| 329 | caggtccagc tggtgcagtc tggggctgag gtgaagaagc ctgggtcctc ggtgaaggtc tcctgcaagg cttctggagg caccttcaac acctatgttc tcagctgggt gcgacaggcc cctggacaag ggcttgagtg gatgggagag atcatccta tcttaggtgc agcaaactac gcacagaact tccagggcag agtcactttt accacggacg aatccacgaa tacagcctac atggacctga gcagcctaag atctgaggac acggccgtgt attactgtgc gagagatcgg acctccgggg ggttcgaccc ctggggccag ggaaccctgg tcactgtctc ctca | DNA nucleotide sequence |
| 330 | QVQLVQSGAE VKKPGSSVKV SCKASGGTFN TYVLSWVRQA PGQGLEWMGE IIPILGAANY AQNFQGRVTF TTDESTNTAY MDLSSLRSED TAVYYCARDR TSGGFDPWGQ GTLVTVSS | AA amino acid sequence |
| 331 | ggaggcacct tcaacaccta tgtt | DNA nucleotide sequence |
| 332 | GGTFNTYV | AA amino acid sequence |
| 333 | atcatcccta tottaggtgc agca | DNA nucleotide sequence |

TABLE 24-continued

Informal Sequence Listing

| SEQ. ID. NO. | SEQUENCE | DESCRIPTION |
|---|---|---|
| 334 | IIPILGAA | AA amino acid sequence |
| 335 | gcgagagatc ggacctccgg ggggttcgac ccc | DNA nucleotide sequence |
| 336 | ARDRTSGGFD P | AA amino acid sequence |
| 337 | caggttcagc tggtgcagtc tggagctgag gtggagaagc ctggggcctc agtgaaggtc tcctgcaagg cttctggtta catctttacc cactatggta tcagctgggt gcgacaggcc cctggacaag gacttgagtg ggtgggctgg atcagccctt acaatggtta cacagactat gcacagaaac tccagggcag agtcaccttg accacagaca catccacgac cacagcctac atggagctga ggaacctgag atctgacgac acggccatgt attactgttc gagagggagg ggcccttact ggtccttcga tctctggggc cgtggcaccc tggtcaccgt ctcctca | DNA nucleotide sequence |
| 338 | QVQLVQSGAE VEKPGASVKV SCKASGYIFT HYGISWVRQA PGQGLEWVGW ISPYNGYTDY AQKLQGRVTL TTDTSTTTAY MELRNLRSDD TAMYYCSRGR GPYWSFDLWG RGTLVTVSS | AA amino acid sequence |
| 339 | ggttacatct ttacccacta tggt | DNA nucleotide sequence |
| 340 | GYIFTHYG | AA amino acid sequence |
| 341 | atcagccctt acaatggtta caca | DNA nucleotide sequence |
| 342 | ISPYNGYT | AA amino acid sequence |
| 343 | tcgagaggga ggggcccytta ctggtccttc gatctc | DNA nucleotide sequence |
| 344 | SRGRGPYWSF DL | AA amino acid sequence |

What is claimed is:

1. A compound of Formula (III):

wherein A is an antibody or antigen binding fragment thereof that binds monomeric human program death ligand 1 (PD-L1), wherein:

the antibody or antigen-binding fragment thereof comprises a heavy chain complementarity determining region 1 (HCDR1) comprising the amino acid sequence of SEQ ID NO: 84 with no more than one amino acid substitution; an HCDR2 comprising the amino acid sequence of SEQ ID NO: 86 with no more than one amino acid substitution; an HCDR3 comprising the amino acid sequence of SEQ ID NO: 88 with no more than one amino acid substitution; a light chain complementarity determining region 1 (LCDR1) comprising the amino acid sequence of SEQ ID NO: 92 with no more than one amino acid substitution; an LCDR2 comprising the amino acid sequence of VAS with no more than one amino acid substitution; and an LCDR3 comprising the amino acid sequence of SEQ ID NO: 96 with no more than one amino acid substitution;

and k is an integer from 1-30.

2. The compound of claim 1, wherein k is 1 or 2.

3. The compound of claim 1, wherein the antibody or antigen-binding fragment thereof comprises a heavy chain variable region (HCVR) having an amino acid sequence with at least 95% sequence identity to SEQ ID NO: 82.

4. The compound of claim 1, wherein the antibody or antigen-binding fragment thereof comprises an HCVR having an amino acid sequence with at least 99% sequence identity to SEQ ID NO: 82.

5. The compound of claim 1, wherein the antibody or antigen-binding fragment thereof comprises an HCVR hav-ing an amino acid sequence of SEQ ID NO: 82 with no more than 5 amino acid substitutions.

6. The compound of claim 1, wherein the antibody or antigen-binding fragment thereof comprises an HCVR hav-ing an amino acid sequence of SEQ ID NO: 82 with no more than one amino acid substitution.

7. The compound of claim 1, wherein the antibody or antigen-binding fragment thereof comprises an HCVR hav-ing an amino acid sequence of SEQ ID NO: 82.

8. The compound of claim 1, wherein the antibody or antigen-binding fragment thereof comprises a light chain variable region (LCVR) having an amino acid sequence with at least 95% sequence identity to SEQ ID NO: 90.

9. The compound of claim 1, wherein the antibody or antigen-binding fragment thereof comprises an LCVR hav-ing an amino acid sequence with at least 99% sequence identity to SEQ ID NO: 90.

10. The compound of claim 1, wherein the antibody or antigen-binding fragment thereof comprises an LCVR hav-ing an amino acid sequence of SEQ ID NO: 90 with no more than 5 amino acid substitutions.

11. The compound of claim 1, wherein the antibody or antigen-binding fragment thereof comprises an LCVR hav-ing an amino acid sequence of SEQ ID NO: 90 with no more than one amino acid substitution.

12. The compound of claim 1, wherein the antibody or antigen-binding fragment thereof comprises an LCVR hav-ing an amino acid sequence of SEQ ID NO: 90.

13. The compound of claim 1, wherein the antibody or antigen-binding fragment thereof comprises an HCVR hav-ing an amino acid sequence of SEQ ID NO: 82 with no more than one amino acid substitution and an LCVR having an amino acid sequence of SEQ ID NO: 90 with no more than one amino acid substitution.

14. The compound of claim 1, wherein the antibody or antigen-binding fragment thereof comprises the HCDR1 comprising the amino acid sequence of SEQ ID NO: 84; the HCDR2 comprising the amino acid sequence of SEQ ID NO: 86; the HCDR3 comprising the amino acid sequence of SEQ ID NO: 88; the LCDR1 comprising the amino acid sequence of SEQ ID NO: 92; the LCDR2 comprising the amino acid sequence of VAS; and the LCDR3 comprising the amino acid sequence of SEQ ID NO: 96.

15. The compound of claim 1, wherein the antibody or antigen-binding fragment thereof comprises an HCVR hav-ing an amino acid sequence of SEQ ID NO: 82 and an LCVR having an amino acid sequence of SEQ ID NO: 90.

*    *    *    *    *